US007989395B2

(12) United States Patent  
Morgan et al.

(10) Patent No.: US 7,989,395 B2  
(45) Date of Patent: *Aug. 2, 2011

(54) METHODS FOR IDENTIFYING COMPOUNDS OF INTEREST USING ENCODED LIBRARIES

(75) Inventors: Barry Morgan, Franklin, MA (US); Stephen Hale, Belmont, MA (US); Christopher C. Arico-Muendel, West Roxbury, MA (US); Matthew Clark, Bedford, MA (US); Richard Wagner, Cambridge, MA (US); David I. Israel, Concord, MA (US); Malcolm L. Gefter, Lincoln, MA (US); Dennis Benjamin, Redmond, WA (US); Nils Jakob Vest Hansen, Copenhagen V (DK); Malcolm J. Kavarana, Burlington, MA (US); Steffen Phillip Creaser, Cambridge, MA (US); George J. Franklin, Lynn, MA (US); Paolo A. Centrella, Acton, MA (US); Raksha A. Acharya, Bedford, MA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 784 days.

This patent is subject to a terminal disclaimer.

(21) Appl. No.: 11/584,880

(22) Filed: Oct. 23, 2006

(65) Prior Publication Data

US 2007/0224607 A1     Sep. 27, 2007

Related U.S. Application Data

(60) Provisional application No. 60/731,464, filed on Oct. 28, 2005.

(51) Int. Cl.  
*C40B 50/16* (2006.01)

(52) U.S. Cl. .................. 506/31; 506/23; 506/16; 506/5; 435/6; 435/91.2; 536/23.1; 536/24.2

(58) Field of Classification Search ........................ None  
See application file for complete search history.

(56) References Cited

U.S. PATENT DOCUMENTS

| 5,573,905 | A | 11/1996 | Lerner et al. |
| 5,708,153 | A | 1/1998 | Dower et al. |
| 5,723,598 | A | 3/1998 | Lerner et al. |
| 6,060,596 | A | 5/2000 | Lerner et al. |
| 6,537,776 | B1 | 3/2003 | Short |
| 2005/0130173 | A1* | 6/2005 | Leamon et al. ........... 435/6 |
| 2005/0158765 | A1 | 7/2005 | Morgan et al. |
| 2007/0042401 | A1 | 2/2007 | Morgan et al. |
| 2009/0062147 | A1 | 3/2009 | Morgan et al. |

FOREIGN PATENT DOCUMENTS

| WO | WO-91/05058 A1 | 4/1991 |
| WO | WO-92/02536 A1 | 2/1992 |
| WO | WO-93/06121 A1 | 4/1993 |
| WO | WO-93/20242 A1 | 10/1993 |
| WO | WO-94/13623 A1 | 6/1994 |
| WO | WO-00/23458 A1 | 4/2000 |
| WO | WO-02/074929 A2 | 9/2002 |
| WO | WO-02/102820 A1 | 12/2002 |
| WO | WO-02/103008 A2 | 12/2002 |
| WO | WO-03/078050 A2 | 9/2003 |
| WO | WO-03/078445 A2 | 9/2003 |
| WO | WO-03/078446 A2 | 9/2003 |
| WO | WO-03/078625 A2 | 9/2003 |
| WO | WO-03/078625 A3 | 9/2003 |
| WO | WO-03/078626 A2 | 9/2003 |
| WO | WO-03/078627 A2 | 9/2003 |
| WO | WO-03/101972 A1 | 12/2003 |
| WO | WO-04/001042 A2 | 12/2003 |
| WO | WO-2004/009814 A1 | 1/2004 |
| WO | WO-2004/013070 A2 | 2/2004 |
| WO | WO-2004/013070 A3 | 2/2004 |
| WO | WO-2004/016767 A2 | 2/2004 |
| WO | WO-2004/074429 A2 | 2/2004 |
| WO | WO-2004/074429 A3 | 2/2004 |
| WO | WO-2004/024929 A2 | 3/2004 |
| WO | WO-2004/039825 A2 | 5/2004 |
| WO | WO-2004/056994 A2 | 7/2004 |
| WO | WO-2004/074501 A2 | 9/2004 |
| WO | WO-2004/083427 A2 | 9/2004 |
| WO | WO-2004/099441 A2 | 11/2004 |
| WO | WO-2004/110964 A2 | 12/2004 |
| WO | WO-2005/003778 A2 | 1/2005 |
| WO | WO-2005/026387 A1 | 3/2005 |
| WO | WO-2005/058479 A2 | 6/2005 |
| WO | WO-2005/078122 A2 | 8/2005 |
| WO | WO-2005/090566 A2 | 9/2005 |
| WO | WO-2006/053571 A2 | 5/2006 |

OTHER PUBLICATIONS

Ansoy, K., et al. "Some reactions of 2,4,6-trichloro-s-triazine." *Journal of Qafgaz University*. 1997; 1:131-7.

Brenner, Sydney et al., "Encoded combinatorial chemistry," Proc. Natl. Acad. Sci. USA, vol. 89:5381-5383 (1992).

Calderone, Christopher T. et al., "Directing Otherwise Incompatible Reactions in a Single Solution by Using DNA-Templated Organic Synthesis," *Angew. Chem. Int. Ed.*, vol. 41(21):4104-4108 (2002).

Calderone, Christopher T. et al., "Nucleic-acid-templated synthesis as a model system for ancient translation," *Current Opinion in Chemical Biology*, vol. 8:645-653 (2004).

Czlapinski, Jennifer L. et al., "Nucleic Acid Template-Directed Assembly of Metallosalen-DNA Conjugates," *J. Am. Chem. Soc.*, vol. 123:8618-8619 (2001).

Gartner, Zev J. et al., "DNA-Templated Organic Synthesis and Selection of a Library of Macrocycles," Science, vol. 305:1601-1605 (2004).

Gryaznov, Sergei M. et al., "Chemical Ligation of Oligonucleotides in the Presence and Absence of a Template," *J. Am. Chem. Soc.*, vol. 115:3808-3809 (1993).

Halpin, D., et al. "DNA display I. Sequence-encoded routing of DNA populations." *PLoS Biology*. 2004; 2(7):1015-21.

(Continued)

*Primary Examiner* — Christopher M Gross  
(74) *Attorney, Agent, or Firm* — McCarter & English, LLP; Maria Laccotripe Zacharakis; Deborah L. Nagle

(57) ABSTRACT

The present invention provides a method for identifying a compound of interest by screening libraries of molecules which include an encoding oligonucleotide tag.

46 Claims, 11 Drawing Sheets

OTHER PUBLICATIONS

Halpin, D., et al. "DNA display II. Genetic manipulation of combinatorial chemistry libraries for small-molecule evolution." *PLoS Biology*. 2004; 2(7):1022-30.

Halpin, D., et al. "DNA display III. Solid-phase organic synthesis on unprotected DNA." *PLoS Biology*. 2004; 2(7):1031-8.

Kanan, Matthew W. et al., "Reaction discovery enabled by DNA-templated synthesis and in vitro selection," Nature, vol. 431:545-549 (2004).

Kinoshita, Y., et al. "Enzymatic synthesis of code regions for encoded combinatorial chemistry (ECC)." *Nucleic Acids Symp Ser*. 1995; (34):201-2.

Li, Xiaoyu et al., "Translation of DNA into Synthetic N-Acyloxazolidines," *J. Am. Chem. Soc.*, vol. 126:5090-5092 (2004).

Needels, M., et al. "Generation and screening of an oligonucleotide-encoded synthetic peptide library." *Proc Natl Acad Sci USA*. Nov, 15, 1993; 90(22):10700-4.

Nielsen, John et al., "Synthetic Methods for the Implementation of Encoded Combinatorial Chemistry," *J. Am. Chem. Soc.*, vol. 115(21):9812-9813 (1993).

Nielsen, John et al., "Toward Chemical Implementation of Encoded Combinatorial Libraries," *Methods: A Comparison to Methods in Enzymology*, vol. 6:361-371 (1994).

International Search Report for Application No. PCT/US2006/041356, dated Aug. 21, 2007.

International Search Report for Application No. PCT/US2006/022555, dated Mar. 23, 2007.

International Search Report for Application No. PCT/US2004/042964, dated Aug. 16, 2005.

International Preliminary Report on Patentability for Application No. PCT/US2006/022555, dated Dec. 11, 2007.

Jäschke et al. "Synthesis and properties of oligodeoxyribonucleotide-polyethylene glycol conjugates," *Nucleic Acids Research* vol. 22(22):4810-4817 (1994).

Shchepinov et al."Trityl tags for encoding in combinatorial synthesis," *Tetrahedron* vol. 56:2713-2724 (2000).

Behrens et al. "Synthesis of achiral linker reagents for direct labeling of oligonucleotides on solid supports," Nucleosides, Nucleotides and Nucleic Acids vol. 18(2):291-305 (19999).

* cited by examiner

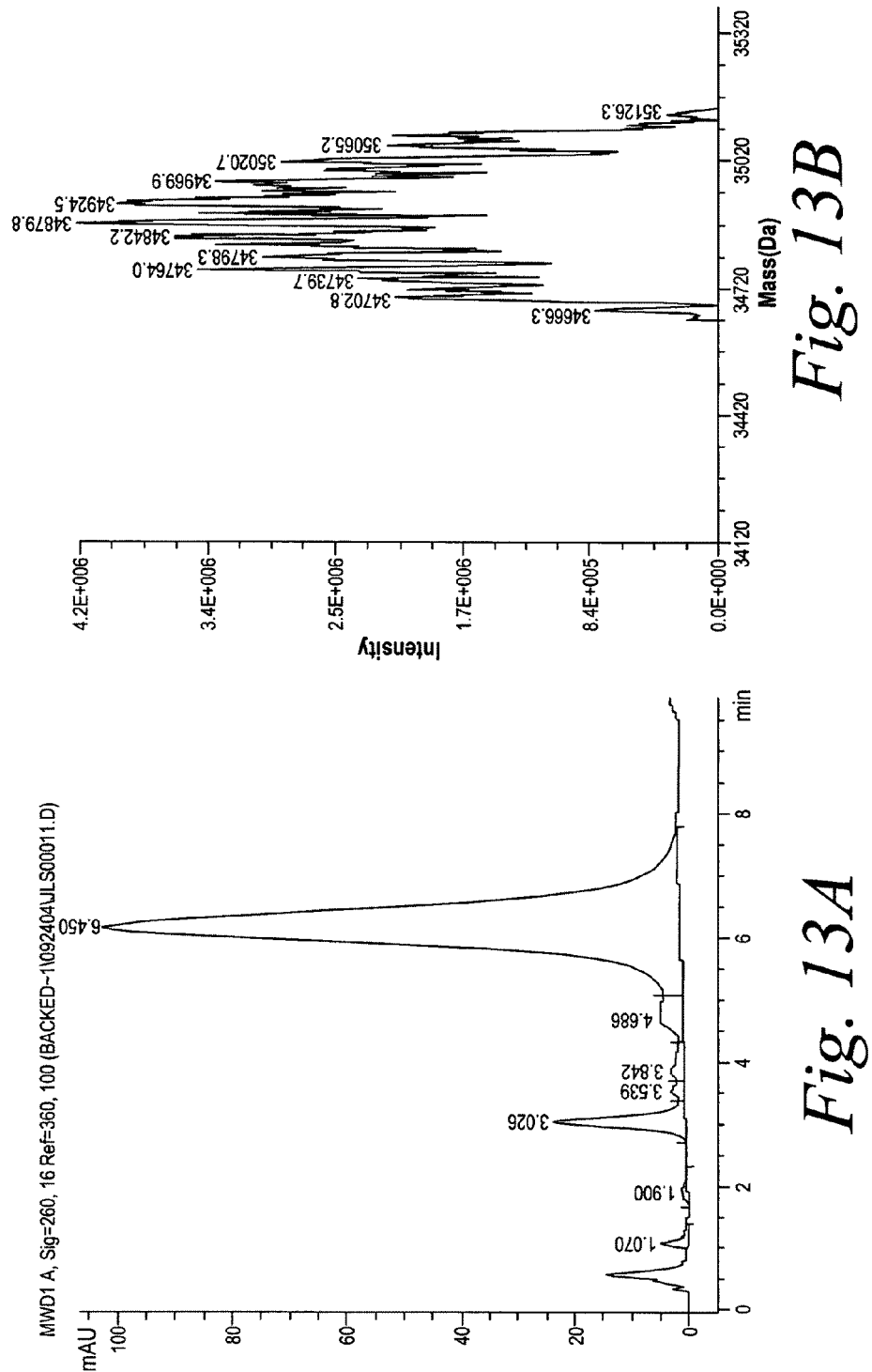

SEQUENCE LISTING

<160> NUMBER OF SEQ ID NOS: 890

<210> SEQ ID NO 1
<211> LENGTH: 9
<212> TYPE: DNA
<213> ORGANISM: Artificial Sequence
<220> FEATURE:
<223> OTHER INFORMATION: synthetic construct

<400> SEQUENCE: 1 gcaacgaag                                                            9

<210> SEQ ID NO 2
<211> LENGTH: 9
<212> TYPE: DNA
<213> ORGANISM: Artificial Sequence
<220> FEATURE:
<223> OTHER INFORMATION: synthetic construct

<400> SEQUENCE: 2 tcgttgcca                                                            9

<210> SEQ ID NO 3

```
<211> LENGTH: 9
<212> TYPE: DNA
<213> ORGANISM: Artificial Sequence
<220> FEATURE:
<223> OTHER INFORMATION: synthetic construct

<400> SEQUENCE: 3 gcgtacaag                                                                  9

<210> SEQ ID NO 4
<211> LENGTH: 9
<212> TYPE: DNA
<213> ORGANISM: Artificial Sequence
<220> FEATURE:
<223> OTHER INFORMATION: synthetic construct

<400> SEQUENCE: 4 tgtacgcca                                                                  9

<210> SEQ ID NO 5
<211> LENGTH: 9
<212> TYPE: DNA
<213> ORGANISM: Artificial Sequence
<220> FEATURE:
<223> OTHER INFORMATION: synthetic construct

<400> SEQUENCE: 5 gctctgtag                                                                  9

<210> SEQ ID NO 6
<211> LENGTH: 9
<212> TYPE: DNA
<213> ORGANISM: Artificial Sequence
<220> FEATURE:
<223> OTHER INFORMATION: synthetic construct

<400> SEQUENCE: 6 acagagcca                                                                  9

<210> SEQ ID NO 7
<211> LENGTH: 9
<212> TYPE: DNA
<213> ORGANISM: Artificial Sequence
<220> FEATURE:
<223> OTHER INFORMATION: synthetic construct

<400> SEQUENCE: 7 gtgccatag                                                                  9

<210> SEQ ID NO 8
<211> LENGTH: 9
<212> TYPE: DNA
<213> ORGANISM: Artificial Sequence
<220> FEATURE:
<223> OTHER INFORMATION: synthetic construct

<400> SEQUENCE: 8 atggcacca                                                                  9

<210> SEQ ID NO 9
<211> LENGTH: 9
<212> TYPE: DNA
<213> ORGANISM: Artificial Sequence
<220> FEATURE:
<223> OTHER INFORMATION: synthetic construct

<400> SEQUENCE: 9
``` gttgaccag                                                                      9

<210> SEQ ID NO 10
<211> LENGTH: 9
<212> TYPE: DNA
<213> ORGANISM: Artificial Sequence
<220> FEATURE:
<223> OTHER INFORMATION: synthetic construct

<400> SEQUENCE: 10 ggtcaacca                                                                      9

<210> SEQ ID NO 11
<211> LENGTH: 9
<212> TYPE: DNA
<213> ORGANISM: Artificial Sequence
<220> FEATURE:
<223> OTHER INFORMATION: synthetic construct

<400> SEQUENCE: 11 cgacttgac                                                                      9

<210> SEQ ID NO 12
<211> LENGTH: 9
<212> TYPE: DNA
<213> ORGANISM: Artificial Sequence
<220> FEATURE:
<223> OTHER INFORMATION: synthetic construct

<400> SEQUENCE: 12 acgctgaac                                                                      9

<210> SEQ ID NO 13
<211> LENGTH: 9
<212> TYPE: DNA
<213> ORGANISM: Artificial Sequence
<220> FEATURE:
<223> OTHER INFORMATION: synthetic construct

<400> SEQUENCE: 13 cgtagtcag                                                                      9

<210> SEQ ID NO 14
<211> LENGTH: 9
<212> TYPE: DNA
<213> ORGANISM: Artificial Sequence
<220> FEATURE:
<223> OTHER INFORMATION: synthetic construct

<400> SEQUENCE: 14 gactacgca                                                                      9

<210> SEQ ID NO 15
<211> LENGTH: 9
<212> TYPE: DNA
<213> ORGANISM: Artificial Sequence
<220> FEATURE:
<223> OTHER INFORMATION: synthetic construct

<400> SEQUENCE: 15 ccagcatag                                                                      9

<210> SEQ ID NO 16
<211> LENGTH: 9
<212> TYPE: DNA
<213> ORGANISM: Artificial Sequence
<220> FEATURE:

<223> OTHER INFORMATION: synthetic construct

<400> SEQUENCE: 16 atgctggca                                                                         9

<210> SEQ ID NO 17
<211> LENGTH: 9
<212> TYPE: DNA
<213> ORGANISM: Artificial Sequence
<220> FEATURE:
<223> OTHER INFORMATION: synthetic construct

<400> SEQUENCE: 17 cctacagag                                                                         9

<210> SEQ ID NO 18
<211> LENGTH: 9
<212> TYPE: DNA
<213> ORGANISM: Artificial Sequence
<220> FEATURE:
<223> OTHER INFORMATION: synthetic construct

<400> SEQUENCE: 18 ctgtaggca                                                                         9

<210> SEQ ID NO 19
<211> LENGTH: 9
<212> TYPE: DNA
<213> ORGANISM: Artificial Sequence
<220> FEATURE:
<223> OTHER INFORMATION: synthetic construct

<400> SEQUENCE: 19 ctgaacgag                                                                         9

<210> SEQ ID NO 20
<211> LENGTH: 9
<212> TYPE: DNA
<213> ORGANISM: Artificial Sequence
<220> FEATURE:
<223> OTHER INFORMATION: synthetic construct

<400> SEQUENCE: 20 acgacttgc                                                                         9

<210> SEQ ID NO 21
<211> LENGTH: 9
<212> TYPE: DNA
<213> ORGANISM: Artificial Sequence
<220> FEATURE:
<223> OTHER INFORMATION: synthetic construct

<400> SEQUENCE: 21 ctccagtag                                                                         9

<210> SEQ ID NO 22
<211> LENGTH: 9
<212> TYPE: DNA
<213> ORGANISM: Artificial Sequence
<220> FEATURE:
<223> OTHER INFORMATION: synthetic construct

<400> SEQUENCE: 22 actggagca                                                                         9

<210> SEQ ID NO 23

```
<211> LENGTH: 9
<212> TYPE: DNA
<213> ORGANISM: Artificial Sequence
<220> FEATURE:
<223> OTHER INFORMATION: synthetic construct

<400> SEQUENCE: 23 taggtccag                                                                  9

<210> SEQ ID NO 24
<211> LENGTH: 9
<212> TYPE: DNA
<213> ORGANISM: Artificial Sequence
<220> FEATURE:
<223> OTHER INFORMATION: synthetic construct

<400> SEQUENCE: 24 ggacctaca                                                                  9

<210> SEQ ID NO 25
<211> LENGTH: 9
<212> TYPE: DNA
<213> ORGANISM: Artificial Sequence
<220> FEATURE:
<223> OTHER INFORMATION: synthetic construct

<400> SEQUENCE: 25 gcgtgttgt                                                                  9

<210> SEQ ID NO 26
<211> LENGTH: 9
<212> TYPE: DNA
<213> ORGANISM: Artificial Sequence
<220> FEATURE:
<223> OTHER INFORMATION: synthetic construct

<400> SEQUENCE: 26 aacacgcct                                                                  9

<210> SEQ ID NO 27
<211> LENGTH: 9
<212> TYPE: DNA
<213> ORGANISM: Artificial Sequence
<220> FEATURE:
<223> OTHER INFORMATION: synthetic construct

<400> SEQUENCE: 27 gcttggagt                                                                  9

<210> SEQ ID NO 28
<211> LENGTH: 9
<212> TYPE: DNA
<213> ORGANISM: Artificial Sequence
<220> FEATURE:
<223> OTHER INFORMATION: synthetic construct

<400> SEQUENCE: 28 tccaagcct                                                                  9

<210> SEQ ID NO 29
<211> LENGTH: 9
<212> TYPE: DNA
<213> ORGANISM: Artificial Sequence
<220> FEATURE:
<223> OTHER INFORMATION: synthetic construct

<400> SEQUENCE: 29
```

-continued gtcaagcgt                                                                           9

<210> SEQ ID NO 30
<211> LENGTH: 9
<212> TYPE: DNA
<213> ORGANISM: Artificial Sequence
<220> FEATURE:
<223> OTHER INFORMATION: synthetic construct

<400> SEQUENCE: 30 gcttgacct                                                                           9

<210> SEQ ID NO 31
<211> LENGTH: 9
<212> TYPE: DNA
<213> ORGANISM: Artificial Sequence
<220> FEATURE:
<223> OTHER INFORMATION: synthetic construct

<400> SEQUENCE: 31 caagagcgt                                                                           9

<210> SEQ ID NO 32
<211> LENGTH: 9
<212> TYPE: DNA
<213> ORGANISM: Artificial Sequence
<220> FEATURE:
<223> OTHER INFORMATION: synthetic construct

<400> SEQUENCE: 32 gctcttgct                                                                           9

<210> SEQ ID NO 33
<211> LENGTH: 9
<212> TYPE: DNA
<213> ORGANISM: Artificial Sequence
<220> FEATURE:
<223> OTHER INFORMATION: synthetic construct

<400> SEQUENCE: 33 cagttcggt                                                                           9

<210> SEQ ID NO 34
<211> LENGTH: 9
<212> TYPE: DNA
<213> ORGANISM: Artificial Sequence
<220> FEATURE:
<223> OTHER INFORMATION: synthetic construct

<400> SEQUENCE: 34 cgaactgct                                                                           9

<210> SEQ ID NO 35
<211> LENGTH: 9
<212> TYPE: DNA
<213> ORGANISM: Artificial Sequence
<220> FEATURE:
<223> OTHER INFORMATION: synthetic construct

<400> SEQUENCE: 35 cgaaggagt                                                                           9

<210> SEQ ID NO 36
<211> LENGTH: 9
<212> TYPE: DNA
<213> ORGANISM: Artificial Sequence
<220> FEATURE:

-continued

<223> OTHER INFORMATION: synthetic construct

<400> SEQUENCE: 36 tccttcgct                                                                9

<210> SEQ ID NO 37
<211> LENGTH: 9
<212> TYPE: DNA
<213> ORGANISM: Artificial Sequence
<220> FEATURE:
<223> OTHER INFORMATION: synthetic construct

<400> SEQUENCE: 37 cggtgttgt                                                                9

<210> SEQ ID NO 38
<211> LENGTH: 9
<212> TYPE: DNA
<213> ORGANISM: Artificial Sequence
<220> FEATURE:
<223> OTHER INFORMATION: synthetic construct

<400> SEQUENCE: 38 aacaccgct                                                                9

<210> SEQ ID NO 39
<211> LENGTH: 9
<212> TYPE: DNA
<213> ORGANISM: Artificial Sequence
<220> FEATURE:
<223> OTHER INFORMATION: synthetic construct

<400> SEQUENCE: 39 cgttgctgt                                                                9

<210> SEQ ID NO 40
<211> LENGTH: 9
<212> TYPE: DNA
<213> ORGANISM: Artificial Sequence
<220> FEATURE:
<223> OTHER INFORMATION: synthetic construct

<400> SEQUENCE: 40 agcaacgct                                                                9

<210> SEQ ID NO 41
<211> LENGTH: 9
<212> TYPE: DNA
<213> ORGANISM: Artificial Sequence
<220> FEATURE:
<223> OTHER INFORMATION: synthetic construct

<400> SEQUENCE: 41 ccgatctgt                                                                9

<210> SEQ ID NO 42
<211> LENGTH: 9
<212> TYPE: DNA
<213> ORGANISM: Artificial Sequence
<220> FEATURE:
<223> OTHER INFORMATION: synthetic construct

<400> SEQUENCE: 42 agatcggct                                                                9

<210> SEQ ID NO 43

-continued

```
<211> LENGTH: 9
<212> TYPE: DNA
<213> ORGANISM: Artificial Sequence
<220> FEATURE:
<223> OTHER INFORMATION: synthetic construct

<400> SEQUENCE: 43 ccttctcgt                                                                 9

<210> SEQ ID NO 44
<211> LENGTH: 9
<212> TYPE: DNA
<213> ORGANISM: Artificial Sequence
<220> FEATURE:
<223> OTHER INFORMATION: synthetic construct

<400> SEQUENCE: 44 gagaaggct                                                                 9

<210> SEQ ID NO 45
<211> LENGTH: 9
<212> TYPE: DNA
<213> ORGANISM: Artificial Sequence
<220> FEATURE:
<223> OTHER INFORMATION: synthetic construct

<400> SEQUENCE: 45 tgagtccgt                                                                 9

<210> SEQ ID NO 46
<211> LENGTH: 9
<212> TYPE: DNA
<213> ORGANISM: Artificial Sequence
<220> FEATURE:
<223> OTHER INFORMATION: synthetic construct

<400> SEQUENCE: 46 ggactcact                                                                 9

<210> SEQ ID NO 47
<211> LENGTH: 9
<212> TYPE: DNA
<213> ORGANISM: Artificial Sequence
<220> FEATURE:
<223> OTHER INFORMATION: synthetic construct

<400> SEQUENCE: 47 tgctacggt                                                                 9

<210> SEQ ID NO 48
<211> LENGTH: 9
<212> TYPE: DNA
<213> ORGANISM: Artificial Sequence
<220> FEATURE:
<223> OTHER INFORMATION: synthetic construct

<400> SEQUENCE: 48 cgttagact                                                                 9

<210> SEQ ID NO 49
<211> LENGTH: 9
<212> TYPE: DNA
<213> ORGANISM: Artificial Sequence
<220> FEATURE:
<223> OTHER INFORMATION: synthetic construct

<400> SEQUENCE: 49
```

```
gtgcgttga                                                                    9

<210> SEQ ID NO 50
<211> LENGTH: 9
<212> TYPE: DNA
<213> ORGANISM: Artificial Sequence
<220> FEATURE:
<223> OTHER INFORMATION: synthetic construct

<400> SEQUENCE: 50 aacgcacac                                                                    9

<210> SEQ ID NO 51
<211> LENGTH: 9
<212> TYPE: DNA
<213> ORGANISM: Artificial Sequence
<220> FEATURE:
<223> OTHER INFORMATION: synthetic construct

<400> SEQUENCE: 51 gttggcaga                                                                    9

<210> SEQ ID NO 52
<211> LENGTH: 9
<212> TYPE: DNA
<213> ORGANISM: Artificial Sequence
<220> FEATURE:
<223> OTHER INFORMATION: synthetic construct

<400> SEQUENCE: 52 tgccaacac                                                                    9

<210> SEQ ID NO 53
<211> LENGTH: 9
<212> TYPE: DNA
<213> ORGANISM: Artificial Sequence
<220> FEATURE:
<223> OTHER INFORMATION: synthetic construct

<400> SEQUENCE: 53 cctgtagga                                                                    9

<210> SEQ ID NO 54
<211> LENGTH: 9
<212> TYPE: DNA
<213> ORGANISM: Artificial Sequence
<220> FEATURE:
<223> OTHER INFORMATION: synthetic construct

<400> SEQUENCE: 54 ctacaggac                                                                    9

<210> SEQ ID NO 55
<211> LENGTH: 9
<212> TYPE: DNA
<213> ORGANISM: Artificial Sequence
<220> FEATURE:
<223> OTHER INFORMATION: synthetic construct

<400> SEQUENCE: 55 ctgcgtaga                                                                    9

<210> SEQ ID NO 56
<211> LENGTH: 9
<212> TYPE: DNA
<213> ORGANISM: Artificial Sequence
<220> FEATURE:
```

<223> OTHER INFORMATION: synthetic construct

<400> SEQUENCE: 56 tacgcagac                                                                                          9

<210> SEQ ID NO 57
<211> LENGTH: 9
<212> TYPE: DNA
<213> ORGANISM: Artificial Sequence
<220> FEATURE:
<223> OTHER INFORMATION: synthetic construct

<400> SEQUENCE: 57 cttacgcga                                                                                          9

<210> SEQ ID NO 58
<211> LENGTH: 9
<212> TYPE: DNA
<213> ORGANISM: Artificial Sequence
<220> FEATURE:
<223> OTHER INFORMATION: synthetic construct

<400> SEQUENCE: 58 gcgtaagac                                                                                          9

<210> SEQ ID NO 59
<211> LENGTH: 9
<212> TYPE: DNA
<213> ORGANISM: Artificial Sequence
<220> FEATURE:
<223> OTHER INFORMATION: synthetic construct

<400> SEQUENCE: 59 tggtcacga                                                                                          9

<210> SEQ ID NO 60
<211> LENGTH: 9
<212> TYPE: DNA
<213> ORGANISM: Artificial Sequence
<220> FEATURE:
<223> OTHER INFORMATION: synthetic construct

<400> SEQUENCE: 60 gtgaccaac                                                                                          9

<210> SEQ ID NO 61
<211> LENGTH: 9
<212> TYPE: DNA
<213> ORGANISM: Artificial Sequence
<220> FEATURE:
<223> OTHER INFORMATION: synthetic construct

<400> SEQUENCE: 61 tcagagcga                                                                                          9

<210> SEQ ID NO 62
<211> LENGTH: 9
<212> TYPE: DNA
<213> ORGANISM: Artificial Sequence
<220> FEATURE:
<223> OTHER INFORMATION: synthetic construct

<400> SEQUENCE: 62 gctctgaac                                                                                          9

<210> SEQ ID NO 63

```
<211> LENGTH: 9
<212> TYPE: DNA
<213> ORGANISM: Artificial Sequence
<220> FEATURE:
<223> OTHER INFORMATION: synthetic construct

<400> SEQUENCE: 63 ttgctcgga                                                                        9

<210> SEQ ID NO 64
<211> LENGTH: 9
<212> TYPE: DNA
<213> ORGANISM: Artificial Sequence
<220> FEATURE:
<223> OTHER INFORMATION: synthetic construct

<400> SEQUENCE: 64 cgagcaaac                                                                        9

<210> SEQ ID NO 65
<211> LENGTH: 9
<212> TYPE: DNA
<213> ORGANISM: Artificial Sequence
<220> FEATURE:
<223> OTHER INFORMATION: synthetic construct

<400> SEQUENCE: 65 gcagttgga                                                                        9

<210> SEQ ID NO 66
<211> LENGTH: 9
<212> TYPE: DNA
<213> ORGANISM: Artificial Sequence
<220> FEATURE:
<223> OTHER INFORMATION: synthetic construct

<400> SEQUENCE: 66 caactgcac                                                                        9

<210> SEQ ID NO 67
<211> LENGTH: 9
<212> TYPE: DNA
<213> ORGANISM: Artificial Sequence
<220> FEATURE:
<223> OTHER INFORMATION: synthetic construct

<400> SEQUENCE: 67 gcctgaaga                                                                        9

<210> SEQ ID NO 68
<211> LENGTH: 9
<212> TYPE: DNA
<213> ORGANISM: Artificial Sequence
<220> FEATURE:
<223> OTHER INFORMATION: synthetic construct

<400> SEQUENCE: 68 ttcaggcac                                                                        9

<210> SEQ ID NO 69
<211> LENGTH: 9
<212> TYPE: DNA
<213> ORGANISM: Artificial Sequence
<220> FEATURE:
<223> OTHER INFORMATION: synthetic construct

<400> SEQUENCE: 69
```

-continued gtagccaga                                                          9

<210> SEQ ID NO 70
<211> LENGTH: 9
<212> TYPE: DNA
<213> ORGANISM: Artificial Sequence
<220> FEATURE:
<223> OTHER INFORMATION: synthetic construct

<400> SEQUENCE: 70 tggctacac                                                          9

<210> SEQ ID NO 71
<211> LENGTH: 9
<212> TYPE: DNA
<213> ORGANISM: Artificial Sequence
<220> FEATURE:
<223> OTHER INFORMATION: synthetic construct

<400> SEQUENCE: 71 gtcgcttga                                                          9

<210> SEQ ID NO 72
<211> LENGTH: 9
<212> TYPE: DNA
<213> ORGANISM: Artificial Sequence
<220> FEATURE:
<223> OTHER INFORMATION: synthetic construct

<400> SEQUENCE: 72 aagcgacac                                                          9

<210> SEQ ID NO 73
<211> LENGTH: 9
<212> TYPE: DNA
<213> ORGANISM: Artificial Sequence
<220> FEATURE:
<223> OTHER INFORMATION: synthetic construct

<400> SEQUENCE: 73 gcctaagtt                                                          9

<210> SEQ ID NO 74
<211> LENGTH: 9
<212> TYPE: DNA
<213> ORGANISM: Artificial Sequence
<220> FEATURE:
<223> OTHER INFORMATION: synthetic construct

<400> SEQUENCE: 74 cttaggctc                                                          9

<210> SEQ ID NO 75
<211> LENGTH: 9
<212> TYPE: DNA
<213> ORGANISM: Artificial Sequence
<220> FEATURE:
<223> OTHER INFORMATION: synthetic construct

<400> SEQUENCE: 75 gtagtgctt                                                          9

<210> SEQ ID NO 76
<211> LENGTH: 9
<212> TYPE: DNA
<213> ORGANISM: Artificial Sequence
<220> FEATURE:

```
<223> OTHER INFORMATION: synthetic construct

<400> SEQUENCE: 76 gcactactc                                                                  9

<210> SEQ ID NO 77
<211> LENGTH: 9
<212> TYPE: DNA
<213> ORGANISM: Artificial Sequence
<220> FEATURE:
<223> OTHER INFORMATION: synthetic construct

<400> SEQUENCE: 77 gtcgaagtt                                                                  9

<210> SEQ ID NO 78
<211> LENGTH: 9
<212> TYPE: DNA
<213> ORGANISM: Artificial Sequence
<220> FEATURE:
<223> OTHER INFORMATION: synthetic construct

<400> SEQUENCE: 78 cttcgactc                                                                  9

<210> SEQ ID NO 79
<211> LENGTH: 9
<212> TYPE: DNA
<213> ORGANISM: Artificial Sequence
<220> FEATURE:
<223> OTHER INFORMATION: synthetic construct

<400> SEQUENCE: 79 gtttcggtt                                                                  9

<210> SEQ ID NO 80
<211> LENGTH: 9
<212> TYPE: DNA
<213> ORGANISM: Artificial Sequence
<220> FEATURE:
<223> OTHER INFORMATION: synthetic construct

<400> SEQUENCE: 80 ccgaaactc                                                                  9

<210> SEQ ID NO 81
<211> LENGTH: 9
<212> TYPE: DNA
<213> ORGANISM: Artificial Sequence
<220> FEATURE:
<223> OTHER INFORMATION: synthetic construct

<400> SEQUENCE: 81 cagcgtttt                                                                  9

<210> SEQ ID NO 82
<211> LENGTH: 9
<212> TYPE: DNA
<213> ORGANISM: Artificial Sequence
<220> FEATURE:
<223> OTHER INFORMATION: synthetic construct

<400> SEQUENCE: 82 aacgctgtc                                                                  9

<210> SEQ ID NO 83
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 83 catacgctt                                                                          9

<210> SEQ ID NO 84
<211> LENGTH: 9
<212> TYPE: DNA
<213> ORGANISM: Artificial Sequence
<220> FEATURE:
<223> OTHER INFORMATION: synthetic construct

<400> SEQUENCE: 84 gcgtatgtc                                                                          9

<210> SEQ ID NO 85
<211> LENGTH: 9
<212> TYPE: DNA
<213> ORGANISM: Artificial Sequence
<220> FEATURE:
<223> OTHER INFORMATION: synthetic construct

<400> SEQUENCE: 85 cgatctgtt                                                                          9

<210> SEQ ID NO 86
<211> LENGTH: 9
<212> TYPE: DNA
<213> ORGANISM: Artificial Sequence
<220> FEATURE:
<223> OTHER INFORMATION: synthetic construct

<400> SEQUENCE: 86 cagatcgtc                                                                          9

<210> SEQ ID NO 87
<211> LENGTH: 9
<212> TYPE: DNA
<213> ORGANISM: Artificial Sequence
<220> FEATURE:
<223> OTHER INFORMATION: synthetic construct

<400> SEQUENCE: 87 cgctttgtt                                                                          9

<210> SEQ ID NO 88
<211> LENGTH: 9
<212> TYPE: DNA
<213> ORGANISM: Artificial Sequence
<220> FEATURE:
<223> OTHER INFORMATION: synthetic construct

<400> SEQUENCE: 88 caaagcgtc                                                                          9

<210> SEQ ID NO 89
<211> LENGTH: 9
<212> TYPE: DNA
<213> ORGANISM: Artificial Sequence
<220> FEATURE:
<223> OTHER INFORMATION: synthetic construct

<400> SEQUENCE: 89
``` ccacagttt                                                                        9

<210> SEQ ID NO 90
<211> LENGTH: 9
<212> TYPE: DNA
<213> ORGANISM: Artificial Sequence
<220> FEATURE:
<223> OTHER INFORMATION: synthetic construct

<400> SEQUENCE: 90 actgtggtc                                                                        9

<210> SEQ ID NO 91
<211> LENGTH: 9
<212> TYPE: DNA
<213> ORGANISM: Artificial Sequence
<220> FEATURE:
<223> OTHER INFORMATION: synthetic construct

<400> SEQUENCE: 91 cctgaagtt                                                                        9

<210> SEQ ID NO 92
<211> LENGTH: 9
<212> TYPE: DNA
<213> ORGANISM: Artificial Sequence
<220> FEATURE:
<223> OTHER INFORMATION: synthetic construct

<400> SEQUENCE: 92 cttcaggtc                                                                        9

<210> SEQ ID NO 93
<211> LENGTH: 9
<212> TYPE: DNA
<213> ORGANISM: Artificial Sequence
<220> FEATURE:
<223> OTHER INFORMATION: synthetic construct

<400> SEQUENCE: 93 ctgacgatt                                                                        9

<210> SEQ ID NO 94
<211> LENGTH: 9
<212> TYPE: DNA
<213> ORGANISM: Artificial Sequence
<220> FEATURE:
<223> OTHER INFORMATION: synthetic construct

<400> SEQUENCE: 94 tcgtcagtc                                                                        9

<210> SEQ ID NO 95
<211> LENGTH: 9
<212> TYPE: DNA
<213> ORGANISM: Artificial Sequence
<220> FEATURE:
<223> OTHER INFORMATION: synthetic construct

<400> SEQUENCE: 95 ctccacttt                                                                        9

<210> SEQ ID NO 96
<211> LENGTH: 9
<212> TYPE: DNA
<213> ORGANISM: Artificial Sequence
<220> FEATURE:

<223> OTHER INFORMATION: synthetic construct

<400> SEQUENCE: 96 agtggagtc                                                                        9

<210> SEQ ID NO 97
<211> LENGTH: 9
<212> TYPE: DNA
<213> ORGANISM: Artificial Sequence
<220> FEATURE:
<223> OTHER INFORMATION: synthetic construct

<400> SEQUENCE: 97 accagagcc                                                                        9

<210> SEQ ID NO 98
<211> LENGTH: 9
<212> TYPE: DNA
<213> ORGANISM: Artificial Sequence
<220> FEATURE:
<223> OTHER INFORMATION: synthetic construct

<400> SEQUENCE: 98 ctctggtaa                                                                        9

<210> SEQ ID NO 99
<211> LENGTH: 9
<212> TYPE: DNA
<213> ORGANISM: Artificial Sequence
<220> FEATURE:
<223> OTHER INFORMATION: synthetic construct

<400> SEQUENCE: 99 atccgcacc                                                                        9

<210> SEQ ID NO 100
<211> LENGTH: 9
<212> TYPE: DNA
<213> ORGANISM: Artificial Sequence
<220> FEATURE:
<223> OTHER INFORMATION: synthetic construct

<400> SEQUENCE: 100 tgcggataa                                                                        9

<210> SEQ ID NO 101
<211> LENGTH: 9
<212> TYPE: DNA
<213> ORGANISM: Artificial Sequence
<220> FEATURE:
<223> OTHER INFORMATION: synthetic construct

<400> SEQUENCE: 101 gacgacacc                                                                        9

<210> SEQ ID NO 102
<211> LENGTH: 9
<212> TYPE: DNA
<213> ORGANISM: Artificial Sequence
<220> FEATURE:
<223> OTHER INFORMATION: synthetic construct

<400> SEQUENCE: 102 tgtcgtcaa                                                                        9

<210> SEQ ID NO 103

```
<211> LENGTH: 9
<212> TYPE: DNA
<213> ORGANISM: Artificial Sequence
<220> FEATURE:
<223> OTHER INFORMATION: synthetic construct

<400> SEQUENCE: 103 ggatggacc                                                                     9

<210> SEQ ID NO 104
<211> LENGTH: 9
<212> TYPE: DNA
<213> ORGANISM: Artificial Sequence
<220> FEATURE:
<223> OTHER INFORMATION: synthetic construct

<400> SEQUENCE: 104 tccatccaa                                                                     9

<210> SEQ ID NO 105
<211> LENGTH: 9
<212> TYPE: DNA
<213> ORGANISM: Artificial Sequence
<220> FEATURE:
<223> OTHER INFORMATION: synthetic construct

<400> SEQUENCE: 105 gcagaagcc                                                                     9

<210> SEQ ID NO 106
<211> LENGTH: 9
<212> TYPE: DNA
<213> ORGANISM: Artificial Sequence
<220> FEATURE:
<223> OTHER INFORMATION: synthetic construct

<400> SEQUENCE: 106 cttctgcaa                                                                     9

<210> SEQ ID NO 107
<211> LENGTH: 9
<212> TYPE: DNA
<213> ORGANISM: Artificial Sequence
<220> FEATURE:
<223> OTHER INFORMATION: synthetic construct

<400> SEQUENCE: 107 gccatgtcc                                                                     9

<210> SEQ ID NO 108
<211> LENGTH: 9
<212> TYPE: DNA
<213> ORGANISM: Artificial Sequence
<220> FEATURE:
<223> OTHER INFORMATION: synthetic construct

<400> SEQUENCE: 108 acatggcaa                                                                     9

<210> SEQ ID NO 109
<211> LENGTH: 9
<212> TYPE: DNA
<213> ORGANISM: Artificial Sequence
<220> FEATURE:
<223> OTHER INFORMATION: synthetic construct

<400> SEQUENCE: 109
``` gtctgctcc                                                                       9

<210> SEQ ID NO 110
<211> LENGTH: 9
<212> TYPE: DNA
<213> ORGANISM: Artificial Sequence
<220> FEATURE:
<223> OTHER INFORMATION: synthetic construct

<400> SEQUENCE: 110 agcagacaa                                                                       9

<210> SEQ ID NO 111
<211> LENGTH: 9
<212> TYPE: DNA
<213> ORGANISM: Artificial Sequence
<220> FEATURE:
<223> OTHER INFORMATION: synthetic construct

<400> SEQUENCE: 111 cgacagacc                                                                       9

<210> SEQ ID NO 112
<211> LENGTH: 9
<212> TYPE: DNA
<213> ORGANISM: Artificial Sequence
<220> FEATURE:
<223> OTHER INFORMATION: synthetic construct

<400> SEQUENCE: 112 tctgtcgaa                                                                       9

<210> SEQ ID NO 113
<211> LENGTH: 9
<212> TYPE: DNA
<213> ORGANISM: Artificial Sequence
<220> FEATURE:
<223> OTHER INFORMATION: synthetic construct

<400> SEQUENCE: 113 cgctactcc                                                                       9

<210> SEQ ID NO 114
<211> LENGTH: 9
<212> TYPE: DNA
<213> ORGANISM: Artificial Sequence
<220> FEATURE:
<223> OTHER INFORMATION: synthetic construct

<400> SEQUENCE: 114 agtagcgaa                                                                       9

<210> SEQ ID NO 115
<211> LENGTH: 9
<212> TYPE: DNA
<213> ORGANISM: Artificial Sequence
<220> FEATURE:
<223> OTHER INFORMATION: synthetic construct

<400> SEQUENCE: 115 ccacagacc                                                                       9

<210> SEQ ID NO 116
<211> LENGTH: 9
<212> TYPE: DNA
<213> ORGANISM: Artificial Sequence
<220> FEATURE:

-continued

```
<223> OTHER INFORMATION: synthetic construct

<400> SEQUENCE: 116 tctgtggaa                                                                  9

<210> SEQ ID NO 117
<211> LENGTH: 9
<212> TYPE: DNA
<213> ORGANISM: Artificial Sequence
<220> FEATURE:
<223> OTHER INFORMATION: synthetic construct

<400> SEQUENCE: 117 cctctctcc                                                                  9

<210> SEQ ID NO 118
<211> LENGTH: 9
<212> TYPE: DNA
<213> ORGANISM: Artificial Sequence
<220> FEATURE:
<223> OTHER INFORMATION: synthetic construct

<400> SEQUENCE: 118 agagaggaa                                                                  9

<210> SEQ ID NO 119
<211> LENGTH: 9
<212> TYPE: DNA
<213> ORGANISM: Artificial Sequence
<220> FEATURE:
<223> OTHER INFORMATION: synthetic construct

<400> SEQUENCE: 119 ctcgtagcc                                                                  9

<210> SEQ ID NO 120
<211> LENGTH: 9
<212> TYPE: DNA
<213> ORGANISM: Artificial Sequence
<220> FEATURE:
<223> OTHER INFORMATION: synthetic construct

<400> SEQUENCE: 120 ctacgagaa                                                                  9

<210> SEQ ID NO 121
<211> LENGTH: 20
<212> TYPE: DNA
<213> ORGANISM: Artificial Sequence
<220> FEATURE:
<223> OTHER INFORMATION: synthetic construct

<400> SEQUENCE: 121
aaatcgatgt ggtcactcag                                                     20

<210> SEQ ID NO 122
<211> LENGTH: 20
<212> TYPE: DNA
<213> ORGANISM: Artificial Sequence
<220> FEATURE:
<223> OTHER INFORMATION: synthetic construct

<400> SEQUENCE: 122
gagtgaccac atcgatttgg                                                     20

<210> SEQ ID NO 123
```

-continued

```
<211> LENGTH: 20
<212> TYPE: DNA
<213> ORGANISM: Artificial Sequence
<220> FEATURE:
<223> OTHER INFORMATION: synthetic construct

<400> SEQUENCE: 123
aaatcgatgt ggactaggag                                                   20

<210> SEQ ID NO 124
<211> LENGTH: 20
<212> TYPE: DNA
<213> ORGANISM: Artificial Sequence
<220> FEATURE:
<223> OTHER INFORMATION: synthetic construct

<400> SEQUENCE: 124
cctagtccac atcgatttgg                                                   20

<210> SEQ ID NO 125
<211> LENGTH: 20
<212> TYPE: DNA
<213> ORGANISM: Artificial Sequence
<220> FEATURE:
<223> OTHER INFORMATION: synthetic construct

<400> SEQUENCE: 125
aaatcgatgt gccgtatgag                                                   20

<210> SEQ ID NO 126
<211> LENGTH: 20
<212> TYPE: DNA
<213> ORGANISM: Artificial Sequence
<220> FEATURE:
<223> OTHER INFORMATION: synthetic construct

<400> SEQUENCE: 126
catacggcac atcgatttgg                                                   20

<210> SEQ ID NO 127
<211> LENGTH: 20
<212> TYPE: DNA
<213> ORGANISM: Artificial Sequence
<220> FEATURE:
<223> OTHER INFORMATION: synthetic construct

<400> SEQUENCE: 127
aaatcgatgt gctgaaggag                                                   20

<210> SEQ ID NO 128
<211> LENGTH: 20
<212> TYPE: DNA
<213> ORGANISM: Artificial Sequence
<220> FEATURE:
<223> OTHER INFORMATION: synthetic construct

<400> SEQUENCE: 128
ccttcagcac atcgatttgg                                                   20

<210> SEQ ID NO 129
<211> LENGTH: 20
<212> TYPE: DNA
<213> ORGANISM: Artificial Sequence
<220> FEATURE:
<223> OTHER INFORMATION: synthetic construct

<400> SEQUENCE: 129
```
aaatcgatgt ggactagcag                                              20

<210> SEQ ID NO 130
<211> LENGTH: 20
<212> TYPE: DNA
<213> ORGANISM: Artificial Sequence
<220> FEATURE:
<223> OTHER INFORMATION: synthetic construct

<400> SEQUENCE: 130
gctagtccac atcgatttgg                                              20

<210> SEQ ID NO 131
<211> LENGTH: 20
<212> TYPE: DNA
<213> ORGANISM: Artificial Sequence
<220> FEATURE:
<223> OTHER INFORMATION: synthetic construct

<400> SEQUENCE: 131
aaatcgatgt gcgctaagag                                              20

<210> SEQ ID NO 132
<211> LENGTH: 20
<212> TYPE: DNA
<213> ORGANISM: Artificial Sequence
<220> FEATURE:
<223> OTHER INFORMATION: synthetic construct

<400> SEQUENCE: 132
cttagcgcac atcgatttgg                                              20

<210> SEQ ID NO 133
<211> LENGTH: 20
<212> TYPE: DNA
<213> ORGANISM: Artificial Sequence
<220> FEATURE:
<223> OTHER INFORMATION: synthetic construct

<400> SEQUENCE: 133
aaatcgatgt gagccgagag                                              20

<210> SEQ ID NO 134
<211> LENGTH: 20
<212> TYPE: DNA
<213> ORGANISM: Artificial Sequence
<220> FEATURE:
<223> OTHER INFORMATION: synthetic construct

<400> SEQUENCE: 134
ctcggctcac atcgatttgg                                              20

<210> SEQ ID NO 135
<211> LENGTH: 20
<212> TYPE: DNA
<213> ORGANISM: Artificial Sequence
<220> FEATURE:
<223> OTHER INFORMATION: synthetic construct

<400> SEQUENCE: 135
aaatcgatgt gccgtatcag                                              20

<210> SEQ ID NO 136
<211> LENGTH: 20
<212> TYPE: DNA
<213> ORGANISM: Artificial Sequence
<220> FEATURE:

<223> OTHER INFORMATION: synthetic construct

<400> SEQUENCE: 136
gatacggcac atcgatttgg                                                    20

<210> SEQ ID NO 137
<211> LENGTH: 20
<212> TYPE: DNA
<213> ORGANISM: Artificial Sequence
<220> FEATURE:
<223> OTHER INFORMATION: synthetic construct

<400> SEQUENCE: 137
aaatcgatgt gctgaagcag                                                    20

<210> SEQ ID NO 138
<211> LENGTH: 20
<212> TYPE: DNA
<213> ORGANISM: Artificial Sequence
<220> FEATURE:
<223> OTHER INFORMATION: synthetic construct

<400> SEQUENCE: 138
gcttcagcac atcgatttgg                                                    20

<210> SEQ ID NO 139
<211> LENGTH: 20
<212> TYPE: DNA
<213> ORGANISM: Artificial Sequence
<220> FEATURE:
<223> OTHER INFORMATION: synthetic construct

<400> SEQUENCE: 139
aaatcgatgt gtgcgagtag                                                    20

<210> SEQ ID NO 140
<211> LENGTH: 20
<212> TYPE: DNA
<213> ORGANISM: Artificial Sequence
<220> FEATURE:
<223> OTHER INFORMATION: synthetic construct

<400> SEQUENCE: 140
actcgcacac atcgatttgg                                                    20

<210> SEQ ID NO 141
<211> LENGTH: 20
<212> TYPE: DNA
<213> ORGANISM: Artificial Sequence
<220> FEATURE:
<223> OTHER INFORMATION: synthetic construct

<400> SEQUENCE: 141
aaatcgatgt gtttggcgag                                                    20

<210> SEQ ID NO 142
<211> LENGTH: 20
<212> TYPE: DNA
<213> ORGANISM: Artificial Sequence
<220> FEATURE:
<223> OTHER INFORMATION: synthetic construct

<400> SEQUENCE: 142
cgccaaacac atcgatttgg                                                    20

<210> SEQ ID NO 143

```
<211> LENGTH: 20
<212> TYPE: DNA
<213> ORGANISM: Artificial Sequence
<220> FEATURE:
<223> OTHER INFORMATION: synthetic construct

<400> SEQUENCE: 143
aaatcgatgt gcgctaacag                                           20

<210> SEQ ID NO 144
<211> LENGTH: 20
<212> TYPE: DNA
<213> ORGANISM: Artificial Sequence
<220> FEATURE:
<223> OTHER INFORMATION: synthetic construct

<400> SEQUENCE: 144
gttagcgcac atcgatttgg                                           20

<210> SEQ ID NO 145
<211> LENGTH: 20
<212> TYPE: DNA
<213> ORGANISM: Artificial Sequence
<220> FEATURE:
<223> OTHER INFORMATION: synthetic construct

<400> SEQUENCE: 145
aaatcgatgt gagccgacag                                           20

<210> SEQ ID NO 146
<211> LENGTH: 20
<212> TYPE: DNA
<213> ORGANISM: Artificial Sequence
<220> FEATURE:
<223> OTHER INFORMATION: synthetic construct

<400> SEQUENCE: 146
gtcggctcac atcgatttgg                                           20

<210> SEQ ID NO 147
<211> LENGTH: 20
<212> TYPE: DNA
<213> ORGANISM: Artificial Sequence
<220> FEATURE:
<223> OTHER INFORMATION: synthetic construct

<400> SEQUENCE: 147
aaatcgatgt gagccgaaag                                           20

<210> SEQ ID NO 148
<211> LENGTH: 20
<212> TYPE: DNA
<213> ORGANISM: Artificial Sequence
<220> FEATURE:
<223> OTHER INFORMATION: synthetic construct

<400> SEQUENCE: 148
ttcggctcac atcgatttgg                                           20

<210> SEQ ID NO 149
<211> LENGTH: 20
<212> TYPE: DNA
<213> ORGANISM: Artificial Sequence
<220> FEATURE:
<223> OTHER INFORMATION: synthetic construct

<400> SEQUENCE: 149
```
aaatcgatgt gtcggtagag                                           20

<210> SEQ ID NO 150
<211> LENGTH: 20
<212> TYPE: DNA
<213> ORGANISM: Artificial Sequence
<220> FEATURE:
<223> OTHER INFORMATION: synthetic construct

<400> SEQUENCE: 150
ctaccgacac atcgatttgg                                           20

<210> SEQ ID NO 151
<211> LENGTH: 20
<212> TYPE: DNA
<213> ORGANISM: Artificial Sequence
<220> FEATURE:
<223> OTHER INFORMATION: synthetic construct

<400> SEQUENCE: 151
aaatcgatgt ggttgccgag                                           20

<210> SEQ ID NO 152
<211> LENGTH: 20
<212> TYPE: DNA
<213> ORGANISM: Artificial Sequence
<220> FEATURE:
<223> OTHER INFORMATION: synthetic construct

<400> SEQUENCE: 152
cggcaaccac atcgatttgg                                           20

<210> SEQ ID NO 153
<211> LENGTH: 20
<212> TYPE: DNA
<213> ORGANISM: Artificial Sequence
<220> FEATURE:
<223> OTHER INFORMATION: synthetic construct

<400> SEQUENCE: 153
aaatcgatgt gagtgcgtag                                           20

<210> SEQ ID NO 154
<211> LENGTH: 20
<212> TYPE: DNA
<213> ORGANISM: Artificial Sequence
<220> FEATURE:
<223> OTHER INFORMATION: synthetic construct

<400> SEQUENCE: 154
acgcactcac atcgatttgg                                           20

<210> SEQ ID NO 155
<211> LENGTH: 20
<212> TYPE: DNA
<213> ORGANISM: Artificial Sequence
<220> FEATURE:
<223> OTHER INFORMATION: synthetic construct

<400> SEQUENCE: 155
aaatcgatgt ggttgccaag                                           20

<210> SEQ ID NO 156
<211> LENGTH: 20
<212> TYPE: DNA
<213> ORGANISM: Artificial Sequence
<220> FEATURE:

<223> OTHER INFORMATION: synthetic construct

<400> SEQUENCE: 156
tggcaaccac atcgatttgg                                          20

<210> SEQ ID NO 157
<211> LENGTH: 20
<212> TYPE: DNA
<213> ORGANISM: Artificial Sequence
<220> FEATURE:
<223> OTHER INFORMATION: synthetic construct

<400> SEQUENCE: 157
aaatcgatgt gtgcgaggag                                          20

<210> SEQ ID NO 158
<211> LENGTH: 20
<212> TYPE: DNA
<213> ORGANISM: Artificial Sequence
<220> FEATURE:
<223> OTHER INFORMATION: synthetic construct

<400> SEQUENCE: 158
cctcgcacac atcgatttgg                                          20

<210> SEQ ID NO 159
<211> LENGTH: 20
<212> TYPE: DNA
<213> ORGANISM: Artificial Sequence
<220> FEATURE:
<223> OTHER INFORMATION: synthetic construct

<400> SEQUENCE: 159
aaatcgatgt ggaacacgag                                          20

<210> SEQ ID NO 160
<211> LENGTH: 20
<212> TYPE: DNA
<213> ORGANISM: Artificial Sequence
<220> FEATURE:
<223> OTHER INFORMATION: synthetic construct

<400> SEQUENCE: 160
cgtgttccac atcgatttgg                                          20

<210> SEQ ID NO 161
<211> LENGTH: 20
<212> TYPE: DNA
<213> ORGANISM: Artificial Sequence
<220> FEATURE:
<223> OTHER INFORMATION: synthetic construct

<400> SEQUENCE: 161
aaatcgatgt gcttgtcgag                                          20

<210> SEQ ID NO 162
<211> LENGTH: 20
<212> TYPE: DNA
<213> ORGANISM: Artificial Sequence
<220> FEATURE:
<223> OTHER INFORMATION: synthetic construct

<400> SEQUENCE: 162
cgacaagcac atcgatttgg                                          20

<210> SEQ ID NO 163

```
<211> LENGTH: 20
<212> TYPE: DNA
<213> ORGANISM: Artificial Sequence
<220> FEATURE:
<223> OTHER INFORMATION: synthetic construct

<400> SEQUENCE: 163
aaatcgatgt gttccggtag                                               20

<210> SEQ ID NO 164
<211> LENGTH: 20
<212> TYPE: DNA
<213> ORGANISM: Artificial Sequence
<220> FEATURE:
<223> OTHER INFORMATION: synthetic construct

<400> SEQUENCE: 164
accggaacac atcgatttgg                                               20

<210> SEQ ID NO 165
<211> LENGTH: 20
<212> TYPE: DNA
<213> ORGANISM: Artificial Sequence
<220> FEATURE:
<223> OTHER INFORMATION: synthetic construct

<400> SEQUENCE: 165
aaatcgatgt gtgcgagcag                                               20

<210> SEQ ID NO 166
<211> LENGTH: 20
<212> TYPE: DNA
<213> ORGANISM: Artificial Sequence
<220> FEATURE:
<223> OTHER INFORMATION: synthetic construct

<400> SEQUENCE: 166
gctcgcacac atcgatttgg                                               20

<210> SEQ ID NO 167
<211> LENGTH: 20
<212> TYPE: DNA
<213> ORGANISM: Artificial Sequence
<220> FEATURE:
<223> OTHER INFORMATION: synthetic construct

<400> SEQUENCE: 167
aaatcgatgt ggtcaggtag                                               20

<210> SEQ ID NO 168
<211> LENGTH: 20
<212> TYPE: DNA
<213> ORGANISM: Artificial Sequence
<220> FEATURE:
<223> OTHER INFORMATION: synthetic construct

<400> SEQUENCE: 168
acctgaccac atcgatttgg                                               20

<210> SEQ ID NO 169
<211> LENGTH: 20
<212> TYPE: DNA
<213> ORGANISM: Artificial Sequence
<220> FEATURE:
<223> OTHER INFORMATION: synthetic construct

<400> SEQUENCE: 169
```

```
aaatcgatgt ggcctgttag                                              20

<210> SEQ ID NO 170
<211> LENGTH: 20
<212> TYPE: DNA
<213> ORGANISM: Artificial Sequence
<220> FEATURE:
<223> OTHER INFORMATION: synthetic construct

<400> SEQUENCE: 170
aacaggccac atcgatttgg                                              20

<210> SEQ ID NO 171
<211> LENGTH: 20
<212> TYPE: DNA
<213> ORGANISM: Artificial Sequence
<220> FEATURE:
<223> OTHER INFORMATION: synthetic construct

<400> SEQUENCE: 171
aaatcgatgt ggaacaccag                                              20

<210> SEQ ID NO 172
<211> LENGTH: 20
<212> TYPE: DNA
<213> ORGANISM: Artificial Sequence
<220> FEATURE:
<223> OTHER INFORMATION: synthetic construct

<400> SEQUENCE: 172
ggtgttccac atcgatttgg                                              20

<210> SEQ ID NO 173
<211> LENGTH: 20
<212> TYPE: DNA
<213> ORGANISM: Artificial Sequence
<220> FEATURE:
<223> OTHER INFORMATION: synthetic construct

<400> SEQUENCE: 173
aaatcgatgt gcttgtccag                                              20

<210> SEQ ID NO 174
<211> LENGTH: 20
<212> TYPE: DNA
<213> ORGANISM: Artificial Sequence
<220> FEATURE:
<223> OTHER INFORMATION: synthetic construct

<400> SEQUENCE: 174
ggacaagcac atcgatttgg                                              20

<210> SEQ ID NO 175
<211> LENGTH: 20
<212> TYPE: DNA
<213> ORGANISM: Artificial Sequence
<220> FEATURE:
<223> OTHER INFORMATION: synthetic construct

<400> SEQUENCE: 175
aaatcgatgt gtgcgagaag                                              20

<210> SEQ ID NO 176
<211> LENGTH: 20
<212> TYPE: DNA
<213> ORGANISM: Artificial Sequence
<220> FEATURE:
```

-continued

<223> OTHER INFORMATION: synthetic construct

<400> SEQUENCE: 176
tctcgcacac atcgatttgg        20

<210> SEQ ID NO 177
<211> LENGTH: 20
<212> TYPE: DNA
<213> ORGANISM: Artificial Sequence
<220> FEATURE:
<223> OTHER INFORMATION: synthetic construct

<400> SEQUENCE: 177
aaatcgatgt gagtgcggag        20

<210> SEQ ID NO 178
<211> LENGTH: 20
<212> TYPE: DNA
<213> ORGANISM: Artificial Sequence
<220> FEATURE:
<223> OTHER INFORMATION: synthetic construct

<400> SEQUENCE: 178
ccgcactcac atcgatttgg        20

<210> SEQ ID NO 179
<211> LENGTH: 20
<212> TYPE: DNA
<213> ORGANISM: Artificial Sequence
<220> FEATURE:
<223> OTHER INFORMATION: synthetic construct

<400> SEQUENCE: 179
aaatcgatgt gttgtccgag        20

<210> SEQ ID NO 180
<211> LENGTH: 20
<212> TYPE: DNA
<213> ORGANISM: Artificial Sequence
<220> FEATURE:
<223> OTHER INFORMATION: synthetic construct

<400> SEQUENCE: 180
cggacaacac atcgatttgg        20

<210> SEQ ID NO 181
<211> LENGTH: 20
<212> TYPE: DNA
<213> ORGANISM: Artificial Sequence
<220> FEATURE:
<223> OTHER INFORMATION: synthetic construct

<400> SEQUENCE: 181
aaatcgatgt gtggaacgag        20

<210> SEQ ID NO 182
<211> LENGTH: 20
<212> TYPE: DNA
<213> ORGANISM: Artificial Sequence
<220> FEATURE:
<223> OTHER INFORMATION: synthetic construct

<400> SEQUENCE: 182
cgttccacac atcgatttgg        20

<210> SEQ ID NO 183

```
<211> LENGTH: 20
<212> TYPE: DNA
<213> ORGANISM: Artificial Sequence
<220> FEATURE:
<223> OTHER INFORMATION: synthetic construct

<400> SEQUENCE: 183
aaatcgatgt gagtgcgaag                                                      20

<210> SEQ ID NO 184
<211> LENGTH: 20
<212> TYPE: DNA
<213> ORGANISM: Artificial Sequence
<220> FEATURE:
<223> OTHER INFORMATION: synthetic construct

<400> SEQUENCE: 184
tcgcactcac atcgatttgg                                                      20

<210> SEQ ID NO 185
<211> LENGTH: 20
<212> TYPE: DNA
<213> ORGANISM: Artificial Sequence
<220> FEATURE:
<223> OTHER INFORMATION: synthetic construct

<400> SEQUENCE: 185
aaatcgatgt gtggaaccag                                                      20

<210> SEQ ID NO 186
<211> LENGTH: 20
<212> TYPE: DNA
<213> ORGANISM: Artificial Sequence
<220> FEATURE:
<223> OTHER INFORMATION: synthetic construct

<400> SEQUENCE: 186
ggttccacac atcgatttgg                                                      20

<210> SEQ ID NO 187
<211> LENGTH: 20
<212> TYPE: DNA
<213> ORGANISM: Artificial Sequence
<220> FEATURE:
<223> OTHER INFORMATION: synthetic construct

<400> SEQUENCE: 187
aaatcgatgt gttaggcgag                                                      20

<210> SEQ ID NO 188
<211> LENGTH: 20
<212> TYPE: DNA
<213> ORGANISM: Artificial Sequence
<220> FEATURE:
<223> OTHER INFORMATION: synthetic construct

<400> SEQUENCE: 188
cgcctaacac atcgatttgg                                                      20

<210> SEQ ID NO 189
<211> LENGTH: 20
<212> TYPE: DNA
<213> ORGANISM: Artificial Sequence
<220> FEATURE:
<223> OTHER INFORMATION: synthetic construct

<400> SEQUENCE: 189
```

| | |
|---|---|
| aaatcgatgt ggcctgtgag | 20 |

<210> SEQ ID NO 190
<211> LENGTH: 20
<212> TYPE: DNA
<213> ORGANISM: Artificial Sequence
<220> FEATURE:
<223> OTHER INFORMATION: synthetic construct

<400> SEQUENCE: 190

| | |
|---|---|
| cacaggccac atcgatttgg | 20 |

<210> SEQ ID NO 191
<211> LENGTH: 20
<212> TYPE: DNA
<213> ORGANISM: Artificial Sequence
<220> FEATURE:
<223> OTHER INFORMATION: synthetic construct

<400> SEQUENCE: 191

| | |
|---|---|
| aaatcgatgt gctcctgtag | 20 |

<210> SEQ ID NO 192
<211> LENGTH: 20
<212> TYPE: DNA
<213> ORGANISM: Artificial Sequence
<220> FEATURE:
<223> OTHER INFORMATION: synthetic construct

<400> SEQUENCE: 192

| | |
|---|---|
| acaggagcac atcgatttgg | 20 |

<210> SEQ ID NO 193
<211> LENGTH: 20
<212> TYPE: DNA
<213> ORGANISM: Artificial Sequence
<220> FEATURE:
<223> OTHER INFORMATION: synthetic construct

<400> SEQUENCE: 193

| | |
|---|---|
| aaatcgatgt ggtcaggcag | 20 |

<210> SEQ ID NO 194
<211> LENGTH: 20
<212> TYPE: DNA
<213> ORGANISM: Artificial Sequence
<220> FEATURE:
<223> OTHER INFORMATION: synthetic construct

<400> SEQUENCE: 194

| | |
|---|---|
| gcctgaccac atcgatttgg | 20 |

<210> SEQ ID NO 195
<211> LENGTH: 20
<212> TYPE: DNA
<213> ORGANISM: Artificial Sequence
<220> FEATURE:
<223> OTHER INFORMATION: synthetic construct

<400> SEQUENCE: 195

| | |
|---|---|
| aaatcgatgt ggtcaggaag | 20 |

<210> SEQ ID NO 196
<211> LENGTH: 20
<212> TYPE: DNA
<213> ORGANISM: Artificial Sequence
<220> FEATURE:

```
<223> OTHER INFORMATION: synthetic construct

<400> SEQUENCE: 196
tcctgaccac atcgatttgg                                                    20

<210> SEQ ID NO 197
<211> LENGTH: 20
<212> TYPE: DNA
<213> ORGANISM: Artificial Sequence
<220> FEATURE:
<223> OTHER INFORMATION: synthetic construct

<400> SEQUENCE: 197
aaatcgatgt ggtagccgag                                                    20

<210> SEQ ID NO 198
<211> LENGTH: 20
<212> TYPE: DNA
<213> ORGANISM: Artificial Sequence
<220> FEATURE:
<223> OTHER INFORMATION: synthetic construct

<400> SEQUENCE: 198
cggctaccac atcgatttgg                                                    20

<210> SEQ ID NO 199
<211> LENGTH: 20
<212> TYPE: DNA
<213> ORGANISM: Artificial Sequence
<220> FEATURE:
<223> OTHER INFORMATION: synthetic construct

<400> SEQUENCE: 199
aaatcgatgt ggcctgtaag                                                    20

<210> SEQ ID NO 200
<211> LENGTH: 20
<212> TYPE: DNA
<213> ORGANISM: Artificial Sequence
<220> FEATURE:
<223> OTHER INFORMATION: synthetic construct

<400> SEQUENCE: 200
tacaggccac atcgatttgg                                                    20

<210> SEQ ID NO 201
<211> LENGTH: 20
<212> TYPE: DNA
<213> ORGANISM: Artificial Sequence
<220> FEATURE:
<223> OTHER INFORMATION: synthetic construct

<400> SEQUENCE: 201
aaatcgatgt gctttcggag                                                    20

<210> SEQ ID NO 202
<211> LENGTH: 20
<212> TYPE: DNA
<213> ORGANISM: Artificial Sequence
<220> FEATURE:
<223> OTHER INFORMATION: synthetic construct

<400> SEQUENCE: 202
ccgaaagcac atcgatttgg                                                    20

<210> SEQ ID NO 203
```

```
<211> LENGTH: 20
<212> TYPE: DNA
<213> ORGANISM: Artificial Sequence
<220> FEATURE:
<223> OTHER INFORMATION: synthetic construct

<400> SEQUENCE: 203
aaatcgatgt gcgtaaggag                                            20

<210> SEQ ID NO 204
<211> LENGTH: 20
<212> TYPE: DNA
<213> ORGANISM: Artificial Sequence
<220> FEATURE:
<223> OTHER INFORMATION: synthetic construct

<400> SEQUENCE: 204
ccttacgcac atcgatttgg                                            20

<210> SEQ ID NO 205
<211> LENGTH: 20
<212> TYPE: DNA
<213> ORGANISM: Artificial Sequence
<220> FEATURE:
<223> OTHER INFORMATION: synthetic construct

<400> SEQUENCE: 205
aaatcgatgt gagagcgtag                                            20

<210> SEQ ID NO 206
<211> LENGTH: 20
<212> TYPE: DNA
<213> ORGANISM: Artificial Sequence
<220> FEATURE:
<223> OTHER INFORMATION: synthetic construct

<400> SEQUENCE: 206
acgctctcac atcgatttgg                                            20

<210> SEQ ID NO 207
<211> LENGTH: 20
<212> TYPE: DNA
<213> ORGANISM: Artificial Sequence
<220> FEATURE:
<223> OTHER INFORMATION: synthetic construct

<400> SEQUENCE: 207
aaatcgatgt ggacggcaag                                            20

<210> SEQ ID NO 208
<211> LENGTH: 20
<212> TYPE: DNA
<213> ORGANISM: Artificial Sequence
<220> FEATURE:
<223> OTHER INFORMATION: synthetic construct

<400> SEQUENCE: 208
tgccgtccac atcgatttgg                                            20

<210> SEQ ID NO 209
<211> LENGTH: 20
<212> TYPE: DNA
<213> ORGANISM: Artificial Sequence
<220> FEATURE:
<223> OTHER INFORMATION: synthetic construct

<400> SEQUENCE: 209
```

```
aaatcgatgt gctttcgcag                                            20

<210> SEQ ID NO 210
<211> LENGTH: 20
<212> TYPE: DNA
<213> ORGANISM: Artificial Sequence
<220> FEATURE:
<223> OTHER INFORMATION: synthetic construct

<400> SEQUENCE: 210
gcgaaagcac atcgatttgg                                            20

<210> SEQ ID NO 211
<211> LENGTH: 20
<212> TYPE: DNA
<213> ORGANISM: Artificial Sequence
<220> FEATURE:
<223> OTHER INFORMATION: synthetic construct

<400> SEQUENCE: 211
aaatcgatgt gcgtaagcag                                            20

<210> SEQ ID NO 212
<211> LENGTH: 20
<212> TYPE: DNA
<213> ORGANISM: Artificial Sequence
<220> FEATURE:
<223> OTHER INFORMATION: synthetic construct

<400> SEQUENCE: 212
gcttacgcac atcgatttgg                                            20

<210> SEQ ID NO 213
<211> LENGTH: 20
<212> TYPE: DNA
<213> ORGANISM: Artificial Sequence
<220> FEATURE:
<223> OTHER INFORMATION: synthetic construct

<400> SEQUENCE: 213
aaatcgatgt ggctatggag                                            20

<210> SEQ ID NO 214
<211> LENGTH: 20
<212> TYPE: DNA
<213> ORGANISM: Artificial Sequence
<220> FEATURE:
<223> OTHER INFORMATION: synthetic construct

<400> SEQUENCE: 214
ccatagccac atcgatttgg                                            20

<210> SEQ ID NO 215
<211> LENGTH: 20
<212> TYPE: DNA
<213> ORGANISM: Artificial Sequence
<220> FEATURE:
<223> OTHER INFORMATION: synthetic construct

<400> SEQUENCE: 215
aaatcgatgt gactctggag                                            20

<210> SEQ ID NO 216
<211> LENGTH: 20
<212> TYPE: DNA
<213> ORGANISM: Artificial Sequence
<220> FEATURE:
```

```
<223> OTHER INFORMATION: synthetic construct

<400> SEQUENCE: 216
ccagagtcac atcgatttgg                                              20

<210> SEQ ID NO 217
<211> LENGTH: 19
<212> TYPE: DNA
<213> ORGANISM: Artificial Sequence
<220> FEATURE:
<223> OTHER INFORMATION: synthetic construct

<400> SEQUENCE: 217
aaatcgatgt gctggaaag                                               19

<210> SEQ ID NO 218
<211> LENGTH: 19
<212> TYPE: DNA
<213> ORGANISM: Artificial Sequence
<220> FEATURE:
<223> OTHER INFORMATION: synthetic construct

<400> SEQUENCE: 218
ttccagcaca tcgatttgg                                               19

<210> SEQ ID NO 219
<211> LENGTH: 20
<212> TYPE: DNA
<213> ORGANISM: Artificial Sequence
<220> FEATURE:
<223> OTHER INFORMATION: synthetic construct

<400> SEQUENCE: 219
aaatcgatgt gccgaagtag                                              20

<210> SEQ ID NO 220
<211> LENGTH: 20
<212> TYPE: DNA
<213> ORGANISM: Artificial Sequence
<220> FEATURE:
<223> OTHER INFORMATION: synthetic construct

<400> SEQUENCE: 220
acttcggcac atcgatttgg                                              20

<210> SEQ ID NO 221
<211> LENGTH: 20
<212> TYPE: DNA
<213> ORGANISM: Artificial Sequence
<220> FEATURE:
<223> OTHER INFORMATION: synthetic construct

<400> SEQUENCE: 221
aaatcgatgt gctcctgaag                                              20

<210> SEQ ID NO 222
<211> LENGTH: 20
<212> TYPE: DNA
<213> ORGANISM: Artificial Sequence
<220> FEATURE:
<223> OTHER INFORMATION: synthetic construct

<400> SEQUENCE: 222
tcaggagcac atcgatttgg                                              20

<210> SEQ ID NO 223
```

```
<211> LENGTH: 20
<212> TYPE: DNA
<213> ORGANISM: Artificial Sequence
<220> FEATURE:
<223> OTHER INFORMATION: synthetic construct

<400> SEQUENCE: 223
aaatcgatgt gtccagtcag                                               20

<210> SEQ ID NO 224
<211> LENGTH: 20
<212> TYPE: DNA
<213> ORGANISM: Artificial Sequence
<220> FEATURE:
<223> OTHER INFORMATION: synthetic construct

<400> SEQUENCE: 224
gactggacac atcgatttgg                                               20

<210> SEQ ID NO 225
<211> LENGTH: 20
<212> TYPE: DNA
<213> ORGANISM: Artificial Sequence
<220> FEATURE:
<223> OTHER INFORMATION: synthetic construct

<400> SEQUENCE: 225
aaatcgatgt gagagcggag                                               20

<210> SEQ ID NO 226
<211> LENGTH: 20
<212> TYPE: DNA
<213> ORGANISM: Artificial Sequence
<220> FEATURE:
<223> OTHER INFORMATION: synthetic construct

<400> SEQUENCE: 226
ccgctctcac atcgatttgg                                               20

<210> SEQ ID NO 227
<211> LENGTH: 20
<212> TYPE: DNA
<213> ORGANISM: Artificial Sequence
<220> FEATURE:
<223> OTHER INFORMATION: synthetic construct

<400> SEQUENCE: 227
aaatcgatgt gagagcgaag                                               20

<210> SEQ ID NO 228
<211> LENGTH: 20
<212> TYPE: DNA
<213> ORGANISM: Artificial Sequence
<220> FEATURE:
<223> OTHER INFORMATION: synthetic construct

<400> SEQUENCE: 228
tcgctctcac atcgatttgg                                               20

<210> SEQ ID NO 229
<211> LENGTH: 20
<212> TYPE: DNA
<213> ORGANISM: Artificial Sequence
<220> FEATURE:
<223> OTHER INFORMATION: synthetic construct

<400> SEQUENCE: 229
```

```
aaatcgatgt gccgaaggag                                               20

<210> SEQ ID NO 230
<211> LENGTH: 20
<212> TYPE: DNA
<213> ORGANISM: Artificial Sequence
<220> FEATURE:
<223> OTHER INFORMATION: synthetic construct

<400> SEQUENCE: 230
ccttcggcac atcgatttgg                                               20

<210> SEQ ID NO 231
<211> LENGTH: 20
<212> TYPE: DNA
<213> ORGANISM: Artificial Sequence
<220> FEATURE:
<223> OTHER INFORMATION: synthetic construct

<400> SEQUENCE: 231
aaatcgatgt gccgaagcag                                               20

<210> SEQ ID NO 232
<211> LENGTH: 20
<212> TYPE: DNA
<213> ORGANISM: Artificial Sequence
<220> FEATURE:
<223> OTHER INFORMATION: synthetic construct

<400> SEQUENCE: 232
gcttcggcac atcgatttgg                                               20

<210> SEQ ID NO 233
<211> LENGTH: 20
<212> TYPE: DNA
<213> ORGANISM: Artificial Sequence
<220> FEATURE:
<223> OTHER INFORMATION: synthetic construct

<400> SEQUENCE: 233
aaatcgatgt gtgttccgag                                               20

<210> SEQ ID NO 234
<211> LENGTH: 20
<212> TYPE: DNA
<213> ORGANISM: Artificial Sequence
<220> FEATURE:
<223> OTHER INFORMATION: synthetic construct

<400> SEQUENCE: 234
cggaacacac atcgatttgg                                               20

<210> SEQ ID NO 235
<211> LENGTH: 20
<212> TYPE: DNA
<213> ORGANISM: Artificial Sequence
<220> FEATURE:
<223> OTHER INFORMATION: synthetic construct

<400> SEQUENCE: 235
aaatcgatgt gtctggcgag                                               20

<210> SEQ ID NO 236
<211> LENGTH: 20
<212> TYPE: DNA
<213> ORGANISM: Artificial Sequence
<220> FEATURE:
```

<223> OTHER INFORMATION: synthetic construct

<400> SEQUENCE: 236
cgccagacac atcgatttgg                                               20

<210> SEQ ID NO 237
<211> LENGTH: 20
<212> TYPE: DNA
<213> ORGANISM: Artificial Sequence
<220> FEATURE:
<223> OTHER INFORMATION: synthetic construct

<400> SEQUENCE: 237
aaatcgatgt gctatcggag                                               20

<210> SEQ ID NO 238
<211> LENGTH: 20
<212> TYPE: DNA
<213> ORGANISM: Artificial Sequence
<220> FEATURE:
<223> OTHER INFORMATION: synthetic construct

<400> SEQUENCE: 238
ccgatagcac atcgatttgg                                               20

<210> SEQ ID NO 239
<211> LENGTH: 20
<212> TYPE: DNA
<213> ORGANISM: Artificial Sequence
<220> FEATURE:
<223> OTHER INFORMATION: synthetic construct

<400> SEQUENCE: 239
aaatcgatgt gcgaaaggag                                               20

<210> SEQ ID NO 240
<211> LENGTH: 20
<212> TYPE: DNA
<213> ORGANISM: Artificial Sequence
<220> FEATURE:
<223> OTHER INFORMATION: synthetic construct

<400> SEQUENCE: 240
cctttcgcac atcgatttgg                                               20

<210> SEQ ID NO 241
<211> LENGTH: 20
<212> TYPE: DNA
<213> ORGANISM: Artificial Sequence
<220> FEATURE:
<223> OTHER INFORMATION: synthetic construct

<400> SEQUENCE: 241
aaatcgatgt gccgaagaag                                               20

<210> SEQ ID NO 242
<211> LENGTH: 20
<212> TYPE: DNA
<213> ORGANISM: Artificial Sequence
<220> FEATURE:
<223> OTHER INFORMATION: synthetic construct

<400> SEQUENCE: 242
tcttcggcac atcgatttgg                                               20

<210> SEQ ID NO 243

```
<211> LENGTH: 20
<212> TYPE: DNA
<213> ORGANISM: Artificial Sequence
<220> FEATURE:
<223> OTHER INFORMATION: synthetic construct

<400> SEQUENCE: 243
aaatcgatgt ggttgcagag                                              20

<210> SEQ ID NO 244
<211> LENGTH: 20
<212> TYPE: DNA
<213> ORGANISM: Artificial Sequence
<220> FEATURE:
<223> OTHER INFORMATION: synthetic construct

<400> SEQUENCE: 244
ctgcaaccac atcgatttgg                                              20

<210> SEQ ID NO 245
<211> LENGTH: 20
<212> TYPE: DNA
<213> ORGANISM: Artificial Sequence
<220> FEATURE:
<223> OTHER INFORMATION: synthetic construct

<400> SEQUENCE: 245
aaatcgatgt ggatggtgag                                              20

<210> SEQ ID NO 246
<211> LENGTH: 20
<212> TYPE: DNA
<213> ORGANISM: Artificial Sequence
<220> FEATURE:
<223> OTHER INFORMATION: synthetic construct

<400> SEQUENCE: 246
caccatccac atcgatttgg                                              20

<210> SEQ ID NO 247
<211> LENGTH: 20
<212> TYPE: DNA
<213> ORGANISM: Artificial Sequence
<220> FEATURE:
<223> OTHER INFORMATION: synthetic construct

<400> SEQUENCE: 247
aaatcgatgt gctatcgcag                                              20

<210> SEQ ID NO 248
<211> LENGTH: 20
<212> TYPE: DNA
<213> ORGANISM: Artificial Sequence
<220> FEATURE:
<223> OTHER INFORMATION: synthetic construct

<400> SEQUENCE: 248
gcgatagcac atcgatttgg                                              20

<210> SEQ ID NO 249
<211> LENGTH: 20
<212> TYPE: DNA
<213> ORGANISM: Artificial Sequence
<220> FEATURE:
<223> OTHER INFORMATION: synthetic construct

<400> SEQUENCE: 249
```
aaatcgatgt gcgaaagcag					20

<210> SEQ ID NO 250
<211> LENGTH: 20
<212> TYPE: DNA
<213> ORGANISM: Artificial Sequence
<220> FEATURE:
<223> OTHER INFORMATION: synthetic construct

<400> SEQUENCE: 250
gctttcgcac atcgatttgg					20

<210> SEQ ID NO 251
<211> LENGTH: 20
<212> TYPE: DNA
<213> ORGANISM: Artificial Sequence
<220> FEATURE:
<223> OTHER INFORMATION: synthetic construct

<400> SEQUENCE: 251
aaatcgatgt gacactggag					20

<210> SEQ ID NO 252
<211> LENGTH: 20
<212> TYPE: DNA
<213> ORGANISM: Artificial Sequence
<220> FEATURE:
<223> OTHER INFORMATION: synthetic construct

<400> SEQUENCE: 252
ccagtgtcac atcgatttgg					20

<210> SEQ ID NO 253
<211> LENGTH: 20
<212> TYPE: DNA
<213> ORGANISM: Artificial Sequence
<220> FEATURE:
<223> OTHER INFORMATION: synthetic construct

<400> SEQUENCE: 253
aaatcgatgt gtctggcaag					20

<210> SEQ ID NO 254
<211> LENGTH: 20
<212> TYPE: DNA
<213> ORGANISM: Artificial Sequence
<220> FEATURE:
<223> OTHER INFORMATION: synthetic construct

<400> SEQUENCE: 254
tgccagacac atcgatttgg					20

<210> SEQ ID NO 255
<211> LENGTH: 20
<212> TYPE: DNA
<213> ORGANISM: Artificial Sequence
<220> FEATURE:
<223> OTHER INFORMATION: synthetic construct

<400> SEQUENCE: 255
aaatcgatgt ggatggtcag					20

<210> SEQ ID NO 256
<211> LENGTH: 20
<212> TYPE: DNA
<213> ORGANISM: Artificial Sequence
<220> FEATURE:

```
<223> OTHER INFORMATION: synthetic construct

<400> SEQUENCE: 256
gaccatccac atcgatttgg                                              20

<210> SEQ ID NO 257
<211> LENGTH: 20
<212> TYPE: DNA
<213> ORGANISM: Artificial Sequence
<220> FEATURE:
<223> OTHER INFORMATION: synthetic construct

<400> SEQUENCE: 257
aaatcgatgt ggttgcacag                                              20

<210> SEQ ID NO 258
<211> LENGTH: 20
<212> TYPE: DNA
<213> ORGANISM: Artificial Sequence
<220> FEATURE:
<223> OTHER INFORMATION: synthetic construct

<400> SEQUENCE: 258
gtgcaaccac atcgatttgg                                              20

<210> SEQ ID NO 259
<211> LENGTH: 20
<212> TYPE: DNA
<213> ORGANISM: Artificial Sequence
<220> FEATURE:
<223> OTHER INFORMATION: synthetic construct

<400> SEQUENCE: 259
aaatcgatgt gggcatcgag                                              20

<210> SEQ ID NO 260
<211> LENGTH: 20
<212> TYPE: DNA
<213> ORGANISM: Artificial Sequence
<220> FEATURE:
<223> OTHER INFORMATION: synthetic construct

<400> SEQUENCE: 260
cgatgcccca tccgatttgg                                              20

<210> SEQ ID NO 261
<211> LENGTH: 20
<212> TYPE: DNA
<213> ORGANISM: Artificial Sequence
<220> FEATURE:
<223> OTHER INFORMATION: synthetic construct

<400> SEQUENCE: 261
aaatcgatgt gtgcctccag                                              20

<210> SEQ ID NO 262
<211> LENGTH: 20
<212> TYPE: DNA
<213> ORGANISM: Artificial Sequence
<220> FEATURE:
<223> OTHER INFORMATION: synthetic construct

<400> SEQUENCE: 262
ggaggcacac atcgatttgg                                              20

<210> SEQ ID NO 263
```

```
<211> LENGTH: 20
<212> TYPE: DNA
<213> ORGANISM: Artificial Sequence
<220> FEATURE:
<223> OTHER INFORMATION: synthetic construct

<400> SEQUENCE: 263
aaatcgatgt gtgcctcaag                                               20

<210> SEQ ID NO 264
<211> LENGTH: 20
<212> TYPE: DNA
<213> ORGANISM: Artificial Sequence
<220> FEATURE:
<223> OTHER INFORMATION: synthetic construct

<400> SEQUENCE: 264
tgaggcacac atcgatttgg                                               20

<210> SEQ ID NO 265
<211> LENGTH: 20
<212> TYPE: DNA
<213> ORGANISM: Artificial Sequence
<220> FEATURE:
<223> OTHER INFORMATION: synthetic construct

<400> SEQUENCE: 265
aaatcgatgt gggcatccag                                               20

<210> SEQ ID NO 266
<211> LENGTH: 20
<212> TYPE: DNA
<213> ORGANISM: Artificial Sequence
<220> FEATURE:
<223> OTHER INFORMATION: synthetic construct

<400> SEQUENCE: 266
ggatgcccac atcgatttgg                                               20

<210> SEQ ID NO 267
<211> LENGTH: 20
<212> TYPE: DNA
<213> ORGANISM: Artificial Sequence
<220> FEATURE:
<223> OTHER INFORMATION: synthetic construct

<400> SEQUENCE: 267
aaatcgatgt gggcatcaag                                               20

<210> SEQ ID NO 268
<211> LENGTH: 20
<212> TYPE: DNA
<213> ORGANISM: Artificial Sequence
<220> FEATURE:
<223> OTHER INFORMATION: synthetic construct

<400> SEQUENCE: 268
tgatgcccac atcgatttgg                                               20

<210> SEQ ID NO 269
<211> LENGTH: 20
<212> TYPE: DNA
<213> ORGANISM: Artificial Sequence
<220> FEATURE:
<223> OTHER INFORMATION: synthetic construct

<400> SEQUENCE: 269
```
aaatcgatgt gcctgtcgag    20

<210> SEQ ID NO 270
<211> LENGTH: 20
<212> TYPE: DNA
<213> ORGANISM: Artificial Sequence
<220> FEATURE:
<223> OTHER INFORMATION: synthetic construct

<400> SEQUENCE: 270
cgacaggcac atcgatttgg    20

<210> SEQ ID NO 271
<211> LENGTH: 20
<212> TYPE: DNA
<213> ORGANISM: Artificial Sequence
<220> FEATURE:
<223> OTHER INFORMATION: synthetic construct

<400> SEQUENCE: 271
aaatcgatgt ggacggatag    20

<210> SEQ ID NO 272
<211> LENGTH: 20
<212> TYPE: DNA
<213> ORGANISM: Artificial Sequence
<220> FEATURE:
<223> OTHER INFORMATION: synthetic construct

<400> SEQUENCE: 272
atccgtccac atcgatttgg    20

<210> SEQ ID NO 273
<211> LENGTH: 20
<212> TYPE: DNA
<213> ORGANISM: Artificial Sequence
<220> FEATURE:
<223> OTHER INFORMATION: synthetic construct

<400> SEQUENCE: 273
aaatcgatgt gcctgtccag    20

<210> SEQ ID NO 274
<211> LENGTH: 20
<212> TYPE: DNA
<213> ORGANISM: Artificial Sequence
<220> FEATURE:
<223> OTHER INFORMATION: synthetic construct

<400> SEQUENCE: 274
ggacaggcac atcgatttgg    20

<210> SEQ ID NO 275
<211> LENGTH: 20
<212> TYPE: DNA
<213> ORGANISM: Artificial Sequence
<220> FEATURE:
<223> OTHER INFORMATION: synthetic construct

<400> SEQUENCE: 275
aaatcgatgt gaagcacgag    20

<210> SEQ ID NO 276
<211> LENGTH: 20
<212> TYPE: DNA
<213> ORGANISM: Artificial Sequence
<220> FEATURE:

```
<223> OTHER INFORMATION: synthetic construct

<400> SEQUENCE: 276
cgtgcttcac atcgatttgg                                                    20

<210> SEQ ID NO 277
<211> LENGTH: 20
<212> TYPE: DNA
<213> ORGANISM: Artificial Sequence
<220> FEATURE:
<223> OTHER INFORMATION: synthetic construct

<400> SEQUENCE: 277
aaatcgatgt gcctgtcaag                                                    20

<210> SEQ ID NO 278
<211> LENGTH: 20
<212> TYPE: DNA
<213> ORGANISM: Artificial Sequence
<220> FEATURE:
<223> OTHER INFORMATION: synthetic construct

<400> SEQUENCE: 278
tgacaggcac atcgatttgg                                                    20

<210> SEQ ID NO 279
<211> LENGTH: 20
<212> TYPE: DNA
<213> ORGANISM: Artificial Sequence
<220> FEATURE:
<223> OTHER INFORMATION: synthetic construct

<400> SEQUENCE: 279
aaatcgatgt gaagcaccag                                                    20

<210> SEQ ID NO 280
<211> LENGTH: 20
<212> TYPE: DNA
<213> ORGANISM: Artificial Sequence
<220> FEATURE:
<223> OTHER INFORMATION: synthetic construct

<400> SEQUENCE: 280
ggtgcttcac atcgatttgg                                                    20

<210> SEQ ID NO 281
<211> LENGTH: 20
<212> TYPE: DNA
<213> ORGANISM: Artificial Sequence
<220> FEATURE:
<223> OTHER INFORMATION: synthetic construct

<400> SEQUENCE: 281
aaatcgatgt gccttcgtag                                                    20

<210> SEQ ID NO 282
<211> LENGTH: 20
<212> TYPE: DNA
<213> ORGANISM: Artificial Sequence
<220> FEATURE:
<223> OTHER INFORMATION: synthetic construct

<400> SEQUENCE: 282
acgaaggcac atcgatttgg                                                    20

<210> SEQ ID NO 283
```

-continued

```
<211> LENGTH: 20
<212> TYPE: DNA
<213> ORGANISM: Artificial Sequence
<220> FEATURE:
<223> OTHER INFORMATION: synthetic construct

<400> SEQUENCE: 283
aaatcgatgt gtcgtccgag                                               20

<210> SEQ ID NO 284
<211> LENGTH: 20
<212> TYPE: DNA
<213> ORGANISM: Artificial Sequence
<220> FEATURE:
<223> OTHER INFORMATION: synthetic construct

<400> SEQUENCE: 284
cggacgacac atcgatttgg                                               20

<210> SEQ ID NO 285
<211> LENGTH: 20
<212> TYPE: DNA
<213> ORGANISM: Artificial Sequence
<220> FEATURE:
<223> OTHER INFORMATION: synthetic construct

<400> SEQUENCE: 285
aaatcgatgt ggagtctgag                                               20

<210> SEQ ID NO 286
<211> LENGTH: 20
<212> TYPE: DNA
<213> ORGANISM: Artificial Sequence
<220> FEATURE:
<223> OTHER INFORMATION: synthetic construct

<400> SEQUENCE: 286
cagactccac atcgatttgg                                               20

<210> SEQ ID NO 287
<211> LENGTH: 20
<212> TYPE: DNA
<213> ORGANISM: Artificial Sequence
<220> FEATURE:
<223> OTHER INFORMATION: synthetic construct

<400> SEQUENCE: 287
aaatcgatgt gtgatccgag                                               20

<210> SEQ ID NO 288
<211> LENGTH: 20
<212> TYPE: DNA
<213> ORGANISM: Artificial Sequence
<220> FEATURE:
<223> OTHER INFORMATION: synthetic construct

<400> SEQUENCE: 288
cggatcacac atcgatttgg                                               20

<210> SEQ ID NO 289
<211> LENGTH: 20
<212> TYPE: DNA
<213> ORGANISM: Artificial Sequence
<220> FEATURE:
<223> OTHER INFORMATION: synthetic construct

<400> SEQUENCE: 289
```
aaatcgatgt gtcaggcgag                                                      20

<210> SEQ ID NO 290
<211> LENGTH: 20
<212> TYPE: DNA
<213> ORGANISM: Artificial Sequence
<220> FEATURE:
<223> OTHER INFORMATION: synthetic construct

<400> SEQUENCE: 290
cgcctgacac atcgatttgg                                                      20

<210> SEQ ID NO 291
<211> LENGTH: 20
<212> TYPE: DNA
<213> ORGANISM: Artificial Sequence
<220> FEATURE:
<223> OTHER INFORMATION: synthetic construct

<400> SEQUENCE: 291
aaatcgatgt gtcgtccaag                                                      20

<210> SEQ ID NO 292
<211> LENGTH: 20
<212> TYPE: DNA
<213> ORGANISM: Artificial Sequence
<220> FEATURE:
<223> OTHER INFORMATION: synthetic construct

<400> SEQUENCE: 292
tggacgacac atcgatttgg                                                      20

<210> SEQ ID NO 293
<211> LENGTH: 20
<212> TYPE: DNA
<213> ORGANISM: Artificial Sequence
<220> FEATURE:
<223> OTHER INFORMATION: synthetic construct

<400> SEQUENCE: 293
aaatcgatgt ggacggagag                                                      20

<210> SEQ ID NO 294
<211> LENGTH: 20
<212> TYPE: DNA
<213> ORGANISM: Artificial Sequence
<220> FEATURE:
<223> OTHER INFORMATION: synthetic construct

<400> SEQUENCE: 294
ctccgtccac atcgatttgg                                                      20

<210> SEQ ID NO 295
<211> LENGTH: 20
<212> TYPE: DNA
<213> ORGANISM: Artificial Sequence
<220> FEATURE:
<223> OTHER INFORMATION: synthetic construct

<400> SEQUENCE: 295
aaatcgatgt ggtagcagag                                                      20

<210> SEQ ID NO 296
<211> LENGTH: 20
<212> TYPE: DNA
<213> ORGANISM: Artificial Sequence
<220> FEATURE:

```
<223> OTHER INFORMATION: synthetic construct

<400> SEQUENCE: 296
ctgctaccac atcgatttgg                                                      20

<210> SEQ ID NO 297
<211> LENGTH: 20
<212> TYPE: DNA
<213> ORGANISM: Artificial Sequence
<220> FEATURE:
<223> OTHER INFORMATION: synthetic construct

<400> SEQUENCE: 297
aaatcgatgt ggctgtgtag                                                      20

<210> SEQ ID NO 298
<211> LENGTH: 20
<212> TYPE: DNA
<213> ORGANISM: Artificial Sequence
<220> FEATURE:
<223> OTHER INFORMATION: synthetic construct

<400> SEQUENCE: 298
acacagccac atcgatttgg                                                      20

<210> SEQ ID NO 299
<211> LENGTH: 20
<212> TYPE: DNA
<213> ORGANISM: Artificial Sequence
<220> FEATURE:
<223> OTHER INFORMATION: synthetic construct

<400> SEQUENCE: 299
aaatcgatgt ggacggacag                                                      20

<210> SEQ ID NO 300
<211> LENGTH: 20
<212> TYPE: DNA
<213> ORGANISM: Artificial Sequence
<220> FEATURE:
<223> OTHER INFORMATION: synthetic construct

<400> SEQUENCE: 300
gtccgtccac atcgatttgg                                                      20

<210> SEQ ID NO 301
<211> LENGTH: 20
<212> TYPE: DNA
<213> ORGANISM: Artificial Sequence
<220> FEATURE:
<223> OTHER INFORMATION: synthetic construct

<400> SEQUENCE: 301
aaatcgatgt gtcaggcaag                                                      20

<210> SEQ ID NO 302
<211> LENGTH: 20
<212> TYPE: DNA
<213> ORGANISM: Artificial Sequence
<220> FEATURE:
<223> OTHER INFORMATION: synthetic construct

<400> SEQUENCE: 302
tgcctgacac atcgatttgg                                                      20

<210> SEQ ID NO 303
```

```
<211> LENGTH: 20
<212> TYPE: DNA
<213> ORGANISM: Artificial Sequence
<220> FEATURE:
<223> OTHER INFORMATION: synthetic construct

<400> SEQUENCE: 303
aaatcgatgt ggctcgaaag                                              20

<210> SEQ ID NO 304
<211> LENGTH: 20
<212> TYPE: DNA
<213> ORGANISM: Artificial Sequence
<220> FEATURE:
<223> OTHER INFORMATION: synthetic construct

<400> SEQUENCE: 304
ttcgagccac atcgatttgg                                              20

<210> SEQ ID NO 305
<211> LENGTH: 20
<212> TYPE: DNA
<213> ORGANISM: Artificial Sequence
<220> FEATURE:
<223> OTHER INFORMATION: synthetic construct

<400> SEQUENCE: 305
aaatcgatgt gccttcggag                                              20

<210> SEQ ID NO 306
<211> LENGTH: 20
<212> TYPE: DNA
<213> ORGANISM: Artificial Sequence
<220> FEATURE:
<223> OTHER INFORMATION: synthetic construct

<400> SEQUENCE: 306
ccgaaggcac atcgatttgg                                              20

<210> SEQ ID NO 307
<211> LENGTH: 20
<212> TYPE: DNA
<213> ORGANISM: Artificial Sequence
<220> FEATURE:
<223> OTHER INFORMATION: synthetic construct

<400> SEQUENCE: 307
aaatcgatgt ggtagcacag                                              20

<210> SEQ ID NO 308
<211> LENGTH: 20
<212> TYPE: DNA
<213> ORGANISM: Artificial Sequence
<220> FEATURE:
<223> OTHER INFORMATION: synthetic construct

<400> SEQUENCE: 308
gtgctaccac atcgatttgg                                              20

<210> SEQ ID NO 309
<211> LENGTH: 20
<212> TYPE: DNA
<213> ORGANISM: Artificial Sequence
<220> FEATURE:
<223> OTHER INFORMATION: synthetic construct

<400> SEQUENCE: 309
```

```
aaatcgatgt ggaaggtcag                                                    20

<210> SEQ ID NO 310
<211> LENGTH: 20
<212> TYPE: DNA
<213> ORGANISM: Artificial Sequence
<220> FEATURE:
<223> OTHER INFORMATION: synthetic construct

<400> SEQUENCE: 310
gaccttccac atcgatttgg                                                    20

<210> SEQ ID NO 311
<211> LENGTH: 20
<212> TYPE: DNA
<213> ORGANISM: Artificial Sequence
<220> FEATURE:
<223> OTHER INFORMATION: synthetic construct

<400> SEQUENCE: 311
aaatcgatgt ggtgctgtag                                                    20

<210> SEQ ID NO 312
<211> LENGTH: 20
<212> TYPE: DNA
<213> ORGANISM: Artificial Sequence
<220> FEATURE:
<223> OTHER INFORMATION: synthetic construct

<400> SEQUENCE: 312
acagcaccac atcgatttgg                                                    20

<210> SEQ ID NO 313
<211> LENGTH: 9
<212> TYPE: DNA
<213> ORGANISM: Artificial Sequence
<220> FEATURE:
<223> OTHER INFORMATION: synthetic construct

<400> SEQUENCE: 313 gttgcctgt                                                                 9

<210> SEQ ID NO 314
<211> LENGTH: 9
<212> TYPE: DNA
<213> ORGANISM: Artificial Sequence
<220> FEATURE:
<223> OTHER INFORMATION: synthetic construct

<400> SEQUENCE: 314 aggcaacct                                                                 9

<210> SEQ ID NO 315
<211> LENGTH: 9
<212> TYPE: DNA
<213> ORGANISM: Artificial Sequence
<220> FEATURE:
<223> OTHER INFORMATION: synthetic construct

<400> SEQUENCE: 315 caggacggt                                                                 9

<210> SEQ ID NO 316
<211> LENGTH: 9
<212> TYPE: DNA
<213> ORGANISM: Artificial Sequence
<220> FEATURE:
```

```
<223> OTHER INFORMATION: synthetic construct

<400> SEQUENCE: 316 cgtcctgct                                                                  9

<210> SEQ ID NO 317
<211> LENGTH: 9
<212> TYPE: DNA
<213> ORGANISM: Artificial Sequence
<220> FEATURE:
<223> OTHER INFORMATION: synthetic construct

<400> SEQUENCE: 317 agacgtggt                                                                  9

<210> SEQ ID NO 318
<211> LENGTH: 9
<212> TYPE: DNA
<213> ORGANISM: Artificial Sequence
<220> FEATURE:
<223> OTHER INFORMATION: synthetic construct

<400> SEQUENCE: 318 cacgtctct                                                                  9

<210> SEQ ID NO 319
<211> LENGTH: 9
<212> TYPE: DNA
<213> ORGANISM: Artificial Sequence
<220> FEATURE:
<223> OTHER INFORMATION: synthetic construct

<400> SEQUENCE: 319 caggaccgt                                                                  9

<210> SEQ ID NO 320
<211> LENGTH: 9
<212> TYPE: DNA
<213> ORGANISM: Artificial Sequence
<220> FEATURE:
<223> OTHER INFORMATION: synthetic construct

<400> SEQUENCE: 320 ggtcctgct                                                                  9

<210> SEQ ID NO 321
<211> LENGTH: 9
<212> TYPE: DNA
<213> ORGANISM: Artificial Sequence
<220> FEATURE:
<223> OTHER INFORMATION: synthetic construct

<400> SEQUENCE: 321 caggacagt                                                                  9

<210> SEQ ID NO 322
<211> LENGTH: 9
<212> TYPE: DNA
<213> ORGANISM: Artificial Sequence
<220> FEATURE:
<223> OTHER INFORMATION: synthetic construct

<400> SEQUENCE: 322 tgtcctgct                                                                  9

<210> SEQ ID NO 323
```

-continued

```
<211> LENGTH: 9
<212> TYPE: DNA
<213> ORGANISM: Artificial Sequence
<220> FEATURE:
<223> OTHER INFORMATION: synthetic construct

<400> SEQUENCE: 323 cactctggt                                                                 9

<210> SEQ ID NO 324
<211> LENGTH: 9
<212> TYPE: DNA
<213> ORGANISM: Artificial Sequence
<220> FEATURE:
<223> OTHER INFORMATION: synthetic construct

<400> SEQUENCE: 324 cagagtgct                                                                 9

<210> SEQ ID NO 325
<211> LENGTH: 9
<212> TYPE: DNA
<213> ORGANISM: Artificial Sequence
<220> FEATURE:
<223> OTHER INFORMATION: synthetic construct

<400> SEQUENCE: 325 gacggctgt                                                                 9

<210> SEQ ID NO 326
<211> LENGTH: 9
<212> TYPE: DNA
<213> ORGANISM: Artificial Sequence
<220> FEATURE:
<223> OTHER INFORMATION: synthetic construct

<400> SEQUENCE: 326 agccgtcct                                                                 9

<210> SEQ ID NO 327
<211> LENGTH: 9
<212> TYPE: DNA
<213> ORGANISM: Artificial Sequence
<220> FEATURE:
<223> OTHER INFORMATION: synthetic construct

<400> SEQUENCE: 327 cactctcgt                                                                 9

<210> SEQ ID NO 328
<211> LENGTH: 9
<212> TYPE: DNA
<213> ORGANISM: Artificial Sequence
<220> FEATURE:
<223> OTHER INFORMATION: synthetic construct

<400> SEQUENCE: 328 gagagtgct                                                                 9

<210> SEQ ID NO 329
<211> LENGTH: 9
<212> TYPE: DNA
<213> ORGANISM: Artificial Sequence
<220> FEATURE:
<223> OTHER INFORMATION: synthetic construct

<400> SEQUENCE: 329
```

```
gtagcctgt                                                                    9

<210> SEQ ID NO 330
<211> LENGTH: 9
<212> TYPE: DNA
<213> ORGANISM: Artificial Sequence
<220> FEATURE:
<223> OTHER INFORMATION: synthetic construct

<400> SEQUENCE: 330 aggctacct                                                                    9

<210> SEQ ID NO 331
<211> LENGTH: 9
<212> TYPE: DNA
<213> ORGANISM: Artificial Sequence
<220> FEATURE:
<223> OTHER INFORMATION: synthetic construct

<400> SEQUENCE: 331 gccacttgt                                                                    9

<210> SEQ ID NO 332
<211> LENGTH: 9
<212> TYPE: DNA
<213> ORGANISM: Artificial Sequence
<220> FEATURE:
<223> OTHER INFORMATION: synthetic construct

<400> SEQUENCE: 332 aagtggcct                                                                    9

<210> SEQ ID NO 333
<211> LENGTH: 9
<212> TYPE: DNA
<213> ORGANISM: Artificial Sequence
<220> FEATURE:
<223> OTHER INFORMATION: synthetic construct

<400> SEQUENCE: 333 catcgctgt                                                                    9

<210> SEQ ID NO 334
<211> LENGTH: 9
<212> TYPE: DNA
<213> ORGANISM: Artificial Sequence
<220> FEATURE:
<223> OTHER INFORMATION: synthetic construct

<400> SEQUENCE: 334 agcgatgct                                                                    9

<210> SEQ ID NO 335
<211> LENGTH: 9
<212> TYPE: DNA
<213> ORGANISM: Artificial Sequence
<220> FEATURE:
<223> OTHER INFORMATION: synthetic construct

<400> SEQUENCE: 335 cactggtgt                                                                    9

<210> SEQ ID NO 336
<211> LENGTH: 9
<212> TYPE: DNA
<213> ORGANISM: Artificial Sequence
<220> FEATURE:
```

```
<223> OTHER INFORMATION: synthetic construct

<400> SEQUENCE: 336 accagtgct                                                                     9

<210> SEQ ID NO 337
<211> LENGTH: 9
<212> TYPE: DNA
<213> ORGANISM: Artificial Sequence
<220> FEATURE:
<223> OTHER INFORMATION: synthetic construct

<400> SEQUENCE: 337 gccactggt                                                                     9

<210> SEQ ID NO 338
<211> LENGTH: 9
<212> TYPE: DNA
<213> ORGANISM: Artificial Sequence
<220> FEATURE:
<223> OTHER INFORMATION: synthetic construct

<400> SEQUENCE: 338 cagtggcct                                                                     9

<210> SEQ ID NO 339
<211> LENGTH: 9
<212> TYPE: DNA
<213> ORGANISM: Artificial Sequence
<220> FEATURE:
<223> OTHER INFORMATION: synthetic construct

<400> SEQUENCE: 339 tctggctgt                                                                     9

<210> SEQ ID NO 340
<211> LENGTH: 9
<212> TYPE: DNA
<213> ORGANISM: Artificial Sequence
<220> FEATURE:
<223> OTHER INFORMATION: synthetic construct

<400> SEQUENCE: 340 agccagact                                                                     9

<210> SEQ ID NO 341
<211> LENGTH: 9
<212> TYPE: DNA
<213> ORGANISM: Artificial Sequence
<220> FEATURE:
<223> OTHER INFORMATION: synthetic construct

<400> SEQUENCE: 341 gccactcgt                                                                     9

<210> SEQ ID NO 342
<211> LENGTH: 9
<212> TYPE: DNA
<213> ORGANISM: Artificial Sequence
<220> FEATURE:
<223> OTHER INFORMATION: synthetic construct

<400> SEQUENCE: 342 gagtggcct                                                                     9

<210> SEQ ID NO 343
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 343 tgcctctgt                                                                   9

<210> SEQ ID NO 344
<211> LENGTH: 9
<212> TYPE: DNA
<213> ORGANISM: Artificial Sequence
<220> FEATURE:
<223> OTHER INFORMATION: synthetic construct

<400> SEQUENCE: 344 agaggcact                                                                   9

<210> SEQ ID NO 345
<211> LENGTH: 9
<212> TYPE: DNA
<213> ORGANISM: Artificial Sequence
<220> FEATURE:
<223> OTHER INFORMATION: synthetic construct

<400> SEQUENCE: 345 catcgcagt                                                                   9

<210> SEQ ID NO 346
<211> LENGTH: 9
<212> TYPE: DNA
<213> ORGANISM: Artificial Sequence
<220> FEATURE:
<223> OTHER INFORMATION: synthetic construct

<400> SEQUENCE: 346 tgcgatgct                                                                   9

<210> SEQ ID NO 347
<211> LENGTH: 9
<212> TYPE: DNA
<213> ORGANISM: Artificial Sequence
<220> FEATURE:
<223> OTHER INFORMATION: synthetic construct

<400> SEQUENCE: 347 caggaaggt                                                                   9

<210> SEQ ID NO 348
<211> LENGTH: 9
<212> TYPE: DNA
<213> ORGANISM: Artificial Sequence
<220> FEATURE:
<223> OTHER INFORMATION: synthetic construct

<400> SEQUENCE: 348 cttcctgct                                                                   9

<210> SEQ ID NO 349
<211> LENGTH: 9
<212> TYPE: DNA
<213> ORGANISM: Artificial Sequence
<220> FEATURE:
<223> OTHER INFORMATION: synthetic construct

<400> SEQUENCE: 349
``` ggcatctgt 9

<210> SEQ ID NO 350
<211> LENGTH: 9
<212> TYPE: DNA
<213> ORGANISM: Artificial Sequence
<220> FEATURE:
<223> OTHER INFORMATION: synthetic construct

<400> SEQUENCE: 350 agatgccct 9

<210> SEQ ID NO 351
<211> LENGTH: 9
<212> TYPE: DNA
<213> ORGANISM: Artificial Sequence
<220> FEATURE:
<223> OTHER INFORMATION: synthetic construct

<400> SEQUENCE: 351 cggtgctgt 9

<210> SEQ ID NO 352
<211> LENGTH: 9
<212> TYPE: DNA
<213> ORGANISM: Artificial Sequence
<220> FEATURE:
<223> OTHER INFORMATION: synthetic construct

<400> SEQUENCE: 352 agcaccgct 9

<210> SEQ ID NO 353
<211> LENGTH: 9
<212> TYPE: DNA
<213> ORGANISM: Artificial Sequence
<220> FEATURE:
<223> OTHER INFORMATION: synthetic construct

<400> SEQUENCE: 353 cactggcgt 9

<210> SEQ ID NO 354
<211> LENGTH: 9
<212> TYPE: DNA
<213> ORGANISM: Artificial Sequence
<220> FEATURE:
<223> OTHER INFORMATION: synthetic construct

<400> SEQUENCE: 354 gccagtgct 9

<210> SEQ ID NO 355
<211> LENGTH: 9
<212> TYPE: DNA
<213> ORGANISM: Artificial Sequence
<220> FEATURE:
<223> OTHER INFORMATION: synthetic construct

<400> SEQUENCE: 355 tctcctcgt 9

<210> SEQ ID NO 356
<211> LENGTH: 9
<212> TYPE: DNA
<213> ORGANISM: Artificial Sequence
<220> FEATURE:

```
<223> OTHER INFORMATION: synthetic construct

<400> SEQUENCE: 356 gaggagact                                                              9

<210> SEQ ID NO 357
<211> LENGTH: 9
<212> TYPE: DNA
<213> ORGANISM: Artificial Sequence
<220> FEATURE:
<223> OTHER INFORMATION: synthetic construct

<400> SEQUENCE: 357 cctgtctgt                                                              9

<210> SEQ ID NO 358
<211> LENGTH: 9
<212> TYPE: DNA
<213> ORGANISM: Artificial Sequence
<220> FEATURE:
<223> OTHER INFORMATION: synthetic construct

<400> SEQUENCE: 358 agacaggct                                                              9

<210> SEQ ID NO 359
<211> LENGTH: 9
<212> TYPE: DNA
<213> ORGANISM: Artificial Sequence
<220> FEATURE:
<223> OTHER INFORMATION: synthetic construct

<400> SEQUENCE: 359 caacgctgt                                                              9

<210> SEQ ID NO 360
<211> LENGTH: 9
<212> TYPE: DNA
<213> ORGANISM: Artificial Sequence
<220> FEATURE:
<223> OTHER INFORMATION: synthetic construct

<400> SEQUENCE: 360 agcgttgct                                                              9

<210> SEQ ID NO 361
<211> LENGTH: 9
<212> TYPE: DNA
<213> ORGANISM: Artificial Sequence
<220> FEATURE:
<223> OTHER INFORMATION: synthetic construct

<400> SEQUENCE: 361 tgcctcggt                                                              9

<210> SEQ ID NO 362
<211> LENGTH: 9
<212> TYPE: DNA
<213> ORGANISM: Artificial Sequence
<220> FEATURE:
<223> OTHER INFORMATION: synthetic construct

<400> SEQUENCE: 362 cgaggcact                                                              9

<210> SEQ ID NO 363
```

<211> LENGTH: 9
<212> TYPE: DNA
<213> ORGANISM: Artificial Sequence
<220> FEATURE:
<223> OTHER INFORMATION: synthetic construct

<400> SEQUENCE: 363 acactgcgt                                                                9

<210> SEQ ID NO 364
<211> LENGTH: 9
<212> TYPE: DNA
<213> ORGANISM: Artificial Sequence
<220> FEATURE:
<223> OTHER INFORMATION: synthetic construct

<400> SEQUENCE: 364 gcagtgtct                                                                9

<210> SEQ ID NO 365
<211> LENGTH: 9
<212> TYPE: DNA
<213> ORGANISM: Artificial Sequence
<220> FEATURE:
<223> OTHER INFORMATION: synthetic construct

<400> SEQUENCE: 365 tcgtcctgt                                                                9

<210> SEQ ID NO 366
<211> LENGTH: 9
<212> TYPE: DNA
<213> ORGANISM: Artificial Sequence
<220> FEATURE:
<223> OTHER INFORMATION: synthetic construct

<400> SEQUENCE: 366 aggacgact                                                                9

<210> SEQ ID NO 367
<211> LENGTH: 9
<212> TYPE: DNA
<213> ORGANISM: Artificial Sequence
<220> FEATURE:
<223> OTHER INFORMATION: synthetic construct

<400> SEQUENCE: 367 gctgccagt                                                                9

<210> SEQ ID NO 368
<211> LENGTH: 9
<212> TYPE: DNA
<213> ORGANISM: Artificial Sequence
<220> FEATURE:
<223> OTHER INFORMATION: synthetic construct

<400> SEQUENCE: 368 tggcagcct                                                                9

<210> SEQ ID NO 369
<211> LENGTH: 9
<212> TYPE: DNA
<213> ORGANISM: Artificial Sequence
<220> FEATURE:
<223> OTHER INFORMATION: synthetic construct

<400> SEQUENCE: 369 tcaggctgt                                                                          9

<210> SEQ ID NO 370
<211> LENGTH: 9
<212> TYPE: DNA
<213> ORGANISM: Artificial Sequence
<220> FEATURE:
<223> OTHER INFORMATION: synthetic construct

<400> SEQUENCE: 370 agcctgact                                                                          9

<210> SEQ ID NO 371
<211> LENGTH: 9
<212> TYPE: DNA
<213> ORGANISM: Artificial Sequence
<220> FEATURE:
<223> OTHER INFORMATION: synthetic construct

<400> SEQUENCE: 371 gccaggtgt                                                                          9

<210> SEQ ID NO 372
<211> LENGTH: 9
<212> TYPE: DNA
<213> ORGANISM: Artificial Sequence
<220> FEATURE:
<223> OTHER INFORMATION: synthetic construct

<400> SEQUENCE: 372 acctggcct                                                                          9

<210> SEQ ID NO 373
<211> LENGTH: 9
<212> TYPE: DNA
<213> ORGANISM: Artificial Sequence
<220> FEATURE:
<223> OTHER INFORMATION: synthetic construct

<400> SEQUENCE: 373 cggacctgt                                                                          9

<210> SEQ ID NO 374
<211> LENGTH: 9
<212> TYPE: DNA
<213> ORGANISM: Artificial Sequence
<220> FEATURE:
<223> OTHER INFORMATION: synthetic construct

<400> SEQUENCE: 374 aggtccgct                                                                          9

<210> SEQ ID NO 375
<211> LENGTH: 9
<212> TYPE: DNA
<213> ORGANISM: Artificial Sequence
<220> FEATURE:
<223> OTHER INFORMATION: synthetic construct

<400> SEQUENCE: 375 caacgcagt                                                                          9

<210> SEQ ID NO 376
<211> LENGTH: 9
<212> TYPE: DNA
<213> ORGANISM: Artificial Sequence
<220> FEATURE:

```
<223> OTHER INFORMATION: synthetic construct

<400> SEQUENCE: 376 tgcgttgct                                                                        9

<210> SEQ ID NO 377
<211> LENGTH: 9
<212> TYPE: DNA
<213> ORGANISM: Artificial Sequence
<220> FEATURE:
<223> OTHER INFORMATION: synthetic construct

<400> SEQUENCE: 377 cacacgagt                                                                        9

<210> SEQ ID NO 378
<211> LENGTH: 9
<212> TYPE: DNA
<213> ORGANISM: Artificial Sequence
<220> FEATURE:
<223> OTHER INFORMATION: synthetic construct

<400> SEQUENCE: 378 tcgtgtgct                                                                        9

<210> SEQ ID NO 379
<211> LENGTH: 9
<212> TYPE: DNA
<213> ORGANISM: Artificial Sequence
<220> FEATURE:
<223> OTHER INFORMATION: synthetic construct

<400> SEQUENCE: 379 atggcctgt                                                                        9

<210> SEQ ID NO 380
<211> LENGTH: 9
<212> TYPE: DNA
<213> ORGANISM: Artificial Sequence
<220> FEATURE:
<223> OTHER INFORMATION: synthetic construct

<400> SEQUENCE: 380 aggccatct                                                                        9

<210> SEQ ID NO 381
<211> LENGTH: 9
<212> TYPE: DNA
<213> ORGANISM: Artificial Sequence
<220> FEATURE:
<223> OTHER INFORMATION: synthetic construct

<400> SEQUENCE: 381 ccagtctgt                                                                        9

<210> SEQ ID NO 382
<211> LENGTH: 9
<212> TYPE: DNA
<213> ORGANISM: Artificial Sequence
<220> FEATURE:
<223> OTHER INFORMATION: synthetic construct

<400> SEQUENCE: 382 agactggct                                                                        9

<210> SEQ ID NO 383
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 383 gccaggagt                                                                 9

<210> SEQ ID NO 384
<211> LENGTH: 9
<212> TYPE: DNA
<213> ORGANISM: Artificial Sequence
<220> FEATURE:
<223> OTHER INFORMATION: synthetic construct

<400> SEQUENCE: 384 tcctggcct                                                                 9

<210> SEQ ID NO 385
<211> LENGTH: 9
<212> TYPE: DNA
<213> ORGANISM: Artificial Sequence
<220> FEATURE:
<223> OTHER INFORMATION: synthetic construct

<400> SEQUENCE: 385 cggaccagt                                                                 9

<210> SEQ ID NO 386
<211> LENGTH: 9
<212> TYPE: DNA
<213> ORGANISM: Artificial Sequence
<220> FEATURE:
<223> OTHER INFORMATION: synthetic construct

<400> SEQUENCE: 386 tggtccgct                                                                 9

<210> SEQ ID NO 387
<211> LENGTH: 9
<212> TYPE: DNA
<213> ORGANISM: Artificial Sequence
<220> FEATURE:
<223> OTHER INFORMATION: synthetic construct

<400> SEQUENCE: 387 ccttcgcgt                                                                 9

<210> SEQ ID NO 388
<211> LENGTH: 9
<212> TYPE: DNA
<213> ORGANISM: Artificial Sequence
<220> FEATURE:
<223> OTHER INFORMATION: synthetic construct

<400> SEQUENCE: 388 gcgaaggct                                                                 9

<210> SEQ ID NO 389
<211> LENGTH: 9
<212> TYPE: DNA
<213> ORGANISM: Artificial Sequence
<220> FEATURE:
<223> OTHER INFORMATION: synthetic construct

<400> SEQUENCE: 389
```

```
gcagccagt                                                                    9

<210> SEQ ID NO 390
<211> LENGTH: 9
<212> TYPE: DNA
<213> ORGANISM: Artificial Sequence
<220> FEATURE:
<223> OTHER INFORMATION: synthetic construct

<400> SEQUENCE: 390 tggctgcct                                                                    9

<210> SEQ ID NO 391
<211> LENGTH: 9
<212> TYPE: DNA
<213> ORGANISM: Artificial Sequence
<220> FEATURE:
<223> OTHER INFORMATION: synthetic construct

<400> SEQUENCE: 391 ccagtcggt                                                                    9

<210> SEQ ID NO 392
<211> LENGTH: 9
<212> TYPE: DNA
<213> ORGANISM: Artificial Sequence
<220> FEATURE:
<223> OTHER INFORMATION: synthetic construct

<400> SEQUENCE: 392 cgactggct                                                                    9

<210> SEQ ID NO 393
<211> LENGTH: 9
<212> TYPE: DNA
<213> ORGANISM: Artificial Sequence
<220> FEATURE:
<223> OTHER INFORMATION: synthetic construct

<400> SEQUENCE: 393 actgagcgt                                                                    9

<210> SEQ ID NO 394
<211> LENGTH: 9
<212> TYPE: DNA
<213> ORGANISM: Artificial Sequence
<220> FEATURE:
<223> OTHER INFORMATION: synthetic construct

<400> SEQUENCE: 394 gctcagtct                                                                    9

<210> SEQ ID NO 395
<211> LENGTH: 9
<212> TYPE: DNA
<213> ORGANISM: Artificial Sequence
<220> FEATURE:
<223> OTHER INFORMATION: synthetic construct

<400> SEQUENCE: 395 ccagtccgt                                                                    9

<210> SEQ ID NO 396
<211> LENGTH: 9
<212> TYPE: DNA
<213> ORGANISM: Artificial Sequence
<220> FEATURE:
```

<223> OTHER INFORMATION: synthetic construct

<400> SEQUENCE: 396 ggactggct                                                                      9

<210> SEQ ID NO 397
<211> LENGTH: 9
<212> TYPE: DNA
<213> ORGANISM: Artificial Sequence
<220> FEATURE:
<223> OTHER INFORMATION: synthetic construct

<400> SEQUENCE: 397 ccagtcagt                                                                      9

<210> SEQ ID NO 398
<211> LENGTH: 9
<212> TYPE: DNA
<213> ORGANISM: Artificial Sequence
<220> FEATURE:
<223> OTHER INFORMATION: synthetic construct

<400> SEQUENCE: 398 tgactggct                                                                      9

<210> SEQ ID NO 399
<211> LENGTH: 9
<212> TYPE: DNA
<213> ORGANISM: Artificial Sequence
<220> FEATURE:
<223> OTHER INFORMATION: synthetic construct

<400> SEQUENCE: 399 catcgaggt                                                                      9

<210> SEQ ID NO 400
<211> LENGTH: 9
<212> TYPE: DNA
<213> ORGANISM: Artificial Sequence
<220> FEATURE:
<223> OTHER INFORMATION: synthetic construct

<400> SEQUENCE: 400 ctcgatgct                                                                      9

<210> SEQ ID NO 401
<211> LENGTH: 9
<212> TYPE: DNA
<213> ORGANISM: Artificial Sequence
<220> FEATURE:
<223> OTHER INFORMATION: synthetic construct

<400> SEQUENCE: 401 ccatcgtgt                                                                      9

<210> SEQ ID NO 402
<211> LENGTH: 9
<212> TYPE: DNA
<213> ORGANISM: Artificial Sequence
<220> FEATURE:
<223> OTHER INFORMATION: synthetic construct

<400> SEQUENCE: 402 acgatggct                                                                      9

<210> SEQ ID NO 403

```
<211> LENGTH: 9
<212> TYPE: DNA
<213> ORGANISM: Artificial Sequence
<220> FEATURE:
<223> OTHER INFORMATION: synthetic construct

<400> SEQUENCE: 403 gtgctgcgt                                                                9

<210> SEQ ID NO 404
<211> LENGTH: 9
<212> TYPE: DNA
<213> ORGANISM: Artificial Sequence
<220> FEATURE:
<223> OTHER INFORMATION: synthetic construct

<400> SEQUENCE: 404 gcagcacct                                                                9

<210> SEQ ID NO 405
<211> LENGTH: 9
<212> TYPE: DNA
<213> ORGANISM: Artificial Sequence
<220> FEATURE:
<223> OTHER INFORMATION: synthetic construct

<400> SEQUENCE: 405 gactacggt                                                                9

<210> SEQ ID NO 406
<211> LENGTH: 9
<212> TYPE: DNA
<213> ORGANISM: Artificial Sequence
<220> FEATURE:
<223> OTHER INFORMATION: synthetic construct

<400> SEQUENCE: 406 cgtagtcct                                                                9

<210> SEQ ID NO 407
<211> LENGTH: 9
<212> TYPE: DNA
<213> ORGANISM: Artificial Sequence
<220> FEATURE:
<223> OTHER INFORMATION: synthetic construct

<400> SEQUENCE: 407 gtgctgagt                                                                9

<210> SEQ ID NO 408
<211> LENGTH: 9
<212> TYPE: DNA
<213> ORGANISM: Artificial Sequence
<220> FEATURE:
<223> OTHER INFORMATION: synthetic construct

<400> SEQUENCE: 408 tcagcacct                                                                9

<210> SEQ ID NO 409
<211> LENGTH: 9
<212> TYPE: DNA
<213> ORGANISM: Artificial Sequence
<220> FEATURE:
<223> OTHER INFORMATION: synthetic construct

<400> SEQUENCE: 409
```

```
gctgcatgt                                                                    9

<210> SEQ ID NO 410
<211> LENGTH: 9
<212> TYPE: DNA
<213> ORGANISM: Artificial Sequence
<220> FEATURE:
<223> OTHER INFORMATION: synthetic construct

<400> SEQUENCE: 410 atgcagcct                                                                    9

<210> SEQ ID NO 411
<211> LENGTH: 9
<212> TYPE: DNA
<213> ORGANISM: Artificial Sequence
<220> FEATURE:
<223> OTHER INFORMATION: synthetic construct

<400> SEQUENCE: 411 gagtggtgt                                                                    9

<210> SEQ ID NO 412
<211> LENGTH: 9
<212> TYPE: DNA
<213> ORGANISM: Artificial Sequence
<220> FEATURE:
<223> OTHER INFORMATION: synthetic construct

<400> SEQUENCE: 412 accactcct                                                                    9

<210> SEQ ID NO 413
<211> LENGTH: 9
<212> TYPE: DNA
<213> ORGANISM: Artificial Sequence
<220> FEATURE:
<223> OTHER INFORMATION: synthetic construct

<400> SEQUENCE: 413 gactaccgt                                                                    9

<210> SEQ ID NO 414
<211> LENGTH: 9
<212> TYPE: DNA
<213> ORGANISM: Artificial Sequence
<220> FEATURE:
<223> OTHER INFORMATION: synthetic construct

<400> SEQUENCE: 414 ggtagtcct                                                                    9

<210> SEQ ID NO 415
<211> LENGTH: 9
<212> TYPE: DNA
<213> ORGANISM: Artificial Sequence
<220> FEATURE:
<223> OTHER INFORMATION: synthetic construct

<400> SEQUENCE: 415 cggtgatgt                                                                    9

<210> SEQ ID NO 416
<211> LENGTH: 9
<212> TYPE: DNA
<213> ORGANISM: Artificial Sequence
<220> FEATURE:
```

```
<223> OTHER INFORMATION: synthetic construct

<400> SEQUENCE: 416 atcaccgct                                                                    9

<210> SEQ ID NO 417
<211> LENGTH: 9
<212> TYPE: DNA
<213> ORGANISM: Artificial Sequence
<220> FEATURE:
<223> OTHER INFORMATION: synthetic construct

<400> SEQUENCE: 417 tgcgactgt                                                                    9

<210> SEQ ID NO 418
<211> LENGTH: 9
<212> TYPE: DNA
<213> ORGANISM: Artificial Sequence
<220> FEATURE:
<223> OTHER INFORMATION: synthetic construct

<400> SEQUENCE: 418 agtcgcact                                                                    9

<210> SEQ ID NO 419
<211> LENGTH: 9
<212> TYPE: DNA
<213> ORGANISM: Artificial Sequence
<220> FEATURE:
<223> OTHER INFORMATION: synthetic construct

<400> SEQUENCE: 419 tctggaggt                                                                    9

<210> SEQ ID NO 420
<211> LENGTH: 9
<212> TYPE: DNA
<213> ORGANISM: Artificial Sequence
<220> FEATURE:
<223> OTHER INFORMATION: synthetic construct

<400> SEQUENCE: 420 ctccagact                                                                    9

<210> SEQ ID NO 421
<211> LENGTH: 9
<212> TYPE: DNA
<213> ORGANISM: Artificial Sequence
<220> FEATURE:
<223> OTHER INFORMATION: synthetic construct

<400> SEQUENCE: 421 agcactggt                                                                    9

<210> SEQ ID NO 422
<211> LENGTH: 9
<212> TYPE: DNA
<213> ORGANISM: Artificial Sequence
<220> FEATURE:
<223> OTHER INFORMATION: synthetic construct

<400> SEQUENCE: 422 cagtgctct                                                                    9

<210> SEQ ID NO 423
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 423 tcgcttggt                                                                   9

<210> SEQ ID NO 424
<211> LENGTH: 9
<212> TYPE: DNA
<213> ORGANISM: Artificial Sequence
<220> FEATURE:
<223> OTHER INFORMATION: synthetic construct

<400> SEQUENCE: 424 caagcgact                                                                   9

<210> SEQ ID NO 425
<211> LENGTH: 9
<212> TYPE: DNA
<213> ORGANISM: Artificial Sequence
<220> FEATURE:
<223> OTHER INFORMATION: synthetic construct

<400> SEQUENCE: 425 agcactcgt                                                                   9

<210> SEQ ID NO 426
<211> LENGTH: 9
<212> TYPE: DNA
<213> ORGANISM: Artificial Sequence
<220> FEATURE:
<223> OTHER INFORMATION: synthetic construct

<400> SEQUENCE: 426 gagtgctct                                                                   9

<210> SEQ ID NO 427
<211> LENGTH: 9
<212> TYPE: DNA
<213> ORGANISM: Artificial Sequence
<220> FEATURE:
<223> OTHER INFORMATION: synthetic construct

<400> SEQUENCE: 427 gcgattggt                                                                   9

<210> SEQ ID NO 428
<211> LENGTH: 9
<212> TYPE: DNA
<213> ORGANISM: Artificial Sequence
<220> FEATURE:
<223> OTHER INFORMATION: synthetic construct

<400> SEQUENCE: 428 caatcgcct                                                                   9

<210> SEQ ID NO 429
<211> LENGTH: 9
<212> TYPE: DNA
<213> ORGANISM: Artificial Sequence
<220> FEATURE:
<223> OTHER INFORMATION: synthetic construct

<400> SEQUENCE: 429
```

```
ccatcgcgt                                                            9

<210> SEQ ID NO 430
<211> LENGTH: 9
<212> TYPE: DNA
<213> ORGANISM: Artificial Sequence
<220> FEATURE:
<223> OTHER INFORMATION: synthetic construct

<400> SEQUENCE: 430 gcgatggct                                                            9

<210> SEQ ID NO 431
<211> LENGTH: 9
<212> TYPE: DNA
<213> ORGANISM: Artificial Sequence
<220> FEATURE:
<223> OTHER INFORMATION: synthetic construct

<400> SEQUENCE: 431 tcgcttcgt                                                            9

<210> SEQ ID NO 432
<211> LENGTH: 9
<212> TYPE: DNA
<213> ORGANISM: Artificial Sequence
<220> FEATURE:
<223> OTHER INFORMATION: synthetic construct

<400> SEQUENCE: 432 gaagcgact                                                            9

<210> SEQ ID NO 433
<211> LENGTH: 9
<212> TYPE: DNA
<213> ORGANISM: Artificial Sequence
<220> FEATURE:
<223> OTHER INFORMATION: synthetic construct

<400> SEQUENCE: 433 agtgcctgt                                                            9

<210> SEQ ID NO 434
<211> LENGTH: 9
<212> TYPE: DNA
<213> ORGANISM: Artificial Sequence
<220> FEATURE:
<223> OTHER INFORMATION: synthetic construct

<400> SEQUENCE: 434 aggcactct                                                            9

<210> SEQ ID NO 435
<211> LENGTH: 9
<212> TYPE: DNA
<213> ORGANISM: Artificial Sequence
<220> FEATURE:
<223> OTHER INFORMATION: synthetic construct

<400> SEQUENCE: 435 ggcataggt                                                            9

<210> SEQ ID NO 436
<211> LENGTH: 9
<212> TYPE: DNA
<213> ORGANISM: Artificial Sequence
<220> FEATURE:
```

```
<223> OTHER INFORMATION: synthetic construct

<400> SEQUENCE: 436 ctatgccct                                                                 9

<210> SEQ ID NO 437
<211> LENGTH: 9
<212> TYPE: DNA
<213> ORGANISM: Artificial Sequence
<220> FEATURE:
<223> OTHER INFORMATION: synthetic construct

<400> SEQUENCE: 437 gcgattcgt                                                                 9

<210> SEQ ID NO 438
<211> LENGTH: 9
<212> TYPE: DNA
<213> ORGANISM: Artificial Sequence
<220> FEATURE:
<223> OTHER INFORMATION: synthetic construct

<400> SEQUENCE: 438 gaatcgcct                                                                 9

<210> SEQ ID NO 439
<211> LENGTH: 9
<212> TYPE: DNA
<213> ORGANISM: Artificial Sequence
<220> FEATURE:
<223> OTHER INFORMATION: synthetic construct

<400> SEQUENCE: 439 tgcgacggt                                                                 9

<210> SEQ ID NO 440
<211> LENGTH: 9
<212> TYPE: DNA
<213> ORGANISM: Artificial Sequence
<220> FEATURE:
<223> OTHER INFORMATION: synthetic construct

<400> SEQUENCE: 440 cgtcgcact                                                                 9

<210> SEQ ID NO 441
<211> LENGTH: 9
<212> TYPE: DNA
<213> ORGANISM: Artificial Sequence
<220> FEATURE:
<223> OTHER INFORMATION: synthetic construct

<400> SEQUENCE: 441 gagtggcgt                                                                 9

<210> SEQ ID NO 442
<211> LENGTH: 9
<212> TYPE: DNA
<213> ORGANISM: Artificial Sequence
<220> FEATURE:
<223> OTHER INFORMATION: synthetic construct

<400> SEQUENCE: 442 gccactcct                                                                 9

<210> SEQ ID NO 443
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 443 cggtgaggt                                                                    9

<210> SEQ ID NO 444
<211> LENGTH: 9
<212> TYPE: DNA
<213> ORGANISM: Artificial Sequence
<220> FEATURE:
<223> OTHER INFORMATION: synthetic construct

<400> SEQUENCE: 444 ctcaccgct                                                                    9

<210> SEQ ID NO 445
<211> LENGTH: 9
<212> TYPE: DNA
<213> ORGANISM: Artificial Sequence
<220> FEATURE:
<223> OTHER INFORMATION: synthetic construct

<400> SEQUENCE: 445 gctgcaagt                                                                    9

<210> SEQ ID NO 446
<211> LENGTH: 9
<212> TYPE: DNA
<213> ORGANISM: Artificial Sequence
<220> FEATURE:
<223> OTHER INFORMATION: synthetic construct

<400> SEQUENCE: 446 ttgcagcct                                                                    9

<210> SEQ ID NO 447
<211> LENGTH: 9
<212> TYPE: DNA
<213> ORGANISM: Artificial Sequence
<220> FEATURE:
<223> OTHER INFORMATION: synthetic construct

<400> SEQUENCE: 447 ttccgctgt                                                                    9

<210> SEQ ID NO 448
<211> LENGTH: 9
<212> TYPE: DNA
<213> ORGANISM: Artificial Sequence
<220> FEATURE:
<223> OTHER INFORMATION: synthetic construct

<400> SEQUENCE: 448 agcggaact                                                                    9

<210> SEQ ID NO 449
<211> LENGTH: 9
<212> TYPE: DNA
<213> ORGANISM: Artificial Sequence
<220> FEATURE:
<223> OTHER INFORMATION: synthetic construct

<400> SEQUENCE: 449
```

```
gagtggagt                                                              9

<210> SEQ ID NO 450
<211> LENGTH: 9
<212> TYPE: DNA
<213> ORGANISM: Artificial Sequence
<220> FEATURE:
<223> OTHER INFORMATION: synthetic construct

<400> SEQUENCE: 450 tccactcct                                                              9

<210> SEQ ID NO 451
<211> LENGTH: 9
<212> TYPE: DNA
<213> ORGANISM: Artificial Sequence
<220> FEATURE:
<223> OTHER INFORMATION: synthetic construct

<400> SEQUENCE: 451 acagagcgt                                                              9

<210> SEQ ID NO 452
<211> LENGTH: 9
<212> TYPE: DNA
<213> ORGANISM: Artificial Sequence
<220> FEATURE:
<223> OTHER INFORMATION: synthetic construct

<400> SEQUENCE: 452 gctctgtct                                                              9

<210> SEQ ID NO 453
<211> LENGTH: 9
<212> TYPE: DNA
<213> ORGANISM: Artificial Sequence
<220> FEATURE:
<223> OTHER INFORMATION: synthetic construct

<400> SEQUENCE: 453 tgcgaccgt                                                              9

<210> SEQ ID NO 454
<211> LENGTH: 9
<212> TYPE: DNA
<213> ORGANISM: Artificial Sequence
<220> FEATURE:
<223> OTHER INFORMATION: synthetic construct

<400> SEQUENCE: 454 ggtcgcact                                                              9

<210> SEQ ID NO 455
<211> LENGTH: 9
<212> TYPE: DNA
<213> ORGANISM: Artificial Sequence
<220> FEATURE:
<223> OTHER INFORMATION: synthetic construct

<400> SEQUENCE: 455 cctgtaggt                                                              9

<210> SEQ ID NO 456
<211> LENGTH: 9
<212> TYPE: DNA
<213> ORGANISM: Artificial Sequence
<220> FEATURE:
```

<223> OTHER INFORMATION: synthetic construct

<400> SEQUENCE: 456 ctacaggct                                                                9

<210> SEQ ID NO 457
<211> LENGTH: 9
<212> TYPE: DNA
<213> ORGANISM: Artificial Sequence
<220> FEATURE:
<223> OTHER INFORMATION: synthetic construct

<400> SEQUENCE: 457 tagccgtgt                                                                9

<210> SEQ ID NO 458
<211> LENGTH: 9
<212> TYPE: DNA
<213> ORGANISM: Artificial Sequence
<220> FEATURE:
<223> OTHER INFORMATION: synthetic construct

<400> SEQUENCE: 458 acggctact                                                                9

<210> SEQ ID NO 459
<211> LENGTH: 9
<212> TYPE: DNA
<213> ORGANISM: Artificial Sequence
<220> FEATURE:
<223> OTHER INFORMATION: synthetic construct

<400> SEQUENCE: 459 tgcgacagt                                                                9

<210> SEQ ID NO 460
<211> LENGTH: 9
<212> TYPE: DNA
<213> ORGANISM: Artificial Sequence
<220> FEATURE:
<223> OTHER INFORMATION: synthetic construct

<400> SEQUENCE: 460 tgtcgcact                                                                9

<210> SEQ ID NO 461
<211> LENGTH: 9
<212> TYPE: DNA
<213> ORGANISM: Artificial Sequence
<220> FEATURE:
<223> OTHER INFORMATION: synthetic construct

<400> SEQUENCE: 461 ggtctgtgt                                                                9

<210> SEQ ID NO 462
<211> LENGTH: 9
<212> TYPE: DNA
<213> ORGANISM: Artificial Sequence
<220> FEATURE:
<223> OTHER INFORMATION: synthetic construct

<400> SEQUENCE: 462 acagaccct                                                                9

<210> SEQ ID NO 463

```
<211> LENGTH: 9
<212> TYPE: DNA
<213> ORGANISM: Artificial Sequence
<220> FEATURE:
<223> OTHER INFORMATION: synthetic construct

<400> SEQUENCE: 463 cggtgaagt                                                                  9

<210> SEQ ID NO 464
<211> LENGTH: 9
<212> TYPE: DNA
<213> ORGANISM: Artificial Sequence
<220> FEATURE:
<223> OTHER INFORMATION: synthetic construct

<400> SEQUENCE: 464 ttcaccgct                                                                  9

<210> SEQ ID NO 465
<211> LENGTH: 9
<212> TYPE: DNA
<213> ORGANISM: Artificial Sequence
<220> FEATURE:
<223> OTHER INFORMATION: synthetic construct

<400> SEQUENCE: 465 caacgaggt                                                                  9

<210> SEQ ID NO 466
<211> LENGTH: 9
<212> TYPE: DNA
<213> ORGANISM: Artificial Sequence
<220> FEATURE:
<223> OTHER INFORMATION: synthetic construct

<400> SEQUENCE: 466 ctcgttgct                                                                  9

<210> SEQ ID NO 467
<211> LENGTH: 9
<212> TYPE: DNA
<213> ORGANISM: Artificial Sequence
<220> FEATURE:
<223> OTHER INFORMATION: synthetic construct

<400> SEQUENCE: 467 gcagcatgt                                                                  9

<210> SEQ ID NO 468
<211> LENGTH: 9
<212> TYPE: DNA
<213> ORGANISM: Artificial Sequence
<220> FEATURE:
<223> OTHER INFORMATION: synthetic construct

<400> SEQUENCE: 468 atgctgcct                                                                  9

<210> SEQ ID NO 469
<211> LENGTH: 9
<212> TYPE: DNA
<213> ORGANISM: Artificial Sequence
<220> FEATURE:
<223> OTHER INFORMATION: synthetic construct

<400> SEQUENCE: 469
```

-continued tcgtcaggt 9

<210> SEQ ID NO 470
<211> LENGTH: 9
<212> TYPE: DNA
<213> ORGANISM: Artificial Sequence
<220> FEATURE:
<223> OTHER INFORMATION: synthetic construct

<400> SEQUENCE: 470 ctgacgact 9

<210> SEQ ID NO 471
<211> LENGTH: 9
<212> TYPE: DNA
<213> ORGANISM: Artificial Sequence
<220> FEATURE:
<223> OTHER INFORMATION: synthetic construct

<400> SEQUENCE: 471 agtgccagt 9

<210> SEQ ID NO 472
<211> LENGTH: 9
<212> TYPE: DNA
<213> ORGANISM: Artificial Sequence
<220> FEATURE:
<223> OTHER INFORMATION: synthetic construct

<400> SEQUENCE: 472 tggcactct 9

<210> SEQ ID NO 473
<211> LENGTH: 9
<212> TYPE: DNA
<213> ORGANISM: Artificial Sequence
<220> FEATURE:
<223> OTHER INFORMATION: synthetic construct

<400> SEQUENCE: 473 tagaggcgt 9

<210> SEQ ID NO 474
<211> LENGTH: 9
<212> TYPE: DNA
<213> ORGANISM: Artificial Sequence
<220> FEATURE:
<223> OTHER INFORMATION: synthetic construct

<400> SEQUENCE: 474 gcctctact 9

<210> SEQ ID NO 475
<211> LENGTH: 9
<212> TYPE: DNA
<213> ORGANISM: Artificial Sequence
<220> FEATURE:
<223> OTHER INFORMATION: synthetic construct

<400> SEQUENCE: 475 gtcagcggt 9

<210> SEQ ID NO 476
<211> LENGTH: 9
<212> TYPE: DNA
<213> ORGANISM: Artificial Sequence
<220> FEATURE:

-continued

<223> OTHER INFORMATION: synthetic construct

<400> SEQUENCE: 476 cgctgacct                                                                          9

<210> SEQ ID NO 477
<211> LENGTH: 9
<212> TYPE: DNA
<213> ORGANISM: Artificial Sequence
<220> FEATURE:
<223> OTHER INFORMATION: synthetic construct

<400> SEQUENCE: 477 tcaggaggt                                                                          9

<210> SEQ ID NO 478
<211> LENGTH: 9
<212> TYPE: DNA
<213> ORGANISM: Artificial Sequence
<220> FEATURE:
<223> OTHER INFORMATION: synthetic construct

<400> SEQUENCE: 478 ctcctgact                                                                          9

<210> SEQ ID NO 479
<211> LENGTH: 9
<212> TYPE: DNA
<213> ORGANISM: Artificial Sequence
<220> FEATURE:
<223> OTHER INFORMATION: synthetic construct

<400> SEQUENCE: 479 agcaggtgt                                                                          9

<210> SEQ ID NO 480
<211> LENGTH: 9
<212> TYPE: DNA
<213> ORGANISM: Artificial Sequence
<220> FEATURE:
<223> OTHER INFORMATION: synthetic construct

<400> SEQUENCE: 480 acctgctct                                                                          9

<210> SEQ ID NO 481
<211> LENGTH: 9
<212> TYPE: DNA
<213> ORGANISM: Artificial Sequence
<220> FEATURE:
<223> OTHER INFORMATION: synthetic construct

<400> SEQUENCE: 481 ttccgcagt                                                                          9

<210> SEQ ID NO 482
<211> LENGTH: 9
<212> TYPE: DNA
<213> ORGANISM: Artificial Sequence
<220> FEATURE:
<223> OTHER INFORMATION: synthetic construct

<400> SEQUENCE: 482 tgcggaact                                                                          9

<210> SEQ ID NO 483

```
<211> LENGTH: 9
<212> TYPE: DNA
<213> ORGANISM: Artificial Sequence
<220> FEATURE:
<223> OTHER INFORMATION: synthetic construct

<400> SEQUENCE: 483 gtcagccgt                                                              9

<210> SEQ ID NO 484
<211> LENGTH: 9
<212> TYPE: DNA
<213> ORGANISM: Artificial Sequence
<220> FEATURE:
<223> OTHER INFORMATION: synthetic construct

<400> SEQUENCE: 484 ggctgacct                                                              9

<210> SEQ ID NO 485
<211> LENGTH: 9
<212> TYPE: DNA
<213> ORGANISM: Artificial Sequence
<220> FEATURE:
<223> OTHER INFORMATION: synthetic construct

<400> SEQUENCE: 485 ggtctgcgt                                                              9

<210> SEQ ID NO 486
<211> LENGTH: 9
<212> TYPE: DNA
<213> ORGANISM: Artificial Sequence
<220> FEATURE:
<223> OTHER INFORMATION: synthetic construct

<400> SEQUENCE: 486 gcagaccct                                                              9

<210> SEQ ID NO 487
<211> LENGTH: 9
<212> TYPE: DNA
<213> ORGANISM: Artificial Sequence
<220> FEATURE:
<223> OTHER INFORMATION: synthetic construct

<400> SEQUENCE: 487 tagccgagt                                                              9

<210> SEQ ID NO 488
<211> LENGTH: 9
<212> TYPE: DNA
<213> ORGANISM: Artificial Sequence
<220> FEATURE:
<223> OTHER INFORMATION: synthetic construct

<400> SEQUENCE: 488 tcggctact                                                              9

<210> SEQ ID NO 489
<211> LENGTH: 9
<212> TYPE: DNA
<213> ORGANISM: Artificial Sequence
<220> FEATURE:
<223> OTHER INFORMATION: synthetic construct

<400> SEQUENCE: 489
``` gtcagcagt 9

<210> SEQ ID NO 490
<211> LENGTH: 9
<212> TYPE: DNA
<213> ORGANISM: Artificial Sequence
<220> FEATURE:
<223> OTHER INFORMATION: synthetic construct

<400> SEQUENCE: 490 tgctgacct 9

<210> SEQ ID NO 491
<211> LENGTH: 9
<212> TYPE: DNA
<213> ORGANISM: Artificial Sequence
<220> FEATURE:
<223> OTHER INFORMATION: synthetic construct

<400> SEQUENCE: 491 ggtctgagt 9

<210> SEQ ID NO 492
<211> LENGTH: 9
<212> TYPE: DNA
<213> ORGANISM: Artificial Sequence
<220> FEATURE:
<223> OTHER INFORMATION: synthetic construct

<400> SEQUENCE: 492 tcagaccct 9

<210> SEQ ID NO 493
<211> LENGTH: 9
<212> TYPE: DNA
<213> ORGANISM: Artificial Sequence
<220> FEATURE:
<223> OTHER INFORMATION: synthetic construct

<400> SEQUENCE: 493 cggacaggt 9

<210> SEQ ID NO 494
<211> LENGTH: 9
<212> TYPE: DNA
<213> ORGANISM: Artificial Sequence
<220> FEATURE:
<223> OTHER INFORMATION: synthetic construct

<400> SEQUENCE: 494 ctgtccgct 9

<210> SEQ ID NO 495
<211> LENGTH: 9
<212> TYPE: DNA
<213> ORGANISM: Artificial Sequence
<220> FEATURE:
<223> OTHER INFORMATION: synthetic construct

<400> SEQUENCE: 495 ttagccggt 9

<210> SEQ ID NO 496
<211> LENGTH: 9
<212> TYPE: DNA
<213> ORGANISM: Artificial Sequence
<220> FEATURE:

```
<223> OTHER INFORMATION: synthetic construct

<400> SEQUENCE: 496 cggctaact                                                                9

<210> SEQ ID NO 497
<211> LENGTH: 9
<212> TYPE: DNA
<213> ORGANISM: Artificial Sequence
<220> FEATURE:
<223> OTHER INFORMATION: synthetic construct

<400> SEQUENCE: 497 gagacgagt                                                                9

<210> SEQ ID NO 498
<211> LENGTH: 9
<212> TYPE: DNA
<213> ORGANISM: Artificial Sequence
<220> FEATURE:
<223> OTHER INFORMATION: synthetic construct

<400> SEQUENCE: 498 tcgtctcct                                                                9

<210> SEQ ID NO 499
<211> LENGTH: 9
<212> TYPE: DNA
<213> ORGANISM: Artificial Sequence
<220> FEATURE:
<223> OTHER INFORMATION: synthetic construct

<400> SEQUENCE: 499 cgtaaccgt                                                                9

<210> SEQ ID NO 500
<211> LENGTH: 9
<212> TYPE: DNA
<213> ORGANISM: Artificial Sequence
<220> FEATURE:
<223> OTHER INFORMATION: synthetic construct

<400> SEQUENCE: 500 ggttacgct                                                                9

<210> SEQ ID NO 501
<211> LENGTH: 9
<212> TYPE: DNA
<213> ORGANISM: Artificial Sequence
<220> FEATURE:
<223> OTHER INFORMATION: synthetic construct

<400> SEQUENCE: 501 ttggcgtgt                                                                9

<210> SEQ ID NO 502
<211> LENGTH: 9
<212> TYPE: DNA
<213> ORGANISM: Artificial Sequence
<220> FEATURE:
<223> OTHER INFORMATION: synthetic construct

<400> SEQUENCE: 502 acgccaact                                                                9

<210> SEQ ID NO 503
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 503 atggcaggt                                                                 9

<210> SEQ ID NO 504
<211> LENGTH: 9
<212> TYPE: DNA
<213> ORGANISM: Artificial Sequence
<220> FEATURE:
<223> OTHER INFORMATION: synthetic construct

<400> SEQUENCE: 504 ctgccatct                                                                 9

<210> SEQ ID NO 505
<211> LENGTH: 9
<212> TYPE: DNA
<213> ORGANISM: Artificial Sequence
<220> FEATURE:
<223> OTHER INFORMATION: synthetic construct

<400> SEQUENCE: 505 cagctacga                                                                 9

<210> SEQ ID NO 506
<211> LENGTH: 9
<212> TYPE: DNA
<213> ORGANISM: Artificial Sequence
<220> FEATURE:
<223> OTHER INFORMATION: synthetic construct

<400> SEQUENCE: 506 gtagctgac                                                                 9

<210> SEQ ID NO 507
<211> LENGTH: 9
<212> TYPE: DNA
<213> ORGANISM: Artificial Sequence
<220> FEATURE:
<223> OTHER INFORMATION: synthetic construct

<400> SEQUENCE: 507 ctcctgcga                                                                 9

<210> SEQ ID NO 508
<211> LENGTH: 9
<212> TYPE: DNA
<213> ORGANISM: Artificial Sequence
<220> FEATURE:
<223> OTHER INFORMATION: synthetic construct

<400> SEQUENCE: 508 gcaggagac                                                                 9

<210> SEQ ID NO 509
<211> LENGTH: 9
<212> TYPE: DNA
<213> ORGANISM: Artificial Sequence
<220> FEATURE:
<223> OTHER INFORMATION: synthetic construct

<400> SEQUENCE: 509
```

```
gctgcctga                                                                    9

<210> SEQ ID NO 510
<211> LENGTH: 9
<212> TYPE: DNA
<213> ORGANISM: Artificial Sequence
<220> FEATURE:
<223> OTHER INFORMATION: synthetic construct

<400> SEQUENCE: 510 aggcagcac                                                                    9

<210> SEQ ID NO 511
<211> LENGTH: 9
<212> TYPE: DNA
<213> ORGANISM: Artificial Sequence
<220> FEATURE:
<223> OTHER INFORMATION: synthetic construct

<400> SEQUENCE: 511 caggaacga                                                                    9

<210> SEQ ID NO 512
<211> LENGTH: 9
<212> TYPE: DNA
<213> ORGANISM: Artificial Sequence
<220> FEATURE:
<223> OTHER INFORMATION: synthetic construct

<400> SEQUENCE: 512 gttcctgac                                                                    9

<210> SEQ ID NO 513
<211> LENGTH: 9
<212> TYPE: DNA
<213> ORGANISM: Artificial Sequence
<220> FEATURE:
<223> OTHER INFORMATION: synthetic construct

<400> SEQUENCE: 513 cacacgcga                                                                    9

<210> SEQ ID NO 514
<211> LENGTH: 9
<212> TYPE: DNA
<213> ORGANISM: Artificial Sequence
<220> FEATURE:
<223> OTHER INFORMATION: synthetic construct

<400> SEQUENCE: 514 gcgtgtgac                                                                    9

<210> SEQ ID NO 515
<211> LENGTH: 9
<212> TYPE: DNA
<213> ORGANISM: Artificial Sequence
<220> FEATURE:
<223> OTHER INFORMATION: synthetic construct

<400> SEQUENCE: 515 gcagcctga                                                                    9

<210> SEQ ID NO 516
<211> LENGTH: 9
<212> TYPE: DNA
<213> ORGANISM: Artificial Sequence
<220> FEATURE:
```

```
<223> OTHER INFORMATION: synthetic construct

<400> SEQUENCE: 516 aggctgcac                                                                9

<210> SEQ ID NO 517
<211> LENGTH: 9
<212> TYPE: DNA
<213> ORGANISM: Artificial Sequence
<220> FEATURE:
<223> OTHER INFORMATION: synthetic construct

<400> SEQUENCE: 517 ctgaacgga                                                                9

<210> SEQ ID NO 518
<211> LENGTH: 9
<212> TYPE: DNA
<213> ORGANISM: Artificial Sequence
<220> FEATURE:
<223> OTHER INFORMATION: synthetic construct

<400> SEQUENCE: 518 cgttcagac                                                                9

<210> SEQ ID NO 519
<211> LENGTH: 9
<212> TYPE: DNA
<213> ORGANISM: Artificial Sequence
<220> FEATURE:
<223> OTHER INFORMATION: synthetic construct

<400> SEQUENCE: 519 ctgaaccga                                                                9

<210> SEQ ID NO 520
<211> LENGTH: 9
<212> TYPE: DNA
<213> ORGANISM: Artificial Sequence
<220> FEATURE:
<223> OTHER INFORMATION: synthetic construct

<400> SEQUENCE: 520 ggttcagac                                                                9

<210> SEQ ID NO 521
<211> LENGTH: 9
<212> TYPE: DNA
<213> ORGANISM: Artificial Sequence
<220> FEATURE:
<223> OTHER INFORMATION: synthetic construct

<400> SEQUENCE: 521 tctggacga                                                                9

<210> SEQ ID NO 522
<211> LENGTH: 9
<212> TYPE: DNA
<213> ORGANISM: Artificial Sequence
<220> FEATURE:
<223> OTHER INFORMATION: synthetic construct

<400> SEQUENCE: 522 gtccagaac                                                                9

<210> SEQ ID NO 523
```

-continued

```
<211> LENGTH: 9
<212> TYPE: DNA
<213> ORGANISM: Artificial Sequence
<220> FEATURE:
<223> OTHER INFORMATION: synthetic construct

<400> SEQUENCE: 523 tgcctacga                                                                  9

<210> SEQ ID NO 524
<211> LENGTH: 9
<212> TYPE: DNA
<213> ORGANISM: Artificial Sequence
<220> FEATURE:
<223> OTHER INFORMATION: synthetic construct

<400> SEQUENCE: 524 gtaggcaac                                                                  9

<210> SEQ ID NO 525
<211> LENGTH: 9
<212> TYPE: DNA
<213> ORGANISM: Artificial Sequence
<220> FEATURE:
<223> OTHER INFORMATION: synthetic construct

<400> SEQUENCE: 525 ggcatacga                                                                  9

<210> SEQ ID NO 526
<211> LENGTH: 9
<212> TYPE: DNA
<213> ORGANISM: Artificial Sequence
<220> FEATURE:
<223> OTHER INFORMATION: synthetic construct

<400> SEQUENCE: 526 gtatgccac                                                                  9

<210> SEQ ID NO 527
<211> LENGTH: 9
<212> TYPE: DNA
<213> ORGANISM: Artificial Sequence
<220> FEATURE:
<223> OTHER INFORMATION: synthetic construct

<400> SEQUENCE: 527 cggtgacga                                                                  9

<210> SEQ ID NO 528
<211> LENGTH: 9
<212> TYPE: DNA
<213> ORGANISM: Artificial Sequence
<220> FEATURE:
<223> OTHER INFORMATION: synthetic construct

<400> SEQUENCE: 528 gtcaccgac                                                                  9

<210> SEQ ID NO 529
<211> LENGTH: 9
<212> TYPE: DNA
<213> ORGANISM: Artificial Sequence
<220> FEATURE:
<223> OTHER INFORMATION: synthetic construct

<400> SEQUENCE: 529
``` caacgacga                                                                9

<210> SEQ ID NO 530
<211> LENGTH: 9
<212> TYPE: DNA
<213> ORGANISM: Artificial Sequence
<220> FEATURE:
<223> OTHER INFORMATION: synthetic construct

<400> SEQUENCE: 530 gtcgttgac                                                                9

<210> SEQ ID NO 531
<211> LENGTH: 9
<212> TYPE: DNA
<213> ORGANISM: Artificial Sequence
<220> FEATURE:
<223> OTHER INFORMATION: synthetic construct

<400> SEQUENCE: 531 ctcctctga                                                                9

<210> SEQ ID NO 532
<211> LENGTH: 9
<212> TYPE: DNA
<213> ORGANISM: Artificial Sequence
<220> FEATURE:
<223> OTHER INFORMATION: synthetic construct

<400> SEQUENCE: 532 agaggagac                                                                9

<210> SEQ ID NO 533
<211> LENGTH: 9
<212> TYPE: DNA
<213> ORGANISM: Artificial Sequence
<220> FEATURE:
<223> OTHER INFORMATION: synthetic construct

<400> SEQUENCE: 533 tcaggacga                                                                9

<210> SEQ ID NO 534
<211> LENGTH: 9
<212> TYPE: DNA
<213> ORGANISM: Artificial Sequence
<220> FEATURE:
<223> OTHER INFORMATION: synthetic construct

<400> SEQUENCE: 534 gtcctgaac                                                                9

<210> SEQ ID NO 535
<211> LENGTH: 9
<212> TYPE: DNA
<213> ORGANISM: Artificial Sequence
<220> FEATURE:
<223> OTHER INFORMATION: synthetic construct

<400> SEQUENCE: 535 aaaggcgga                                                                9

<210> SEQ ID NO 536
<211> LENGTH: 9
<212> TYPE: DNA
<213> ORGANISM: Artificial Sequence
<220> FEATURE:

<223> OTHER INFORMATION: synthetic construct

<400> SEQUENCE: 536 cgcctttac                                                                          9

<210> SEQ ID NO 537
<211> LENGTH: 9
<212> TYPE: DNA
<213> ORGANISM: Artificial Sequence
<220> FEATURE:
<223> OTHER INFORMATION: synthetic construct

<400> SEQUENCE: 537 ctcctcgga                                                                          9

<210> SEQ ID NO 538
<211> LENGTH: 9
<212> TYPE: DNA
<213> ORGANISM: Artificial Sequence
<220> FEATURE:
<223> OTHER INFORMATION: synthetic construct

<400> SEQUENCE: 538 cgaggagac                                                                          9

<210> SEQ ID NO 539
<211> LENGTH: 9
<212> TYPE: DNA
<213> ORGANISM: Artificial Sequence
<220> FEATURE:
<223> OTHER INFORMATION: synthetic construct

<400> SEQUENCE: 539 cagatgcga                                                                          9

<210> SEQ ID NO 540
<211> LENGTH: 9
<212> TYPE: DNA
<213> ORGANISM: Artificial Sequence
<220> FEATURE:
<223> OTHER INFORMATION: synthetic construct

<400> SEQUENCE: 540 gcatctgac                                                                          9

<210> SEQ ID NO 541
<211> LENGTH: 9
<212> TYPE: DNA
<213> ORGANISM: Artificial Sequence
<220> FEATURE:
<223> OTHER INFORMATION: synthetic construct

<400> SEQUENCE: 541 gcagcaaga                                                                          9

<210> SEQ ID NO 542
<211> LENGTH: 9
<212> TYPE: DNA
<213> ORGANISM: Artificial Sequence
<220> FEATURE:
<223> OTHER INFORMATION: synthetic construct

<400> SEQUENCE: 542 ttgctgcac                                                                          9

<210> SEQ ID NO 543

```
<211> LENGTH: 9
<212> TYPE: DNA
<213> ORGANISM: Artificial Sequence
<220> FEATURE:
<223> OTHER INFORMATION: synthetic construct

<400> SEQUENCE: 543 gtggagtga                                                                  9

<210> SEQ ID NO 544
<211> LENGTH: 9
<212> TYPE: DNA
<213> ORGANISM: Artificial Sequence
<220> FEATURE:
<223> OTHER INFORMATION: synthetic construct

<400> SEQUENCE: 544 actccacac                                                                  9

<210> SEQ ID NO 545
<211> LENGTH: 9
<212> TYPE: DNA
<213> ORGANISM: Artificial Sequence
<220> FEATURE:
<223> OTHER INFORMATION: synthetic construct

<400> SEQUENCE: 545 ccagtagga                                                                  9

<210> SEQ ID NO 546
<211> LENGTH: 9
<212> TYPE: DNA
<213> ORGANISM: Artificial Sequence
<220> FEATURE:
<223> OTHER INFORMATION: synthetic construct

<400> SEQUENCE: 546 ctactggac                                                                  9

<210> SEQ ID NO 547
<211> LENGTH: 9
<212> TYPE: DNA
<213> ORGANISM: Artificial Sequence
<220> FEATURE:
<223> OTHER INFORMATION: synthetic construct

<400> SEQUENCE: 547 atggcacga                                                                  9

<210> SEQ ID NO 548
<211> LENGTH: 9
<212> TYPE: DNA
<213> ORGANISM: Artificial Sequence
<220> FEATURE:
<223> OTHER INFORMATION: synthetic construct

<400> SEQUENCE: 548 gtgccatac                                                                  9

<210> SEQ ID NO 549
<211> LENGTH: 9
<212> TYPE: DNA
<213> ORGANISM: Artificial Sequence
<220> FEATURE:
<223> OTHER INFORMATION: synthetic construct

<400> SEQUENCE: 549
``` ggactgtga 9

<210> SEQ ID NO 550
<211> LENGTH: 9
<212> TYPE: DNA
<213> ORGANISM: Artificial Sequence
<220> FEATURE:
<223> OTHER INFORMATION: synthetic construct

<400> SEQUENCE: 550 acagtccac 9

<210> SEQ ID NO 551
<211> LENGTH: 9
<212> TYPE: DNA
<213> ORGANISM: Artificial Sequence
<220> FEATURE:
<223> OTHER INFORMATION: synthetic construct

<400> SEQUENCE: 551 ccgaactga 9

<210> SEQ ID NO 552
<211> LENGTH: 9
<212> TYPE: DNA
<213> ORGANISM: Artificial Sequence
<220> FEATURE:
<223> OTHER INFORMATION: synthetic construct

<400> SEQUENCE: 552 agttcggac 9

<210> SEQ ID NO 553
<211> LENGTH: 9
<212> TYPE: DNA
<213> ORGANISM: Artificial Sequence
<220> FEATURE:
<223> OTHER INFORMATION: synthetic construct

<400> SEQUENCE: 553 ctcctcaga 9

<210> SEQ ID NO 554
<211> LENGTH: 9
<212> TYPE: DNA
<213> ORGANISM: Artificial Sequence
<220> FEATURE:
<223> OTHER INFORMATION: synthetic construct

<400> SEQUENCE: 554 tgaggagac 9

<210> SEQ ID NO 555
<211> LENGTH: 9
<212> TYPE: DNA
<213> ORGANISM: Artificial Sequence
<220> FEATURE:
<223> OTHER INFORMATION: synthetic construct

<400> SEQUENCE: 555 cactgctga 9

<210> SEQ ID NO 556
<211> LENGTH: 9
<212> TYPE: DNA
<213> ORGANISM: Artificial Sequence
<220> FEATURE:

```
<223> OTHER INFORMATION: synthetic construct

<400> SEQUENCE: 556 agcagtgac                                                                          9

<210> SEQ ID NO 557
<211> LENGTH: 9
<212> TYPE: DNA
<213> ORGANISM: Artificial Sequence
<220> FEATURE:
<223> OTHER INFORMATION: synthetic construct

<400> SEQUENCE: 557 agcaggcga                                                                          9

<210> SEQ ID NO 558
<211> LENGTH: 9
<212> TYPE: DNA
<213> ORGANISM: Artificial Sequence
<220> FEATURE:
<223> OTHER INFORMATION: synthetic construct

<400> SEQUENCE: 558 gcctgctac                                                                          9

<210> SEQ ID NO 559
<211> LENGTH: 9
<212> TYPE: DNA
<213> ORGANISM: Artificial Sequence
<220> FEATURE:
<223> OTHER INFORMATION: synthetic construct

<400> SEQUENCE: 559 agcaggaga                                                                          9

<210> SEQ ID NO 560
<211> LENGTH: 9
<212> TYPE: DNA
<213> ORGANISM: Artificial Sequence
<220> FEATURE:
<223> OTHER INFORMATION: synthetic construct

<400> SEQUENCE: 560 tcctgctac                                                                          9

<210> SEQ ID NO 561
<211> LENGTH: 9
<212> TYPE: DNA
<213> ORGANISM: Artificial Sequence
<220> FEATURE:
<223> OTHER INFORMATION: synthetic construct

<400> SEQUENCE: 561 agagccaga                                                                          9

<210> SEQ ID NO 562
<211> LENGTH: 9
<212> TYPE: DNA
<213> ORGANISM: Artificial Sequence
<220> FEATURE:
<223> OTHER INFORMATION: synthetic construct

<400> SEQUENCE: 562 tggctctac                                                                          9

<210> SEQ ID NO 563
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 563 gtcgttgga                                                                  9

<210> SEQ ID NO 564
<211> LENGTH: 9
<212> TYPE: DNA
<213> ORGANISM: Artificial Sequence
<220> FEATURE:
<223> OTHER INFORMATION: synthetic construct

<400> SEQUENCE: 564 caacgacac                                                                  9

<210> SEQ ID NO 565
<211> LENGTH: 9
<212> TYPE: DNA
<213> ORGANISM: Artificial Sequence
<220> FEATURE:
<223> OTHER INFORMATION: synthetic construct

<400> SEQUENCE: 565 ccgaacgga                                                                  9

<210> SEQ ID NO 566
<211> LENGTH: 9
<212> TYPE: DNA
<213> ORGANISM: Artificial Sequence
<220> FEATURE:
<223> OTHER INFORMATION: synthetic construct

<400> SEQUENCE: 566 cgttcggac                                                                  9

<210> SEQ ID NO 567
<211> LENGTH: 9
<212> TYPE: DNA
<213> ORGANISM: Artificial Sequence
<220> FEATURE:
<223> OTHER INFORMATION: synthetic construct

<400> SEQUENCE: 567 cactgcgga                                                                  9

<210> SEQ ID NO 568
<211> LENGTH: 9
<212> TYPE: DNA
<213> ORGANISM: Artificial Sequence
<220> FEATURE:
<223> OTHER INFORMATION: synthetic construct

<400> SEQUENCE: 568 cgcagtgac                                                                  9

<210> SEQ ID NO 569
<211> LENGTH: 9
<212> TYPE: DNA
<213> ORGANISM: Artificial Sequence
<220> FEATURE:
<223> OTHER INFORMATION: synthetic construct

<400> SEQUENCE: 569
```

```
gtggagcga                                                                      9

<210> SEQ ID NO 570
<211> LENGTH: 9
<212> TYPE: DNA
<213> ORGANISM: Artificial Sequence
<220> FEATURE:
<223> OTHER INFORMATION: synthetic construct

<400> SEQUENCE: 570 gctccacac                                                                      9

<210> SEQ ID NO 571
<211> LENGTH: 9
<212> TYPE: DNA
<213> ORGANISM: Artificial Sequence
<220> FEATURE:
<223> OTHER INFORMATION: synthetic construct

<400> SEQUENCE: 571 gtggagaga                                                                      9

<210> SEQ ID NO 572
<211> LENGTH: 9
<212> TYPE: DNA
<213> ORGANISM: Artificial Sequence
<220> FEATURE:
<223> OTHER INFORMATION: synthetic construct

<400> SEQUENCE: 572 tctccacac                                                                      9

<210> SEQ ID NO 573
<211> LENGTH: 9
<212> TYPE: DNA
<213> ORGANISM: Artificial Sequence
<220> FEATURE:
<223> OTHER INFORMATION: synthetic construct

<400> SEQUENCE: 573 ggactgcga                                                                      9

<210> SEQ ID NO 574
<211> LENGTH: 9
<212> TYPE: DNA
<213> ORGANISM: Artificial Sequence
<220> FEATURE:
<223> OTHER INFORMATION: synthetic construct

<400> SEQUENCE: 574 gcagtccac                                                                      9

<210> SEQ ID NO 575
<211> LENGTH: 9
<212> TYPE: DNA
<213> ORGANISM: Artificial Sequence
<220> FEATURE:
<223> OTHER INFORMATION: synthetic construct

<400> SEQUENCE: 575 ccgaaccga                                                                      9

<210> SEQ ID NO 576
<211> LENGTH: 9
<212> TYPE: DNA
<213> ORGANISM: Artificial Sequence
<220> FEATURE:
```

-continued

<223> OTHER INFORMATION: synthetic construct

<400> SEQUENCE: 576 ggttcggac                                                                        9

<210> SEQ ID NO 577
<211> LENGTH: 9
<212> TYPE: DNA
<213> ORGANISM: Artificial Sequence
<220> FEATURE:
<223> OTHER INFORMATION: synthetic construct

<400> SEQUENCE: 577 cactgccga                                                                        9

<210> SEQ ID NO 578
<211> LENGTH: 9
<212> TYPE: DNA
<213> ORGANISM: Artificial Sequence
<220> FEATURE:
<223> OTHER INFORMATION: synthetic construct

<400> SEQUENCE: 578 ggcagtgac                                                                        9

<210> SEQ ID NO 579
<211> LENGTH: 9
<212> TYPE: DNA
<213> ORGANISM: Artificial Sequence
<220> FEATURE:
<223> OTHER INFORMATION: synthetic construct

<400> SEQUENCE: 579 cgaaacgga                                                                        9

<210> SEQ ID NO 580
<211> LENGTH: 9
<212> TYPE: DNA
<213> ORGANISM: Artificial Sequence
<220> FEATURE:
<223> OTHER INFORMATION: synthetic construct

<400> SEQUENCE: 580 cgtttcgac                                                                        9

<210> SEQ ID NO 581
<211> LENGTH: 9
<212> TYPE: DNA
<213> ORGANISM: Artificial Sequence
<220> FEATURE:
<223> OTHER INFORMATION: synthetic construct

<400> SEQUENCE: 581 ggactgaga                                                                        9

<210> SEQ ID NO 582
<211> LENGTH: 9
<212> TYPE: DNA
<213> ORGANISM: Artificial Sequence
<220> FEATURE:
<223> OTHER INFORMATION: synthetic construct

<400> SEQUENCE: 582 tcagtccac                                                                        9

<210> SEQ ID NO 583

```
<211> LENGTH: 9
<212> TYPE: DNA
<213> ORGANISM: Artificial Sequence
<220> FEATURE:
<223> OTHER INFORMATION: synthetic construct

<400> SEQUENCE: 583 ccgaacaga                                                                  9

<210> SEQ ID NO 584
<211> LENGTH: 9
<212> TYPE: DNA
<213> ORGANISM: Artificial Sequence
<220> FEATURE:
<223> OTHER INFORMATION: synthetic construct

<400> SEQUENCE: 584 tgttcggac                                                                  9

<210> SEQ ID NO 585
<211> LENGTH: 9
<212> TYPE: DNA
<213> ORGANISM: Artificial Sequence
<220> FEATURE:
<223> OTHER INFORMATION: synthetic construct

<400> SEQUENCE: 585 cgaaaccga                                                                  9

<210> SEQ ID NO 586
<211> LENGTH: 9
<212> TYPE: DNA
<213> ORGANISM: Artificial Sequence
<220> FEATURE:
<223> OTHER INFORMATION: synthetic construct

<400> SEQUENCE: 586 ggtttcgac                                                                  9

<210> SEQ ID NO 587
<211> LENGTH: 9
<212> TYPE: DNA
<213> ORGANISM: Artificial Sequence
<220> FEATURE:
<223> OTHER INFORMATION: synthetic construct

<400> SEQUENCE: 587 ctggcttga                                                                  9

<210> SEQ ID NO 588
<211> LENGTH: 9
<212> TYPE: DNA
<213> ORGANISM: Artificial Sequence
<220> FEATURE:
<223> OTHER INFORMATION: synthetic construct

<400> SEQUENCE: 588 aagccagac                                                                  9

<210> SEQ ID NO 589
<211> LENGTH: 9
<212> TYPE: DNA
<213> ORGANISM: Artificial Sequence
<220> FEATURE:
<223> OTHER INFORMATION: synthetic construct

<400> SEQUENCE: 589
``` cacacctga 9

<210> SEQ ID NO 590
<211> LENGTH: 9
<212> TYPE: DNA
<213> ORGANISM: Artificial Sequence
<220> FEATURE:
<223> OTHER INFORMATION: synthetic construct

<400> SEQUENCE: 590 aggtgtgac 9

<210> SEQ ID NO 591
<211> LENGTH: 9
<212> TYPE: DNA
<213> ORGANISM: Artificial Sequence
<220> FEATURE:
<223> OTHER INFORMATION: synthetic construct

<400> SEQUENCE: 591 aacgaccga 9

<210> SEQ ID NO 592
<211> LENGTH: 9
<212> TYPE: DNA
<213> ORGANISM: Artificial Sequence
<220> FEATURE:
<223> OTHER INFORMATION: synthetic construct

<400> SEQUENCE: 592 ggtcgttac 9

<210> SEQ ID NO 593
<211> LENGTH: 9
<212> TYPE: DNA
<213> ORGANISM: Artificial Sequence
<220> FEATURE:
<223> OTHER INFORMATION: synthetic construct

<400> SEQUENCE: 593 atccagcga 9

<210> SEQ ID NO 594
<211> LENGTH: 9
<212> TYPE: DNA
<213> ORGANISM: Artificial Sequence
<220> FEATURE:
<223> OTHER INFORMATION: synthetic construct

<400> SEQUENCE: 594 gctggatac 9

<210> SEQ ID NO 595
<211> LENGTH: 9
<212> TYPE: DNA
<213> ORGANISM: Artificial Sequence
<220> FEATURE:
<223> OTHER INFORMATION: synthetic construct

<400> SEQUENCE: 595 tgcgaagga 9

<210> SEQ ID NO 596
<211> LENGTH: 9
<212> TYPE: DNA
<213> ORGANISM: Artificial Sequence
<220> FEATURE:

-continued

<223> OTHER INFORMATION: synthetic construct

<400> SEQUENCE: 596 cttcgcaac					9

<210> SEQ ID NO 597
<211> LENGTH: 9
<212> TYPE: DNA
<213> ORGANISM: Artificial Sequence
<220> FEATURE:
<223> OTHER INFORMATION: synthetic construct

<400> SEQUENCE: 597 tgcgaacga					9

<210> SEQ ID NO 598
<211> LENGTH: 9
<212> TYPE: DNA
<213> ORGANISM: Artificial Sequence
<220> FEATURE:
<223> OTHER INFORMATION: synthetic construct

<400> SEQUENCE: 598 gttcgcaac					9

<210> SEQ ID NO 599
<211> LENGTH: 9
<212> TYPE: DNA
<213> ORGANISM: Artificial Sequence
<220> FEATURE:
<223> OTHER INFORMATION: synthetic construct

<400> SEQUENCE: 599 ctggctgga					9

<210> SEQ ID NO 600
<211> LENGTH: 9
<212> TYPE: DNA
<213> ORGANISM: Artificial Sequence
<220> FEATURE:
<223> OTHER INFORMATION: synthetic construct

<400> SEQUENCE: 600 cagccagac					9

<210> SEQ ID NO 601
<211> LENGTH: 9
<212> TYPE: DNA
<213> ORGANISM: Artificial Sequence
<220> FEATURE:
<223> OTHER INFORMATION: synthetic construct

<400> SEQUENCE: 601 cacaccgga					9

<210> SEQ ID NO 602
<211> LENGTH: 9
<212> TYPE: DNA
<213> ORGANISM: Artificial Sequence
<220> FEATURE:
<223> OTHER INFORMATION: synthetic construct

<400> SEQUENCE: 602 cggtgtgac					9

<210> SEQ ID NO 603

```
<211> LENGTH: 9
<212> TYPE: DNA
<213> ORGANISM: Artificial Sequence
<220> FEATURE:
<223> OTHER INFORMATION: synthetic construct

<400> SEQUENCE: 603 agtgcagga                                                                  9

<210> SEQ ID NO 604
<211> LENGTH: 9
<212> TYPE: DNA
<213> ORGANISM: Artificial Sequence
<220> FEATURE:
<223> OTHER INFORMATION: synthetic construct

<400> SEQUENCE: 604 ctgcactac                                                                  9

<210> SEQ ID NO 605
<211> LENGTH: 9
<212> TYPE: DNA
<213> ORGANISM: Artificial Sequence
<220> FEATURE:
<223> OTHER INFORMATION: synthetic construct

<400> SEQUENCE: 605 gaccgttga                                                                  9

<210> SEQ ID NO 606
<211> LENGTH: 9
<212> TYPE: DNA
<213> ORGANISM: Artificial Sequence
<220> FEATURE:
<223> OTHER INFORMATION: synthetic construct

<400> SEQUENCE: 606 aacggtcac                                                                  9

<210> SEQ ID NO 607
<211> LENGTH: 9
<212> TYPE: DNA
<213> ORGANISM: Artificial Sequence
<220> FEATURE:
<223> OTHER INFORMATION: synthetic construct

<400> SEQUENCE: 607 ggtgagtga                                                                  9

<210> SEQ ID NO 608
<211> LENGTH: 9
<212> TYPE: DNA
<213> ORGANISM: Artificial Sequence
<220> FEATURE:
<223> OTHER INFORMATION: synthetic construct

<400> SEQUENCE: 608 actcaccac                                                                  9

<210> SEQ ID NO 609
<211> LENGTH: 9
<212> TYPE: DNA
<213> ORGANISM: Artificial Sequence
<220> FEATURE:
<223> OTHER INFORMATION: synthetic construct

<400> SEQUENCE: 609
```

```
ccttcctga                                                                    9

<210> SEQ ID NO 610
<211> LENGTH: 9
<212> TYPE: DNA
<213> ORGANISM: Artificial Sequence
<220> FEATURE:
<223> OTHER INFORMATION: synthetic construct

<400> SEQUENCE: 610 aggaaggac                                                                    9

<210> SEQ ID NO 611
<211> LENGTH: 9
<212> TYPE: DNA
<213> ORGANISM: Artificial Sequence
<220> FEATURE:
<223> OTHER INFORMATION: synthetic construct

<400> SEQUENCE: 611 ctggctaga                                                                    9

<210> SEQ ID NO 612
<211> LENGTH: 9
<212> TYPE: DNA
<213> ORGANISM: Artificial Sequence
<220> FEATURE:
<223> OTHER INFORMATION: synthetic construct

<400> SEQUENCE: 612 tagccagac                                                                    9

<210> SEQ ID NO 613
<211> LENGTH: 9
<212> TYPE: DNA
<213> ORGANISM: Artificial Sequence
<220> FEATURE:
<223> OTHER INFORMATION: synthetic construct

<400> SEQUENCE: 613 cacaccaga                                                                    9

<210> SEQ ID NO 614
<211> LENGTH: 9
<212> TYPE: DNA
<213> ORGANISM: Artificial Sequence
<220> FEATURE:
<223> OTHER INFORMATION: synthetic construct

<400> SEQUENCE: 614 tggtgtgac                                                                    9

<210> SEQ ID NO 615
<211> LENGTH: 9
<212> TYPE: DNA
<213> ORGANISM: Artificial Sequence
<220> FEATURE:
<223> OTHER INFORMATION: synthetic construct

<400> SEQUENCE: 615 agcggtaga                                                                    9

<210> SEQ ID NO 616
<211> LENGTH: 9
<212> TYPE: DNA
<213> ORGANISM: Artificial Sequence
<220> FEATURE:
```

```
<223> OTHER INFORMATION: synthetic construct

<400> SEQUENCE: 616 taccgctac                                                                9

<210> SEQ ID NO 617
<211> LENGTH: 9
<212> TYPE: DNA
<213> ORGANISM: Artificial Sequence
<220> FEATURE:
<223> OTHER INFORMATION: synthetic construct

<400> SEQUENCE: 617 gtcagagga                                                                9

<210> SEQ ID NO 618
<211> LENGTH: 9
<212> TYPE: DNA
<213> ORGANISM: Artificial Sequence
<220> FEATURE:
<223> OTHER INFORMATION: synthetic construct

<400> SEQUENCE: 618 ctctgacac                                                                9

<210> SEQ ID NO 619
<211> LENGTH: 9
<212> TYPE: DNA
<213> ORGANISM: Artificial Sequence
<220> FEATURE:
<223> OTHER INFORMATION: synthetic construct

<400> SEQUENCE: 619 ttccgacga                                                                9

<210> SEQ ID NO 620
<211> LENGTH: 9
<212> TYPE: DNA
<213> ORGANISM: Artificial Sequence
<220> FEATURE:
<223> OTHER INFORMATION: synthetic construct

<400> SEQUENCE: 620 gtcggaaac                                                                9

<210> SEQ ID NO 621
<211> LENGTH: 9
<212> TYPE: DNA
<213> ORGANISM: Artificial Sequence
<220> FEATURE:
<223> OTHER INFORMATION: synthetic construct

<400> SEQUENCE: 621 aggcgtaga                                                                9

<210> SEQ ID NO 622
<211> LENGTH: 9
<212> TYPE: DNA
<213> ORGANISM: Artificial Sequence
<220> FEATURE:
<223> OTHER INFORMATION: synthetic construct

<400> SEQUENCE: 622 tacgcctac                                                                9

<210> SEQ ID NO 623
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 623 ctcgactga                                                                   9

<210> SEQ ID NO 624
<211> LENGTH: 9
<212> TYPE: DNA
<213> ORGANISM: Artificial Sequence
<220> FEATURE:
<223> OTHER INFORMATION: synthetic construct

<400> SEQUENCE: 624 agtcgagac                                                                   9

<210> SEQ ID NO 625
<211> LENGTH: 9
<212> TYPE: DNA
<213> ORGANISM: Artificial Sequence
<220> FEATURE:
<223> OTHER INFORMATION: synthetic construct

<400> SEQUENCE: 625 tacgctgga                                                                   9

<210> SEQ ID NO 626
<211> LENGTH: 9
<212> TYPE: DNA
<213> ORGANISM: Artificial Sequence
<220> FEATURE:
<223> OTHER INFORMATION: synthetic construct

<400> SEQUENCE: 626 cagcgtaac                                                                   9

<210> SEQ ID NO 627
<211> LENGTH: 9
<212> TYPE: DNA
<213> ORGANISM: Artificial Sequence
<220> FEATURE:
<223> OTHER INFORMATION: synthetic construct

<400> SEQUENCE: 627 gttcggtga                                                                   9

<210> SEQ ID NO 628
<211> LENGTH: 9
<212> TYPE: DNA
<213> ORGANISM: Artificial Sequence
<220> FEATURE:
<223> OTHER INFORMATION: synthetic construct

<400> SEQUENCE: 628 accgaacac                                                                   9

<210> SEQ ID NO 629
<211> LENGTH: 9
<212> TYPE: DNA
<213> ORGANISM: Artificial Sequence
<220> FEATURE:
<223> OTHER INFORMATION: synthetic construct

<400> SEQUENCE: 629
```

-continued gccagcaga 9

<210> SEQ ID NO 630
<211> LENGTH: 9
<212> TYPE: DNA
<213> ORGANISM: Artificial Sequence
<220> FEATURE:
<223> OTHER INFORMATION: synthetic construct

<400> SEQUENCE: 630 tgctggcac 9

<210> SEQ ID NO 631
<211> LENGTH: 9
<212> TYPE: DNA
<213> ORGANISM: Artificial Sequence
<220> FEATURE:
<223> OTHER INFORMATION: synthetic construct

<400> SEQUENCE: 631 gaccgtaga 9

<210> SEQ ID NO 632
<211> LENGTH: 9
<212> TYPE: DNA
<213> ORGANISM: Artificial Sequence
<220> FEATURE:
<223> OTHER INFORMATION: synthetic construct

<400> SEQUENCE: 632 tacggtcac 9

<210> SEQ ID NO 633
<211> LENGTH: 9
<212> TYPE: DNA
<213> ORGANISM: Artificial Sequence
<220> FEATURE:
<223> OTHER INFORMATION: synthetic construct

<400> SEQUENCE: 633 gtgctctga 9

<210> SEQ ID NO 634
<211> LENGTH: 9
<212> TYPE: DNA
<213> ORGANISM: Artificial Sequence
<220> FEATURE:
<223> OTHER INFORMATION: synthetic construct

<400> SEQUENCE: 634 agagcacac 9

<210> SEQ ID NO 635
<211> LENGTH: 9
<212> TYPE: DNA
<213> ORGANISM: Artificial Sequence
<220> FEATURE:
<223> OTHER INFORMATION: synthetic construct

<400> SEQUENCE: 635 ggtgagcga 9

<210> SEQ ID NO 636
<211> LENGTH: 9
<212> TYPE: DNA
<213> ORGANISM: Artificial Sequence
<220> FEATURE:

<223> OTHER INFORMATION: synthetic construct

<400> SEQUENCE: 636 gctcaccac                                                                      9

<210> SEQ ID NO 637
<211> LENGTH: 9
<212> TYPE: DNA
<213> ORGANISM: Artificial Sequence
<220> FEATURE:
<223> OTHER INFORMATION: synthetic construct

<400> SEQUENCE: 637 ggtgagaga                                                                      9

<210> SEQ ID NO 638
<211> LENGTH: 9
<212> TYPE: DNA
<213> ORGANISM: Artificial Sequence
<220> FEATURE:
<223> OTHER INFORMATION: synthetic construct

<400> SEQUENCE: 638 tctcaccac                                                                      9

<210> SEQ ID NO 639
<211> LENGTH: 9
<212> TYPE: DNA
<213> ORGANISM: Artificial Sequence
<220> FEATURE:
<223> OTHER INFORMATION: synthetic construct

<400> SEQUENCE: 639 ccttccaga                                                                      9

<210> SEQ ID NO 640
<211> LENGTH: 9
<212> TYPE: DNA
<213> ORGANISM: Artificial Sequence
<220> FEATURE:
<223> OTHER INFORMATION: synthetic construct

<400> SEQUENCE: 640 tggaaggac                                                                      9

<210> SEQ ID NO 641
<211> LENGTH: 9
<212> TYPE: DNA
<213> ORGANISM: Artificial Sequence
<220> FEATURE:
<223> OTHER INFORMATION: synthetic construct

<400> SEQUENCE: 641 ctcctacga                                                                      9

<210> SEQ ID NO 642
<211> LENGTH: 9
<212> TYPE: DNA
<213> ORGANISM: Artificial Sequence
<220> FEATURE:
<223> OTHER INFORMATION: synthetic construct

<400> SEQUENCE: 642 gtaggagac                                                                      9

<210> SEQ ID NO 643

<211> LENGTH: 9
<212> TYPE: DNA
<213> ORGANISM: Artificial Sequence
<220> FEATURE:
<223> OTHER INFORMATION: synthetic construct

<400> SEQUENCE: 643 ctcgacgga                                                                  9

<210> SEQ ID NO 644
<211> LENGTH: 9
<212> TYPE: DNA
<213> ORGANISM: Artificial Sequence
<220> FEATURE:
<223> OTHER INFORMATION: synthetic construct

<400> SEQUENCE: 644 cgtcgagac                                                                  9

<210> SEQ ID NO 645
<211> LENGTH: 9
<212> TYPE: DNA
<213> ORGANISM: Artificial Sequence
<220> FEATURE:
<223> OTHER INFORMATION: synthetic construct

<400> SEQUENCE: 645 gccgtttga                                                                  9

<210> SEQ ID NO 646
<211> LENGTH: 9
<212> TYPE: DNA
<213> ORGANISM: Artificial Sequence
<220> FEATURE:
<223> OTHER INFORMATION: synthetic construct

<400> SEQUENCE: 646 aaacggcac                                                                  9

<210> SEQ ID NO 647
<211> LENGTH: 9
<212> TYPE: DNA
<213> ORGANISM: Artificial Sequence
<220> FEATURE:
<223> OTHER INFORMATION: synthetic construct

<400> SEQUENCE: 647 gcggagtga                                                                  9

<210> SEQ ID NO 648
<211> LENGTH: 9
<212> TYPE: DNA
<213> ORGANISM: Artificial Sequence
<220> FEATURE:
<223> OTHER INFORMATION: synthetic construct

<400> SEQUENCE: 648 actccgcac                                                                  9

<210> SEQ ID NO 649
<211> LENGTH: 9
<212> TYPE: DNA
<213> ORGANISM: Artificial Sequence
<220> FEATURE:
<223> OTHER INFORMATION: synthetic construct

<400> SEQUENCE: 649

```
cgtgcttga                                                                 9

<210> SEQ ID NO 650
<211> LENGTH: 9
<212> TYPE: DNA
<213> ORGANISM: Artificial Sequence
<220> FEATURE:
<223> OTHER INFORMATION: synthetic construct

<400> SEQUENCE: 650 aagcacgac                                                                 9

<210> SEQ ID NO 651
<211> LENGTH: 9
<212> TYPE: DNA
<213> ORGANISM: Artificial Sequence
<220> FEATURE:
<223> OTHER INFORMATION: synthetic construct

<400> SEQUENCE: 651 ctcgaccga                                                                 9

<210> SEQ ID NO 652
<211> LENGTH: 9
<212> TYPE: DNA
<213> ORGANISM: Artificial Sequence
<220> FEATURE:
<223> OTHER INFORMATION: synthetic construct

<400> SEQUENCE: 652 ggtcgagac                                                                 9

<210> SEQ ID NO 653
<211> LENGTH: 9
<212> TYPE: DNA
<213> ORGANISM: Artificial Sequence
<220> FEATURE:
<223> OTHER INFORMATION: synthetic construct

<400> SEQUENCE: 653 agagcagga                                                                 9

<210> SEQ ID NO 654
<211> LENGTH: 9
<212> TYPE: DNA
<213> ORGANISM: Artificial Sequence
<220> FEATURE:
<223> OTHER INFORMATION: synthetic construct

<400> SEQUENCE: 654 ctgctctac                                                                 9

<210> SEQ ID NO 655
<211> LENGTH: 9
<212> TYPE: DNA
<213> ORGANISM: Artificial Sequence
<220> FEATURE:
<223> OTHER INFORMATION: synthetic construct

<400> SEQUENCE: 655 gtgctcgga                                                                 9

<210> SEQ ID NO 656
<211> LENGTH: 9
<212> TYPE: DNA
<213> ORGANISM: Artificial Sequence
<220> FEATURE:
```

<223> OTHER INFORMATION: synthetic construct

<400> SEQUENCE: 656 cgagcacac                                                                         9

<210> SEQ ID NO 657
<211> LENGTH: 9
<212> TYPE: DNA
<213> ORGANISM: Artificial Sequence
<220> FEATURE:
<223> OTHER INFORMATION: synthetic construct

<400> SEQUENCE: 657 ctcgacaga                                                                         9

<210> SEQ ID NO 658
<211> LENGTH: 9
<212> TYPE: DNA
<213> ORGANISM: Artificial Sequence
<220> FEATURE:
<223> OTHER INFORMATION: synthetic construct

<400> SEQUENCE: 658 tgtcgagac                                                                         9

<210> SEQ ID NO 659
<211> LENGTH: 9
<212> TYPE: DNA
<213> ORGANISM: Artificial Sequence
<220> FEATURE:
<223> OTHER INFORMATION: synthetic construct

<400> SEQUENCE: 659 ggagagtga                                                                         9

<210> SEQ ID NO 660
<211> LENGTH: 9
<212> TYPE: DNA
<213> ORGANISM: Artificial Sequence
<220> FEATURE:
<223> OTHER INFORMATION: synthetic construct

<400> SEQUENCE: 660 actctccac                                                                         9

<210> SEQ ID NO 661
<211> LENGTH: 9
<212> TYPE: DNA
<213> ORGANISM: Artificial Sequence
<220> FEATURE:
<223> OTHER INFORMATION: synthetic construct

<400> SEQUENCE: 661 aggctgtga                                                                         9

<210> SEQ ID NO 662
<211> LENGTH: 9
<212> TYPE: DNA
<213> ORGANISM: Artificial Sequence
<220> FEATURE:
<223> OTHER INFORMATION: synthetic construct

<400> SEQUENCE: 662 acagcctac                                                                         9

<210> SEQ ID NO 663

```
<211> LENGTH: 9
<212> TYPE: DNA
<213> ORGANISM: Artificial Sequence
<220> FEATURE:
<223> OTHER INFORMATION: synthetic construct

<400> SEQUENCE: 663 agagcacga                                                                9

<210> SEQ ID NO 664
<211> LENGTH: 9
<212> TYPE: DNA
<213> ORGANISM: Artificial Sequence
<220> FEATURE:
<223> OTHER INFORMATION: synthetic construct

<400> SEQUENCE: 664 gtgctctac                                                                9

<210> SEQ ID NO 665
<211> LENGTH: 9
<212> TYPE: DNA
<213> ORGANISM: Artificial Sequence
<220> FEATURE:
<223> OTHER INFORMATION: synthetic construct

<400> SEQUENCE: 665 ccatcctga                                                                9

<210> SEQ ID NO 666
<211> LENGTH: 9
<212> TYPE: DNA
<213> ORGANISM: Artificial Sequence
<220> FEATURE:
<223> OTHER INFORMATION: synthetic construct

<400> SEQUENCE: 666 aggatggac                                                                9

<210> SEQ ID NO 667
<211> LENGTH: 9
<212> TYPE: DNA
<213> ORGANISM: Artificial Sequence
<220> FEATURE:
<223> OTHER INFORMATION: synthetic construct

<400> SEQUENCE: 667 gttcggaga                                                                9

<210> SEQ ID NO 668
<211> LENGTH: 9
<212> TYPE: DNA
<213> ORGANISM: Artificial Sequence
<220> FEATURE:
<223> OTHER INFORMATION: synthetic construct

<400> SEQUENCE: 668 tccgaacac                                                                9

<210> SEQ ID NO 669
<211> LENGTH: 9
<212> TYPE: DNA
<213> ORGANISM: Artificial Sequence
<220> FEATURE:
<223> OTHER INFORMATION: synthetic construct

<400> SEQUENCE: 669
```

-continued tggtagcga                                                                9

<210> SEQ ID NO 670
<211> LENGTH: 9
<212> TYPE: DNA
<213> ORGANISM: Artificial Sequence
<220> FEATURE:
<223> OTHER INFORMATION: synthetic construct

<400> SEQUENCE: 670 gctaccaac                                                                9

<210> SEQ ID NO 671
<211> LENGTH: 9
<212> TYPE: DNA
<213> ORGANISM: Artificial Sequence
<220> FEATURE:
<223> OTHER INFORMATION: synthetic construct

<400> SEQUENCE: 671 gtgctccga                                                                9

<210> SEQ ID NO 672
<211> LENGTH: 9
<212> TYPE: DNA
<213> ORGANISM: Artificial Sequence
<220> FEATURE:
<223> OTHER INFORMATION: synthetic construct

<400> SEQUENCE: 672 ggagcacac                                                                9

<210> SEQ ID NO 673
<211> LENGTH: 9
<212> TYPE: DNA
<213> ORGANISM: Artificial Sequence
<220> FEATURE:
<223> OTHER INFORMATION: synthetic construct

<400> SEQUENCE: 673 gtgctcaga                                                                9

<210> SEQ ID NO 674
<211> LENGTH: 9
<212> TYPE: DNA
<213> ORGANISM: Artificial Sequence
<220> FEATURE:
<223> OTHER INFORMATION: synthetic construct

<400> SEQUENCE: 674 tgagcacac                                                                9

<210> SEQ ID NO 675
<211> LENGTH: 9
<212> TYPE: DNA
<213> ORGANISM: Artificial Sequence
<220> FEATURE:
<223> OTHER INFORMATION: synthetic construct

<400> SEQUENCE: 675 gccgttgga                                                                9

<210> SEQ ID NO 676
<211> LENGTH: 9
<212> TYPE: DNA
<213> ORGANISM: Artificial Sequence
<220> FEATURE:

<223> OTHER INFORMATION: synthetic construct

<400> SEQUENCE: 676 caacggcac                                                                9

<210> SEQ ID NO 677
<211> LENGTH: 9
<212> TYPE: DNA
<213> ORGANISM: Artificial Sequence
<220> FEATURE:
<223> OTHER INFORMATION: synthetic construct

<400> SEQUENCE: 677 gagtgctga                                                                9

<210> SEQ ID NO 678
<211> LENGTH: 9
<212> TYPE: DNA
<213> ORGANISM: Artificial Sequence
<220> FEATURE:
<223> OTHER INFORMATION: synthetic construct

<400> SEQUENCE: 678 agcactcac                                                                9

<210> SEQ ID NO 679
<211> LENGTH: 9
<212> TYPE: DNA
<213> ORGANISM: Artificial Sequence
<220> FEATURE:
<223> OTHER INFORMATION: synthetic construct

<400> SEQUENCE: 679 gctccttga                                                                9

<210> SEQ ID NO 680
<211> LENGTH: 9
<212> TYPE: DNA
<213> ORGANISM: Artificial Sequence
<220> FEATURE:
<223> OTHER INFORMATION: synthetic construct

<400> SEQUENCE: 680 aaggagcac                                                                9

<210> SEQ ID NO 681
<211> LENGTH: 9
<212> TYPE: DNA
<213> ORGANISM: Artificial Sequence
<220> FEATURE:
<223> OTHER INFORMATION: synthetic construct

<400> SEQUENCE: 681 ccgaaagga                                                                9

<210> SEQ ID NO 682
<211> LENGTH: 9
<212> TYPE: DNA
<213> ORGANISM: Artificial Sequence
<220> FEATURE:
<223> OTHER INFORMATION: synthetic construct

<400> SEQUENCE: 682 ctttcggac                                                                9

<210> SEQ ID NO 683

```
<211> LENGTH: 9
<212> TYPE: DNA
<213> ORGANISM: Artificial Sequence
<220> FEATURE:
<223> OTHER INFORMATION: synthetic construct

<400> SEQUENCE: 683 cactgagga                                                                9

<210> SEQ ID NO 684
<211> LENGTH: 9
<212> TYPE: DNA
<213> ORGANISM: Artificial Sequence
<220> FEATURE:
<223> OTHER INFORMATION: synthetic construct

<400> SEQUENCE: 684 ctcagtgac                                                                9

<210> SEQ ID NO 685
<211> LENGTH: 9
<212> TYPE: DNA
<213> ORGANISM: Artificial Sequence
<220> FEATURE:
<223> OTHER INFORMATION: synthetic construct

<400> SEQUENCE: 685 cgtgctgga                                                                9

<210> SEQ ID NO 686
<211> LENGTH: 9
<212> TYPE: DNA
<213> ORGANISM: Artificial Sequence
<220> FEATURE:
<223> OTHER INFORMATION: synthetic construct

<400> SEQUENCE: 686 cagcacgac                                                                9

<210> SEQ ID NO 687
<211> LENGTH: 9
<212> TYPE: DNA
<213> ORGANISM: Artificial Sequence
<220> FEATURE:
<223> OTHER INFORMATION: synthetic construct

<400> SEQUENCE: 687 ccgaaacga                                                                9

<210> SEQ ID NO 688
<211> LENGTH: 9
<212> TYPE: DNA
<213> ORGANISM: Artificial Sequence
<220> FEATURE:
<223> OTHER INFORMATION: synthetic construct

<400> SEQUENCE: 688 gtttcggac                                                                9

<210> SEQ ID NO 689
<211> LENGTH: 9
<212> TYPE: DNA
<213> ORGANISM: Artificial Sequence
<220> FEATURE:
<223> OTHER INFORMATION: synthetic construct

<400> SEQUENCE: 689
```

-continued gcggagaga                                                                    9

<210> SEQ ID NO 690
<211> LENGTH: 9
<212> TYPE: DNA
<213> ORGANISM: Artificial Sequence
<220> FEATURE:
<223> OTHER INFORMATION: synthetic construct

<400> SEQUENCE: 690 tctccgcac                                                                    9

<210> SEQ ID NO 691
<211> LENGTH: 9
<212> TYPE: DNA
<213> ORGANISM: Artificial Sequence
<220> FEATURE:
<223> OTHER INFORMATION: synthetic construct

<400> SEQUENCE: 691 gccgttaga                                                                    9

<210> SEQ ID NO 692
<211> LENGTH: 9
<212> TYPE: DNA
<213> ORGANISM: Artificial Sequence
<220> FEATURE:
<223> OTHER INFORMATION: synthetic construct

<400> SEQUENCE: 692 taacggcac                                                                    9

<210> SEQ ID NO 693
<211> LENGTH: 9
<212> TYPE: DNA
<213> ORGANISM: Artificial Sequence
<220> FEATURE:
<223> OTHER INFORMATION: synthetic construct

<400> SEQUENCE: 693 tctcgtgga                                                                    9

<210> SEQ ID NO 694
<211> LENGTH: 9
<212> TYPE: DNA
<213> ORGANISM: Artificial Sequence
<220> FEATURE:
<223> OTHER INFORMATION: synthetic construct

<400> SEQUENCE: 694 cacgagaac                                                                    9

<210> SEQ ID NO 695
<211> LENGTH: 9
<212> TYPE: DNA
<213> ORGANISM: Artificial Sequence
<220> FEATURE:
<223> OTHER INFORMATION: synthetic construct

<400> SEQUENCE: 695 cgtgctaga                                                                    9

<210> SEQ ID NO 696
<211> LENGTH: 9
<212> TYPE: DNA
<213> ORGANISM: Artificial Sequence
<220> FEATURE:

```
<223> OTHER INFORMATION: synthetic construct

<400> SEQUENCE: 696 tagcacgac                                                                  9

<210> SEQ ID NO 697
<211> LENGTH: 9
<212> TYPE: DNA
<213> ORGANISM: Artificial Sequence
<220> FEATURE:
<223> OTHER INFORMATION: synthetic construct

<400> SEQUENCE: 697 gcctgtctt                                                                  9

<210> SEQ ID NO 698
<211> LENGTH: 9
<212> TYPE: DNA
<213> ORGANISM: Artificial Sequence
<220> FEATURE:
<223> OTHER INFORMATION: synthetic construct

<400> SEQUENCE: 698 gacaggctc                                                                  9

<210> SEQ ID NO 699
<211> LENGTH: 9
<212> TYPE: DNA
<213> ORGANISM: Artificial Sequence
<220> FEATURE:
<223> OTHER INFORMATION: synthetic construct

<400> SEQUENCE: 699 ctcctggtt                                                                  9

<210> SEQ ID NO 700
<211> LENGTH: 9
<212> TYPE: DNA
<213> ORGANISM: Artificial Sequence
<220> FEATURE:
<223> OTHER INFORMATION: synthetic construct

<400> SEQUENCE: 700 ccaggagtc                                                                  9

<210> SEQ ID NO 701
<211> LENGTH: 9
<212> TYPE: DNA
<213> ORGANISM: Artificial Sequence
<220> FEATURE:
<223> OTHER INFORMATION: synthetic construct

<400> SEQUENCE: 701 actctgctt                                                                  9

<210> SEQ ID NO 702
<211> LENGTH: 9
<212> TYPE: DNA
<213> ORGANISM: Artificial Sequence
<220> FEATURE:
<223> OTHER INFORMATION: synthetic construct

<400> SEQUENCE: 702 gcagagttc                                                                  9

<210> SEQ ID NO 703
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 703 catcgcctt                                                                 9

<210> SEQ ID NO 704
<211> LENGTH: 9
<212> TYPE: DNA
<213> ORGANISM: Artificial Sequence
<220> FEATURE:
<223> OTHER INFORMATION: synthetic construct

<400> SEQUENCE: 704 ggcgatgtc                                                                 9

<210> SEQ ID NO 705
<211> LENGTH: 9
<212> TYPE: DNA
<213> ORGANISM: Artificial Sequence
<220> FEATURE:
<223> OTHER INFORMATION: synthetic construct

<400> SEQUENCE: 705 gccactatt                                                                 9

<210> SEQ ID NO 706
<211> LENGTH: 9
<212> TYPE: DNA
<213> ORGANISM: Artificial Sequence
<220> FEATURE:
<223> OTHER INFORMATION: synthetic construct

<400> SEQUENCE: 706 tagtggctc                                                                 9

<210> SEQ ID NO 707
<211> LENGTH: 9
<212> TYPE: DNA
<213> ORGANISM: Artificial Sequence
<220> FEATURE:
<223> OTHER INFORMATION: synthetic construct

<400> SEQUENCE: 707 cacacggtt                                                                 9

<210> SEQ ID NO 708
<211> LENGTH: 9
<212> TYPE: DNA
<213> ORGANISM: Artificial Sequence
<220> FEATURE:
<223> OTHER INFORMATION: synthetic construct

<400> SEQUENCE: 708 ccgtgtgtc                                                                 9

<210> SEQ ID NO 709
<211> LENGTH: 9
<212> TYPE: DNA
<213> ORGANISM: Artificial Sequence
<220> FEATURE:
<223> OTHER INFORMATION: synthetic construct

<400> SEQUENCE: 709
``` caacgcctt                                                                    9

<210> SEQ ID NO 710
<211> LENGTH: 9
<212> TYPE: DNA
<213> ORGANISM: Artificial Sequence
<220> FEATURE:
<223> OTHER INFORMATION: synthetic construct

<400> SEQUENCE: 710 ggcgttgtc                                                                    9

<210> SEQ ID NO 711
<211> LENGTH: 9
<212> TYPE: DNA
<213> ORGANISM: Artificial Sequence
<220> FEATURE:
<223> OTHER INFORMATION: synthetic construct

<400> SEQUENCE: 711 actgaggtt                                                                    9

<210> SEQ ID NO 712
<211> LENGTH: 9
<212> TYPE: DNA
<213> ORGANISM: Artificial Sequence
<220> FEATURE:
<223> OTHER INFORMATION: synthetic construct

<400> SEQUENCE: 712 cctcagttc                                                                    9

<210> SEQ ID NO 713
<211> LENGTH: 9
<212> TYPE: DNA
<213> ORGANISM: Artificial Sequence
<220> FEATURE:
<223> OTHER INFORMATION: synthetic construct

<400> SEQUENCE: 713 gtgctggtt                                                                    9

<210> SEQ ID NO 714
<211> LENGTH: 9
<212> TYPE: DNA
<213> ORGANISM: Artificial Sequence
<220> FEATURE:
<223> OTHER INFORMATION: synthetic construct

<400> SEQUENCE: 714 ccagcactc                                                                    9

<210> SEQ ID NO 715
<211> LENGTH: 9
<212> TYPE: DNA
<213> ORGANISM: Artificial Sequence
<220> FEATURE:
<223> OTHER INFORMATION: synthetic construct

<400> SEQUENCE: 715 catcgactt                                                                    9

<210> SEQ ID NO 716
<211> LENGTH: 9
<212> TYPE: DNA
<213> ORGANISM: Artificial Sequence
<220> FEATURE:

<223> OTHER INFORMATION: synthetic construct

<400> SEQUENCE: 716 gtcgatgtc                                                                  9

<210> SEQ ID NO 717
<211> LENGTH: 9
<212> TYPE: DNA
<213> ORGANISM: Artificial Sequence
<220> FEATURE:
<223> OTHER INFORMATION: synthetic construct

<400> SEQUENCE: 717 ccatcggtt                                                                  9

<210> SEQ ID NO 718
<211> LENGTH: 9
<212> TYPE: DNA
<213> ORGANISM: Artificial Sequence
<220> FEATURE:
<223> OTHER INFORMATION: synthetic construct

<400> SEQUENCE: 718 ccgatggtc                                                                  9

<210> SEQ ID NO 719
<211> LENGTH: 9
<212> TYPE: DNA
<213> ORGANISM: Artificial Sequence
<220> FEATURE:
<223> OTHER INFORMATION: synthetic construct

<400> SEQUENCE: 719 gctgcactt                                                                  9

<210> SEQ ID NO 720
<211> LENGTH: 9
<212> TYPE: DNA
<213> ORGANISM: Artificial Sequence
<220> FEATURE:
<223> OTHER INFORMATION: synthetic construct

<400> SEQUENCE: 720 gtgcagctc                                                                  9

<210> SEQ ID NO 721
<211> LENGTH: 9
<212> TYPE: DNA
<213> ORGANISM: Artificial Sequence
<220> FEATURE:
<223> OTHER INFORMATION: synthetic construct

<400> SEQUENCE: 721 acagaggtt                                                                  9

<210> SEQ ID NO 722
<211> LENGTH: 9
<212> TYPE: DNA
<213> ORGANISM: Artificial Sequence
<220> FEATURE:
<223> OTHER INFORMATION: synthetic construct

<400> SEQUENCE: 722 cctctgttc                                                                  9

<210> SEQ ID NO 723

```
<211> LENGTH: 9
<212> TYPE: DNA
<213> ORGANISM: Artificial Sequence
<220> FEATURE:
<223> OTHER INFORMATION: synthetic construct

<400> SEQUENCE: 723 agtgccgtt                                                                  9

<210> SEQ ID NO 724
<211> LENGTH: 9
<212> TYPE: DNA
<213> ORGANISM: Artificial Sequence
<220> FEATURE:
<223> OTHER INFORMATION: synthetic construct

<400> SEQUENCE: 724 cggcacttc                                                                  9

<210> SEQ ID NO 725
<211> LENGTH: 9
<212> TYPE: DNA
<213> ORGANISM: Artificial Sequence
<220> FEATURE:
<223> OTHER INFORMATION: synthetic construct

<400> SEQUENCE: 725 cggacattt                                                                  9

<210> SEQ ID NO 726
<211> LENGTH: 9
<212> TYPE: DNA
<213> ORGANISM: Artificial Sequence
<220> FEATURE:
<223> OTHER INFORMATION: synthetic construct

<400> SEQUENCE: 726 atgtccgtc                                                                  9

<210> SEQ ID NO 727
<211> LENGTH: 9
<212> TYPE: DNA
<213> ORGANISM: Artificial Sequence
<220> FEATURE:
<223> OTHER INFORMATION: synthetic construct

<400> SEQUENCE: 727 ggtctggtt                                                                  9

<210> SEQ ID NO 728
<211> LENGTH: 9
<212> TYPE: DNA
<213> ORGANISM: Artificial Sequence
<220> FEATURE:
<223> OTHER INFORMATION: synthetic construct

<400> SEQUENCE: 728 ccagacctc                                                                  9

<210> SEQ ID NO 729
<211> LENGTH: 9
<212> TYPE: DNA
<213> ORGANISM: Artificial Sequence
<220> FEATURE:
<223> OTHER INFORMATION: synthetic construct

<400> SEQUENCE: 729
```

```
gagacggtt                                                          9

<210> SEQ ID NO 730
<211> LENGTH: 9
<212> TYPE: DNA
<213> ORGANISM: Artificial Sequence
<220> FEATURE:
<223> OTHER INFORMATION: synthetic construct

<400> SEQUENCE: 730 ccgtctctc                                                          9

<210> SEQ ID NO 731
<211> LENGTH: 9
<212> TYPE: DNA
<213> ORGANISM: Artificial Sequence
<220> FEATURE:
<223> OTHER INFORMATION: synthetic construct

<400> SEQUENCE: 731 ctttccgtt                                                          9

<210> SEQ ID NO 732
<211> LENGTH: 9
<212> TYPE: DNA
<213> ORGANISM: Artificial Sequence
<220> FEATURE:
<223> OTHER INFORMATION: synthetic construct

<400> SEQUENCE: 732 cggaaagtc                                                          9

<210> SEQ ID NO 733
<211> LENGTH: 9
<212> TYPE: DNA
<213> ORGANISM: Artificial Sequence
<220> FEATURE:
<223> OTHER INFORMATION: synthetic construct

<400> SEQUENCE: 733 cagatggtt                                                          9

<210> SEQ ID NO 734
<211> LENGTH: 9
<212> TYPE: DNA
<213> ORGANISM: Artificial Sequence
<220> FEATURE:
<223> OTHER INFORMATION: synthetic construct

<400> SEQUENCE: 734 ccatctgtc                                                          9

<210> SEQ ID NO 735
<211> LENGTH: 9
<212> TYPE: DNA
<213> ORGANISM: Artificial Sequence
<220> FEATURE:
<223> OTHER INFORMATION: synthetic construct

<400> SEQUENCE: 735 cggacactt                                                          9

<210> SEQ ID NO 736
<211> LENGTH: 9
<212> TYPE: DNA
<213> ORGANISM: Artificial Sequence
<220> FEATURE:
```

<223> OTHER INFORMATION: synthetic construct

<400> SEQUENCE: 736 gtgtccgtc                                                                9

<210> SEQ ID NO 737
<211> LENGTH: 9
<212> TYPE: DNA
<213> ORGANISM: Artificial Sequence
<220> FEATURE:
<223> OTHER INFORMATION: synthetic construct

<400> SEQUENCE: 737 actctcgtt                                                                9

<210> SEQ ID NO 738
<211> LENGTH: 9
<212> TYPE: DNA
<213> ORGANISM: Artificial Sequence
<220> FEATURE:
<223> OTHER INFORMATION: synthetic construct

<400> SEQUENCE: 738 cgagagttc                                                                9

<210> SEQ ID NO 739
<211> LENGTH: 9
<212> TYPE: DNA
<213> ORGANISM: Artificial Sequence
<220> FEATURE:
<223> OTHER INFORMATION: synthetic construct

<400> SEQUENCE: 739 gcagcactt                                                                9

<210> SEQ ID NO 740
<211> LENGTH: 9
<212> TYPE: DNA
<213> ORGANISM: Artificial Sequence
<220> FEATURE:
<223> OTHER INFORMATION: synthetic construct

<400> SEQUENCE: 740 gtgctgctc                                                                9

<210> SEQ ID NO 741
<211> LENGTH: 9
<212> TYPE: DNA
<213> ORGANISM: Artificial Sequence
<220> FEATURE:
<223> OTHER INFORMATION: synthetic construct

<400> SEQUENCE: 741 actctcctt                                                                9

<210> SEQ ID NO 742
<211> LENGTH: 9
<212> TYPE: DNA
<213> ORGANISM: Artificial Sequence
<220> FEATURE:
<223> OTHER INFORMATION: synthetic construct

<400> SEQUENCE: 742 ggagagttc                                                                9

<210> SEQ ID NO 743

<211> LENGTH: 9
<212> TYPE: DNA
<213> ORGANISM: Artificial Sequence
<220> FEATURE:
<223> OTHER INFORMATION: synthetic construct

<400> SEQUENCE: 743 accttggtt                                                                9

<210> SEQ ID NO 744
<211> LENGTH: 9
<212> TYPE: DNA
<213> ORGANISM: Artificial Sequence
<220> FEATURE:
<223> OTHER INFORMATION: synthetic construct

<400> SEQUENCE: 744 ccaaggttc                                                                9

<210> SEQ ID NO 745
<211> LENGTH: 9
<212> TYPE: DNA
<213> ORGANISM: Artificial Sequence
<220> FEATURE:
<223> OTHER INFORMATION: synthetic construct

<400> SEQUENCE: 745 agagccgtt                                                                9

<210> SEQ ID NO 746
<211> LENGTH: 9
<212> TYPE: DNA
<213> ORGANISM: Artificial Sequence
<220> FEATURE:
<223> OTHER INFORMATION: synthetic construct

<400> SEQUENCE: 746 cggctcttc                                                                9

<210> SEQ ID NO 747
<211> LENGTH: 9
<212> TYPE: DNA
<213> ORGANISM: Artificial Sequence
<220> FEATURE:
<223> OTHER INFORMATION: synthetic construct

<400> SEQUENCE: 747 accttgctt                                                                9

<210> SEQ ID NO 748
<211> LENGTH: 9
<212> TYPE: DNA
<213> ORGANISM: Artificial Sequence
<220> FEATURE:
<223> OTHER INFORMATION: synthetic construct

<400> SEQUENCE: 748 gcaaggttc                                                                9

<210> SEQ ID NO 749
<211> LENGTH: 9
<212> TYPE: DNA
<213> ORGANISM: Artificial Sequence
<220> FEATURE:
<223> OTHER INFORMATION: synthetic construct

<400> SEQUENCE: 749

-continued aagtccgtt 9

<210> SEQ ID NO 750
<211> LENGTH: 9
<212> TYPE: DNA
<213> ORGANISM: Artificial Sequence
<220> FEATURE:
<223> OTHER INFORMATION: synthetic construct

<400> SEQUENCE: 750 cggactttc 9

<210> SEQ ID NO 751
<211> LENGTH: 9
<212> TYPE: DNA
<213> ORGANISM: Artificial Sequence
<220> FEATURE:
<223> OTHER INFORMATION: synthetic construct

<400> SEQUENCE: 751 ggactggtt 9

<210> SEQ ID NO 752
<211> LENGTH: 9
<212> TYPE: DNA
<213> ORGANISM: Artificial Sequence
<220> FEATURE:
<223> OTHER INFORMATION: synthetic construct

<400> SEQUENCE: 752 ccagtcctc 9

<210> SEQ ID NO 753
<211> LENGTH: 9
<212> TYPE: DNA
<213> ORGANISM: Artificial Sequence
<220> FEATURE:
<223> OTHER INFORMATION: synthetic construct

<400> SEQUENCE: 753 gtcgttctt 9

<210> SEQ ID NO 754
<211> LENGTH: 9
<212> TYPE: DNA
<213> ORGANISM: Artificial Sequence
<220> FEATURE:
<223> OTHER INFORMATION: synthetic construct

<400> SEQUENCE: 754 gaacgactc 9

<210> SEQ ID NO 755
<211> LENGTH: 9
<212> TYPE: DNA
<213> ORGANISM: Artificial Sequence
<220> FEATURE:
<223> OTHER INFORMATION: synthetic construct

<400> SEQUENCE: 755 cagcatctt 9

<210> SEQ ID NO 756
<211> LENGTH: 9
<212> TYPE: DNA
<213> ORGANISM: Artificial Sequence
<220> FEATURE:

```
<223> OTHER INFORMATION: synthetic construct

<400> SEQUENCE: 756 gatgctgtc                                                                    9

<210> SEQ ID NO 757
<211> LENGTH: 9
<212> TYPE: DNA
<213> ORGANISM: Artificial Sequence
<220> FEATURE:
<223> OTHER INFORMATION: synthetic construct

<400> SEQUENCE: 757 ctatccgtt                                                                    9

<210> SEQ ID NO 758
<211> LENGTH: 9
<212> TYPE: DNA
<213> ORGANISM: Artificial Sequence
<220> FEATURE:
<223> OTHER INFORMATION: synthetic construct

<400> SEQUENCE: 758 cggatagtc                                                                    9

<210> SEQ ID NO 759
<211> LENGTH: 9
<212> TYPE: DNA
<213> ORGANISM: Artificial Sequence
<220> FEATURE:
<223> OTHER INFORMATION: synthetic construct

<400> SEQUENCE: 759 acactcgtt                                                                    9

<210> SEQ ID NO 760
<211> LENGTH: 9
<212> TYPE: DNA
<213> ORGANISM: Artificial Sequence
<220> FEATURE:
<223> OTHER INFORMATION: synthetic construct

<400> SEQUENCE: 760 cgagtgttc                                                                    9

<210> SEQ ID NO 761
<211> LENGTH: 9
<212> TYPE: DNA
<213> ORGANISM: Artificial Sequence
<220> FEATURE:
<223> OTHER INFORMATION: synthetic construct

<400> SEQUENCE: 761 atccaggtt                                                                    9

<210> SEQ ID NO 762
<211> LENGTH: 9
<212> TYPE: DNA
<213> ORGANISM: Artificial Sequence
<220> FEATURE:
<223> OTHER INFORMATION: synthetic construct

<400> SEQUENCE: 762 cctggattc                                                                    9

<210> SEQ ID NO 763
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 763 gttcctgtt                                                                9

<210> SEQ ID NO 764
<211> LENGTH: 9
<212> TYPE: DNA
<213> ORGANISM: Artificial Sequence
<220> FEATURE:
<223> OTHER INFORMATION: synthetic construct

<400> SEQUENCE: 764 caggaactc                                                                9

<210> SEQ ID NO 765
<211> LENGTH: 9
<212> TYPE: DNA
<213> ORGANISM: Artificial Sequence
<220> FEATURE:
<223> OTHER INFORMATION: synthetic construct

<400> SEQUENCE: 765 acactcctt                                                                9

<210> SEQ ID NO 766
<211> LENGTH: 9
<212> TYPE: DNA
<213> ORGANISM: Artificial Sequence
<220> FEATURE:
<223> OTHER INFORMATION: synthetic construct

<400> SEQUENCE: 766 ggagtgttc                                                                9

<210> SEQ ID NO 767
<211> LENGTH: 9
<212> TYPE: DNA
<213> ORGANISM: Artificial Sequence
<220> FEATURE:
<223> OTHER INFORMATION: synthetic construct

<400> SEQUENCE: 767 gttcctctt                                                                9

<210> SEQ ID NO 768
<211> LENGTH: 9
<212> TYPE: DNA
<213> ORGANISM: Artificial Sequence
<220> FEATURE:
<223> OTHER INFORMATION: synthetic construct

<400> SEQUENCE: 768 gaggaactc                                                                9

<210> SEQ ID NO 769
<211> LENGTH: 9
<212> TYPE: DNA
<213> ORGANISM: Artificial Sequence
<220> FEATURE:
<223> OTHER INFORMATION: synthetic construct

<400> SEQUENCE: 769
``` ctggctctt 9

<210> SEQ ID NO 770
<211> LENGTH: 9
<212> TYPE: DNA
<213> ORGANISM: Artificial Sequence
<220> FEATURE:
<223> OTHER INFORMATION: synthetic construct

<400> SEQUENCE: 770 gagccagtc 9

<210> SEQ ID NO 771
<211> LENGTH: 9
<212> TYPE: DNA
<213> ORGANISM: Artificial Sequence
<220> FEATURE:
<223> OTHER INFORMATION: synthetic construct

<400> SEQUENCE: 771 acggcattt 9

<210> SEQ ID NO 772
<211> LENGTH: 9
<212> TYPE: DNA
<213> ORGANISM: Artificial Sequence
<220> FEATURE:
<223> OTHER INFORMATION: synthetic construct

<400> SEQUENCE: 772 atgccgttc 9

<210> SEQ ID NO 773
<211> LENGTH: 9
<212> TYPE: DNA
<213> ORGANISM: Artificial Sequence
<220> FEATURE:
<223> OTHER INFORMATION: synthetic construct

<400> SEQUENCE: 773 ggtgaggtt 9

<210> SEQ ID NO 774
<211> LENGTH: 9
<212> TYPE: DNA
<213> ORGANISM: Artificial Sequence
<220> FEATURE:
<223> OTHER INFORMATION: synthetic construct

<400> SEQUENCE: 774 cctcacctc 9

<210> SEQ ID NO 775
<211> LENGTH: 9
<212> TYPE: DNA
<213> ORGANISM: Artificial Sequence
<220> FEATURE:
<223> OTHER INFORMATION: synthetic construct

<400> SEQUENCE: 775 ccttccgtt 9

<210> SEQ ID NO 776
<211> LENGTH: 9
<212> TYPE: DNA
<213> ORGANISM: Artificial Sequence
<220> FEATURE:

```
<223> OTHER INFORMATION: synthetic construct

<400> SEQUENCE: 776 cggaaggtc                                                                 9

<210> SEQ ID NO 777
<211> LENGTH: 9
<212> TYPE: DNA
<213> ORGANISM: Artificial Sequence
<220> FEATURE:
<223> OTHER INFORMATION: synthetic construct

<400> SEQUENCE: 777 tacgctctt                                                                 9

<210> SEQ ID NO 778
<211> LENGTH: 9
<212> TYPE: DNA
<213> ORGANISM: Artificial Sequence
<220> FEATURE:
<223> OTHER INFORMATION: synthetic construct

<400> SEQUENCE: 778 gagcgtatc                                                                 9

<210> SEQ ID NO 779
<211> LENGTH: 9
<212> TYPE: DNA
<213> ORGANISM: Artificial Sequence
<220> FEATURE:
<223> OTHER INFORMATION: synthetic construct

<400> SEQUENCE: 779 acggcagtt                                                                 9

<210> SEQ ID NO 780
<211> LENGTH: 9
<212> TYPE: DNA
<213> ORGANISM: Artificial Sequence
<220> FEATURE:
<223> OTHER INFORMATION: synthetic construct

<400> SEQUENCE: 780 ctgccgttc                                                                 9

<210> SEQ ID NO 781
<211> LENGTH: 9
<212> TYPE: DNA
<213> ORGANISM: Artificial Sequence
<220> FEATURE:
<223> OTHER INFORMATION: synthetic construct

<400> SEQUENCE: 781 actgacgtt                                                                 9

<210> SEQ ID NO 782
<211> LENGTH: 9
<212> TYPE: DNA
<213> ORGANISM: Artificial Sequence
<220> FEATURE:
<223> OTHER INFORMATION: synthetic construct

<400> SEQUENCE: 782 cgtcagttc                                                                 9

<210> SEQ ID NO 783
```

<211> LENGTH: 9
<212> TYPE: DNA
<213> ORGANISM: Artificial Sequence
<220> FEATURE:
<223> OTHER INFORMATION: synthetic construct

<400> SEQUENCE: 783 acggcactt                                                                  9

<210> SEQ ID NO 784
<211> LENGTH: 9
<212> TYPE: DNA
<213> ORGANISM: Artificial Sequence
<220> FEATURE:
<223> OTHER INFORMATION: synthetic construct

<400> SEQUENCE: 784 gtgccgttc                                                                  9

<210> SEQ ID NO 785
<211> LENGTH: 9
<212> TYPE: DNA
<213> ORGANISM: Artificial Sequence
<220> FEATURE:
<223> OTHER INFORMATION: synthetic construct

<400> SEQUENCE: 785 actgacctt                                                                  9

<210> SEQ ID NO 786
<211> LENGTH: 9
<212> TYPE: DNA
<213> ORGANISM: Artificial Sequence
<220> FEATURE:
<223> OTHER INFORMATION: synthetic construct

<400> SEQUENCE: 786 ggtcagttc                                                                  9

<210> SEQ ID NO 787
<211> LENGTH: 9
<212> TYPE: DNA
<213> ORGANISM: Artificial Sequence
<220> FEATURE:
<223> OTHER INFORMATION: synthetic construct

<400> SEQUENCE: 787 tttgcggtt                                                                  9

<210> SEQ ID NO 788
<211> LENGTH: 9
<212> TYPE: DNA
<213> ORGANISM: Artificial Sequence
<220> FEATURE:
<223> OTHER INFORMATION: synthetic construct

<400> SEQUENCE: 788 ccgcaaatc                                                                  9

<210> SEQ ID NO 789
<211> LENGTH: 9
<212> TYPE: DNA
<213> ORGANISM: Artificial Sequence
<220> FEATURE:
<223> OTHER INFORMATION: synthetic construct

<400> SEQUENCE: 789 tggtaggtt                                                                    9

<210> SEQ ID NO 790
<211> LENGTH: 9
<212> TYPE: DNA
<213> ORGANISM: Artificial Sequence
<220> FEATURE:
<223> OTHER INFORMATION: synthetic construct

<400> SEQUENCE: 790 cctaccatc                                                                    9

<210> SEQ ID NO 791
<211> LENGTH: 9
<212> TYPE: DNA
<213> ORGANISM: Artificial Sequence
<220> FEATURE:
<223> OTHER INFORMATION: synthetic construct

<400> SEQUENCE: 791 gttcggctt                                                                    9

<210> SEQ ID NO 792
<211> LENGTH: 9
<212> TYPE: DNA
<213> ORGANISM: Artificial Sequence
<220> FEATURE:
<223> OTHER INFORMATION: synthetic construct

<400> SEQUENCE: 792 gccgaactc                                                                    9

<210> SEQ ID NO 793
<211> LENGTH: 9
<212> TYPE: DNA
<213> ORGANISM: Artificial Sequence
<220> FEATURE:
<223> OTHER INFORMATION: synthetic construct

<400> SEQUENCE: 793 gccgttctt                                                                    9

<210> SEQ ID NO 794
<211> LENGTH: 9
<212> TYPE: DNA
<213> ORGANISM: Artificial Sequence
<220> FEATURE:
<223> OTHER INFORMATION: synthetic construct

<400> SEQUENCE: 794 gaacggctc                                                                    9

<210> SEQ ID NO 795
<211> LENGTH: 9
<212> TYPE: DNA
<213> ORGANISM: Artificial Sequence
<220> FEATURE:
<223> OTHER INFORMATION: synthetic construct

<400> SEQUENCE: 795 ggagaggtt                                                                    9

<210> SEQ ID NO 796
<211> LENGTH: 9
<212> TYPE: DNA
<213> ORGANISM: Artificial Sequence
<220> FEATURE:

<223> OTHER INFORMATION: synthetic construct

<400> SEQUENCE: 796 cctctcctc                                                                        9

<210> SEQ ID NO 797
<211> LENGTH: 9
<212> TYPE: DNA
<213> ORGANISM: Artificial Sequence
<220> FEATURE:
<223> OTHER INFORMATION: synthetic construct

<400> SEQUENCE: 797 cactgactt                                                                        9

<210> SEQ ID NO 798
<211> LENGTH: 9
<212> TYPE: DNA
<213> ORGANISM: Artificial Sequence
<220> FEATURE:
<223> OTHER INFORMATION: synthetic construct

<400> SEQUENCE: 798 gtcagtgtc                                                                        9

<210> SEQ ID NO 799
<211> LENGTH: 9
<212> TYPE: DNA
<213> ORGANISM: Artificial Sequence
<220> FEATURE:
<223> OTHER INFORMATION: synthetic construct

<400> SEQUENCE: 799 cgtgctctt                                                                        9

<210> SEQ ID NO 800
<211> LENGTH: 9
<212> TYPE: DNA
<213> ORGANISM: Artificial Sequence
<220> FEATURE:
<223> OTHER INFORMATION: synthetic construct

<400> SEQUENCE: 800 gagcacgtc                                                                        9

<210> SEQ ID NO 801
<211> LENGTH: 9
<212> TYPE: DNA
<213> ORGANISM: Artificial Sequence
<220> FEATURE:
<223> OTHER INFORMATION: synthetic construct

<400> SEQUENCE: 801 aatccgctt                                                                        9

<210> SEQ ID NO 802
<211> LENGTH: 9
<212> TYPE: DNA
<213> ORGANISM: Artificial Sequence
<220> FEATURE:
<223> OTHER INFORMATION: synthetic construct

<400> SEQUENCE: 802 gcggatttc                                                                        9

<210> SEQ ID NO 803

```
<211> LENGTH: 9
<212> TYPE: DNA
<213> ORGANISM: Artificial Sequence
<220> FEATURE:
<223> OTHER INFORMATION: synthetic construct

<400> SEQUENCE: 803 aggctggtt                                                                 9

<210> SEQ ID NO 804
<211> LENGTH: 9
<212> TYPE: DNA
<213> ORGANISM: Artificial Sequence
<220> FEATURE:
<223> OTHER INFORMATION: synthetic construct

<400> SEQUENCE: 804 ccagccttc                                                                 9

<210> SEQ ID NO 805
<211> LENGTH: 9
<212> TYPE: DNA
<213> ORGANISM: Artificial Sequence
<220> FEATURE:
<223> OTHER INFORMATION: synthetic construct

<400> SEQUENCE: 805 gctagtgtt                                                                 9

<210> SEQ ID NO 806
<211> LENGTH: 9
<212> TYPE: DNA
<213> ORGANISM: Artificial Sequence
<220> FEATURE:
<223> OTHER INFORMATION: synthetic construct

<400> SEQUENCE: 806 cactagctc                                                                 9

<210> SEQ ID NO 807
<211> LENGTH: 9
<212> TYPE: DNA
<213> ORGANISM: Artificial Sequence
<220> FEATURE:
<223> OTHER INFORMATION: synthetic construct

<400> SEQUENCE: 807 ggagagctt                                                                 9

<210> SEQ ID NO 808
<211> LENGTH: 9
<212> TYPE: DNA
<213> ORGANISM: Artificial Sequence
<220> FEATURE:
<223> OTHER INFORMATION: synthetic construct

<400> SEQUENCE: 808 gctctcctc                                                                 9

<210> SEQ ID NO 809
<211> LENGTH: 9
<212> TYPE: DNA
<213> ORGANISM: Artificial Sequence
<220> FEATURE:
<223> OTHER INFORMATION: synthetic construct

<400> SEQUENCE: 809
```

-continued ggagagatt 9

<210> SEQ ID NO 810
<211> LENGTH: 9
<212> TYPE: DNA
<213> ORGANISM: Artificial Sequence
<220> FEATURE:
<223> OTHER INFORMATION: synthetic construct

<400> SEQUENCE: 810 tctctcctc 9

<210> SEQ ID NO 811
<211> LENGTH: 9
<212> TYPE: DNA
<213> ORGANISM: Artificial Sequence
<220> FEATURE:
<223> OTHER INFORMATION: synthetic construct

<400> SEQUENCE: 811 aggctgctt 9

<210> SEQ ID NO 812
<211> LENGTH: 9
<212> TYPE: DNA
<213> ORGANISM: Artificial Sequence
<220> FEATURE:
<223> OTHER INFORMATION: synthetic construct

<400> SEQUENCE: 812 gcagccttc 9

<210> SEQ ID NO 813
<211> LENGTH: 9
<212> TYPE: DNA
<213> ORGANISM: Artificial Sequence
<220> FEATURE:
<223> OTHER INFORMATION: synthetic construct

<400> SEQUENCE: 813 gagtgcgtt 9

<210> SEQ ID NO 814
<211> LENGTH: 9
<212> TYPE: DNA
<213> ORGANISM: Artificial Sequence
<220> FEATURE:
<223> OTHER INFORMATION: synthetic construct

<400> SEQUENCE: 814 cgcactctc 9

<210> SEQ ID NO 815
<211> LENGTH: 9
<212> TYPE: DNA
<213> ORGANISM: Artificial Sequence
<220> FEATURE:
<223> OTHER INFORMATION: synthetic construct

<400> SEQUENCE: 815 ccatccatt 9

<210> SEQ ID NO 816
<211> LENGTH: 9
<212> TYPE: DNA
<213> ORGANISM: Artificial Sequence
<220> FEATURE:

```
<223> OTHER INFORMATION: synthetic construct

<400> SEQUENCE: 816 tggatggtc                                                                9

<210> SEQ ID NO 817
<211> LENGTH: 9
<212> TYPE: DNA
<213> ORGANISM: Artificial Sequence
<220> FEATURE:
<223> OTHER INFORMATION: synthetic construct

<400> SEQUENCE: 817 gctagtctt                                                                9

<210> SEQ ID NO 818
<211> LENGTH: 9
<212> TYPE: DNA
<213> ORGANISM: Artificial Sequence
<220> FEATURE:
<223> OTHER INFORMATION: synthetic construct

<400> SEQUENCE: 818 gactagctc                                                                9

<210> SEQ ID NO 819
<211> LENGTH: 9
<212> TYPE: DNA
<213> ORGANISM: Artificial Sequence
<220> FEATURE:
<223> OTHER INFORMATION: synthetic construct

<400> SEQUENCE: 819 aggctgatt                                                                9

<210> SEQ ID NO 820
<211> LENGTH: 9
<212> TYPE: DNA
<213> ORGANISM: Artificial Sequence
<220> FEATURE:
<223> OTHER INFORMATION: synthetic construct

<400> SEQUENCE: 820 tcagccttc                                                                9

<210> SEQ ID NO 821
<211> LENGTH: 9
<212> TYPE: DNA
<213> ORGANISM: Artificial Sequence
<220> FEATURE:
<223> OTHER INFORMATION: synthetic construct

<400> SEQUENCE: 821 acagacgtt                                                                9

<210> SEQ ID NO 822
<211> LENGTH: 9
<212> TYPE: DNA
<213> ORGANISM: Artificial Sequence
<220> FEATURE:
<223> OTHER INFORMATION: synthetic construct

<400> SEQUENCE: 822 cgtctgttc                                                                9

<210> SEQ ID NO 823
```

-continued

```
<211> LENGTH: 9
<212> TYPE: DNA
<213> ORGANISM: Artificial Sequence
<220> FEATURE:
<223> OTHER INFORMATION: synthetic construct

<400> SEQUENCE: 823 gagtgcctt                                                                 9

<210> SEQ ID NO 824
<211> LENGTH: 9
<212> TYPE: DNA
<213> ORGANISM: Artificial Sequence
<220> FEATURE:
<223> OTHER INFORMATION: synthetic construct

<400> SEQUENCE: 824 ggcactctc                                                                 9

<210> SEQ ID NO 825
<211> LENGTH: 9
<212> TYPE: DNA
<213> ORGANISM: Artificial Sequence
<220> FEATURE:
<223> OTHER INFORMATION: synthetic construct

<400> SEQUENCE: 825 acagacctt                                                                 9

<210> SEQ ID NO 826
<211> LENGTH: 9
<212> TYPE: DNA
<213> ORGANISM: Artificial Sequence
<220> FEATURE:
<223> OTHER INFORMATION: synthetic construct

<400> SEQUENCE: 826 ggtctgttc                                                                 9

<210> SEQ ID NO 827
<211> LENGTH: 9
<212> TYPE: DNA
<213> ORGANISM: Artificial Sequence
<220> FEATURE:
<223> OTHER INFORMATION: synthetic construct

<400> SEQUENCE: 827 cgagctttt                                                                 9

<210> SEQ ID NO 828
<211> LENGTH: 9
<212> TYPE: DNA
<213> ORGANISM: Artificial Sequence
<220> FEATURE:
<223> OTHER INFORMATION: synthetic construct

<400> SEQUENCE: 828 aagctcgtc                                                                 9

<210> SEQ ID NO 829
<211> LENGTH: 9
<212> TYPE: DNA
<213> ORGANISM: Artificial Sequence
<220> FEATURE:
<223> OTHER INFORMATION: synthetic construct

<400> SEQUENCE: 829
``` ttagcggtt                                                                  9

<210> SEQ ID NO 830
<211> LENGTH: 9
<212> TYPE: DNA
<213> ORGANISM: Artificial Sequence
<220> FEATURE:
<223> OTHER INFORMATION: synthetic construct

<400> SEQUENCE: 830 ccgctaatc                                                                  9

<210> SEQ ID NO 831
<211> LENGTH: 9
<212> TYPE: DNA
<213> ORGANISM: Artificial Sequence
<220> FEATURE:
<223> OTHER INFORMATION: synthetic construct

<400> SEQUENCE: 831 cctcttgtt                                                                  9

<210> SEQ ID NO 832
<211> LENGTH: 9
<212> TYPE: DNA
<213> ORGANISM: Artificial Sequence
<220> FEATURE:
<223> OTHER INFORMATION: synthetic construct

<400> SEQUENCE: 832 caagaggtc                                                                  9

<210> SEQ ID NO 833
<211> LENGTH: 9
<212> TYPE: DNA
<213> ORGANISM: Artificial Sequence
<220> FEATURE:
<223> OTHER INFORMATION: synthetic construct

<400> SEQUENCE: 833 ggtctcttt                                                                  9

<210> SEQ ID NO 834
<211> LENGTH: 9
<212> TYPE: DNA
<213> ORGANISM: Artificial Sequence
<220> FEATURE:
<223> OTHER INFORMATION: synthetic construct

<400> SEQUENCE: 834 agagacctc                                                                  9

<210> SEQ ID NO 835
<211> LENGTH: 9
<212> TYPE: DNA
<213> ORGANISM: Artificial Sequence
<220> FEATURE:
<223> OTHER INFORMATION: synthetic construct

<400> SEQUENCE: 835 gccagattt                                                                  9

<210> SEQ ID NO 836
<211> LENGTH: 9
<212> TYPE: DNA
<213> ORGANISM: Artificial Sequence
<220> FEATURE:

<223> OTHER INFORMATION: synthetic construct

<400> SEQUENCE: 836 atctggctc                                                                9

<210> SEQ ID NO 837
<211> LENGTH: 9
<212> TYPE: DNA
<213> ORGANISM: Artificial Sequence
<220> FEATURE:
<223> OTHER INFORMATION: synthetic construct

<400> SEQUENCE: 837 gagaccttt                                                                9

<210> SEQ ID NO 838
<211> LENGTH: 9
<212> TYPE: DNA
<213> ORGANISM: Artificial Sequence
<220> FEATURE:
<223> OTHER INFORMATION: synthetic construct

<400> SEQUENCE: 838 aggtctctc                                                                9

<210> SEQ ID NO 839
<211> LENGTH: 9
<212> TYPE: DNA
<213> ORGANISM: Artificial Sequence
<220> FEATURE:
<223> OTHER INFORMATION: synthetic construct

<400> SEQUENCE: 839 cacacagtt                                                                9

<210> SEQ ID NO 840
<211> LENGTH: 9
<212> TYPE: DNA
<213> ORGANISM: Artificial Sequence
<220> FEATURE:
<223> OTHER INFORMATION: synthetic construct

<400> SEQUENCE: 840 ctgtgtgtc                                                                9

<210> SEQ ID NO 841
<211> LENGTH: 9
<212> TYPE: DNA
<213> ORGANISM: Artificial Sequence
<220> FEATURE:
<223> OTHER INFORMATION: synthetic construct

<400> SEQUENCE: 841 cctcttctt                                                                9

<210> SEQ ID NO 842
<211> LENGTH: 9
<212> TYPE: DNA
<213> ORGANISM: Artificial Sequence
<220> FEATURE:
<223> OTHER INFORMATION: synthetic construct

<400> SEQUENCE: 842 gaagaggtc                                                                9

<210> SEQ ID NO 843

```
<211> LENGTH: 9
<212> TYPE: DNA
<213> ORGANISM: Artificial Sequence
<220> FEATURE:
<223> OTHER INFORMATION: synthetic construct

<400> SEQUENCE: 843 tagagcgtt                                                                 9

<210> SEQ ID NO 844
<211> LENGTH: 9
<212> TYPE: DNA
<213> ORGANISM: Artificial Sequence
<220> FEATURE:
<223> OTHER INFORMATION: synthetic construct

<400> SEQUENCE: 844 cgctctatc                                                                 9

<210> SEQ ID NO 845
<211> LENGTH: 9
<212> TYPE: DNA
<213> ORGANISM: Artificial Sequence
<220> FEATURE:
<223> OTHER INFORMATION: synthetic construct

<400> SEQUENCE: 845 gcaccttttt                                                                9

<210> SEQ ID NO 846
<211> LENGTH: 9
<212> TYPE: DNA
<213> ORGANISM: Artificial Sequence
<220> FEATURE:
<223> OTHER INFORMATION: synthetic construct

<400> SEQUENCE: 846 aaggtgctc                                                                 9

<210> SEQ ID NO 847
<211> LENGTH: 9
<212> TYPE: DNA
<213> ORGANISM: Artificial Sequence
<220> FEATURE:
<223> OTHER INFORMATION: synthetic construct

<400> SEQUENCE: 847 ggcttgttt                                                                 9

<210> SEQ ID NO 848
<211> LENGTH: 9
<212> TYPE: DNA
<213> ORGANISM: Artificial Sequence
<220> FEATURE:
<223> OTHER INFORMATION: synthetic construct

<400> SEQUENCE: 848 acaagcctc                                                                 9

<210> SEQ ID NO 849
<211> LENGTH: 9
<212> TYPE: DNA
<213> ORGANISM: Artificial Sequence
<220> FEATURE:
<223> OTHER INFORMATION: synthetic construct

<400> SEQUENCE: 849
``` gacgcgatt                                                                    9

<210> SEQ ID NO 850
<211> LENGTH: 9
<212> TYPE: DNA
<213> ORGANISM: Artificial Sequence
<220> FEATURE:
<223> OTHER INFORMATION: synthetic construct

<400> SEQUENCE: 850 tcgcgtctc                                                                    9

<210> SEQ ID NO 851
<211> LENGTH: 9
<212> TYPE: DNA
<213> ORGANISM: Artificial Sequence
<220> FEATURE:
<223> OTHER INFORMATION: synthetic construct

<400> SEQUENCE: 851 cgagctgtt                                                                    9

<210> SEQ ID NO 852
<211> LENGTH: 9
<212> TYPE: DNA
<213> ORGANISM: Artificial Sequence
<220> FEATURE:
<223> OTHER INFORMATION: synthetic construct

<400> SEQUENCE: 852 cagctcgtc                                                                    9

<210> SEQ ID NO 853
<211> LENGTH: 9
<212> TYPE: DNA
<213> ORGANISM: Artificial Sequence
<220> FEATURE:
<223> OTHER INFORMATION: synthetic construct

<400> SEQUENCE: 853 tagagcctt                                                                    9

<210> SEQ ID NO 854
<211> LENGTH: 9
<212> TYPE: DNA
<213> ORGANISM: Artificial Sequence
<220> FEATURE:
<223> OTHER INFORMATION: synthetic construct

<400> SEQUENCE: 854 ggctctatc                                                                    9

<210> SEQ ID NO 855
<211> LENGTH: 9
<212> TYPE: DNA
<213> ORGANISM: Artificial Sequence
<220> FEATURE:
<223> OTHER INFORMATION: synthetic construct

<400> SEQUENCE: 855 catccgttt                                                                    9

<210> SEQ ID NO 856
<211> LENGTH: 9
<212> TYPE: DNA
<213> ORGANISM: Artificial Sequence
<220> FEATURE:

-continued

<223> OTHER INFORMATION: synthetic construct

<400> SEQUENCE: 856 acggatgtc                                                                       9

<210> SEQ ID NO 857
<211> LENGTH: 9
<212> TYPE: DNA
<213> ORGANISM: Artificial Sequence
<220> FEATURE:
<223> OTHER INFORMATION: synthetic construct

<400> SEQUENCE: 857 ggtctcgtt                                                                       9

<210> SEQ ID NO 858
<211> LENGTH: 9
<212> TYPE: DNA
<213> ORGANISM: Artificial Sequence
<220> FEATURE:
<223> OTHER INFORMATION: synthetic construct

<400> SEQUENCE: 858 cgagacctc                                                                       9

<210> SEQ ID NO 859
<211> LENGTH: 9
<212> TYPE: DNA
<213> ORGANISM: Artificial Sequence
<220> FEATURE:
<223> OTHER INFORMATION: synthetic construct

<400> SEQUENCE: 859 gccagagtt                                                                       9

<210> SEQ ID NO 860
<211> LENGTH: 9
<212> TYPE: DNA
<213> ORGANISM: Artificial Sequence
<220> FEATURE:
<223> OTHER INFORMATION: synthetic construct

<400> SEQUENCE: 860 ctctggctc                                                                       9

<210> SEQ ID NO 861
<211> LENGTH: 9
<212> TYPE: DNA
<213> ORGANISM: Artificial Sequence
<220> FEATURE:
<223> OTHER INFORMATION: synthetic construct

<400> SEQUENCE: 861 gagaccgtt                                                                       9

<210> SEQ ID NO 862
<211> LENGTH: 9
<212> TYPE: DNA
<213> ORGANISM: Artificial Sequence
<220> FEATURE:
<223> OTHER INFORMATION: synthetic construct

<400> SEQUENCE: 862 cggtctctc                                                                       9

<210> SEQ ID NO 863

```
<211> LENGTH: 9
<212> TYPE: DNA
<213> ORGANISM: Artificial Sequence
<220> FEATURE:
<223> OTHER INFORMATION: synthetic construct

<400> SEQUENCE: 863 cgagctatt                                                                 9

<210> SEQ ID NO 864
<211> LENGTH: 9
<212> TYPE: DNA
<213> ORGANISM: Artificial Sequence
<220> FEATURE:
<223> OTHER INFORMATION: synthetic construct

<400> SEQUENCE: 864 tagctcgtc                                                                 9

<210> SEQ ID NO 865
<211> LENGTH: 9
<212> TYPE: DNA
<213> ORGANISM: Artificial Sequence
<220> FEATURE:
<223> OTHER INFORMATION: synthetic construct

<400> SEQUENCE: 865 gcaagtgtt                                                                 9

<210> SEQ ID NO 866
<211> LENGTH: 9
<212> TYPE: DNA
<213> ORGANISM: Artificial Sequence
<220> FEATURE:
<223> OTHER INFORMATION: synthetic construct

<400> SEQUENCE: 866 cacttgctc                                                                 9

<210> SEQ ID NO 867
<211> LENGTH: 9
<212> TYPE: DNA
<213> ORGANISM: Artificial Sequence
<220> FEATURE:
<223> OTHER INFORMATION: synthetic construct

<400> SEQUENCE: 867 ggtctcctt                                                                 9

<210> SEQ ID NO 868
<211> LENGTH: 9
<212> TYPE: DNA
<213> ORGANISM: Artificial Sequence
<220> FEATURE:
<223> OTHER INFORMATION: synthetic construct

<400> SEQUENCE: 868 ggagacctc                                                                 9

<210> SEQ ID NO 869
<211> LENGTH: 9
<212> TYPE: DNA
<213> ORGANISM: Artificial Sequence
<220> FEATURE:
<223> OTHER INFORMATION: synthetic construct

<400> SEQUENCE: 869
``` gccagactt 9

<210> SEQ ID NO 870
<211> LENGTH: 9
<212> TYPE: DNA
<213> ORGANISM: Artificial Sequence
<220> FEATURE:
<223> OTHER INFORMATION: synthetic construct

<400> SEQUENCE: 870 gtctggctc 9

<210> SEQ ID NO 871
<211> LENGTH: 9
<212> TYPE: DNA
<213> ORGANISM: Artificial Sequence
<220> FEATURE:
<223> OTHER INFORMATION: synthetic construct

<400> SEQUENCE: 871 ggtctcatt 9

<210> SEQ ID NO 872
<211> LENGTH: 9
<212> TYPE: DNA
<213> ORGANISM: Artificial Sequence
<220> FEATURE:
<223> OTHER INFORMATION: synthetic construct

<400> SEQUENCE: 872 tgagacctc 9

<210> SEQ ID NO 873
<211> LENGTH: 9
<212> TYPE: DNA
<213> ORGANISM: Artificial Sequence
<220> FEATURE:
<223> OTHER INFORMATION: synthetic construct

<400> SEQUENCE: 873 gagaccatt 9

<210> SEQ ID NO 874
<211> LENGTH: 9
<212> TYPE: DNA
<213> ORGANISM: Artificial Sequence
<220> FEATURE:
<223> OTHER INFORMATION: synthetic construct

<400> SEQUENCE: 874 tggtctctc 9

<210> SEQ ID NO 875
<211> LENGTH: 9
<212> TYPE: DNA
<213> ORGANISM: Artificial Sequence
<220> FEATURE:
<223> OTHER INFORMATION: synthetic construct

<400> SEQUENCE: 875 ccttcagtt 9

<210> SEQ ID NO 876
<211> LENGTH: 9
<212> TYPE: DNA
<213> ORGANISM: Artificial Sequence
<220> FEATURE:

```
<223> OTHER INFORMATION: synthetic construct

<400> SEQUENCE: 876 ctgaaggtc                                                                          9

<210> SEQ ID NO 877
<211> LENGTH: 9
<212> TYPE: DNA
<213> ORGANISM: Artificial Sequence
<220> FEATURE:
<223> OTHER INFORMATION: synthetic construct

<400> SEQUENCE: 877 gcacctgtt                                                                          9

<210> SEQ ID NO 878
<211> LENGTH: 9
<212> TYPE: DNA
<213> ORGANISM: Artificial Sequence
<220> FEATURE:
<223> OTHER INFORMATION: synthetic construct

<400> SEQUENCE: 878 caggtgctc                                                                          9

<210> SEQ ID NO 879
<211> LENGTH: 9
<212> TYPE: DNA
<213> ORGANISM: Artificial Sequence
<220> FEATURE:
<223> OTHER INFORMATION: synthetic construct

<400> SEQUENCE: 879 aaaggcgtt                                                                          9

<210> SEQ ID NO 880
<211> LENGTH: 9
<212> TYPE: DNA
<213> ORGANISM: Artificial Sequence
<220> FEATURE:
<223> OTHER INFORMATION: synthetic construct

<400> SEQUENCE: 880 cgccttttc                                                                          9

<210> SEQ ID NO 881
<211> LENGTH: 9
<212> TYPE: DNA
<213> ORGANISM: Artificial Sequence
<220> FEATURE:
<223> OTHER INFORMATION: synthetic construct

<400> SEQUENCE: 881 cagatcgtt                                                                          9

<210> SEQ ID NO 882
<211> LENGTH: 9
<212> TYPE: DNA
<213> ORGANISM: Artificial Sequence
<220> FEATURE:
<223> OTHER INFORMATION: synthetic construct

<400> SEQUENCE: 882 cgatctgtc                                                                          9

<210> SEQ ID NO 883
```

```
<211> LENGTH: 9
<212> TYPE: DNA
<213> ORGANISM: Artificial Sequence
<220> FEATURE:
<223> OTHER INFORMATION: synthetic construct

<400> SEQUENCE: 883 cataggctt                                                                  9

<210> SEQ ID NO 884
<211> LENGTH: 9
<212> TYPE: DNA
<213> ORGANISM: Artificial Sequence
<220> FEATURE:
<223> OTHER INFORMATION: synthetic construct

<400> SEQUENCE: 884 gcctatgtc                                                                  9

<210> SEQ ID NO 885
<211> LENGTH: 9
<212> TYPE: DNA
<213> ORGANISM: Artificial Sequence
<220> FEATURE:
<223> OTHER INFORMATION: synthetic construct

<400> SEQUENCE: 885 ccttcactt                                                                  9

<210> SEQ ID NO 886
<211> LENGTH: 9
<212> TYPE: DNA
<213> ORGANISM: Artificial Sequence
<220> FEATURE:
<223> OTHER INFORMATION: synthetic construct

<400> SEQUENCE: 886 gtgaaggtc                                                                  9

<210> SEQ ID NO 887
<211> LENGTH: 9
<212> TYPE: DNA
<213> ORGANISM: Artificial Sequence
<220> FEATURE:
<223> OTHER INFORMATION: synthetic construct

<400> SEQUENCE: 887 gcacctctt                                                                  9

<210> SEQ ID NO 888
<211> LENGTH: 9
<212> TYPE: DNA
<213> ORGANISM: Artificial Sequence
<220> FEATURE:
<223> OTHER INFORMATION: synthetic construct

<400> SEQUENCE: 888 gaggtgctc                                                                  9

<210> SEQ ID NO 889
<211> LENGTH: 25
<212> TYPE: DNA
<213> ORGANISM: Artificial Sequence
<220> FEATURE:
<223> OTHER INFORMATION: synthetic construct

<400> SEQUENCE: 889
```

```
cagaagacag acaagcttca cctgc                                               25

<210> SEQ ID NO 890
<211> LENGTH: 27
<212> TYPE: DNA
<213> ORGANISM: Artificial Sequence
<220> FEATURE:
<223> OTHER INFORMATION: synthetic construct

<400> SEQUENCE: 890
gcaggtgaag cttgtctgtc ttctgaa                                             27
```

METHODS FOR IDENTIFYING COMPOUNDS OF INTEREST USING ENCODED LIBRARIES

RELATED APPLICATIONS

This application claims priority to U.S. Provisional Application No. 60/731,464, filed Oct. 28, 2005. This application is related to U.S. Patent Application No. 60/689,466, filed Jun. 9, 2005, pending, and U.S. patent application Ser. No. 11/015,458 filed Dec. 17, 2004. This application is also related to U.S. Provisional Patent Application Ser. No. 60/530,854, filed on Dec. 17, 2003; U.S. Provisional Patent Application Ser. No. 60/540,681, filed on Jan. 30, 2004; U.S. Provisional Patent Application Ser. No. 60/553,715 filed Mar. 15, 2004; and U.S. Provisional Patent Application Ser. No. 60/588,672 filed Jul. 16, 2004. The entire contents of each of the foregoing applications are incorporated herein by reference.
Sequence Listing The instant application contains a Sequence Listing which has been submitted via EFS-Web and is hereby incorporated by reference in its entirety. The ASCII copy of the Sequence Listing, created on Mar. 14, 2011, is named SubSeqList.txt, and is 308,417 bytes in size.

BACKGROUND OF THE INVENTION

The search for more efficient methods of identifying compounds having useful biological activities has led to the development of methods for screening vast numbers of distinct compounds, present in collections referred to as combinatorial libraries. Such libraries can include $10^5$ or more distinct compounds. A variety of methods exist for producing combinatorial libraries, and combinatorial syntheses of peptides, peptidomimetics and small organic molecules have been reported.

The two major challenges in the use of combinatorial approaches in drug discovery are the synthesis of libraries of sufficient complexity and the identification of molecules which are active in the screens used. It is generally acknowledged that greater the degree of complexity of a library, i.e., the number of distinct structures present in the library, the greater the probability that the library contains molecules with the activity of interest. Therefore, the chemistry employed in library synthesis must be capable of producing vast numbers of compounds within a reasonable time frame. However, for a given formal or overall concentration, increasing the number of distinct members within the library lowers the concentration of any particular library member. This complicates the identification of active molecules from high complexity libraries.

One approach to overcoming these obstacles has been the development of encoded libraries, and particularly libraries in which each compound includes an amplifiable tag. Such libraries include DNA-encoded libraries, in which a DNA tag identifying a library member can be amplified using techniques of molecular biology, such as the polymerase chain reaction. However, the use of such methods for producing very large libraries is yet to be demonstrated, and it is clear that improved methods for producing such libraries are required for the realization of the potential of this approach to drug discovery.

SUMMARY OF THE INVENTION

Traditional drug discovery methods have relied on multi-step selection processes, often involving the amplification (e.g., PCR amplification) of nucleic acid molecules, and the sequencing of up to 1,000 or more of the top clones. This multi-step selection process and the nucleic acid amplification often lead to the introduction of many biases (as discussed in, for example, Holt, L. J., et al. (2000) *Nucleic Acids Res.* 28(15):E72). The presence of these biases typically leads to the selection of compounds that lack the desired biological activity.

The present invention provides improved methods as compared to the prior art methods in that it provides methods which eliminate the foregoing biases. For example, the present invention provides methods of identifying a compound of interest using a massively parallel sequencing approach which leads to the accurate identification of a compound with a desired biological activity using fewer selection steps. Moreover, as described herein, a unique tagging system has been developed that eliminates biases introduced by nucleic acid amplification, e.g., PCR amplification. In addition, the methods described herein allow for an expansive and extensive analysis of the selected compounds having a desired biological property, which, in turn, allows for related compounds with familial structural relationships to be identified (structure activity relationships). In summary, using the methods of the invention, a single step selection/enrichment cycle can be performed and then sequencing can be performed at the single molecule level, preferably without the need for any nucleic acid amplification.

Accordingly, in one aspect, the invention provides a method for identifying one or more compounds which bind to a biological target. The method comprises synthesizing a library of compounds, wherein the compounds comprise a functional moiety comprising two or more building blocks which is operatively linked to an initial oligonucleotide which identifies the structure of the functional moiety by providing a solution comprising m initiator compounds, wherein m is an integer of 1 or greater, where the initiator compounds consist of a functional moiety comprising n building blocks, where n is an integer of 1 or greater, which is operatively linked to an initial oligonucleotide which identifies the n building blocks, dividing the solution described above into r reaction vessels, wherein r is an integer of 2 or greater, thereby producing r aliquots of the solution, reacting the initiator compounds in each reaction vessel with one of r building blocks, thereby producing r aliquots comprising compounds consisting of a functional moiety comprising n+1 building blocks operatively linked to the initial oligonucleotide, and reacting the initial oligonucleotide in each aliquot with one of a set of r distinct incoming oligonucleotides in the presence of an enzyme which catalyzes the ligation of the incoming oligonucleotide and the initial oligonucleotide, under conditions suitable for enzymatic ligation of the incoming oligonucleotide and the initial oligonucleotide; thereby producing r aliquots of molecules consisting of a functional moiety comprising n+1 building blocks operatively linked to an elongated oligonucleotide which encodes the n+1 building blocks; contacting the biological target with the library of compounds, or a portion thereof, under conditions suitable for at least one member of the library of compounds to bind to the target, removing library members that do not bind to the target, sequencing the encoding oligonucleotides of the at least one member of the library of compounds which binds to the target, and using the foregoing sequences to determine the structure of the functional moieties of the members of the library of compounds which bind to the biological target, thereby identifying one or more compounds which bind to the biological target.

In one embodiment, the methods of the invention may further comprise amplifying the encoding oligonucleotide of the at least one member of the library of compounds which binds to the target prior to sequencing.

In one embodiment, the method of amplifying comprises forming a water-in-oil emulsion to create a plurality of aqueous microreactors, wherein at least one of the microreactors comprises the at least one member of the library of compounds that binds to the target, a single bead capable of binding to the encoding oligonucleotide of the at least one member of the library of compounds that binds to the target, and amplification reaction solution containing reagents necessary to perform nucleic acid amplification, amplifying the encoding oligonucleotide in the microreactors to form amplified copies of the encoding oligonucleotide, and binding the amplified copies of the encoding oligonucleotide to the beads in the microreactors.

In one embodiment, the method of sequencing comprises annealing an effective amount of a sequencing primer to the amplified copies of the encoding oligonucleotide and extending the sequencing primer with a polymerase and a predetermined nucleotide triphosphate to yield a sequencing product and, if the predetermined nucleotide triphosphate is incorporated onto a 3' end of the sequencing primer, a sequencing reaction byproduct, and identifying the sequencing reaction byproduct, thereby determining the sequence of the encoding oligonucleotide.

In one embodiment, sequencing is performed using the polymerase chain reaction. In another embodiment, sequencing is performed using a pyrophosphate sequencing method or using a single molecule sequencing by synthesis method.

BRIEF DESCRIPTION OF THE DRAWINGS

FIG. 13a is a chromatogram of the library produced as described in Example 2 following Cycle 4.

FIG. 13b is a mass spectrum of the library produced as described in Example 2 following Cycle 4.

DETAILED DESCRIPTION OF THE INVENTION

Figure 1:
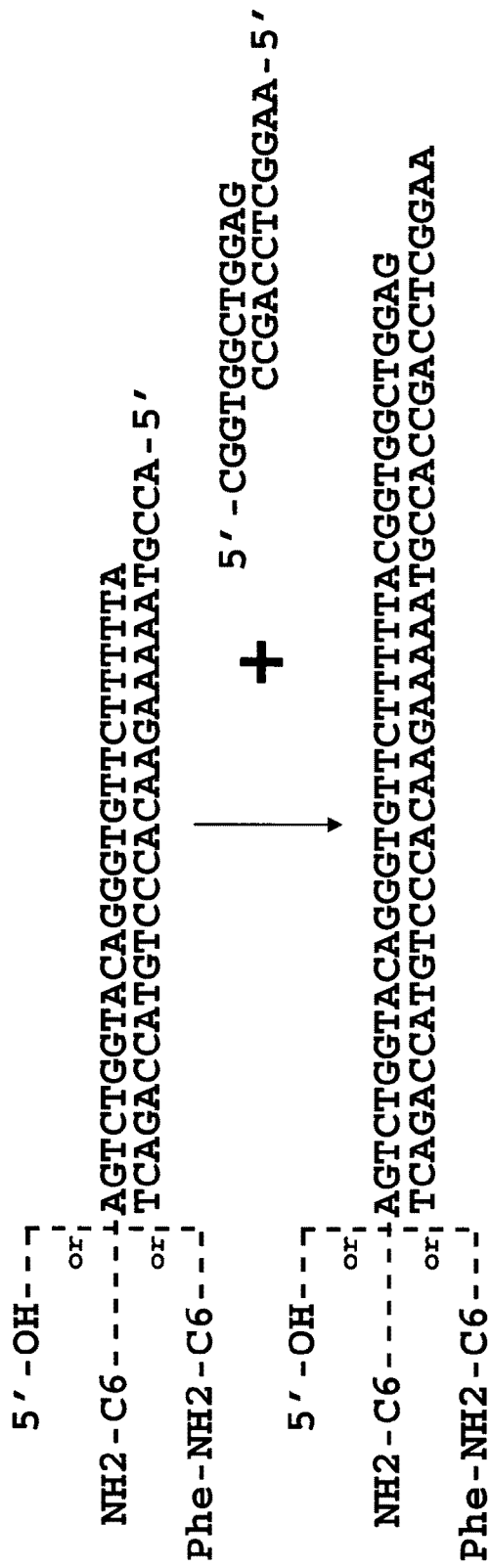
FIG. 1 is a schematic representation of ligation of double stranded oligonucleotides (SEQ ID NOs:923-926), in which the initial oligonucleotide has an overhang which is complementary to the overhang of the incoming oligonucleotide. The initial strand is represented as either free, conjugated to an aminohexyl linker or conjugated to a phenylalanine residue via an aminohexyl linker.

The present invention relates to methods of producing compounds and combinatorial compound libraries, the compounds and libraries produced via the methods of the invention, and methods of using the libraries to identify compounds having a desired property, such as a desired biological activity. The invention further relates to the compounds identified using these methods.

A variety of approaches have been taken to produce and screen combinatorial chemical libraries. Examples include methods in which the individual members of the library are physically separated from each other, such as when a single compound is synthesized in each of a multitude of reaction vessels. However, these libraries are typically screened one compound at a time, or at most, several compounds at a time and do not, therefore, result in the most efficient screening process. In other methods, compounds are synthesized on solid supports. Such solid supports include chips in which specific compounds occupy specific regions of the chip or membrane ("position addressable"). In other methods, compounds are synthesized on beads, with each bead containing a different chemical structure.

Two difficulties that arise in screening large libraries are (1) the number of distinct compounds that can be screened; and (2) the identification of compounds which are active in the screen. In one method, the compounds which are active in the screen are identified by narrowing the original library into ever smaller fractions and subfractions, in each case selecting the fraction or subfraction which contains active compounds and further subdividing until attaining an active subfraction which contains a set of compounds which is sufficiently small that all members of the subset can be individually synthesized and assessed for the desired activity. This is a tedious and time consuming activity.

Another method of deconvoluting the results of a combinatorial library screen is to utilize libraries in which the library members are tagged with an identifying label, that is, each label present in the library is associated with a discreet compound structure present in the library, such that identification of the label tells the structure of the tagged molecule. One approach to tagged libraries utilizes oligonucleotide tags, as described, for example, in U.S. Pat. Nos. 5,573,905; 5,708,153; 5,723,598, 6,060,596 published PCT applications WO 93/06121; WO 93/20242; WO 94/13623; WO 00/23458; WO 02/074929 and WO 02/103008, and by Brenner and Lerner (*Proc. Natl. Acad. Sci. USA* 89, 5381-5383 (1992); Nielsen and Janda (*Methods: A Companion to Methods in Enzymology* 6, 361-371 (1994); and Nielsen, Brenner and Janda (*J. Am. Chem. Soc.* 115, 9812-9813 (1993)), each of which is incorporated herein by reference in its entirety. Such tags can be amplified, using for example, polymerase chain reaction, to produce many copies of the tag and identify the tag by sequencing. The sequence of the tag then identifies the structure of the binding molecule, which can be synthesized in pure form and tested. To date, there has been no report of the use of the methodology disclosed by Lerner et al. to prepare large libraries. The present invention provides an improvement in methods to produce DNA-encoded libraries, as well as the first examples of large ($10^5$ members or greater) libraries of DNA-encoded molecules in which the functional moiety is synthesized using solution phase synthetic methods.

The present invention provides methods which enable facile synthesis of oligonucleotide-encoded combinatorial libraries, and permit an efficient, high-fidelity means of adding such an oligonucleotide tag to each member of a vast collection of molecules.

The methods of the invention include methods for synthesizing bifunctional molecules which comprise a first moiety ("functional moiety") which is made up of building blocks, and a second moiety operatively linked to the first moiety, comprising an oligonucleotide tag which identifies the structure of the first moiety, i.e., the oligonucleotide tag indicates which building blocks were used in the construction of the first moiety, as well as the order in which the building blocks were linked. Generally, the information provided by the oligonucleotide tag is sufficient to determine the building blocks used to construct the active moiety. In certain embodiments, the sequence of the oligonucleotide tag is sufficient to determine the arrangement of the building blocks in the functional moiety, for example, for peptidic moieties, the amino acid sequence.

The term "functional moiety" as used herein, refers to a chemical moiety comprising one or more building blocks. Preferably, the building blocks in the functional moiety are not nucleic acids. The functional moiety can be a linear or branched or cyclic polymer or oligomer or a small organic molecule.

The term "building block", as used herein, is a chemical structural unit which is linked to other chemical structural units or can be linked to other such units. When the functional moiety is polymeric or oligomeric, the building blocks are the monomeric units of the polymer or oligomer. Building blocks can also include a scaffold structure ("scaffold building block") to which is, or can be, attached one or more additional structures ("peripheral building blocks").

It is to be understood that the term "building block" is used herein to refer to a chemical structural unit as it exists in a functional moiety and also in the reactive form used for the synthesis of the functional moiety. Within the functional moiety, a building block will exist without any portion of the building block which is lost as a consequence of incorporating the building block into the functional moiety. For example, in cases in which the bond-forming reaction releases a small molecule (see below), the building block as it exists in the functional moiety is a "building block residue", that is, the remainder of the building block used in the synthesis following loss of the atoms that it contributes to the released molecule.

The building blocks can be any chemical compounds which are complementary, that is the building blocks must be able to react together to form a structure comprising two or more building blocks. Typically, all of the building blocks used will have at least two reactive groups, although it is possible that some of the building blocks (for example the last building block in an oligomeric functional moiety) used will have only one reactive group each. Reactive groups on two different building blocks should be complementary, i.e., capable of reacting together to form a covalent bond, optionally with the concomitant loss of a small molecule, such as water, HCl, HF, and so forth.

For the present purposes, two reactive groups are complementary if they are capable of reacting together to form a covalent bond. In a preferred embodiment, the bond forming reactions occur rapidly under ambient conditions without substantial formation of side products. Preferably, a given reactive group will react with a given complementary reactive group exactly once. In one embodiment, complementary reactive groups of two building blocks react, for example, via nucleophilic substitution, to form a covalent bond. In one embodiment, one member of a pair of complementary reactive groups is an electrophilic group and the other member of the pair is a nucleophilic group.

Complementary electrophilic and nucleophilic groups include any two groups which react via nucleophilic substitution under suitable conditions to form a covalent bond. A variety of suitable bond-forming reactions are known in the art. See, for example, March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Collman et al., Principles and Applications of Organotransition Metal Chemistry, University Science Books, Mill Valley, Calif. (1987), Chapters 13 to 20; each of which is incorporated herein by reference in its entirety. Examples of suitable electrophilic groups include reactive carbonyl groups, such as acyl chloride groups, ester groups, including carbonyl pentafluorophenyl esters and succinimide esters, ketone groups and aldehyde groups; reactive sulfonyl groups, such as sulfonyl chloride groups, and reactive phosphonyl groups. Other electrophilic groups include terminal epoxide groups, isocyanate groups and alkyl halide groups. Suitable nucleophilic groups include primary and secondary amino groups and hydroxyl groups and carboxyl groups.

Suitable complementary reactive groups are set forth below. One of skill in the art can readily determine other reactive group pairs that can be used in the present method, and the examples provided herein are not intended to be limiting.

In a first embodiment, the complementary reactive groups include activated carboxyl groups, reactive sulfonyl groups or reactive phosphonyl groups, or a combination thereof, and primary or secondary amino groups. In this embodiment, the complementary reactive groups react under suitable conditions to form an amide, sulfonamide or phosphonamidate bond.

In a second embodiment, the complementary reactive groups include epoxide groups and primary or secondary amino groups. An epoxide-containing building block reacts with an amine-containing building block under suitable conditions to form a carbon-nitrogen bond, resulting in a β-amino alcohol.

In another embodiment, the complementary reactive groups include aziridine groups and primary or secondary amino groups. Under suitable conditions, an aziridine-containing building block reacts with an amine-containing building block to form a carbon-nitrogen bond, resulting in a 1,2-diamine. In a third embodiment, the complementary reactive groups include isocyanate groups and primary or secondary amino groups. An isocyanate-containing building block will react with an amino-containing building block under suitable conditions to form a carbon-nitrogen bond, resulting in a urea group.

In a fourth embodiment, the complementary reactive groups include isocyanate groups and hydroxyl groups. An isocyanate-containing building block will react with an hydroxyl-containing building block under suitable conditions to form a carbon-oxygen bond, resulting in a carbamate group.

In a fifth embodiment, the complementary reactive groups include amino groups and carbonyl-containing groups, such as aldehyde or ketone groups. Amines react with such groups via reductive amination to form a new carbon-nitrogen bond.

In a sixth embodiment, the complementary reactive groups include phosphorous ylide groups and aldehyde or ketone groups. A phosphorus-ylide-containing building block will react with an aldehyde or ketone-containing building block under suitable conditions to form a carbon-carbon double bond, resulting in an alkene.

Figure 8:
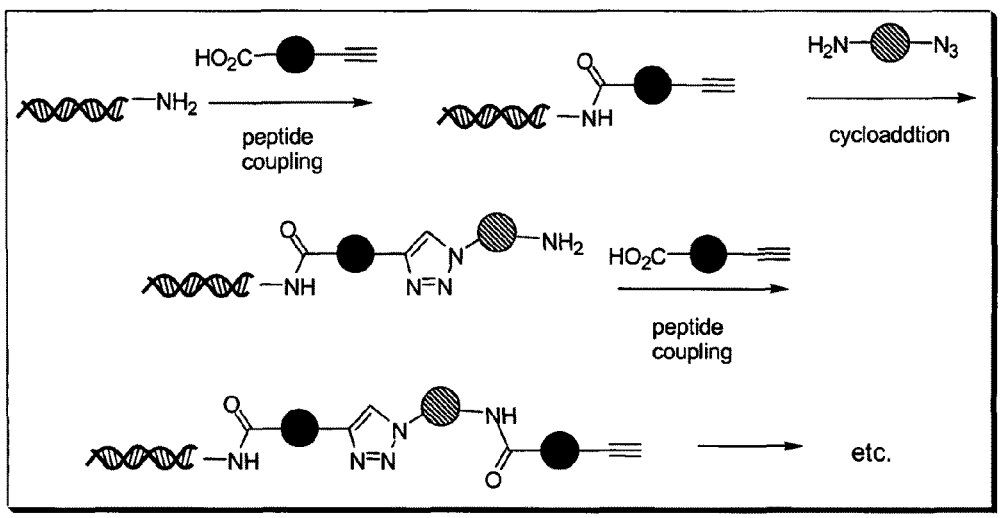
FIG. 8 is a schematic depiction of the coupling of building blocks using azide-alkyne cycloaddition.

In a seventh embodiment, the complementary reactive groups react via cycloaddition to form a cyclic structure. One example of such complementary reactive groups are alkynes and organic azides, which react under suitable conditions to form a triazole ring structure. An example of the use of this reaction to link two building blocks is illustrated in FIG. 8. Suitable conditions for such reactions are known in the art and include those disclosed in WO 03/101972, the entire contents of which are incorporated by reference herein.

In an eighth embodiment, the complementary reactive groups are an alkyl halide and a nucleophile, such as an amino group, a hydroxyl group or a carboxyl group. Such groups react under suitable conditions to form a carbon-nitrogen (alkyl halide plus amine) or carbon oxygen (alkyl halide plus hydroxyl or carboxyl group).

Figure 9:
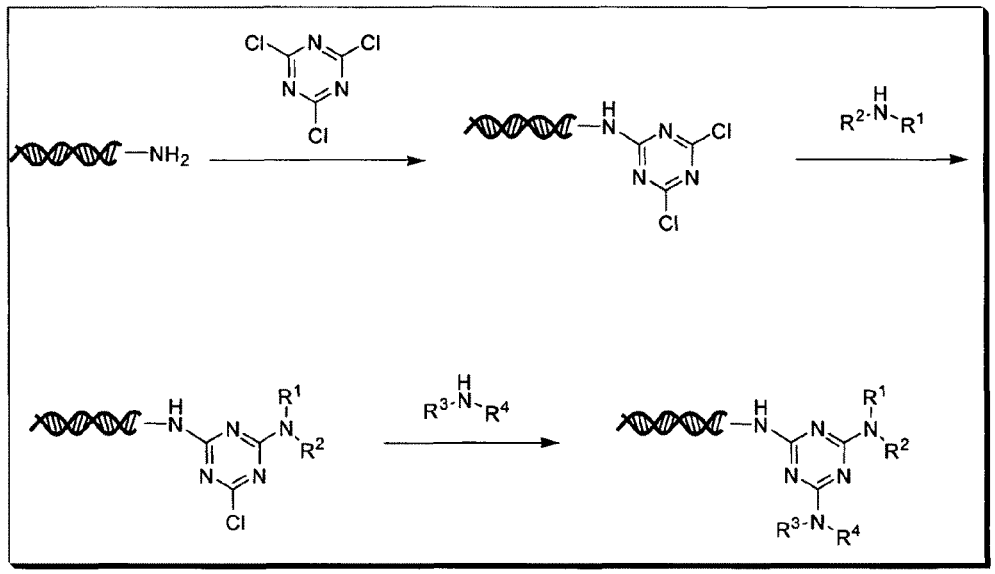
FIGS. 9 and 10 illustrate the coupling of building blocks via nucleophilic aromatic substitution on a chlorinated triazine.
Figure 10:
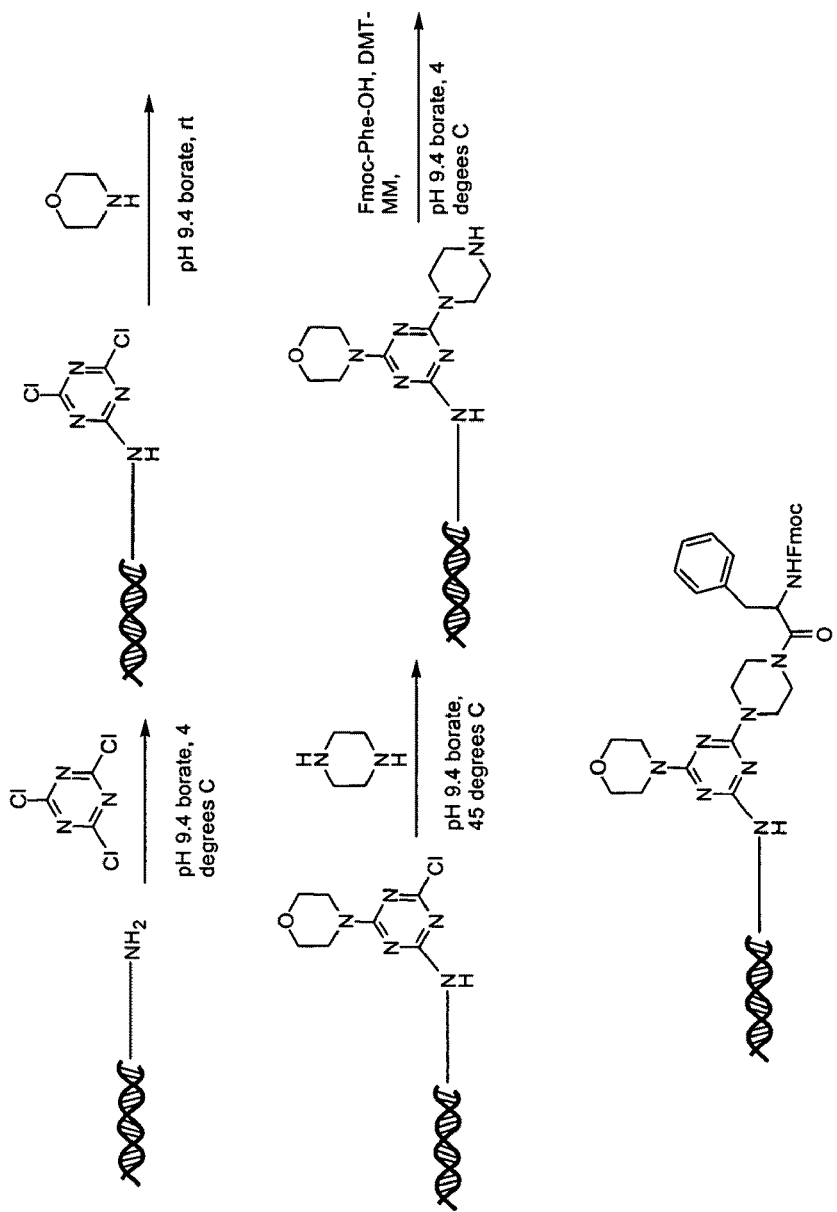
Figure 11:
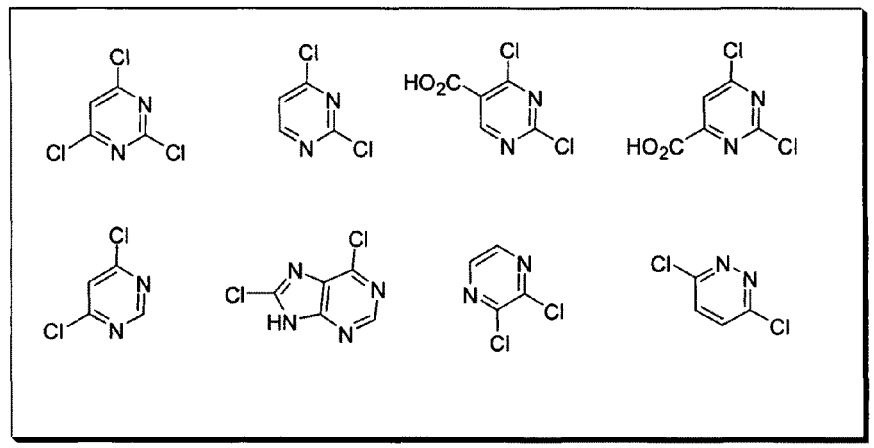
FIG. 11 shows representative chlorinated heteroaromatic structures suitable for use in the synthesis of functional moieties.
Figure 12:
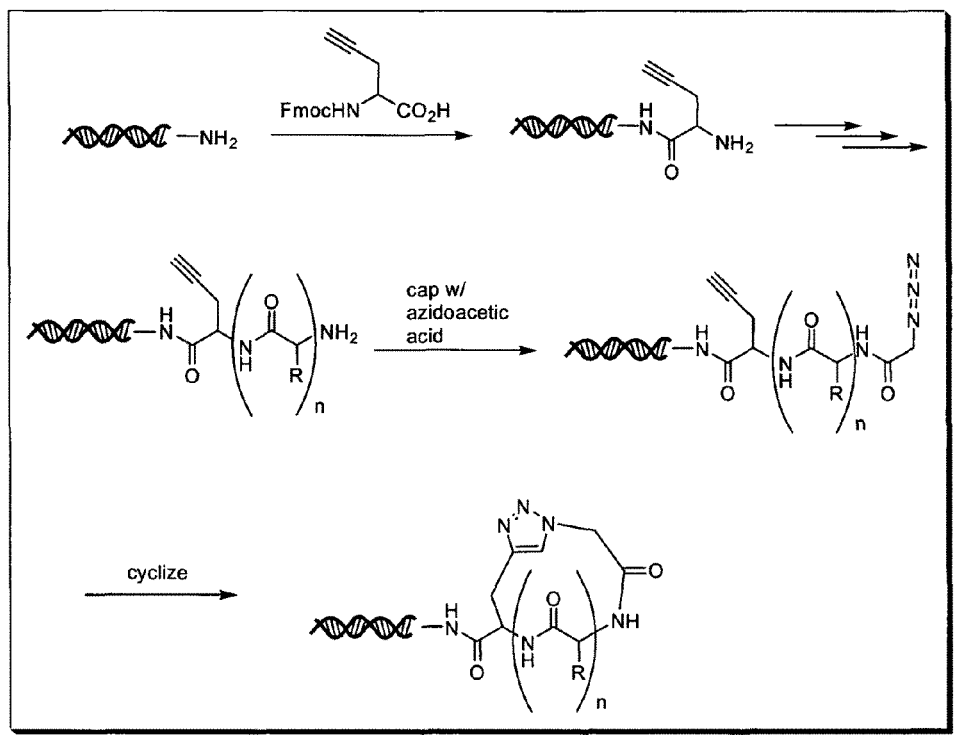
FIG. 12 illustrates the cyclization of a linear peptide using the azide/alkyne cycloaddition reaction.

In a ninth embodiment, the complementary functional groups are a halogenated heteroaromatic group and a nucleophile, and the building blocks are linked under suitable conditions via aromatic nucleophilic substitution. Suitable halogenated heteroaromatic groups include chlorinated pyrimidines, triazines and purines, which react with nucleophiles, such as amines, under mild conditions in aqueous solution. Representative examples of the reaction of an oligonucleotide-tagged trichlorotriazine with amines are shown in FIGS. 9 and 10. Examples of suitable chlorinated heteroaromatic groups are shown in FIG. 11.

Additional bond-forming reactions that can be used to join building blocks in the synthesis of the molecules and libraries of the invention include those shown below. The reactions shown below emphasize the reactive functional groups. Various substituents can be present in the reactants, including those labeled $R_1$, $R_2$, $R_3$ and $R_4$. The possible positions which can be substituted include, but are not limited, to those indicated by $R_1$, $R_2$, $R_3$ and $R_4$. These substituents can include any suitable chemical moieties, but are preferably limited to those which will not interfere with or significantly inhibit the indicated reaction, and, unless otherwise specified, can include hydrogen, alkyl, substituted alkyl, aryl, substituted aryl, heteroaryl, substituted heteroaryl, alkoxy, aryloxy, arylalkyl, substituted arylalkyl, amino, substituted amino and others as are known in the art. Suitable substituents on these groups include alkyl, aryl, heteroaryl, cyano, halogen, hydroxyl, nitro, amino, mercapto, carboxyl, and carboxamide. Where specified, suitable electron-withdrawing groups include nitro, carboxyl, haloalkyl, such as trifluoromethyl and others as are known in the art. Examples of suitable electron-donating groups include alkyl, alkoxy, hydroxyl, amino, halogen, acetamido and others as are known in the art.

Addition of a Primary Amine to an Alkene:

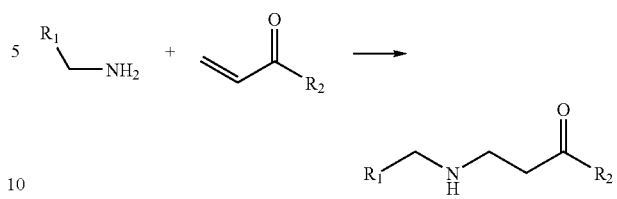

Nucleophilic Substitution:

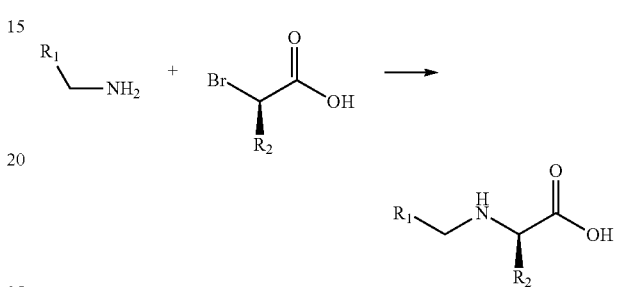

Reductive Alkylation of an Amine:

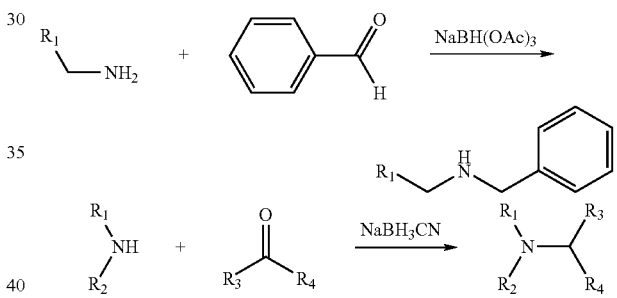

Palladium Catalyzed Carbon-Carbon Bond Forming Reactions:

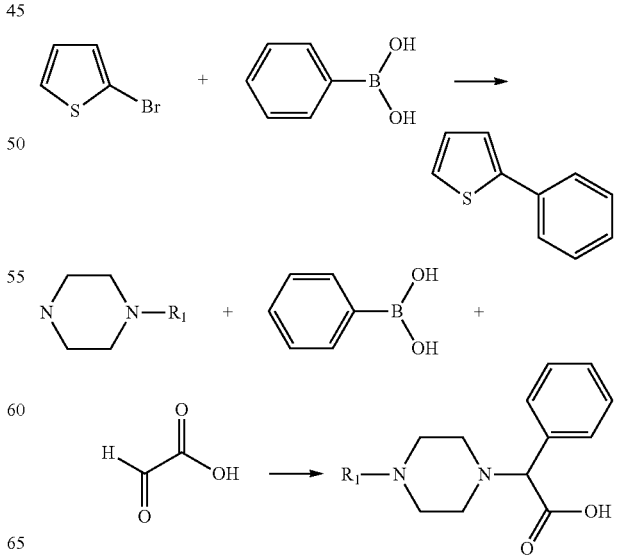

Ugi Condensation Reactions:

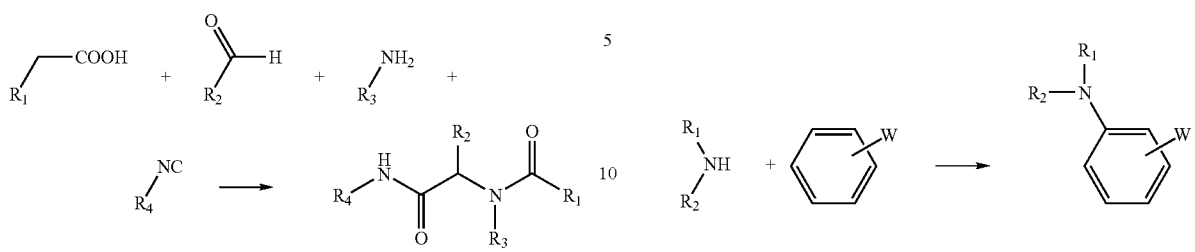

Electrophilic Aromatic Substitution Reactions:

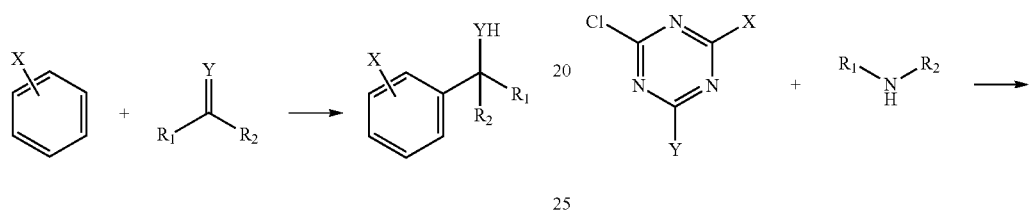

X is an electron-donating group.

Imine/Iminium/Enamine Forming Reactions:

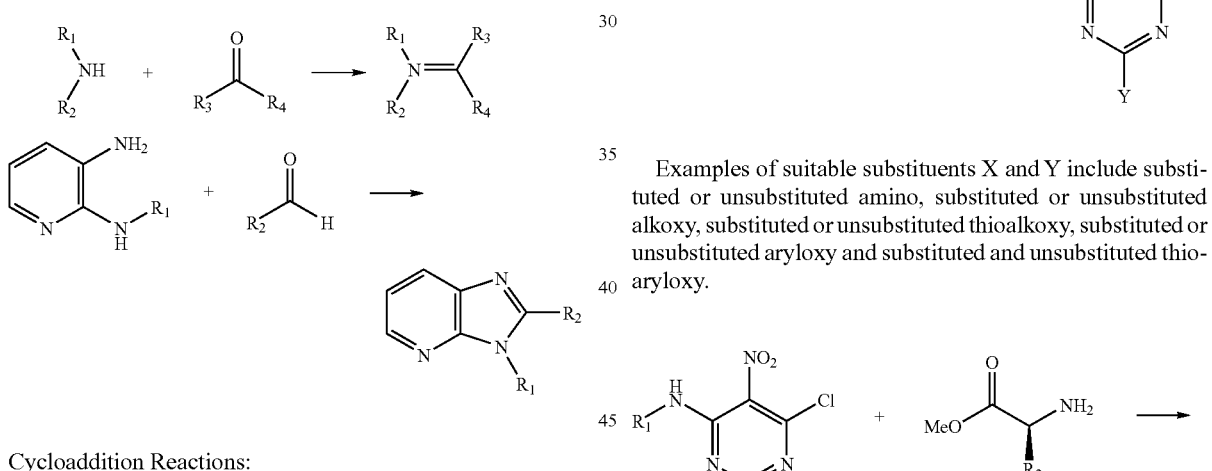

Cycloaddition Reactions:

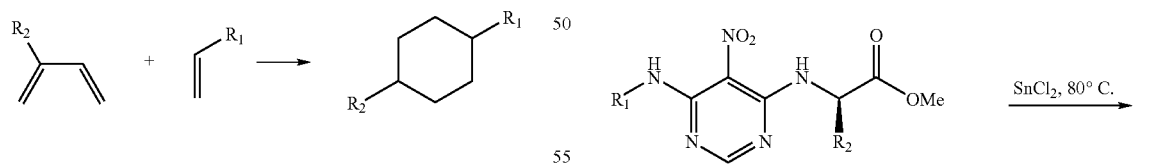

Diels-Alder Cycloaddition

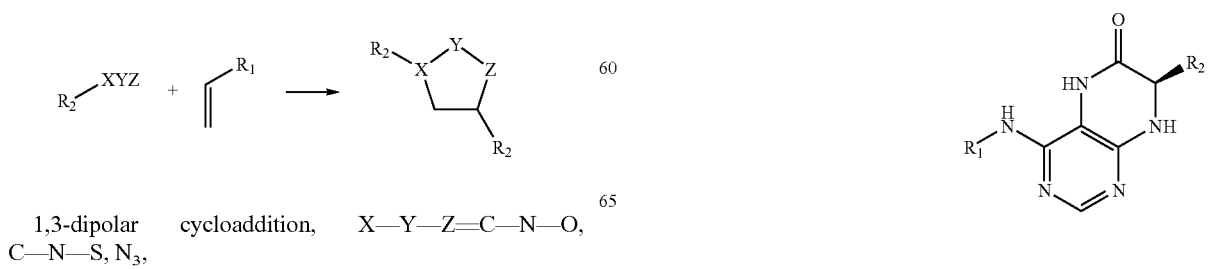

1,3-dipolar cycloaddition, X—Y—Z=C—N—O, C—N—S, $N_3$,

Nucleophilic Aromatic Substitution Reactions:

W is an electron withdrawing group

Examples of suitable substituents X and Y include substituted or unsubstituted amino, substituted or unsubstituted alkoxy, substituted or unsubstituted thioalkoxy, substituted or unsubstituted aryloxy and substituted and unsubstituted thioaryloxy.

Heck Reaction:

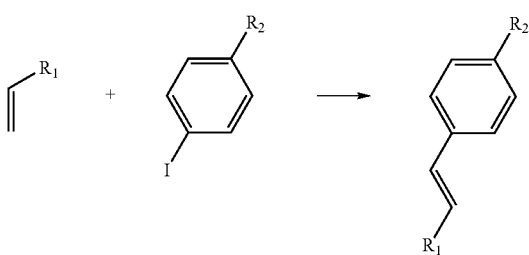

Acetal Formation:

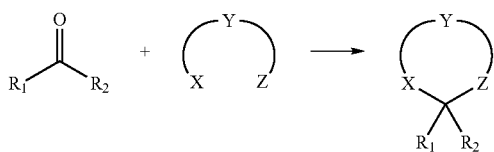

Examples of suitable substituents X and Y include substituted and unsubstituted amino, hydroxyl and sulhydryl; Y is a linker that connects X and Y and is suitable for forming the ring structure found in the product of the reaction Aldol Reactions:

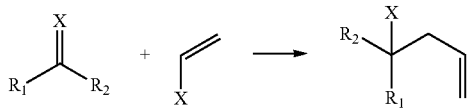

Examples of suitable substituents X include O, S and $NR_3$.

Scaffold building blocks which can be used to form the molecules and libraries of the invention include those which have two or more functional groups which can participate in bond forming reactions with peripheral building block precursors, for example, using one or more of the bond forming reactions discussed above. Scaffold moieties may also be synthesized during construction of the libraries and molecules of the invention, for example, using building block precursors which can react in specific ways to form molecules comprising a central molecular moiety to which are appended peripheral functional groups. In one embodiment, a library of the invention comprises molecules comprising a constant scaffold moiety, but different peripheral moieties or different arrangements of peripheral moieties. In certain libraries, all library members comprise a constant scaffold moiety; other libraries can comprise molecules having two or more different scaffold moieties. Examples of scaffold moiety-forming reactions that can be used in the construction of the molecules and libraries of the invention are set forth in the Table. The references cited in the table are incorporated herein by reference in their entirety. The groups $R_1$, $R_2$, $R_3$ and $R_4$ are limited only in that they should not interfere with, or significantly inhibit, the indicated reaction, and can include hydrogen, alkyl, substituted alkyl, heteroalkyl, substituted heteroalkyl, cycloalkyl, heterocycloalkyl, substituted cycloalkyl, substituted heterocycloalkyl, aryl, substituted aryl, arylalkyl, heteroarylalkyl, substituted arylalkyl, substituted heteroarylalkyl, heteroaryl, substituted heteroaryl, halogen, alkoxy, aryloxy, amino, substituted amino and others as are known in the art. Suitable substituents include, but are not limited to, alkyl, alkoxy, thioalkoxy, nitro, hydroxyl, sulfhydryl, aryloxy, aryl-S—, halogen, carboxy, amino, alkylamino, dialkylamino, arylamino, cyano, cyanate, nitrile, isocyanate, thiocyanate, carbamyl, and substituted carbamyl.

It is to be understood that the synthesis of a functional moiety can proceed via one particular type of coupling reaction, such as, but not limited to, one of the reactions discussed above, or via a combination of two or more coupling reactions, such as two or more of the coupling reactions discussed above. For example, in one embodiment, the building blocks are joined by a combination of amide bond formation (amino and carboxylic acid complementary groups) and reductive amination (amino and aldehyde or ketone complementary groups). Any coupling chemistry can be used, provided that it is compatible with the presence of an oligonucleotide. Double stranded (duplex) oligonucleotide tags, as used in certain embodiments of the present invention, are chemically more robust than single stranded tags, and, therefore, tolerate a broader range of reaction conditions and enable the use of bond-forming reactions that would not be possible with single-stranded tags.

A building block can include one or more functional groups in addition to the reactivem group or groups employed to form the functional moiety. One or more of these additional functional groups can be protected to prevent undesired reactions of these functional groups. Suitable protecting groups are known in the art for a variety of functional groups (Greene and Wuts, Protective Groups in Organic Synthesis, second edition, New York: John Wiley and Sons (1991), incorporated herein by reference). Particularly useful protecting groups include t-butyl esters and ethers, acetals, trityl ethers and amines, acetyl esters, trimethylsilyl ethers, trichloroethyl ethers and esters and carbamates.

In one embodiment, each building block comprises two reactive groups, which can be the same or different. For example, each building block added in cycle s can comprise two reactive groups which are the same, but which are both complementary to the reactive groups of the building blocks added at steps s−1 and s+1. In another embodiment, each building block comprises two reactive groups which are themselves complementary. For example, a library comprising polyamide molecules can be produced via reactions between building blocks comprising two primary amino groups and building blocks comprising two activated carboxyl groups. In the resulting compounds there is no N- or C-terminus, as alternate amide groups have opposite directionality. Alternatively, a polyamide library can be produced using building blocks that each comprise an amino group and an activated carboxyl group. In this embodiment, the building blocks added in step n of the cycle will have a free reactive group which is complementary to the available reactive group on the n−1 building block, while, preferably, the other reactive group on the nth building block is protected. For example, if the members of the library are synthesized from the C to N direction, the building blocks added will comprise an activated carboxyl group and a protected amino group.

The functional moieties can be polymeric or oligomeric moieties, such as peptides, peptidomimetics, peptide nucleic acids or peptoids, or they can be small non-polymeric molecules, for example, molecules having a structure comprising a central scaffold and structures arranged about the periphery of the scaffold. Linear polymeric or oligomeric libraries will result from the use of building blocks having two reactive groups, while branched polymeric or oligomeric libraries will result from the use of building blocks having three or more reactive groups, optionally in combination with building blocks having only two reactive groups. Such molecules can be represented by the general formula $X_1X_2 \ldots X_n$, where each X is a monomeric unit of a polymer comprising n monomeric units, where n is an integer greater than 1 In the case of oligomeric or polymeric compounds, the terminal building blocks need not comprise two functional groups. For example, in the case of a polyamide library, the C-terminal building block can comprise an amino group, but the presence of a carboxyl group is optional. Similarly, the building block at the N-terminus can comprise a carboxyl group, but need not contain an amino group.

Branched oligomeric or polymeric compounds can also be synthesized provided that at least one building block comprises three functional groups which are reactive with other building blocks. A library of the invention can comprise linear molecules, branched molecules or a combination thereof.

Libraries can also be constructed using, for example, a scaffold building block having two or more reactive groups, in combination with other building blocks having only one available reactive group, for example, where any additional reactive groups are either protected or not reactive with the other reactive groups present in the scaffold building block. In one embodiment, for example, the molecules synthesized can be represented by the general formula $X(Y)_n$, where X is a scaffold building block; each Y is a building block linked to X and n is an integer of at least two, and preferably an integer from 2 to about 6. In one preferred embodiment, the initial building block of cycle 1 is a scaffold building block. In molecules of the formula $X(Y)_n$, each Y can be the same or different, but in most members of a typical library, each Y will be different.

In one embodiment, the libraries of the invention comprise polyamide compounds. The polyamide compounds can be composed of building blocks derived from any amino acids, including the twenty naturally occurring α-amino acids, such as alanine (Ala; A), glycine (Gly; G), asparagine (Asn; N), aspartic acid (Asp; D), glutamic acid (Glu; E), histidine (His; H), leucine (Leu; L), lysine (Lys; K), phenylalanine (Phe; F), tyrosine (Tyr; Y), threonine (Thr; T), serine (Ser; S), arginine (Arg; R), valine (Val; V), glutamine (Gln; Q), isoleucine (Ile; I), cysteine (Cys; C), methionine (Met; M), proline (Pro; P) and tryptophan (Trp; W), where the three-letter and one-letter codes for each amino acid are given. In their naturally occurring form, each of the foregoing amino acids exists in the L-configuration, which is to be assumed herein unless otherwise noted. In the present method, however, the D-configuration forms of these amino acids can also be used. These D-amino acids are indicated herein by lower case three- or one-letter code, i.e., ala (a), gly (g), leu (l), gln (q), thr (t), ser (s), and so forth. The building blocks can also be derived from other α-amino acids, including, but not limited to, 3-arylalanines, such as naphthylalanine, phenyl-substituted phenylalanines, including 4-fluoro-, 4-chloro, 4-bromo and 4-methylphenylalanine; 3-heteroarylalanines, such as 3-pyridylalanine, 3-thienylalanine, 3-quinolylalanine, and 3-imidazolylalanine; ornithine; citrulline; homocitrulline; sarcosine; homoproline; homocysteine; substituted proline, such as hydroxyproline and fluoroproline; dehydroproline; norleucine; O-methyltyrosine; O-methylserine; O-methylthreonine and 3-cyclohexylalanine. Each of the preceding amino acids can be utilized in either the D- or L-configuration.

The building blocks can also be amino acids which are not α-amino acids, such as α-azaamino acids; β, γ, δ, ε-amino acids, and N-substituted amino acids, such as N-substituted glycine, where the N-substituent can be, for example, a substituted or unsubstituted alkyl, aryl, heteroaryl, arylalkyl or heteroarylalkyl group. In one embodiment, the N-substituent is a side chain from a naturally-occurring or non-naturally occurring α-amino acid.

The building block can also be a peptidomimetic structure, such as a dipeptide, tripeptide, tetrapeptide or pentapeptide mimetic. Such peptidomimetic building blocks are preferably derived from amino acyl compounds, such that the chemistry of addition of these building blocks to the growing poly (aminoacyl) group is the same as, or similar to, the chemistry used for the other building blocks. The building blocks can also be molecules which are capable of forming bonds which are isosteric with a peptide bond, to form peptidomimetic functional moieties comprising a peptide backbone modification, such as $\psi[CH_2S]$, $\psi[CH_2NH]$, $\psi[CSNH_2]$, $\psi[NHCO]$, $\psi[COCH_2]$, and $\psi[(E)$ or $(Z)CH=CH]$. In the nomenclature used above, $\psi$ indicates the absence of an amide bond. The structure that replaces the amide group is specified within the brackets.

In one embodiment, the invention provides a method of synthesizing a compound comprising or consisting of a functional moiety which is operatively linked to an encoding oligonucleotide. The method includes the steps of: (1) providing an initiator compound consisting of an initial functional moiety comprising n building blocks, where n is an integer of 1 or greater, wherein the initial functional moiety comprises at least one reactive group, and wherein the initial functional moiety is operatively linked to an initial oligonucleotide which encodes the n building blocks; (2) reacting the initiator compound with a building block comprising at least one complementary reactive group, wherein the at least one complementary reactive group is complementary to the reactive group of step (1), under suitable conditions for reaction of the reactive group and the complementary reactive group to form a covalent bond; (3) reacting the initial oligonucleotide with an incoming oligonucleotide in the presence of an enzyme which catalyzes ligation of the initial oligonucleotide and the incoming oligonucleotide, under conditions suitable for ligation of the incoming oligonucleotide and the initial oligonucleotide, thereby producing a molecule which comprises or consists of a functional moiety comprising n+1 building blocks which is operatively linked to an encoding oligonucleotide. If the functional moiety of step (3) comprises a reactive group, steps 1-3 can be repeated one or more times, thereby forming cycles 1 to i, where i is an integer of 2 or greater, with the product of step (3) of a cycle s−1, where s is an integer of i or less, becoming the initiator compound of step (1) of cycle s. In each cycle, one building block is added to the growing functional moiety and one oligonucleotide sequence, which encodes the new building block, is added to the growing encoding oligonucleotide.

In one embodiment, the initial initiator compound(s) is generated by reacting a first building block with an oligonucleotide (e.g., an oligonucleotide which includes PCR primer sequences or an initial oligonucleotide) or with a linker to which such an oligonucleotide is attached. In the embodiment set forth in FIG. 5, the linker comprises a reactive group for attachment of a first building block and is attached to an initial oligonucleotide. In this embodiment, reaction of a building block, or in each of multiple aliquots, one of a collection of building blocks, with the reactive group of the linker and addition of an oligonucleotide encoding the building block to the initial oligonucleotide produces the one or more initial initiator compounds of the process set forth above.

In a preferred embodiment, each individual building block is associated with a distinct oligonucleotide, such that the sequence of nucleotides in the oligonucleotide added in a given cycle identifies the building block added in the same cycle.

The coupling of building blocks and ligation of oligonucleotides will generally occur at similar concentrations of starting materials and reagents. For example, concentrations of reactants on the order of micromolar to millimolar, for example from about 10 μM to about 10 mM, are preferred in order to have efficient coupling of building blocks.

In certain embodiments, the method further comprises, following step (2), the step of scavenging any unreacted initial functional moiety. Scavenging any unreacted initial functional moiety in a particular cycle prevents the initial functional moiety of the cycle from reacting with a building block added in a later cycle. Such reactions could lead to the generation of functional moieties missing one or more building blocks, potentially leading to a range of functional moiety structures which correspond to a particular oligonucleotide sequence. Such scavenging can be accomplished by reacting any remaining initial functional moiety with a compound which reacts with the reactive group of step (2). Preferably, the scavenger compound reacts rapidly with the reactive group of step (2) and includes no additional reactive groups that can react with building blocks added in later cycles. For example, in the synthesis of a compound where the reactive group of step (2) is an amino group, a suitable scavenger compound is an N-hydroxysuccinimide ester, such as acetic acid N-hydroxysuccinimide ester.

In another embodiment, the invention provides a method of producing a library of compounds, wherein each compound comprises a functional moiety comprising two or more building block residues which is operatively linked to an oligonucleotide. In a preferred embodiment, the oligonucleotide present in each molecule provides sufficient information to identify the building blocks within the molecule and, optionally, the order of addition of the building blocks. In this embodiment, the method of the invention comprises a method of synthesizing a library of compounds, wherein the compounds comprise a functional moiety comprising two or more building blocks which is operatively linked to an oligonucleotide which identifies the structure of the functional moiety. The method comprises the steps of (1) providing a solution comprising m initiator compounds, wherein m is an integer of 1 or greater, where the initiator compounds consist of a functional moiety comprising n building blocks, where n is an integer of 1 or greater, which is operatively linked to an initial oligonucleotide which identifies the n building blocks; (2) dividing the solution of step (1) into at least r fractions, wherein r is an integer of 2 or greater; (3) reacting each fraction with one of r building blocks, thereby producing r fractions comprising compounds consisting of a functional moiety comprising n+1 building blocks operatively linked to the initial oligonucleotide; (4) reacting each of the r fractions of step (3) with one of a set of r distinct incoming oligonucleotides under conditions suitable for enzymatic ligation of the incoming oligonucleotide to the initial oligonucleotide, thereby producing r fractions comprising molecules consisting of a functional moiety comprising n+1 building blocks operatively linked to an elongated oligonucleotide which encodes the n+1 building blocks. Optionally, the method can further include the step of (5) recombining the r fractions, produced in step (4), thereby producing a solution comprising molecules consisting of a functional moiety comprising n+1 building blocks, which is operatively linked to an elongated oligonucleotide which encodes the n+1 building blocks. Steps (1) to (5) can be conducted one or more times to yield cycles 1 to i, where i is an integer of 2 or greater. In cycle s+1, where s is an integer of i−1 or less, the solution comprising m initiator compounds of step (1) is the solution of step (5) of cycle s. Likewise, the initiator compounds of step (1) of cycle s+1 are the products of step (4) in cycle s.

Preferably the solution of step (2) is divided into r fractions in each cycle of the library synthesis. In this embodiment, each fract is reacted with a unique building block.

In the methods of the invention, the order of addition of the building block and the incoming oligonucleotide is not critical, and steps (2) and (3) of the synthesis of a molecule, and steps (3) and (4) in the library synthesis can be reversed, i.e., the incoming oligonucleotide can be ligated to the initial oligonucleotide before the new building block is added. In certain embodiments, it may be possible to conduct these two steps simultaneously.

In certain embodiments, the method further comprises, following step (2), the step of scavenging any unreacted initial functional moiety. Scavenging any unreacted initial functional moiety in a particular cycle prevents the initial functional moiety of a the cycle from reacting with a building block added in a later cycle. Such reactions could lead to the generation of functional moieties missing one or more building blocks, potentially leading to a range of functional moiety structures which correspond to a particular oligonucleotide sequence. Such scavenging can be accomplished by reacting any remaining initial functional moiety with a compound which reacts with the reactive group of step (2). Preferably, the scavenger compound reacts rapidly with the reactive group of step (2) and includes no additional reactive groups that can react with building blocks added in later cycles. For example, in the synthesis of a compound where the reactive group of step (2) is an amino group, a suitable scavenger compound is an N-hydroxysuccinimide ester, such as acetic acid N-hydroxysuccinimide ester.

In one embodiment, the building blocks used in the library synthesis are selected from a set of candidate building blocks by evaluating the ability of the candidate building blocks to react with appropriate complementary functional groups under the conditions used for synthesis of the library. Building blocks which are shown to be suitably reactive under such conditions can then be selected for incorporation into the library. The products of a given cycle can, optionally, be purified. When the cycle is an intermediate cycle, i.e., any cycle prior to the final cycle, these products are intermediates and can be purified prior to initiation of the next cycle. If the cycle is the final cycle, the products of the cycle are the final products, and can be purified prior to any use of the compounds. This purification step can, for example, remove unreacted or excess reactants and the enzyme employed for oligonucleotide ligation. Any methods which are suitable for separating the products from other species present in solution can be used, including liquid chromatography, such as high performance liquid chromatography (HPLC) and precipitation with a suitable co-solvent, such as ethanol. Suitable methods for purification will depend upon the nature of the products and the solvent system used for synthesis.

The reactions are, preferably, conducted in aqueous solution, such as a buffered aqueous solution, but can also be conducted in mixed aqueous/organic media consistent with the solubility properties of the building blocks, the oligonucleotides, the intermediates and final products and the enzyme used to catalyze the oligonucleotide ligation.

It is to be understood that the theoretical number of compounds produced by a given cycle in the method described above is the product of the number of different initiator compounds, m, used in the cycle and the number of distinct building blocks added in the cycle, r. The actual number of distinct compounds produced in the cycle can be as high as the product of r and m (r×m), but could be lower, given differences in reactivity of certain building blocks with certain other building blocks. For example, the kinetics of addition of a particular building block to a particular initiator compound may be such that on the time scale of the synthetic cycle, little to none of the product of that reaction may be produced.

In certain embodiments, a common building block is added prior to cycle 1, following the last cycle or in between any two cycles. For example, when the functional moiety is a polyamide, a common N-terminal capping building block can be added after the final cycle. A common building block can also be introduced between any two cycles, for example, to add a functional group, such as an alkyne or azide group, which can be utilized to modify the functional moieties, for example by cyclization, following library synthesis.

The term "operatively linked", as used herein, means that two chemical structures are linked together in such a way as to remain linked through the various manipulations they are expected to undergo. Typically the functional moiety and the encoding oligonucleotide are linked covalently via an appropriate linking group. The linking group is a bivalent moiety with a site of attachment for the oligonucleotide and a site of attachment for the functional moiety. For example, when the functional moiety is a polyamide compound, the polyamide compound can be attached to the linking group at its N-terminus, its C-terminus or via a functional group on one of the side chains. The linking group is sufficient to separate the polyamide compound and the oligonucleotide by at least one atom, and preferably, by more than one atom, such as at least two, at least three, at least four, at least five or at least six atoms. Preferably, the linking group is sufficiently flexible to allow the polyamide compound to bind target molecules in a manner which is independent of the oligonucleotide.

In one embodiment, the linking group is attached to the N-terminus of the polyamide compound and the 5'-phosphate group of the oligonucleotide. For example, the linking group can be derived from a linking group precursor comprising an activated carboxyl group on one end and an activated ester on the other end. Reaction of the linking group precursor with the N-terminal nitrogen atom will form an amide bond connecting the linking group to the polyamide compound or N-terminal building block, while reaction of the linking group precursor with the 5'-hydroxy group of the oligonucleotide will result in attachment of the oligonucleotide to the linking group via an ester linkage. The linking group can comprise, for example, a polymethylene chain, such as a —(CH$_2$)$_n$— chain or a poly(ethylene glycol) chain, such as a —(CH$_2$CH$_2$O)$_n$ chain, where in both cases n is an integer from 1 to about 20. Preferably, n is from 2 to about 12, more preferably from about 4 to about 10. In one embodiment, the linking group comprises a hexamethylene (—(CH$_2$)$_6$—) group.

When the building blocks are amino acid residues, the resulting functional moiety is a polyamide. The amino acids can be coupled using any suitable chemistry for the formation of amide bonds. Preferably, the coupling of the amino acid building blocks is conducted under conditions which are compatible with enzymatic ligation of oligonucleotides, for example, at neutral or near-neutral pH and in aqueous solution. In one embodiment, the polyamide compound is synthesized from the C-terminal to N-terminal direction. In this embodiment, the first, or C-terminal, building block is coupled at its carboxyl group to an oligonucleotide via a suitable linking group. The first building block is reacted with the second building block, which preferably has an activated carboxyl group and a protected amino group. Any activating/protecting group strategy which is suitable for solution phase amide bond formation can be used. For example, suitable activated carboxyl species include acyl fluorides (U.S. Pat. No. 5,360,928, incorporated herein by reference in its entirety), symmetrical anhydrides and N-hydroxysuccinimide esters. The acyl groups can also be activated in situ, as is known in the art, by reaction with a suitable activating compound. Suitable activating compounds include dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDC), n-propane-phosphonic anhydride (PPA), N,N-bis(2-oxo-3-oxazolidinyl)imido-phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), diethylphosphoryl cyanide (DEPCN), 2,5-diphenyl-2,3-dihydro-3-oxo-4-hydroxy-thiophene dioxide (Steglich's reagent; HOTDO), 1,1'-carbonyl-diimidazole (CDI), and 4-(4,6-dimethoxy-1,3,5-triazin-2-yl)-4-methylmorpholinium chloride (DMT-MM). The coupling reagents can be employed alone or in combination with additives such as N. N-dimethyl-4-aminopyridine (DMAP), N-hydroxy-benzotriazole (HOBt), N-hydroxybenzotriazine (HOOBt), N-hydroxysuccinimide (HOSu) N-hydroxyazabenzotriazole (HOAt), azabenzotriazolyl-tetramethyluronium salts (HATU, HAPyU) or 2-hydroxypyridine. In certain embodiments, synthesis of a library requires the use of two or more activation strategies, to enable the use of a structurally diverse set of building blocks. For each building block, one skilled in the art can determine the appropriate activation strategy.

The N-terminal protecting group can be any protecting group which is compatible with the conditions of the process, for example, protecting groups which are suitable for solution phase synthesis conditions. A preferred protecting group is the fluorenylmethoxycarbonyl ("Fmoc") group. Any potentially reactive functional groups on the side chain of the aminoacyl building block may also need to be suitably protected. Preferably the side chain protecting group is orthogonal to the N-terminal protecting group, that is, the side chain protecting group is removed under conditions which are different than those required for removal of the N-terminal protecting group. Suitable side chain protecting groups include the nitroveratryl group, which can be used to protect both side chain carboxyl groups and side chain amino groups. Another suitable side chain amine protecting group is the N-pent-4-enoyl group.

The building blocks can be modified following incorporation into the functional moiety, for example, by a suitable reaction involving a functional group on one or more of the building blocks. Building block modification can take place following addition of the final building block or at any intermediate point in the synthesis of the functional moiety, for example, after any cycle of the synthetic process. When a library of bifunctional molecules of the invention is synthesized, building block modification can be carried out on the entire library or on a portion of the library, thereby increasing the degree of complexity of the library. Suitable building block modifying reactions include those reactions that can be performed under conditions compatible with the functional moiety and the encoding oligonucleotide. Examples of such reactions include acylation and sulfonation of amino groups or hydroxyl groups, alkylation of amino groups, esterification or thioesterification of carboxyl groups, amidation of carboxyl groups, epoxidation of alkenes, and other reactions as are known the art. When the functional moiety includes a building block having an alkyne or an azide functional group, the azide/alkyne cycloaddition reaction can be used to derivatize the building block. For example, a building block including an alkyne can be reacted with an organic azide, or a building block including an azide can be reacted with an alkyne, in either case forming a triazole. Building block modification reactions can take place after addition of the final building block or at an intermediate point in the synthetic process, and can be used to append a variety of chemical structures to the functional moiety, including carbohydrates, metal binding moieties and structures for targeting certain biomolecules or tissue types.

In another embodiment, the functional moiety comprises a linear series of building blocks and this linear series is cyclized using a suitable reaction. For example, if at least two building blocks in the linear array include sulfhydryl groups, the sulfhydryl groups can be oxidized to form a disulfide linkage, thereby cyclizing the linear array. For example, the functional moieties can be oligopeptides which include two or more L or D-cysteine and/or L or D-homocysteine moieties. The building blocks can also include other functional groups capable of reacting together to cyclize the linear array, such as carboxyl groups and amino or hydroxyl groups.

In a preferred embodiment, one of the building blocks in the linear array comprises an alkyne group and another building block in the linear array comprises an azide group. The azide and alkyne groups can be induced to react via cycloaddition, resulting in the formation of a macrocyclic structure. In the example illustrated in FIG. 9, the functional moiety is a polypeptide comprising a propargylglycine building block at its C-terminus and an azidoacetyl group at its N-terminus. Reaction of the alkyne and the azide group under suitable conditions results in formation of a cyclic compound, which includes a triazole structure within the macrocycle. In the case of a library, in one embodiment, each member of the library comprises alkyne- and azide-containing building blocks and can be cyclized in this way. In a second embodiment, all members of the library comprises alkyne- and azide-containing building blocks, but only a portion of the library is cyclized. In a third embodiment, only certain functional moieties include alkyne- and azide-containing building blocks, and only these molecules are cyclized. In the forgoing second and third embodiments, the library, following the cycloaddition reaction, will include both cyclic and linear functional moieties.

In some embodiments of the invention in which the same functional moiety, e.g., triazine, is added to each and all of the fractions of the library during a particular synthesis step, it may not be necessary to add an oligonucleotide tag encoding that function moiety.

Oligonucleotides may be ligated by chemical or enzymatic methods. In one embodiment, oligonucleotides are ligated by chemical means. Chemical ligation of DNA and RNA may be performed using reagents such as water soluble carbodiimide and cyanogen bromide as taught by, for example, Shabarova, et al. (1991) *Nucleic Acids Research,* 19, 4247-4251), Federova, et al. (1996) *Nucleosides and Nucleotides,* 15, 1137-1147, and Carriero and Damha (2003) *Journal of Organic Chemistry,* 68, 8328-8338. In one embodiment, chemical ligation is performed using cyanogen bromide, 5 M in acetonitrile, in a 1:10 v/v ratio with 5' phosphorylated oligonucleotide in a pH 7.6 buffer (1 M MES+20 mM $MgCl_2$) at 0 degrees for 1-5 minutes. The oligonucleotides may be double stranded, preferably with an overhang of about 5 to about 14 bases. The oligonucleotide may also be single stranded, in which case a splint with an overlap of about 6 bases with each of the oligonucleotides to be ligated is employed to position the reactive 5' and 3' moieties in proximity with each other.

In another embodiment, the oligonucleotides are ligated using enzymatic methods. In one embodiment, the initial building block is operatively linked to an initial oligonucleotide. Prior to or following coupling of a second building block to the initial building block, a second oligonucleotide sequence which identifies the second building block is ligated to the initial oligonucleotide. Methods for ligating the initial oligonucleotide sequence and the incoming oligonucleotide sequence are set forth in FIGS. 1 and 2. In FIG. 1, the initial oligonucleotide is double-stranded, and one strand includes an overhang sequence which is complementary to one end of the second oligonucleotide and brings the second oligonucleotide into contact with the initial oligonucleotide. Preferably the overhanging sequence of the initial oligonucleotide and the complementary sequence of the second oligonucleotide are both at least about 4 bases; more preferably both sequences are both the same length. The initial oligonucleotide and the second oligonucleotide can be ligated using a suitable enzyme. If the initial oligonucleotide is linked to the first building block at the 5' end of one of the strands (the "top strand"), then the strand which is complementary to the top strand (the "bottom strand") will include the overhang sequence at its 5' end, and the second oligonucleotide will include a complementary sequence at its 5' end. Following ligation of the second oligonucleotide, a strand can be added which is complementary to the sequence of the second oligonucleotide which is 3' to the overhang complementary sequence, and which includes additional overhang sequence.

Figure 2:
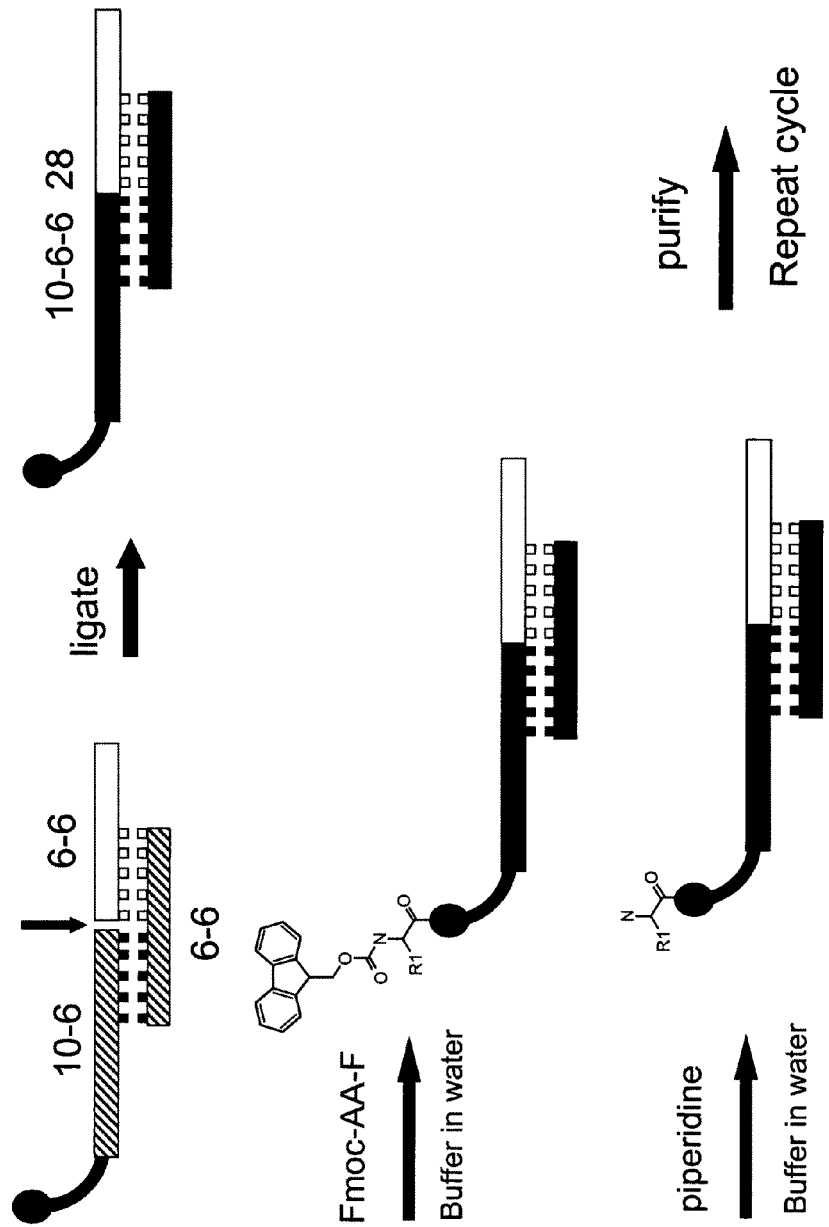
FIG. 2 is a schematic representation of oligonucleotide ligation using a splint strand. In this embodiment, the splint is a 12-mer oligonucleotide with sequences complementary to the single-stranded initial oligonucleotide and the single-stranded incoming oligonucleotide.

In one embodiment, the oligonucleotide is elongated as set forth in FIG. 2. The oligonucleotide bound to the growing functional moiety and the incoming oligonucleotide are positioned for ligation by the use of a "splint" sequence, which includes a region which is complementary to the 3' end of the initial oligonucleotide and a region which is complementary to the 5' end of the incoming oligonucleotide. The splint brings the 5' end of the oligonucleotide into proximity with the 3' end of the incoming oligo and ligation is accomplished using enzymatic ligation. In the example illustrated in FIG. 2, the initial oligonucleotide consists of 16 nucleobases and the splint is complementary to the 6 bases at the 3' end. The incoming oligonucleotide consists of 12 nucleobases, and the splint is complementary to the 6 bases at the 5' terminus. The length of the splint and the lengths of the complementary regions are not critical. However, the complementary regions should be sufficiently long to enable stable dimer formation under the conditions of the ligation, but not so long as to yield an excessively large encoding nucleotide in the final molecules. It is preferred that the complementary regions are from about 4 bases to about 12 bases, more preferably from about 5 bases to about 10 bases, and most preferably from about 5 bases to about 8 bases in length.

The split-and-pool methods used for the methods for library synthesis set forth herein assure that each unique functional moiety is operatively linked to at least one unique oligonucleotide sequence which identifies the functional moiety. If 2 or more different oligonucleotide tags are used for at least one building bock in at least one of the synthetic cycles, each distinct functional moiety comprising that building block will be encoded by multiple oligonucleotides. For example, if 2 oligonucleotide tags are used for each building block during the synthesis of a 4 cycle library, there will be 16 DNA sequences ($2^4$) that encode each unique functional moiety. There are several potential advantages for encoding each unique functional moiety with multiple sequences. First, selection of a different combination of tag sequences encoding the same functional moiety assures that those molecules were independently selected. Second, selection of a different combination of tag sequences encoding the same functional moiety eliminates the possibility that the selection was based on the sequence of the oligonucleotide. Third, technical artifact can be recognized if sequence analysis suggests that a particular functional moiety is highly enriched, but only one sequence combination out of many possibilities appears. Multiple tagging can be accomplished by having independent split reactions with the same building block but a different oligonucleotide tag. Alternatively, multiple tagging can be accomplished by mixing an appropriate ratio of each tag in a single tagging reaction with an individual building block.

Figure 3:
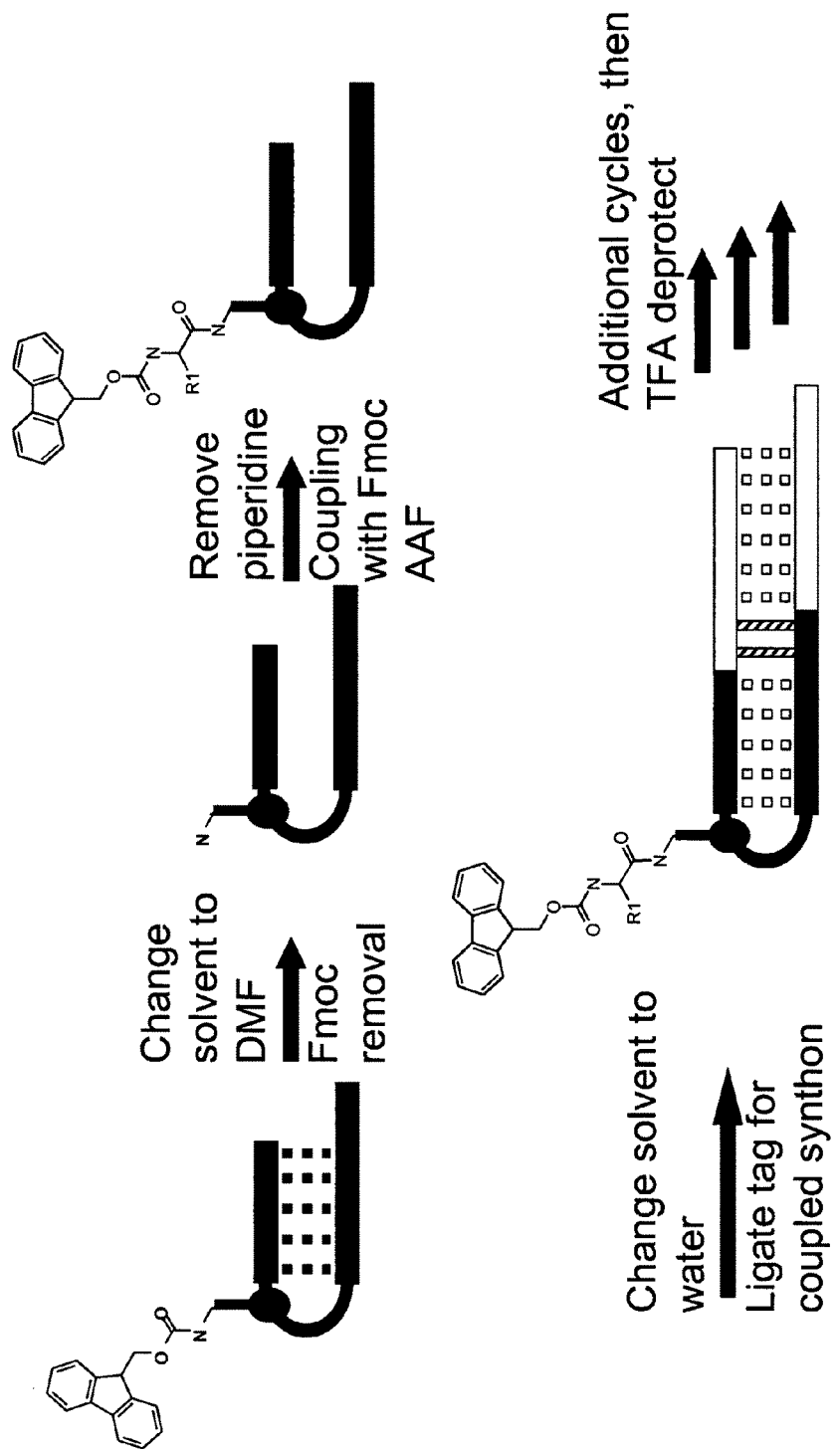
FIG. 3 is a schematic representation of ligation of an initial oligonucleotide and an incoming oligonucleotide, when the initial oligonucleotide is double-stranded with covalently linked strands, and the incoming oligonucleotide is double-stranded.

In one embodiment, the initial oligonucleotide is double-stranded and the two strands are covalently joined. One means of covalently joining the two strands is shown in FIG. 3, in which a linking moiety is used to link the two strands and the functional moiety. The linking moiety can be any chemical structure which comprises a first functional group which is adapted to react with a building block, a second functional group which is adapted to react with the 3'-end of an oligonucleotide, and a third functional group which is adapted to react with the 5'-end of an oligonucleotide. Preferably, the second and third functional groups are oriented so as to position the two oligonucleotide strands in a relative orientation that permits hybridization of the two strands. For example, the linking moiety can have the general structure (I):

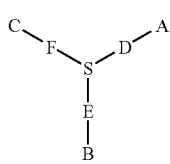
(I)

where A, is a functional group that can form a covalent bond with a building block, B is a functional group that can form a bond with the 5'-end of an oligonucleotide, and C is a functional group that can form a bond with the 3'-end of an oligonucleotide. D, F and E are chemical groups that link functional groups A, C and B to S, which is a core atom or scaffold. Preferably, D, E and F are each independently a chain of atoms, such as an alkylene chain or an oligo(ethylene glycol) chain, and D, E and F can be the same or different, and are preferably effective to allow hybridization of the two oligonucleotides and synthesis of the functional moiety. In one embodiment, the trivalent linker has the structure In this embodiment, the NH group is available for attachment to a building block, while the terminal phosphate groups are available for attachment to an oligonucleotide.

In embodiments in which the initial oligonucleotide is double-stranded, the incoming oligonucleotides are also double-stranded. As shown in FIG. 3, the initial oligonucleotide can have one strand which is longer than the other, providing an overhang sequence. In this embodiment, the incoming oligonucleotide includes an overhang sequence which is complementary to the overhang sequence of the initial oligonucleotide. Hybridization of the two complementary overhang sequences brings the incoming oligonucleotide into position for ligation to the initial oligonucleotide. This ligation can be performed enzymatically using a DNA or RNA ligase. The overhang sequences of the incoming oligonucleotide and the initial oligonucleotide are preferably the same length and consist of two or more nucleotides, preferably from 2 to about 10 nucleotides, more preferably from 2 to about 6 nucleotides. In one preferred embodiment, the incoming oligonucleotide is a double-stranded oligonucleotide having an overhang sequence at each end. The overhang sequence at one end is complementary to the overhang sequence of the initial oligonucleotide, while, after ligation of the incoming oligonucleotide and the initial oligonucleotide, the overhang sequence at the other end becomes the overhang sequence of initial oligonucleotide of the next cycle. In one embodiment, the three overhang sequences are all 2 to 6 nucleotides in length, and the encoding sequence of the incoming oligonucleotide is from 3 to 10 nucleotides in length, preferably 3 to 6 nucleotides in length. In a particular embodiment, the overhang sequences are all 2 nucleotides in length and the encoding sequence is 5 nucleotides in length.

Figure 4:
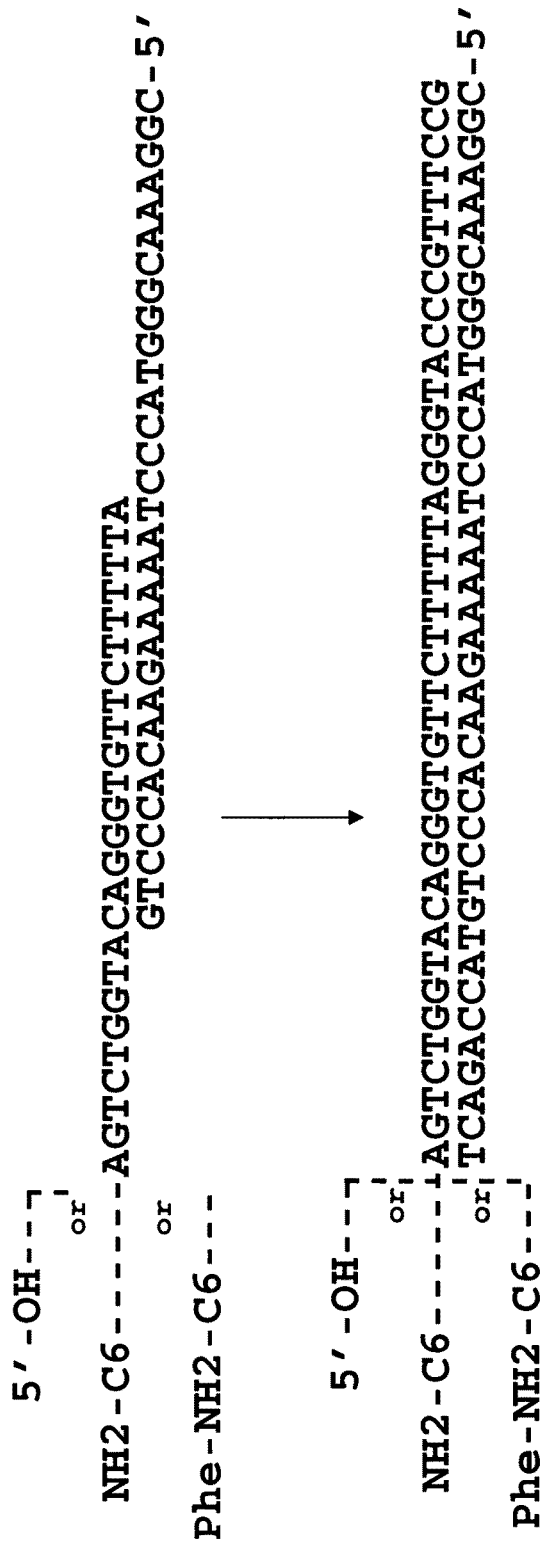
FIG. 4 is a schematic representation of oligonucleotide elongation using a polymerase (SEQ ID NOs:921 & 927-929). The initial strand is represented as either free, conjugated to an aminohexyl linker or conjugated to a phenylalanine residue via an aminohexyl linker.

In the embodiment illustrated in FIG. 4, the incoming strand has a region at its 3' end which is complementary to the 3' end of the initial oligonucleotide, leaving overhangs at the 5' ends of both strands. The 5' ends can be filled in using, for example, a DNA polymerase, such as vent polymerase, resulting in a double-stranded elongated oligonucleotide. The bottom strand of this oligonucleotide can be removed, and additional sequence added to the 3' end of the top strand using the same method.

The encoding oligonucleotide tag is formed as the result of the successive addition of oligonucleotides that identify each successive building block. In one embodiment of the methods of the invention, the successive oligonucleotide tags may be coupled by enzymatic ligation to produce an encoding oligonucleotide.

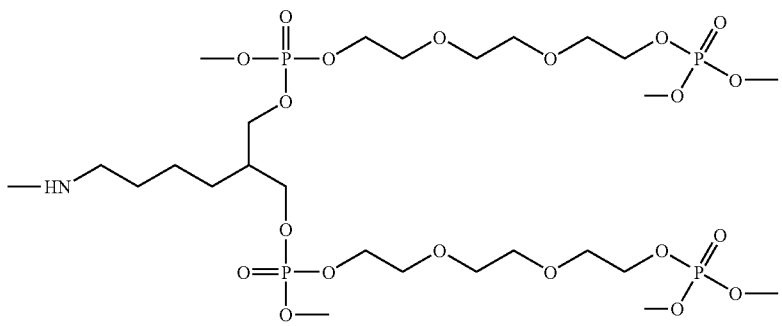

Enzyme-catalyzed ligation of oligonucleotides can be performed using any enzyme that has the ability to ligate nucleic acid fragments. Exemplary enzymes include ligases, polymerases, and topoisomerases. In specific embodiments of the invention, DNA ligase (EC 6.5.1.1), DNA polymerase (EC 2.7.7.7), RNA polymerase (EC 2.7.7.6) or topoisomerase (EC 5.99.1.2) are used to ligate the oligonucleotides. Enzymes contained in each EC class can be found, for example, as described in Bairoch (2000) *Nucleic Acids Research* 28:304-5.

In a preferred embodiment, the oligonucleotides used in the methods of the invention are oligodeoxynucleotides and the enzyme used to catalyze the oligonucleotide ligation is DNA ligase. In order for ligation to occur in the presence of the ligase, i.e., for a phosphodiester bond to be formed between two oligonucleotides, one oligonucleotide must have a free 5' phosphate group and the other oligonucleotide must have a free 3' hydroxyl group. Exemplary DNA ligases that may be used in the methods of the invention include T4 DNA ligase, Taq DNA ligase, $T_4$ RNA ligase, DNA ligase (*E. coli*) (all available from, for example, New England Biolabs, MA).

One of skill in the art will understand that each enzyme used for ligation has optimal activity under specific conditions, e.g., temperature, buffer concentration, pH and time. Each of these conditions can be adjusted, for example, according to the manufacturer's instructions, to obtain optimal ligation of the oligonucleotide tags.

The incoming oligonucleotide can be of any desirable length, but is preferably at least three nucleobases in length. More preferably, the incoming oligonucleotide is 4 or more nucleobases in length. In one embodiment, the incoming oligonucleotide is from 3 to about 12 nucleobases in length. It is preferred that the oligonucleotides of the molecules in the libraries of the invention have a common terminal sequence which can serve as a primer for PCR, as is known in the art. Such a common terminal sequence can be incorporated as the terminal end of the incoming oligonucleotide added in the final cycle of the library synthesis, or it can be added following library synthesis, for example, using the enzymatic ligation methods disclosed herein.

Figure 5:
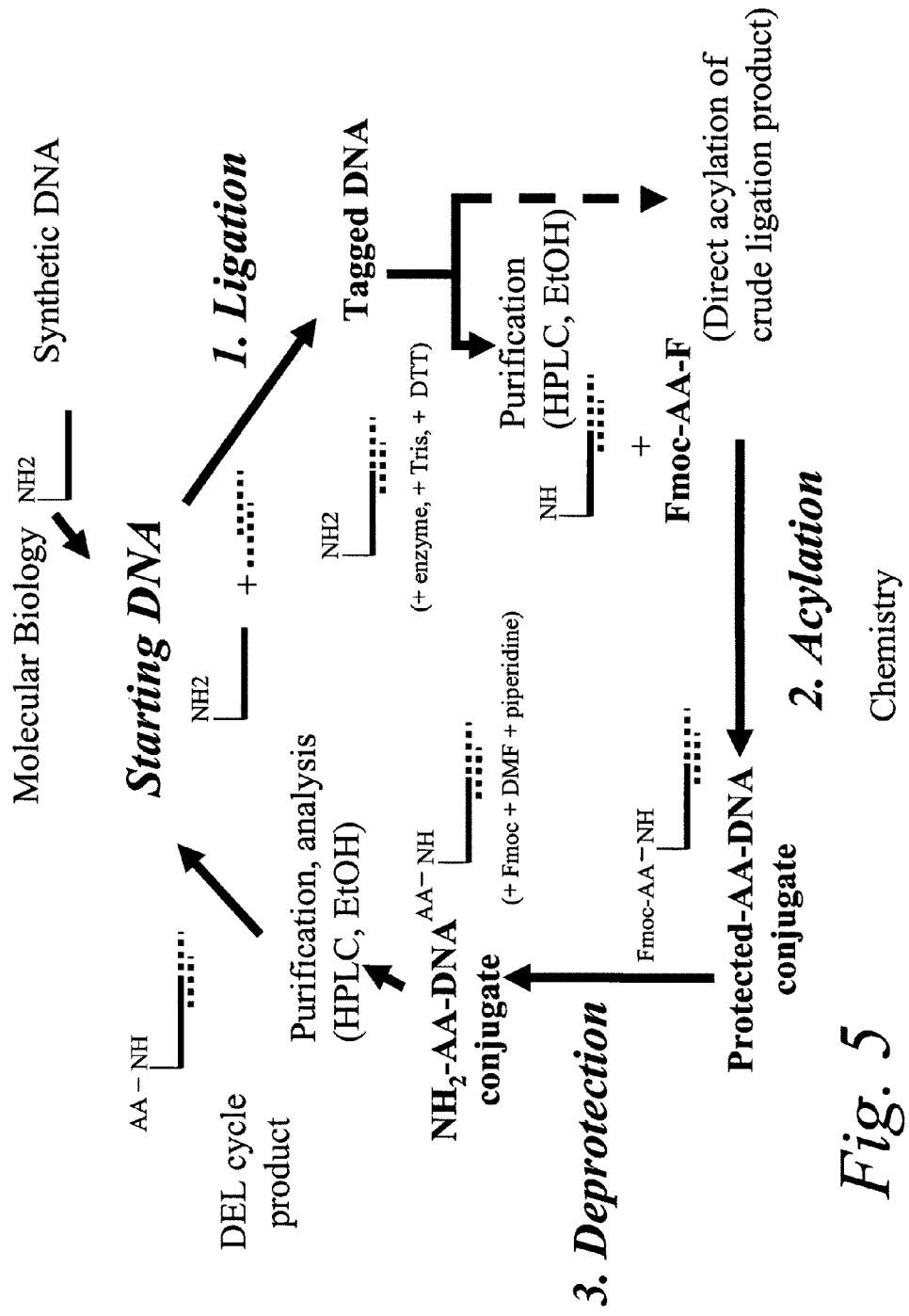
FIG. 5 is a schematic representation of the synthesis cycle of one embodiment of the invention.

A preferred embodiment of the method of the invention is set forth in FIG. 5. The process begins with a synthesized DNA sequence which is attached at its 5' end to a linker which terminates in an amino group. In step 1, this starting DNA sequence is ligated to an incoming DNA sequence in the presence of a splint DNA strand, DNA ligase and dithiothreitol in Tris buffer. This yields a tagged DNA sequence which can then be used directly in the next step or purified, for example, using HPLC or ethanol precipitation, before proceeding to the next step. In step 2 the tagged DNA is reacted with a protected activated amino acid, in this example, an Fmoc-protected amino acid fluoride, yielding a protected amino acid-DNA conjugate. In step 3, the protected amino acid-DNA conjugate is deprotected, for example, in the presence of piperidine, and the resulting deprotected conjugate is, optionally, purified, for example, by HPLC or ethanol precipitation. The deprotected conjugate is the product of the first synthesis cycle, and becomes the starting material for the second cycle, which adds a second amino acid residue to the free amino group of the deprotected conjugate.

In embodiments in which PCR is to be used to amplify and/or sequence the encoding oligonucleotides of selected molecules, the encoding oligonucleotides may include, for example, PCR primer sequences and/or sequencing primers (e.g., primers such as, for example, 3'-GACTACCGCGCTC-CCTCCG-5' (SEQ ID NO:891) and 3'-GACTCGCCCGAC-CGTTCCG-5'(SEQ ID NO:892)). A PCR primer sequence can be included, for example, in the initial oligonucleotide prior to the first cycle of synthesis, and/or it can be included with the first incoming oligonucleotide, and/or it can be ligated to the encoding oligonucleotide following the final cycle of library synthesis, and/or it can be included in the incoming oligonucleotide of the final cycle. The PCR primer sequences added following the final cycle of library synthesis and/or in the incoming oligonucleotide of the final cycle are referred to herein as "capping sequences".

In one embodiment, the PCR primer sequence is designed into the encoding oligonucleotide tag. For example, a PCR primer sequence may be incorporated into the initial oligonucleotide tag and/or it may be incorporated into the final oligonucleotide tag. In one embodiment the same PCR primer sequence is incorporated into the initial and final oligonucleotide tag. In another embodiment, a first PCR sequence is incorporated into the initial oligonucleotide tag and a second PCR primer sequence is incorporated in the final oligonucleotide tag. Alternatively, the second PCR primer sequence may be incorporated into the capping sequence as described herein. In preferred embodiments, the PCR primer sequence is at least about 5, 7, 10, 13, 15, 17, 20, 22, or 25 nucleotides in length.

PCR primer sequences suitable for use in the libraries of the invention are known in the art; suitable primers and methods are set forth, for example, in Innis, et al., eds., *PCR Protocols: A Guide to Methods and Applications*, San Diego: Academic Press (1990), the contents of which are incorporated herein by reference in their entirety. Other suitable primers for use in the construction of the libraries described herein are those primers described in PCT Publications WO 2004/069849 and WO 2005/003375, the contents of which are expressly incorporated herein by reference.

The term "polynucleotide" as used herein in reference to primers, probes and nucleic acid fragments or segments to be synthesized by primer extension is defined as a molecule comprised of two or more deoxyribonucleotides, preferably more than three.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer.

The primers used herein are selected to be "substantially" complementary to the different strands of each specific sequence to be amplified. This means that the primer must be sufficiently complementary so as to non-randomly hybridize with its respective template strand. Therefore, the primer sequence may or may not reflect the exact sequence of the template.

The polynucleotide primers can be prepared using any suitable method, such as, for example, the phosphotriester or phosphodiester methods described in Narang et al., (1979) Meth. Enzymol., 68:90; U.S. Pat. No. 4,356,270, U.S. Pat. No. 4,458,066, U.S. Pat. No. 4,416,988, U.S. Pat. No. 4,293,652; and Brown et al., (1979) Meth. Enzymol., 68:109. The contents of all the foregoing documents are incorporated herein by reference.

In cases in which the PCR primer sequences are included in an incoming oligonucleotide, these incoming oligonucleotides will preferably be significantly longer than the incoming oligonucleotides added in the other cycles, because they will include both an encoding sequence and a PCR primer sequence.

In one embodiment, the capping sequence is added after the addition of the final building block and final incoming oligonucleotide, and the synthesis of a library as set forth herein includes the step of ligating the capping sequence to the encoding oligonucleotide, such that the oligonucleotide portion of substantially all of the library members terminates in a sequence that includes a PCR primer sequence. Preferably, the capping sequence is added by ligation to the pooled

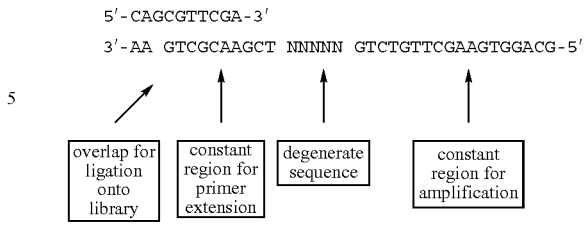

where N can be any of the 4 bases, permitting 1024 different sequences ($4^5$). The primer has the following sequence after its ligation onto the library and primer-extension:

(SEQ ID NO: 895)
5'-CAGCGTTCGA N'N'N'N'N'CAGACAAGCTTCACCTGC-3'

(SEQ ID NO: 896)
3'-AA GTCGCAAGCT N N N N N GTCTGTTCGAAGTGGACG-5'

In another embodiment, the capping primer comprises or has the following sequence:

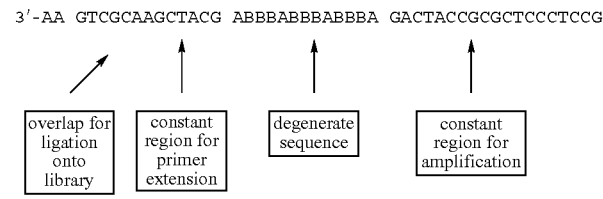

fractions which are products of the final synthetic cycle. The capping sequence can be added using the enzymatic process used in the construction of the library.

In one embodiment, the same capping sequence is ligated to every member of the library. In another embodiment, a plurality of capping sequences are used. In this embodiment, oligonucleotide capping sequences containing variable bases are, for example, ligated onto library members following the final synthetic cycle. In one embodiment, following the final synthetic cycle, the fractions are pooled and then split into fractions again, with each fraction having a different capping sequence added. Alternatively, multiple capping sequences can be added to the pooled library following the final synthesis cycle. In both embodiments, the final library members will include molecules comprising specific functional moieties linked to identifying oligonucleotides including two or more different capping sequences.

In one embodiment, the capping primer comprises an oligonucleotide sequence containing variable, i.e., degenerate, nucleotides. Such degenerate bases within the capping primers permit the identification of library molecules of interest by determining whether a combination of building blocks is the consequence of PCR duplication (identical sequence) or independent occurrences of the molecule (different sequence). For example, such degenerate bases may reduce the potential number of false positives identified during the biological screening of the encoded library.

In one embodiment, a degenerate capping primer comprises or has the following sequence:

where B can be any of C, G or T, permitting 19,683 different sequences ($3^9$). The design of the degenerate region in this primer improves DNA sequence analysis, as the A bases that flank and punctuate the degenerate B bases prevent homopolymeric stretches of greater than 3 bases, and facilitate sequence alignment.

In one embodiment, the degenerate capping oligonucleotide is ligated to the members of the library using a suitable enzyme and the upper strand of the degenerate capping oligonucleotide is subsequently polymerized using a suitable enzyme, such as a DNA polymerase.

In another embodiment, the PCR priming sequence is a "universal adaptor" or "universal primer". As used herein, a "universal adaptor" or "universal primer" is an oligonucleotide that contains a unique PCR priming region, that is, for example, about 5, 7, 10, 13, 15, 17, 20, 22, or 25 nucleotides in length, and is located adjacent to a unique sequencing priming region that is, for example, about 5, 7, 10, 13, 15, 17, 20, 22, or 25 nucleotides in length, and is optionally followed by a unique discriminating key sequence (or sample identifier sequence) consisting of at least one of each of the four deoxyribonucleotides (i.e., A, C, G, T).

As used herein, the term "discriminating key sequence" or "sample identifier sequence" refers to a sequence that may be used to uniquely tag a population of molecules from a sample. Multiple samples, each containing a unique sample identifier sequence, can be mixed, sequenced and re-sorted after DNA sequencing for analysis of individual samples. The same discriminating sequence can be used for an entire library or, alternatively, different discriminating key sequences can be used to track different libraries. In one embodiment, the discriminating key sequence is on either the 5' PCR primer, the 3' PCR primer, or on both primers. If both PCR primers contain a sample identifier sequence, the number of different samples that can be pooled with unique sample identifier sequences is the product of the number of sample identifier sequences on each primer. Thus, 10 different 5' sample identifier sequence primers can be combined with 10 different 3' sample identifier sequence primers to yield 100 different sample identifier sequence combinations.

Non-limiting examples of 5' and 3' unique PCR primers containing discriminating key sequences include the following:

```
5' primers
(variable positions bold and italicized):
                                        (SEQ ID NO: 898)
5' A-GCCTTGCCAGCCCGCTCAGATGACTCCCAAATCGATGTG;

(SEQ ID NO: 899)
5' C-GCCTTGCCAGCCCGCTCAGCTGACTCCCAAATCGATGTG;

(SEQ ID NO: 900)
5' G-GCCTTGCCAGCCCGCTCAGGTGACTCCCAAATCGATGTG;

(SEQ ID NO: 901)
5' T-GCCTTGCCAGCCCGCTCAGTTGACTCCCAAATCGATGTG;

(SEQ ID NO: 902)
5' AA-GCCTTGCCAGCCCGCTCAGAATGACTCCCAAATCGATGTG;

(SEQ ID NO: 903)
5' AC-GCCTTGCCAGCCCGCTCAGACTGACTCCCAAATCGATGTG;

(SEQ ID NO: 904)
5' AG-GCCTTGCCAGCCCGCTCAGAGTGACTCCCAAATCGATGTG;

(SEQ ID NO: 905)
5' AT-GCCTTGCCAGCCCGCTCAGATTGACTCCCAAATCGATGTG;
and (SEQ ID NO: 906)
5' CA-GCCTTGCCAGCCCGCTCAGCATGACTCCCAAATCGATGTG.

3' SID primers
(variable positions bold and italicized):
                                        (SEQ ID NO: 907)
3' A-GCCTCCCTCGCGCCATCAGAGCAGGTGAAGCTTGTCTG;

(SEQ ID NO: 908)
3' C-GCCTCCCTCGCGCCATCAGCGCAGGTGAAGCTTGTCTG;

(SEQ ID NO: 909)
3' G-GCCTCCCTCGCGCCATCAGGGCAGGTGAAGCTTGTCTG;

(SEQ ID NO: 910)
3' T-GCCTCCCTCGCGCCATCAGTGCAGGTGAAGCTTGTCTG;

(SEQ ID NO: 911)
3' AA-GCCTCCCTCGCGCCATCAGAAGCAGGTGAAGCTTGTCTG;

(SEQ ID NO: 912)
3' AC-GCCTCCCTCGCGCCATCAGACGCAGGTGAAGCTTGTCTG;

(SEQ ID NO: 913)
3' AG-GCCTCCCTCGCGCCATCAGAGGCAGGTGAAGCTTGTCTG;

(SEQ ID NO: 914)
3' AT-GCCTCCCTCGCGCCATCAGATGCAGGTGAAGCTTGTCTG;
and (SEQ ID NO: 915)
3' CA-GCCTCCCTCGCGCCATCAGCAGCAGGTGAAGCTTGTCTG
```

In one embodiment, the discriminating key sequence is about 4, 5, 6, 7, 8, 9, or 10 nucleotides in length. In another embodiment, the discriminating key sequence is a combination of about 1-4 nucleotides. In yet another embodiment, each universal adaptor is about forty-four nucleotides in length. In one embodiment the universal adaptors are ligated, using T4 DNA ligase, onto the end of the encoding oligonucleotide. Different universal adaptors may be designed specifically for each library preparation and will, therefore, provide a unique identifier for each library. The size and sequence of the universal adaptors may be modified as deemed necessary by one of skill in the art.

In one embodiment, the universal adaptor added as a capping sequence is linked to a support binding moiety. For example, a 5'-biotin is added to the universal adaptor to allow, for example, isolation of single-stranded DNA template as well as non-covalent coupling of the universal adaptor to the surface of a solid support that is saturated with a biotin-binding protein (i.e., streptavidin, neutravidin or avidin). Other linkages are well known in the art and may be used in place of biotin-streptavidin (for example antibody/antigen-epitope, receptor/ligand and oligonucleotide pairing or complimentarily).

In another embodiment, the capping sequence contains anchor primer sequences such that the members of the library may be attached to a solid substrate. In one embodiment, the anchor primer sequences are annealed to the capping sequences using recognized techniques (see, e.g., Hatch, et al. (1999) *Genet. Anal Biomol Engineer* 15: 35-40; U.S. Pat. No. 5,714,320, and U.S. Pat. No. 5,854,033). In general, any procedure for annealing the anchor primers to the capping sequences is suitable as long as it results in formation of specific, i.e., perfect or nearly perfect, complementarity between the adapter region or regions in the anchor primer sequence and a sequence present in the capping sequences. The anchoring of the encoding oligonucleotide to the solid surface may be reversible or irreversible, e.g., the anchor to the solid surface may be cleavable or non-cleavable.

In one embodiment, the universal primer, is annealed to a solid support that contains oligonucleotide capture primers that are complementary to the PCR priming regions of the universal adaptor ends.

In one embodiment, the solid support is a bead, for example, a sepharose bead. The beads may be of any convenient size and fabricated from any number of known materials. Example of such materials include: inorganics, natural polymers, and synthetic polymers. Specific examples of these materials include: cellulose, cellulose derivatives, acrylic resins, glass; silica gels, polystyrene, gelatin, polyvinyl pyrrolidone, co-polymers of vinyl and acrylamide, polystyrene cross-linked with divinylbenzene or the like (see, Merrifield (1964) *Biochemistry* 3:1385-1390), polyacrylamides, latex gels, polystyrene, dextran, rubber, silicon, plastics, nitrocellulose, celluloses, natural sponges, silica gels, glass, metals plastic, cellulose, cross-linked dextrans (e.g., Sephadex™) and agarose gel (Sepharose™) and solid phase supports known to those of skill in the art.

The encoding oligonucleotides may be attached to the solid support capture bead ("DNA capture bead") in any manner known in the art. Any suitable coupling agent known in the art can be used, such as, for example, water-soluble carbodiimide, to link the 5'-phosphate on the DNA to amine-coated capture beads through a phosphoamidate bond, coupling specific oligonucleotide linkers to the bead using similar chemistry, and using DNA ligase to link the DNA to the linker on the bead, joining the oligonucleotide to the beads using N-hydroxysuccinamide (NHS) and its derivatives, such that one end of the oligonucleotide may contain a reactive group (such as an amide group) which forms a covalent bond with the solid support, while the other end of the linker contains a second reactive group that can bond with the oligonucleotide to be immobilized.

In another embodiment, the oligonucleotide is bound to the DNA capture bead by non-covalent linkage, such as chelation or antigen-antibody complexes, may also be used to join the oligonucleotide to the bead. Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially. These methods are described in detail in U.S. Pat. No. 5,674,743. It is preferred that any method used to immobilize the beads will continue to bind the immobilized oligonucleotide throughout the steps in the methods of the invention.

In one embodiment, the oligonucleotide is attached to a solid support manufactured from, for example, glass, plastic, a nylon membrane, a gel matrix, ceramics, silica, silicon, or any other non-reactive material as described in U.S. Pat. No. 6,787,308, the entire contents of which are incorporated by reference. The supports generally comprise a flat, i.e., planar, surface, or at least an array in which the molecules to be analysed are in the same plane. The oligonucleotide may be attached by specific covalent or non-covalent interactions. In one embodiment of the invention, the surface of a solid support is coated with streptavidin or avidin. In another embodiment of the invention, the solid surface is coated with an epoxide and the molecules are coupled via an amine linkage. In yet another embodiment, the encoding oligonucleotide may be attached to a solid support via hybridization to a complementary nucleic acid molecule previously attached to the solid support.

In one embodiment, the solid support is pretreated to create surface chemistry that facilitates oligonucleotide attachment and subsequent sequence analysis. In one embodiment, the solid support is coated with a polyelectrolyte multilayer (PEM). In another embodiment, the encoding oligonucleotide is attached to the surface of a microfabricated channel or to the surface of reaction chambers that are disposed along a microfabricated flow channel, optionally with streptavidin-biotin links. The methods of each of these attachment methods are described in PCT Publication No. WO 2005/080605, the entire contents of which are incorporated by reference.

In one embodiment, the encoding oligonucleotide is attached to a solid surface at high density and at single molecule resolution. In one embodiment, the encoding oligonucleotide is attached to a solid surface at an individually-addressable location (see, e.g., PCT Publication No. WO 2005/080605).

Attachment of the encoding oligonucleotide to any suitable solid surface can occur prior to the hybridization of a primer for amplification and/or sequencing or alternatively, the encoding oligonucleotide can be attached to any suitable solid surface after the hybridization of a primer for amplification and/or sequencing.

In another embodiment, the oligonucleotide is attached to a particle, such as a microsphere, which is itself attached to a solid support. The microspheres may be of any suitable size, typically in the range of from 10 nm to 100 nm in diameter.

In one embodiment, the universal adaptors are not 5'-phosphorylated. Accordingly, "gaps" or "nicks" can be filled in by using a DNA polymerase enzyme that can bind, strand displace and extend the nicked DNA fragments according to techniques recognized in the art. DNA polymerases that lack 3→5' exonuclease activity but exhibit 5→3' exonuclease activity have the ability to recognize nicks, displace the nicked strands, and extend the strand in a manner that results in the repair of the nicks and in the formation of non-nicked double-stranded DNA (Hamilton, et al. (2001) *BioTechniques* 31:370).

Several modifying enzymes are utilized for the nick repair step, including but not limited to polymerase, ligase and kinase. DNA polymerases that can be used for this application include, for example, *E. coli* DNA pol I, *Thermoanaerobacter thermohydrosulfuricus* pol I, and bacteriophage phi 29. In one embodiment, the strand displacing enzyme *Bacillus stearothermophilus* pol I (Bst DNA polymerase I) is used to repair the nicked dsDNA and results in non-nicked dsDNA. In another embodiment, the ligase is T4 and the kinase is polynucleotide kinase.

The invention further relates to the compounds which can be produced using the methods of the invention, and collections of such compounds, either as isolated species or pooled to form a library of chemical structures. Compounds of the invention include compounds of the formula

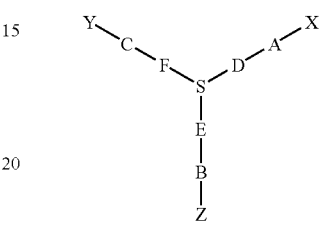

where X is a functional moiety comprising one or more building blocks, Z is an oligonucleotide attached at its 3' terminus to B and Y is an oligonucleotide which is attached to C at its 5' terminus. A is a functional group that forms a covalent bond with X, B is a functional group that forms a bond with the 3'-end of Z and C is a functional group that forms a bond with the 5'-end of Y, D, F and E are chemical groups that link functional groups A, C and B to S, which is a core atom or scaffold. Preferably, D, E and F are each independently a chain of atoms, such as an alkylene chain or an oligo(ethylene glycol) chain, and D, E and F can be the same or different, and are preferably effective to allow hybridization of the two oligonucleotides and synthesis of the functional moiety.

Preferably, Y and Z are substantially complementary and are oriented in the compound so as to enable Watson-Crick base pairing and duplex formation under suitable conditions. Y and Z are the same length or different lengths. Preferably, Y and Z are the same length, or one of Y and Z is from 1 to 10 bases longer than the other. In a preferred embodiment, Y and Z are each 10 or more bases in length and have complementary regions of ten or more base pairs. More preferably, Y and Z are substantially complementary throughout their length, i.e., they have no more than one mismatch per every ten base pairs. Most preferably, Y and Z are complementary throughout their length, i.e., except for any overhang region on Y or Z, the strands hybridize via Watson-Crick base pairing with no mismatches throughout their entire length.

S can be a single atom or a molecular scaffold. For example, S can be a carbon atom, a boron atom, a nitrogen atom or a phosphorus atom, or a polyatomic scaffold, such as a phosphate group or a cyclic group, such as a cycloalkyl, cycloalkenyl, heterocycloalkyl, heterocycloalkenyl, aryl or heteroaryl group. In one embodiment, the linker is a group of the structure

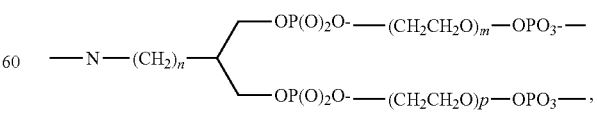

where each of n, m and p is, independently, an integer from 1 to about 20, preferably from 2 to eight, and more preferably from 3 to 6. In one particular embodiment, the linker has the structure shown below.

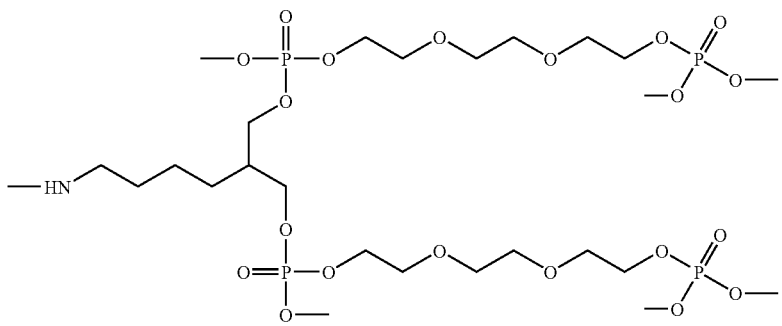

In one embodiment, the libraries of the invention include molecules consisting of a functional moiety composed of building blocks, where each functional moiety is operatively linked to an encoding oligonucleotide. The nucleotide sequence of the encoding oligonucleotide is indicative of the building blocks present in the functional moiety, and in some embodiments, the connectivity or arrangement of the building blocks. The invention provides the advantage that the methodology used to construct the functional moiety and that used to construct the oligonucleotide tag can be performed in the same reaction medium, preferably an aqueous medium, thus simplifying the method of preparing the library compared to methods in the prior art. In certain embodiments in which the oligonucleotide ligation steps and the building block addition steps can both be conducted in aqueous media, each reaction will have a different pH optimum. In these embodiments, the building block addition reaction can be conducted at a suitable pH and temperature in a suitable aqueous buffer. The buffer can then be exchanged for an aqueous buffer which provides a suitable pH for oligonucleotide ligation.

In another embodiment, the invention provides compounds, and libraries comprising such compounds, of Formula II $$Z\text{-}L\,A_t\text{-}X(Y)_n \qquad (II)$$

where X is a molecular scaffold, each Y is independently, a peripheral moiety, and n is an integer from 1 to 6. Each A is independently, a building block and n is an integer from 0 to about 5. L is a linking moiety and Z is a single-stranded or double-stranded oligonucleotide which identifies the structure -$A_t$-X(Y)$_n$. The structure X(Y)$_n$ can be, for example, one of the scaffold structures set forth in Table 8 (see below). In one embodiment, the invention provides compounds, and libraries comprising such compounds, of Formula III:

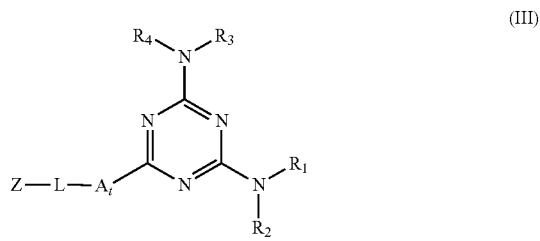

where t is an integer from 0 to about 5, preferably from 0 to 3, and each A is, independently, a building block. L is a linking moiety and Z is a single-stranded or double-stranded oligonucleotide which identifies each A and $R_1$, $R_2$, $R_3$ and $R_4$. $R_1$, $R_2$, $R_3$ and $R_4$ are each independently a substituent selected from hydrogen, alkyl, substituted alkyl, heteroalkyl, substituted heteroalkyl, cycloalkyl, heterocycloalkyl, substituted cycloalkyl, substituted heterocycloalkyl, aryl, substituted aryl, arylalkyl, heteroarylalkyl, substituted arylalkyl, substituted heteroarylalkyl, heteroaryl, substituted heteroaryl, alkoxy, aryloxy, amino, and substituted amino. In one embodiment, each A is an amino acid residue.

Libraries which include compounds of Formula II or Formula III can comprise at least about 100; 1000; 10,000; 100,000; 1,000,000 or 10,000,000 compounds of Formula II or Formula III. In one embodiment, the library is prepared via a method designed to produce a library comprising at least about 100; 1000; 10,000; 100,000; 1,000,000 or 10,000,000 compounds of Formula II or Formula III.

TABLE 8

| Scaffolds | Amine | Aldehyde/Ketone |
|---|---|---|

TABLE 8-continued
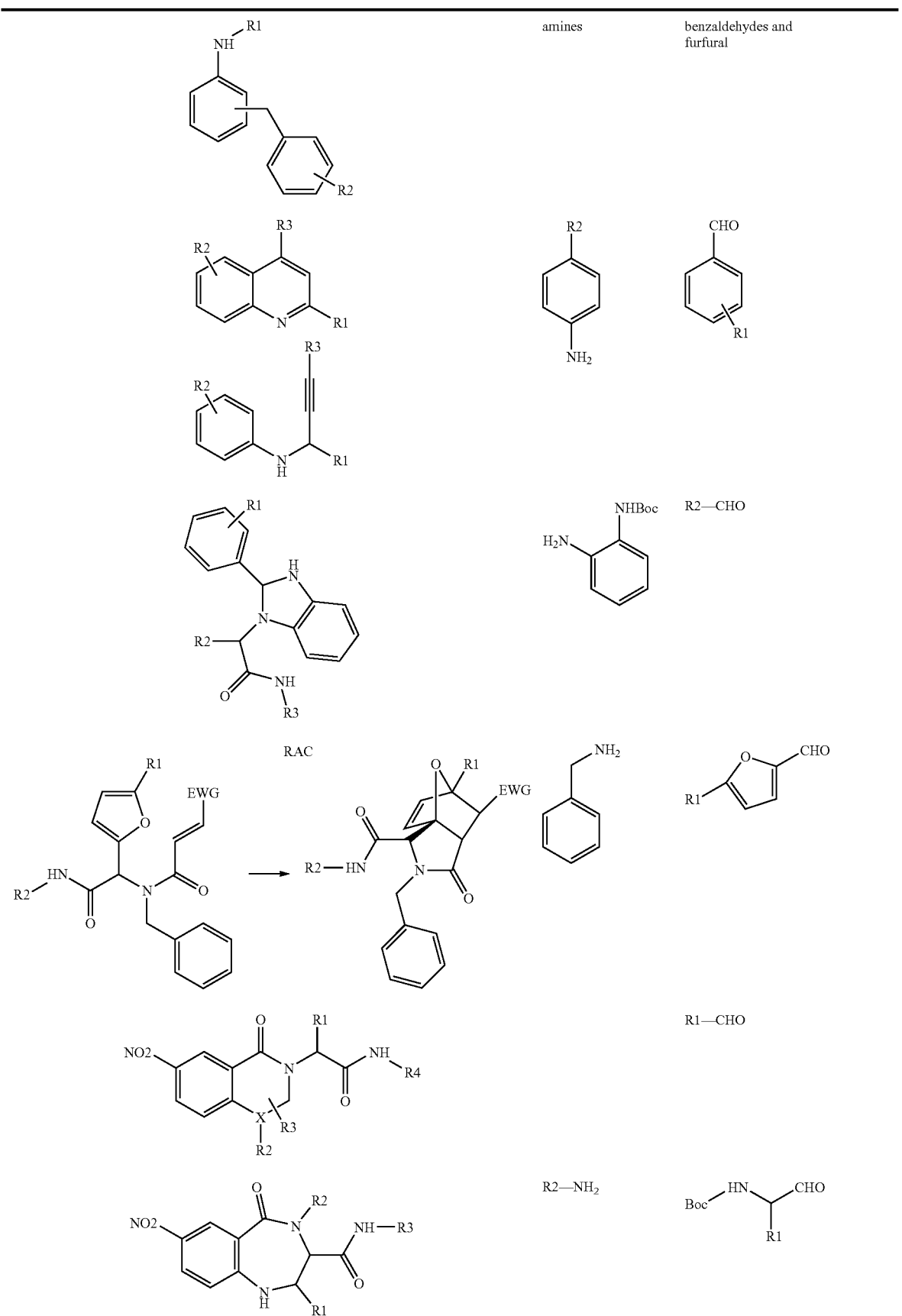

TABLE 8-continued
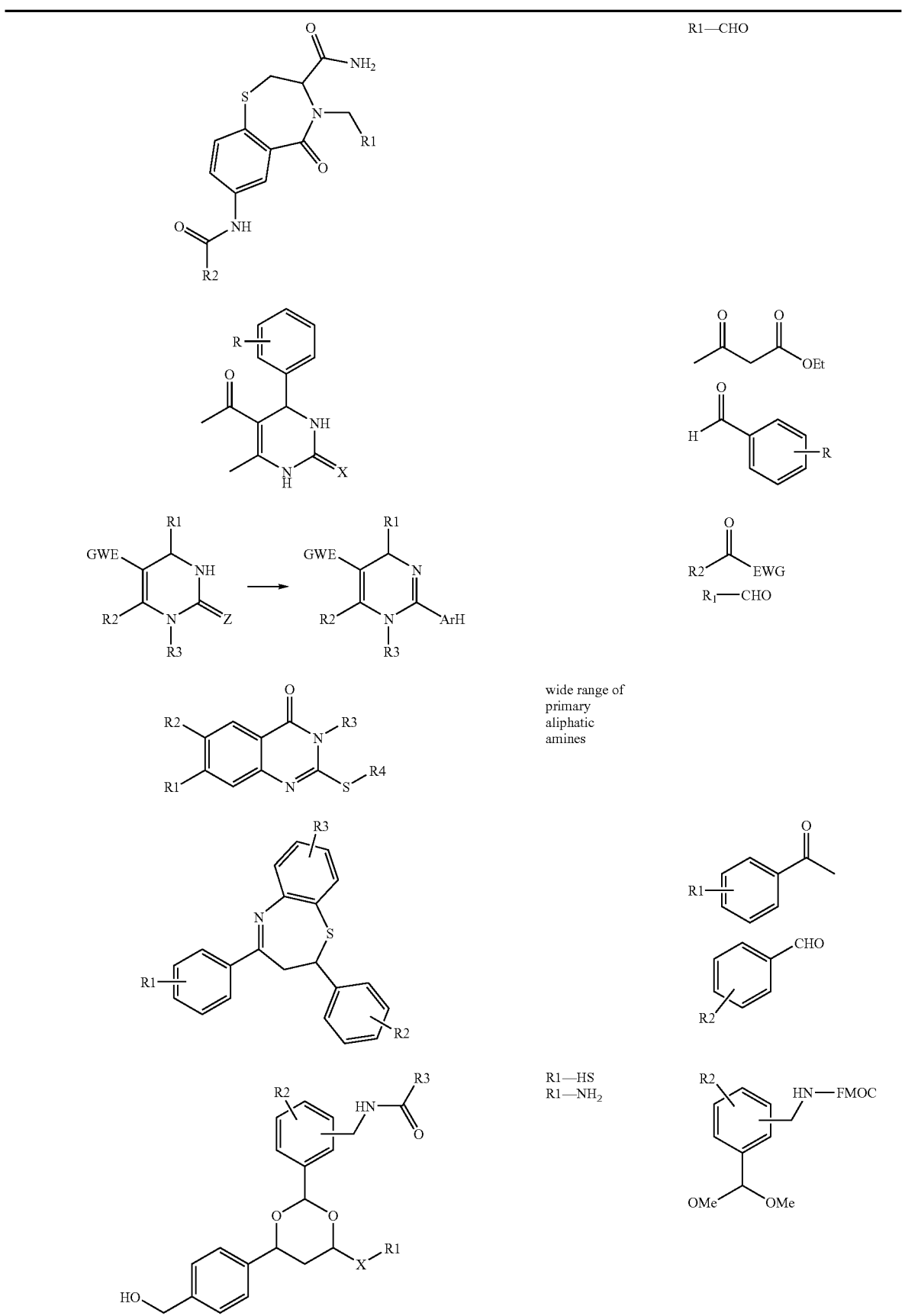

TABLE 8-continued
| | |
|---|---|
| DIA 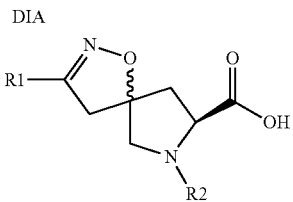 | 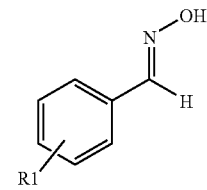 |
| 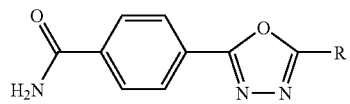 | 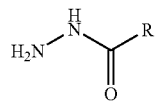 |
| 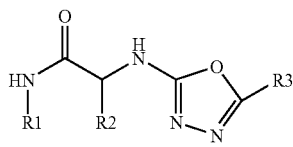 | R1—NH$_2$ |
| 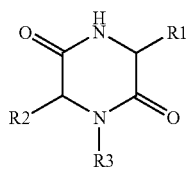 | amino acid |
| 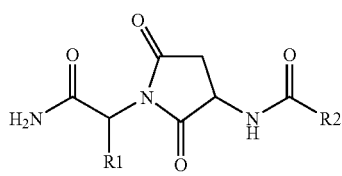 | amino acid |
| RAC 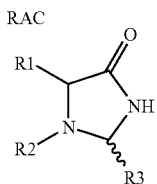 | R2—CHO |
| 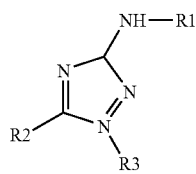 | R1—NH$_2$ |
| 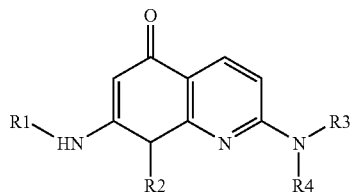 | |

TABLE 8-continued
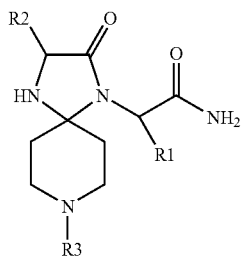
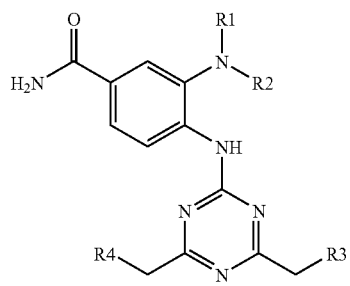
| | Amines | Aldehydes |
|---|---|---|
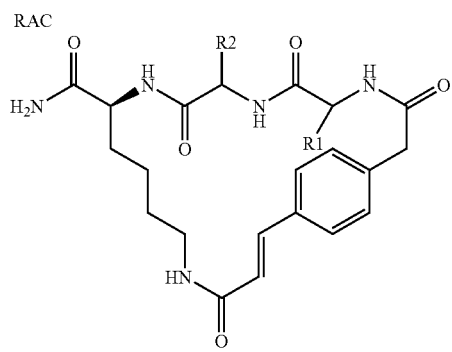
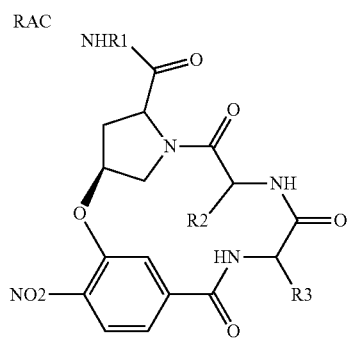
| Carboxylic acid | Other | Reference |
|---|---|---|
| | 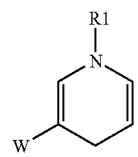 | Carranco, I., et al. (2005) J. Comb. Chem. 7:33-41 |
| | 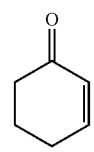 | Rosamilia, A. E., et al. (2005) Organic Letters 7:1525-1528 |

TABLE 8-continued

| Reactant 1 | Reactant 2 | Reference |
|---|---|---|
| R1-C6H4-COOH | ≡—R3 | Syeda Huma, H. Z., et al. (2002) Tet Lett 43:6485-6488 |
| | ≡N—R3 | Tempest, P., et al. (2001) Tet Lett 42:4959-4962 |
| HOOC-CH2CH2-EWG (COOH...EWG) | benzyl isocyanide (PhCH2-NC) | Paulvannan, K. (1999) Tet Lett 40:1851-1854 |
| 5-NO2-2-F-benzoic acid | ≡N—R4 | Tempest, P., et al. (2001) Tet Lett 42:4963-4968 |
| 5-NO2-2-F-benzoic acid | ≡N—R3 | Tempest, P., et al. (2003) Tet Lett 44:1947-1950 |
| R2—COOH | Fmoc-Cys(S-Ar(COOMe)(NO2))-OH | Nefzi, A., et al. (1999) Tet Lett 40:4939-4942 |
| | thiourea (H2N-C(=S)-NH2) | Bose, A. K., et al. (2005) Tet Lett 46:1901-1903 |
| | urea (H2N-C(=O)-NH2) | |
| | R3-HN-C(=Z)-NH2 | Stadler, A. and Kappe, C. O. (2001) J. Comb. Chem. 3:624-630; Lengar, A. and Kappe, C. O. (2004) Organic Letters 6:771-774 |
| R2-, CO2Me, methyl-, NCS-substituted benzene | Cl-CH2-R4 | Ivachtchenko, A. V., et al. (2003) J. Comb. Chem. 5:775-788 |
| | R3-C6H3(SH)(NH2) | Micheli, F., et al. (2001) J. Comb. Chem. 3:224-228 |

TABLE 8-continued

| | | | |
|---|---|---|---|
| 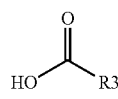 | RAC | 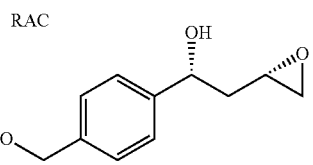 | Sternson, S. M., et al. (2001) Org. Lett. 3:4239-4242 |
| | RAC | 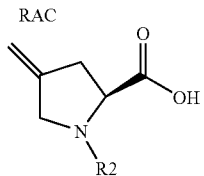 | Cheng, W.-C., et al. (2002) J. Org. Chem. 67:5673-5677; Park, K.-H., et al. (2001) J Comb Chem 3:171-176 |
| 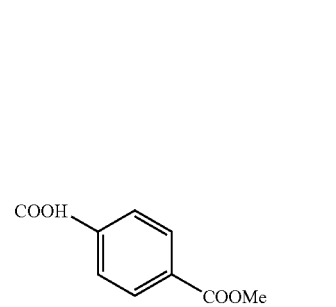 | | | Brown, B. J., et al. (2000) Synlett 1:131-133 |
| | | 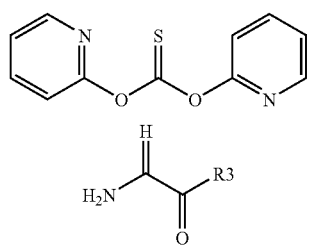 | Kilburn, J. P., et al. (2001) Tet Lett 42:2583-2586 |
| 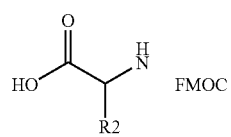 | | | |
| amino acid ester | | | del Fresno, M., et al. (1998) Tet Lett 39:2639-2642 |
| carboxylic acids | | | Alvarez-Gutierrez, J. M., et al. (2000) Tet Lett 41:609-612 |
| 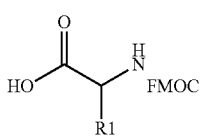 | RAC | 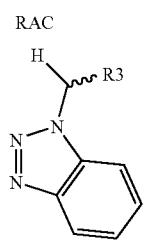 | Rinnová, M., et al. (2002) J. Comb. Chem 4:209-213 |
| 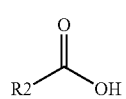 | | 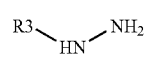 | Makara, G. M., et al. (2002) Organic Lett 4:1751-1754 |
| | | 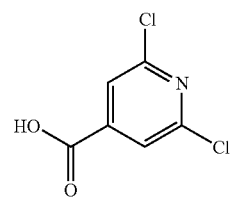 | Schell, P., et al. (2005) J. Comb. Chem 7:96-98 |
| amino acids | | | Feliu, L., et al. (2003) J. Comb. Chem. 5:356-361 |
| amino acids | | | Hiroshige, M., et al. (1995) J. Am. Chem. Soc. 117:11590-11591 |

| | |
|---|---|
| amino acids | Bose, A. K., et al. (2005) Tet Lett 46:1901-1903 |

TABLE 8-continued

One advantage of the methods of the invention is that they can be used to prepare libraries comprising vast numbers of compounds. The ability to amplify encoding oligonucleotide sequences using known methods such as polymerase chain reaction ("PCR") means that selected molecules can be identified even if relatively few copies are recovered. This allows the practical use of very large libraries, which, as a consequence of their high degree of complexity, either comprise relatively few copies of any given library member, or require the use of very large volumes. For example, a library consisting of $10^8$ unique structures in which each structure has $1 \times 10^{12}$ copies (about 1 picomole), requires about 100 L of solution at 1 µM effective concentration. For the same library, if each member is represented by 1,000,000 copies, the volume required is 100 µL at 1 µM effective concentration.

In a preferred embodiment, the library comprises from about $10^3$ to about $10^{15}$ copies of each library member. Given differences in efficiency of synthesis among the library members, it is possible that different library members will have different numbers of copies in any given library. Therefore, although the number of copies of each member theoretically present in the library may be the same, the actual number of copies of any given library member is independent of the number of copies of any other member. More preferably, the compound libraries of the invention include at least about $10^5$, $10^6$ or $10^7$ copies of each library member, or of substantially all library members. By "substantially all" library members is meant at least about 85% of the members of the library, preferably at least about 90%, and more preferably at least about 95% of the members of the library.

Figure 6:
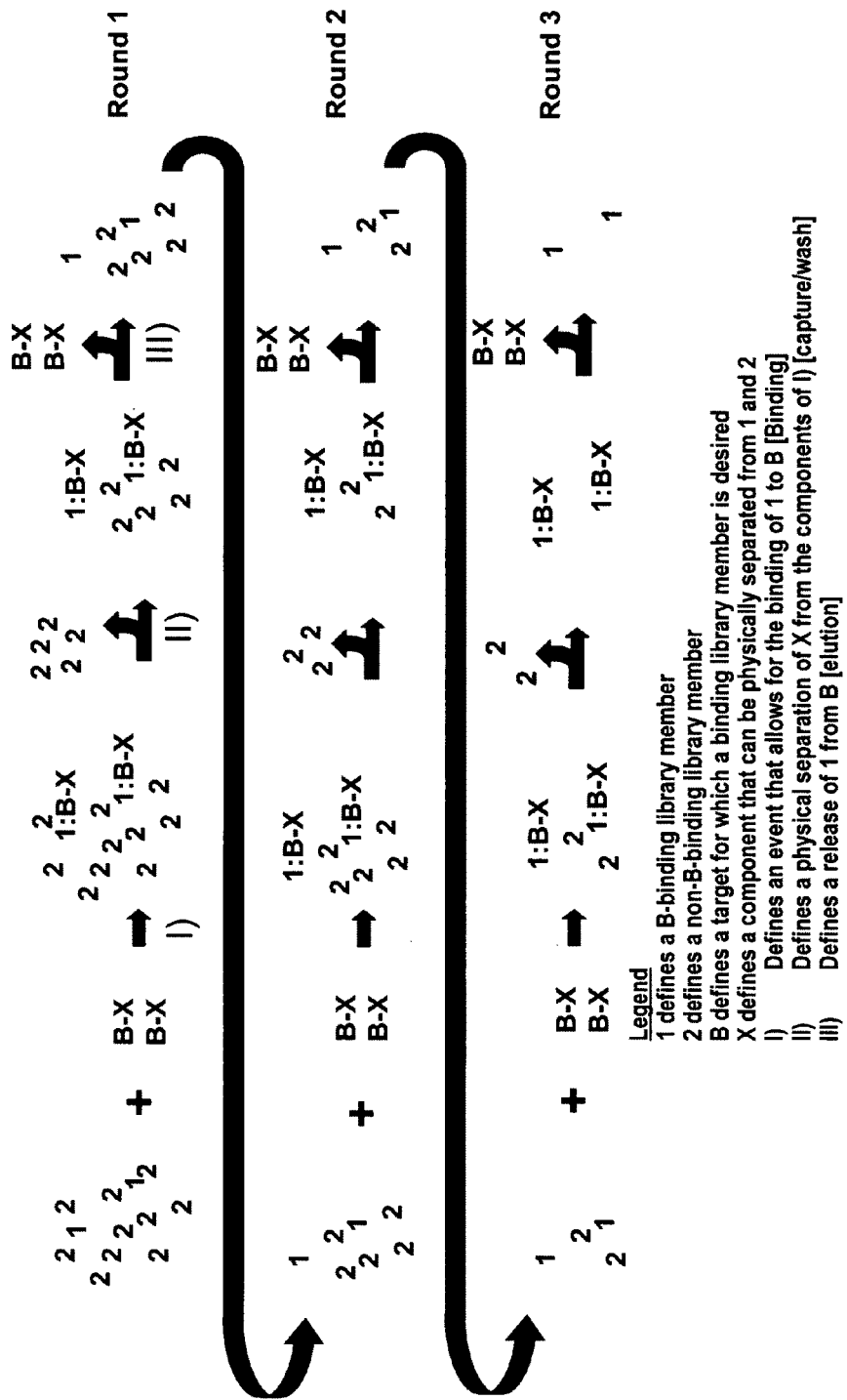
FIG. 6 is a schematic representation of a multiple round selection process using the libraries of the invention.

Preferably, the library includes a sufficient number of copies of each member that multiple rounds (i.e., two or more) of selection against a biological target can be performed, with sufficient quantities of binding molecules remaining following the final round of selection to enable amplification of the oligonucleotide tags of the remaining molecules and, therefore, identification of the functional moieties of the binding molecules. A schematic representation of such a selection process is illustrated in FIG. 6, in which 1 and 2 represent library members, B is a target molecule and X is a moiety operatively linked to B that enables the removal of B from the selection medium. In this example, compound 1 binds to B, while compound 2 does not bind to B. The selection process, as depicted in Round 1, comprises (I) contacting a library comprising compounds 1 and 2 with B-X under conditions suitable for binding of compound 1 to B; (II) removing unbound compound 2, (III) dissociating compound 1 from B and removing BX from the reaction medium. The result of Round 1 is a collection of molecules that is enriched in compound 1 relative to compound 2. Subsequent rounds employing steps I-III result in further enrichment of compound 1 relative to compound 2. Although three rounds of selection are shown in FIG. 6, in practice any number of rounds may be employed, for example from one round to ten rounds, to achieve the desired enrichment of binding molecules relative to non-binding molecules.

In the embodiment shown in FIG. 6, there is no amplification (synthesis of more copies) of the compounds remaining after any of the rounds of selection. Such amplification can lead to a mixture of compounds which is not consistent with the relative amounts of the compounds remaining after the selection. This inconsistency is due to the fact that certain compounds may be more readily synthesized that other compounds, and thus may be amplified in a manner which is not proportional to their presence following selection. For example, if compound 2 is more readily synthesized than compound 1, the amplification of the molecules remaining after Round 2 would result in a disproportionate amplification of compound 2 relative to compound 1, and a resulting mixture of compounds with a much lower (if any) enrichment of compound 1 relative to compound 2.

In one embodiment, the target is immobilized on a solid support by any known immobilization technique. The solid support can be, for example, a water-insoluble matrix contained within a chromatography column or a membrane. The encoded library can be applied to a water-insoluble matrix contained within a chromatography column. The column is then washed to remove non-specific binders. Target-bound compounds can then be dissociated by changing the pH, salt concentration, organic solvent concentration, or other methods, such as competition with a known ligand to the target.

In another embodiment, the target is free in solution and is incubated with the encoded library. Compounds which bind to the target (also referred to herein as "ligands") are selectively isolated by a size separation step such as gel filtration or ultrafiltration. In one embodiment, the mixture of encoded compounds and the target biomolecule are passed through a size exclusion chromatography column (gel filtration), which separates any ligand-target complexes from the unbound compounds. The ligand-target complexes are transferred to a reverse-phase chromatography column, which dissociates the ligands from the target. The dissociated ligands are then analyzed by PCR amplification and sequence analysis of the encoding oligonucleotides. This approach is particularly advantageous in situations where immobilization of the target may result in a loss of activity.

Accordingly, in one aspect of the invention, methods are provided for identifying one or more compounds in a library of compounds, produced as described herein, that bind to a biological target and subsequently determining the structure of the functional moieties of the member(s) of the library of compounds that bind to the biological target.

For example, in one embodiment, one or more compounds which bind to a biological target can be identified by a method comprising the steps of:

(A) synthesizing a library of compounds, wherein the compounds comprise a functional moiety comprising two or more building blocks which is operatively linked to an initial oligonucleotide which identifies the structure of the functional moiety by:

(i) providing a solution comprising m initiator compounds, wherein m is an integer of 1 or greater, where the initiator compounds consist of a functional moiety comprising n building blocks, where n is an integer of 1 or greater, which is operatively linked to an initial oligonucleotide which identifies the n building blocks;

(ii) dividing the solution of step (i) into r reaction vessels, wherein r is an integer of 2 or greater, thereby producing r aliquots of the solution;

(iii) reacting the initiator compounds in each reaction vessel with one of r building blocks, thereby producing r aliquots comprising compounds consisting of a functional moiety comprising n+1 building blocks operatively linked to the initial oligonucleotide; and (iv) reacting the initial oligonucleotide in each aliquot with one of a set of r distinct incoming oligonucleotides in the presence of an enzyme which catalyzes the ligation of the incoming oligonucleotide and the initial oligonucleotide, under conditions suitable for enzymatic ligation of the incoming oligonucleotide and the initial oligonucleotide; thereby producing r aliquots of molecules consisting of a functional moiety comprising n+1 building blocks operatively linked to an elongated oligonucleotide which encodes the n+1 building blocks;

(B) contacting the biological target with the library of compounds, or a portion thereof, under conditions suitable for at least one member of the library of compounds to bind to the target;

(C) removing library members that do not bind to the target;

(D) sequencing the encoding oligonucleotides of the at least one member of the library of compounds which binds to the target, and (E) using the sequences determined in step (D) to determine the structure of the functional moieties of the members of the library of compounds which bind to the biological target, thereby identifying one or more compounds which bind to the biological target.

In one embodiment, the method further comprises ligating a degenerate capping oligonucleotide to the members of the library of compounds in the presence of an enzyme which catalyzes the ligation and polymerizing the degenerate capping oligonucleotide with an enzyme that catalyzes the polymerization of DNA.

In one embodiment, the method may further comprise amplifying the encoding oligonucleotide of the at least one member of the library of compounds which binds to the target prior to sequencing.

In one embodiment of the invention, the selection and enrichment of the library is monitored using an oligonucleotide array. For example, a library of compounds may be hybridized to a solid surface, such as a chip comprising oligonucleotides, e.g., an Affymetrix oligonucleotide chip, which is subsequently fluoresced to detect the oligonucleotide tags bound to the surface. This hybridization can be repeated at each successive step of the screening process for identifying a compound with a desired biological activity.

In one embodiment, the library of compounds comprising encoding oligonucleotides which are optionally attached to capture beads as described above are emulsified as a heat stable water-in-oil emulsion to form a microcapsule according to the methods described in PCT Publications WO 2004/069849, WO 2005/003375, and WO 2005/073410. In one embodiment, the emulsion can be generated by suspending the oligonucleotide tag, with or without attached beads, in amplification solution, e.g., forming a "microreactor." As used herein, the term "amplification solution" means the sufficient mixture of reagents that is necessary to perform amplification of template DNA. One example of an amplification solution, is a PCR amplification solution, that one of skill in the art can readily prepare.

In one embodiment of the invention, the library of compounds comprising encoding oligonucleotides are amplified to increase the copy number of encoding oligonucleotide molecules prior to sequencing. Encoding oligonucleotides may be amplified by any suitable method of DNA amplification including, for example, temperature cycling-polymerase chain reaction (PCR) (see, e.g., Saiki, et al. (1995) *Science* 230:1350-1354; Gingeras, et al. WO 88/10315; Davey, et al. European Patent Application Publication No. 329,822; Miller, et al. WO 89/06700), ligase chain reaction (see, e.g., Barany (1991) *Proc. Natl Acad. Sci. USA* 88:189-193; Barringer, et al. (1990) *Gene* 89:117-122), transcription-based amplification (see, e.g., Kwoh, et al. (1989) *Proc. Natl. Acad. Sci. USA* 86:1173-1177) isothermal amplification systems—self-sustaining, sequence replication (see, e.g., Guatelli, et al. (1990) *Proc. Natl. Acad. Sci. USA* 87:1874-1878); the Qp replicase system (see, e.g., Lizardi, et al. (1988) *BioTechnology* 6: 1197-1202); strand displacement amplification (Walker, et al. (1992) *Nucleic Acids Res* 20(7): 1691-6; the methods described by Walker, et al. (*Proc. Natl. Acad. Sci. USA* (1992) 1:89(1):392-6; the methods described by Kievits, et al. (*J Virol Methods* (1991) 35(3):273-86; "race" (Frohman, In: *PCR Protocols: A Guide to Methods and Applications*, Academic Press, NY (1990)); "one-sided PCR" (Ohara, et al. (1989) *Proc. Natl. Acad. Sci. U.S.A.* 86.5673-5677); "di-oligonucleotide" amplification, isothermal amplification (Walker, et al. (1992) *Proc. Natl. Acad. Sci. U.S.A.* 89:392-396), and rolling circle amplification (reviewed in U.S. Pat. No. 5,714,320).

In one embodiment, the library of compounds comprising encoding oligonucleotides is amplified prior to sequence analysis in order to minimize any potential skew in the population distribution of DNA molecules present in the selected library mix. For example, only a small amount of library is recovered after a selection step and is typically amplified using PCR prior to sequence analysis. PCR has the potential to produce a skew in the population distribution of DNA molecules present in the selected library mix. This is especially problematic when the number of input molecules is small and the input molecules are poor PCR templates. PCR products produced at early cycles are more efficient templates than covalent duplex library, and therefore the frequency of these molecules in the final amplified population may be much higher than in original input template.

Accordingly, in order to minimize this potential PCR skew, in one embodiment of the invention, a population of single-stranded oligonucleotides corresponding to the individual library members is produced by, for example, using one primer in a reaction, followed by PCR amplification using two primers. By doing so, there is a linear accumulation of single-stranded primer-extension product prior to exponential amplification using PCR, and the diversity and distribution of molecules in the accumulated primer-extension product more accurately reflect the diversity and distribution of molecules present in the original input template, since the exponential phase of amplification occurs only after much of the original molecular diversity present is represented in the population of molecules produced during the primer-extension reaction.

Preferably, DNA amplification is performed by PCR. PCR amplification methods are described in detail in U.S. Pat. Nos. 4,683,192, 4,683,202, 4,800,159, and 4,965,188, and at least in PCR Technology: Principles and Applications for DNA Amplification, H. Erlich, ed., Stockton Press, New York (1989); and PCR Protocols: A Guide to Methods and Applications, Innis et al., eds., Academic Press, San Diego, Calif. (1990). The contents of all the foregoing documents are incorporated herein by reference. In one embodiment of the invention, PCR amplification of the template is performed on an oligonucleotide tag bound to a bead, and encapsulated with a PCR solution comprising all the necessary reagents for a PCR reaction. In another embodiment of the invention, PCR amplification of the template is performed on a soluble oligonucleotide tag (i.e., not bound to a bead) which is encapsulated with a PCR solution comprising all the necessary reagents for a PCR reaction. PCR is subsequently performed by exposing the emulsion to any suitable thermocycling regimen known in the art. In one embodiment, between 30 and 50 cycles, preferably about 40 cycles, of amplification are performed. It is desirable, but not necessary, that following the amplification procedure there be one or more hybridization and extension cycles following the cycles of amplification. In a another embodiment, between 10 and 30 cycles, or about 25 cycles, of hybridization and extension are performed. In one embodiment, the template DNA is amplified until about at least two million to fifty million copies or about ten million to thirty million copies of the template DNA are immobilized per bead.

Following amplification of the encoding oligonucleotide tag, the emulsion is "broken" (also referred to as "demulsification" in the art). There are many well known methods of breaking an emulsion (see, e.g., U.S. Pat. No. 5,989,892 and references cited therein) and one of skill in the art would be able to select the proper method. For example, the emulsion may be broken by adding additional oil to cause the emulsion to separate into two phases. The oil phase is then removed, and a suitable organic solvent (e.g., hexanes) is added. After mixing, the oil/organic solvent phase is removed. This step may be repeated several times. Finally, the aqueous layers is removed. If the encoding oligonucleotides are attached to beads, the beads are then washed with an organic solvent/annealing buffer mixture, and then washed again in annealing buffer. Suitable organic solvents include alcohols such as methanol, ethanol and the like.

The amplified encoding oligonucleotides may then be resuspended in aqueous solution for use, for example, in a sequencing reaction according to known technologies. (See, e.g., Sanger, F. et al. (1977) *Proc. Natl. Acad. Sci. U.S.A.* 75:5463-5467; Maxam & Gilbert (1977) *Proc Natl Acad Sci USA* 74:560-564; Ronaghi, et al. (1998) *Science* 281:363, 365; Lysov, et al. (1988) *Dokl Akad Nauk SSSR* 303:1508-1511; Bains & Smith (1988) *J Theor Biol* 135:303-307; Drnanac, R. et al. (1989) *Genomics* 4:114-128; Khrapko, et al. (1989) *FEBS Lett* 256:118-122; Pevzner (1989) *J Biomol Struct Dyn* 7:63-73; Southern, et al. (1992) *Genomics* 13:1008-1017).

If the encoding oligonucleotide attached to a bead is to be used in a pyrophosphate-based sequencing reaction (described, e.g., in U.S. Pat. Nos. 6,274,320, 6,258,568 and 6,210,891, and incorporated herein by reference), then it is necessary to remove the second strand of the PCR product and anneal a sequencing primer to the single stranded template that is bound to the bead.

Briefly, the second strand is melted away using any number of commonly known methods such as NaOH, low ionic (e.g., salt) strength, or heat processing. Following this melting step, the beads are pelleted and the supernatant is discarded. The beads are resuspended in an annealing buffer, the sequencing primer added, and annealed to the bead-attached single stranded template using a standard annealing cycle.

The amplified encoding oligonucleotide, optionally on a bead, may be sequenced either directly or in a different reaction vessel. In one embodiment of the present invention, the encoding oligonucleotide is sequenced directly on the bead by transferring the bead to a reaction vessel and subjecting the DNA to a sequencing reaction (e.g., pyrophosphate or Sanger sequencing). Alternatively, the beads may be isolated and the encoding oligonucleotide may be removed from each bead and sequenced. Nonetheless, the sequencing steps may be performed on each individual bead and/or the beads that contain no nucleic acid template may be removed prior to distribution to a reaction vessel by, for example, biotin-streptavidin magnetic beads. Other suitable methods to separate beads are described in, for example, Bauer, J. (1999) *J. Chromatography B*, 722:55-69 and in Brody et al. (1999) *Applied Physics Lett*. 74:144-146.

Once the encoding oligonucleotide tag has been amplified, the sequence of the tag, and ultimately the composition of the selected molecule, can be determined using nucleic acid sequence analysis, a well known procedure for determining the sequence of nucleotide sequences. Nucleic acid sequence analysis is approached by a combination of (a) physiochemical techniques, based on the hybridization or denaturation of a probe strand plus its complementary target, and (b) enzymatic reactions with polymerases.

The nucleotide sequence of the oligonucleotide tag comprised of polynucleotides that identify the building blocks that make up the functional moiety as described herein, may be determined by the use of any sequencing method known to one of skill in the art. Suitable methods are described in, for example, Sanger, F. et al. (1977) *Proc. Natl. Acad. Sci. U.S.A.* 75:5463-5467; Maxam & Gilbert (1977) *Proc Natl Acad Sci USA* 74:560-564; Ronaghi, et al. (1998) *Science* 281:363, 365; Lysov, et al. (1988) *Dokl Akad Nauk SSSR* 303:1508-1511; Bains & Smith (1988) *J TheorBiol* 135:303-307; Dmanac, R. et al. (1989) *Genomics* 4:114-128; Khrapko, et al. (1989) *FEBS Lett* 256:118-122; Pevzner (1989) *J Biomol Struct Dyn* 7:63-73; Southern, et al. (1992) *Genomics* 13:1008-1017).

In a preferred embodiment, the oligonucleotide tags are sequenced using the apparati and methods described in PCT publications WO 2004/069849, WO 2005/003375, WO 2005/073410, and WO 2005/054431, the entire contents of each of which are incorporated herein by this reference.

In one embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides, such as, for example, α-thio-dATP. The sequence can be determined by detecting a sequence reaction byproduct, using methods known in the art.

In some embodiments, the nucleotide is modified to contain a disulfide-derivative of a hapten, such as biotin. The addition of the modified nucleotide to the nascent primer annealed to an anchored substrate is analyzed by a suitable post-polymerization method. Such methods enable a nucleotide to be identified in a given target position, and the DNA to be sequenced simply and rapidly while avoiding the need for electrophoresis and the use of potentially dangerous radiolabels.

Examples of suitable haptens include, for example, biotin, digoxygenin, the fluorescent dye molecules cy3 and cy5, and fluorescein. The attachment of the hapten can occur through linkages via the sugar, the base, and/or via the phosphate moiety on the nucleotide. Exemplary means for signal amplification following polymerization and extension of the encoding oligonucleotide include fluorescent, electrochemical and enzymatic means. In one embodiment using enzymatic amplification, the enzyme is one for which light-generating substrates are known, such as, for example, alkaline phosphatase (AP), horse-radish peroxidase (HRP), beta-galactosidase, or luciferase, and the means for the detection of these light-generating (chemiluminescent) substrates can include a CCD camera.

A sequencing primer can be of any length or base composition, as long as it is capable of specifically annealing to a region of the nucleic acid template (i.e., the oligonucleotide tag). The oligonucleotide primers of the present invention may be synthesized by conventional technology, e.g., with a commercial oligonucleotide synthesizer and/or by ligating together subfragments that have been so synthesized. No particular structure for the sequencing primer is required so long as it is able to specifically prime a region on the template nucleic acid. The sequencing primer is extended with the DNA polymerase to form a sequence product. The extension is performed in the presence of one or more types of nucleotide triphosphates, and if desired, auxiliary binding proteins. Incorporation of the dNTP is determined by, for example, assaying for the presence of a sequencing byproduct.

In one embodiment, the nucleic acid sequence of the oligonucleotide tag is determined by the use of the polymerase chain reaction (PCR). Briefly, the oligonucleotide tag (optionally attached to a bead) is subjected to a PCR reaction as follows. The appropriate sample is contacted with a PCR primer pair, each member of the pair having a pre-selected nucleotide sequence. The PCR primer pair is capable of initiating primer extension reactions by hybridizing to a PCR primer binding site on the encoding oligonucleotide tag.

The PCR reaction is performed by mixing the PCR primer pair, preferably a predetermined amount thereof, with the nucleic acids of the encoding oligonucleotide tag, preferably a predetermined amount thereof, in a PCR buffer to form a PCR reaction admixture. The admixture is thermocycled for a number of cycles, which is typically predetermined, sufficient for the formation of a PCR reaction product. A sufficient amount of product is one that can be isolated in a sufficient amount to allow for DNA sequence determination.

PCR is typically carried out by thermocycling i.e., repeatedly increasing and decreasing the temperature of a PCR reaction admixture within a temperature range whose lower limit is about 30° C. to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

The PCR reaction is performed using any suitable method. Generally it occurs in a buffered aqueous solution, i.e., a PCR buffer, preferably at a pH of 7-9. Preferably, a molar excess of the primer is present. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.-100° C. for about 1 to 10 minutes, preferably from 1 to 4 minutes. After this heating period the solution is allowed to cool to 54° C., which is preferable for primer hybridization. The synthesis reaction may occur at a temperature ranging from room temperature up to a temperature above which the polymerase (inducing agent) no longer functions efficiently. Thus, for example, if DNA polymerase is used, the temperature is generally no greater than about 40° C. The thermocycling is repeated until the desired amount of PCR product is produced. An exemplary PCR buffer comprises the following reagents: 50 mM KCl; 10 mM Tris-HCl at pH 8.3; 1.5 mM $MgCl_2$; 0.001% (wt/vol) gelatin, 200 µM dATP; 200 µM dTTP; 200 µM dCTP; 200 µM dGTP; and 2.5 units *Thermus aquaticus* (Taq) DNA polymerase 1 per 100 microliters of buffer.

Suitable enzymes for elongating the primer sequences include, for example, E. coli DNA polymerase I, Taq DNA polymerase, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. The newly synthesized DNA strand and its complementary strand form a double-stranded molecule which can be used in the succeeding steps of the analysis process.

In one embodiment, the nucleotide sequence of the oligonucleotide tag is determined by measuring inorganic pyrophosphate (PPi) liberated from a nucleotide triphosphate (dNTP) as the dNMP is incorporated into an extended sequence primer. This method of sequencing, termed Pyrosequencing™ technology (PyroSequencing AB, Stockholm, Sweden) can be performed in solution (liquid phase) or as a solid phase technique. PPi-based sequencing methods are described in, e.g., U.S. Pat. Nos. 6,274,320, 6,258,568 and 6,210,891, WO9813523A1, Ronaghi, et al. (1996) *Anal Biochem.* 242:84-89, Ronaghi, et al. (1998) *Science* 281:363-365, and USSN 2001/0024790. These disclosures of PPi sequencing are incorporated herein in their entirety, by reference. See also, e.g., U.S. Pat. Nos. 6,210,891 and 6,258,568, each of which are fully incorporated herein by this reference.

Pyrophosphate can be detected by a number of different methodologies, and various enzymatic methods have been previously described (see e.g., Reeves, et al. (1969) *Anal Biochem.* 28:282-287; Guillory, et al. (1971) *Anal Biochem.* 39:170-180; Johnson, et al. (1968) *Anal Biochem.* 15:273; Cook, et al. 1978. *Anal Biochem.* 91:557-565; and Drake, et al. (1979) *Anal Biochem.* 94: 117-120).

In one embodiment, PPi is detected enzymatically (e.g., by the generation of light). Such methods enable a nucleotide to be identified in a given target position, and the DNA to be sequenced simply and rapidly while avoiding the need for electrophoresis and the use of potentially dangerous radiolabels.

In one embodiment, the PPi and a coupled luciferase-luciferin reaction is used to generate light for detection. In another embodiment, the PPi and a coupled sulfurylase/luciferase reaction is used to generate light for detection as described in U.S. Pat. No. 6,902,921, the contents of which are hereby expressly incorporated herein by reference. In one embodiment, the sulfurylase is thermostable. In some embodiments, either or both the sulfurylase and luciferase are immobilized on one or more mobile solid supports disposed at each reaction site.

In another embodiment, the nucleotide sequence of the oligonucleotide tag may be determined according to the methods described in PCT Publication No. WO 01/23610, the contents of which are incorporated herein by reference. Briefly, a target nucleotide sequence can be determined by generating its complement using the polymerase reaction to extend a suitable primer, and characterizing the successive incorporation of bases that generate the complement sequence. The target sequence is, typically, immobilized on a solid support. Each of the different bases A, T, G, or C is then brought, by sequential addition, into contact with the target, and any incorporation events are detected via a suitable label attached to the base.

A labeled base is incorporated into the complementary sequence by the use of a polymerase, e.g., a polymerase with a 3' to 5' exonuclease activity (e.g., DNA polymerase I, the Klenow fragment, DNA polymerase III, T4 DNA polymerase, and T7 DNA polymerase). Following detection of the incorporated labeled base, the polymerase replaces the terminally labeled base with a corresponding unlabelled base, thus permitting further sequencing to occur.

In yet another embodiment, the nucleotide sequence of the oligonucleotide tag is determined by the use of single molecule sequencing by synthesis methods described in, for example, PCT Publication No. WO 2005/080605, the entire contents of which are expressly incorporated by reference. The benefit of using this technology is that it eliminates the need for DNA amplification prior to sequencing, thus, abolishing the introduction of amplification errors and bias. Briefly, the encoding oligonucleotide is hybridized to a universal primer immobilized on a solid surface. The oligonucleotide:primer duplexes are visualized by, e.g., illuminating the surface with a laser and imaging with a digital TV camera connected to a microscope, and the positions of all the duplexes on the surface are recorded. DNA polymerase and one type of fluorescently labeled nucleotide, e.g., A, is added to the surface and incorporated into the appropriate primer. Subsequently, the polymerase and the unincorporated nucleotides are washed from the surface and the incorporated nucleotide is visualized by, e.g., illuminating the surface with a laser and imaging with a camera as before to record the positions of the incorporated nucleotides. The fluorescent label is removed from each incorporated nucleotide and the process is repeated with the next nucleotide, e.g., G, stepping through A, C, G, T, until the desired read-length is achieved.

One group of fluorescent dyes suitable for this method of sequencing is fluorescence resonance energy transfer (FRET) dyes, including donor and acceptor energy fluorescent dyes and linkers such as, for example, Cy3 and Cy5. FRET is a phenomenon described in, for example, Selvin (1995) *Methods in Enzym.* 246:300. FRET can detect the incorporation of multiple nucleotides into a single oligonucleotide molecule and is, thus, useful for sequencing the encoding oligonucleotides of the invention. Sequencing methods using FRET are described in, for example, PCT Publication No. WO 2005/080605, the entire contents of which are expressly incorporated by reference. Alternatively, quantum dots can be used as a labeling moiety on the different types of nucleotides for use in sequencing reactions.

Once single ligands are identified by the above-described process, various levels of analysis can be applied to yield structure-activity relationship information and to guide further optimization of the affinity, specificity and bioactivity of the ligand. For ligands derived from the same scaffold, three-dimensional molecular modeling can be employed to identify significant structural features common to the ligands, thereby generating families of small-molecule ligands that presumably bind at a common site on the target biomolecule.

A variety of screening approaches can be used to obtain ligands that possess high affinity for one target but significantly weaker affinity for another closely related target. One screening strategy is to identify ligands for both biomolecules in parallel experiments and to subsequently eliminate common ligands by a cross-referencing comparison. In this method, ligands for each biomolecule can be separately identified as disclosed above. This method is compatible with both immobilized target biomolecules and target biomolecules free in solution.

For immobilized target biomolecules, another strategy is to add a preselection step that eliminates all ligands that bind to the non-target biomolecule from the library. For example, a first biomolecule can be contacted with an encoded library as described above. Compounds which do not bind to the first biomolecule are then separated from any first biomolecule-ligand complexes which form. The second biomolecule is then contacted with the compounds which did not bind to the first biomolecule. Compounds which bind to the second biomolecule can be identified as described above and have significantly greater affinity for the second biomolecule than to the first biomolecule.

A ligand for a biomolecule of unknown function which is identified by the method disclosed above can also be used to determine the biological function of the biomolecule. This is advantageous because although new gene sequences continue to be identified, the functions of the proteins encoded by these sequences and the validity of these proteins as targets for new drug discovery and development are difficult to determine and represent perhaps the most significant obstacle to applying genomic information to the treatment of disease. Target-specific ligands obtained through the process described in this invention can be effectively employed in whole cell biological assays or in appropriate animal models to understand both the function of the target protein and the validity of the target protein for therapeutic intervention. This approach can also confirm that the target is specifically amenable to small molecule drug discovery.

In one embodiment, one or more compounds within a library of the invention are identified as ligands for a particular biomolecule. These compounds can then be assessed in an in vitro assay for the ability to bind to the biomolecule. Preferably, the functional moieties of the binding compounds are synthesized without the oligonucleotide tag or linker moiety, and these functional moieties are assessed for the ability to bind to the biomolecule.

The effect of the binding of the functional moieties to the biomolecule on the function of the biomolecule can also be assessed using in vitro cell-free or cell-based assays. For a biomolecule having a known function, the assay can include a comparison of the activity of the biomolecule in the presence and absence of the ligand, for example, by direct measurement of the activity, such as enzymatic activity, or by an indirect measure, such as a cellular function that is influenced by the biomolecule. If the biomolecule is of unknown function, a cell which expresses the biomolecule can be contacted with the ligand and the effect of the ligand on the viability, function, phenotype, and/or gene expression of the cell is assessed. The in vitro assay can be, for example, a cell death assay, a cell proliferation assay or a viral replication assay. For example, if the biomolecule is a protein expressed by a virus, a cell infected with the virus can be contacted with a ligand for the protein. The affect of the binding of the ligand to the protein on viral viability can then be assessed.

A ligand identified by the method of the invention can also be assessed in an in vivo model or in a human. For example, the ligand can be evaluated in an animal or organism which produces the biomolecule. Any resulting change in the health status (e.g., disease progression) of the animal or organism can be determined.

For a biomolecule, such as a protein or a nucleic acid molecule, of unknown function, the effect of a ligand which binds to the biomolecule on a cell or organism which produces the biomolecule can provide information regarding the biological function of the biomolecule. For example, the observation that a particular cellular process is inhibited in the presence of the ligand indicates that the process depends, at least in part, on the function of the biomolecule.

Ligands identified using the methods of the invention can also be used as affinity reagents for the biomolecule to which they bind. In one embodiment, such ligands are used to effect affinity purification of the biomolecule, for example, via chromatography of a solution comprising the biomolecule using a solid phase to which one or more such ligands are attached.

In addition to the screening of encoded libraries as described herein, other traditional drug discovery methods, such as phage display, differential display (mRNA display), and aptamer/SELEX, could benefit from the methods of the invention which eliminate the introduction of amplification errors and biases. For example, multiple rounds of selection using phage display (described in, for example, PCT Publication Nos. WO91/18980, WO91/19818, and WO92/18619, and U.S. Pat. No. 5,223,409, the entire contents of each of which are incorporated herein by reference) can cause host toxicity and, consequently, loss or under-representation of desired library members (see, e.g., Daugherty, P. S., et al. (1999) *Protein Engineering* 12(7):613-621 and Holt, L. J., et al. (2000) *Nucleic Acids Res.* 28(15):E72). Moreover, methods such as Systematic Evolution of Ligands by EXponential enrichment (also known as SELEX which is described in, for example, U.S. Pat. Nos. 5,654,151, 5,503,978, 5,567,588 and 5,270,163, as well as PCT Publication Nos. WO 96/38579 and WO9927133A1, the entire contents of each of which are incorporated herein by reference) introduce biases due to the need for multiple rounds of selection, i.e., partitioning unbound nucleic acids from those nucleic acids which have bound specifically to a target molecule, and multiple rounds of amplification of the nucleic acids that have bound to the target by reverse transcription and PCR. Similarly, methods of selection like differential display (described in, for example, U.S. Pat. Nos. 5,580,726 and 5,700,644, the entire contents of each of which are incorporated herein by reference) rely on multiple rounds of PCR amplification which also leads to unequal representation of the clones in the library. Thus, the foregoing multi-step selection processes may benefit from the methods described herein which employ massively parallel sequencing approaches (such as, for example, a pyrophosphate-based sequencing method or a single molecule sequencing by synthesis method) which leads to the accurate identification of a compound with a desired biological activity without the need for any nucleic acid amplification.

This invention is further illustrated by the following examples which should not be construed as limiting. The contents of all references, patents and published patent applications cited throughout this application, as well as the Figures and the Sequence Listing, are hereby incorporated in reference.

EXAMPLES

Example 1

Synthesis and Characterization of a Library on the Order of $10^5$ Members

The synthesis of a library comprising on the order of $10^5$ distinct members was accomplished using the following reagents:

Compound 1:

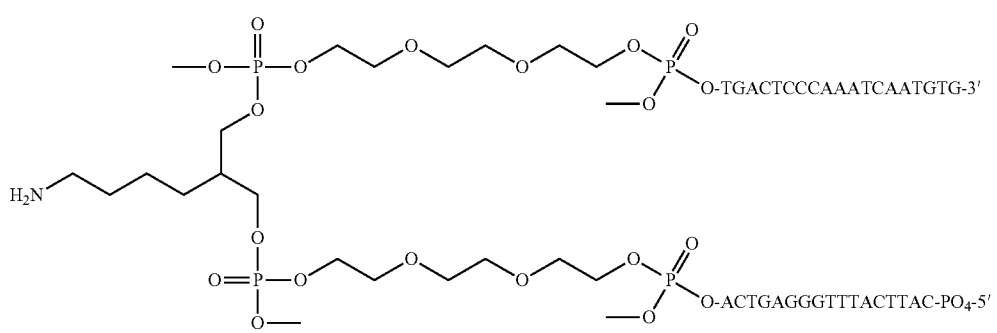

Single Letter Codes for Deoxyribonucleotides:
A=adenosine
C=cytidine
G=guanosine
T=thymidine Building Block Precursors:

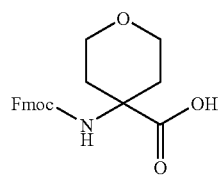

BB1

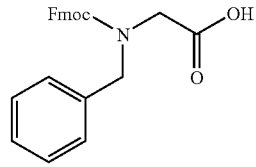

BB2

BB3 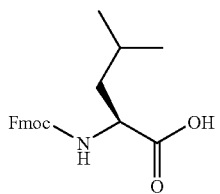

BB4 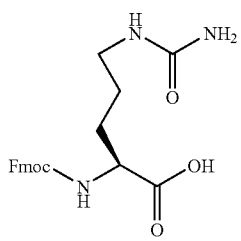

BB5 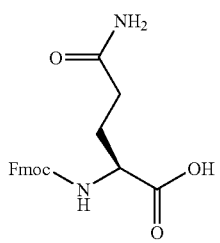

BB6 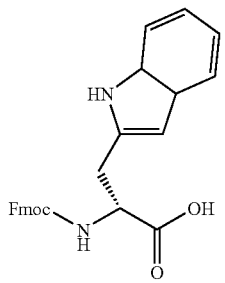

BB7 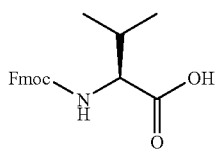

BB8 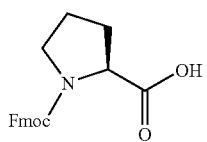

BB9 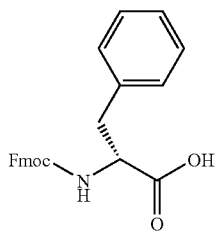

BB10 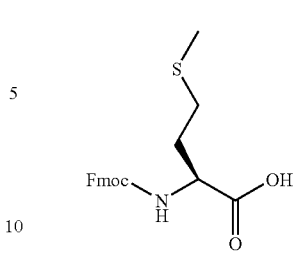

BB11 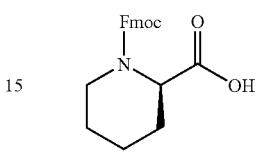

BB12 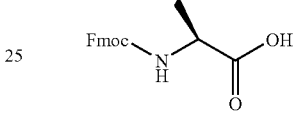

Oligonucleotide Tags:

| Sequence | | Tag number |
|---|---|---|
| 3'-PO$_4$-GCAACGAAG | (SEQ ID NO: 1) | 1.1 |
| ACCGTTGCT-PO$_3$-5' | (SEQ ID NO: 2) | |
| 5'-PO$_3$-GCGTACAAG | (SEQ ID NO: 3) | 1.2 |
| ACCGCATGT-PO$_3$-5' | (SEQ ID NO: 4) | |
| 5'-PO$_3$-GCTCTGTAG | (SEQ ID NO: 5) | 1.3 |
| ACCGAGACA-PO$_3$-5' | (SEQ ID NO: 6) | |
| 5'-PO$_3$-GTGCCATAG | (SEQ ID NO: 7) | 1.4 |
| ACCACGGTA-PO$_3$-5' | (SEQ ID NO: 8) | |
| 5'-PO$_3$-GTTGACCAG | (SEQ ID NO: 9) | 1.5 |
| ACCAACTGG-PO$_3$-5' | (SEQ ID NO: 10) | |
| 5'-PO$_3$-CGACTTGAC | (SEQ ID NO: 11) | 1.6 |
| CAAGTCGCA-PO$_3$-5' | (SEQ ID NO: 12) | |
| 5'-PO$_3$-CGTAGTCAG | (SEQ ID NO: 13) | 1.7 |
| ACGCATCAG-PO$_3$-5' | (SEQ ID NO: 14) | |
| 5'-PO$_3$-CCAGCATAG | (SEQ ID NO: 15) | 1.8 |
| ACGGTCGTA-PO$_3$-5' | (SEQ ID NO: 16) | |
| 5'-PO$_3$-CCTACAGAG | (SEQ ID NO: 17) | 1.9 |
| ACGGATGTC-PO$_3$-5' | (SEQ ID NO: 18) | |
| 5'-PO$_3$-CTGAACGAG | (SEQ ID NO: 19) | 1.10 |
| CGTTCAGCA-PO$_3$-5' | (SEQ ID NO: 20) | |
| 5'-PO$_3$-CTCCAGTAG | (SEQ ID NO: 21) | 1.11 |
| ACGAGGTCA-PO$_3$-5' | (SEQ ID NO: 22) | |
| 5'-PO$_3$-TAGGTCCAG | (SEQ ID NO: 23) | 1.12 |
| ACATCCAGG-PO$_3$-5' | (SEQ ID NO: 24) | |
| 5'-PO$_3$-GCGTGTTGT | (SEQ ID NO: 25) | 2.1 |
| TCCGCACAA-PO$_3$-5' | (SEQ ID NO: 26) | |

| Sequence | | Tag number |
|---|---|---|
| 5'-PO$_3$-GCTTGGAGT | (SEQ ID NO: 27) | 2.2 |
| TCCGAACCT-PO$_3$-5' | (SEQ ID NO: 28) | |
| 5'-PO$_3$-GTCAAGCGT | (SEQ ID NO: 29) | 2.3 |
| TCCAGTTCG-PO$_3$-5' | (SEQ ID NO: 30) | |
| 5'-PO$_3$-CAAGAGCGT | (SEQ ID NO: 31) | 2.4 |
| TCGTTCTCG-PO$_3$-5' | (SEQ ID NO: 32) | |
| 5'-PO$_3$-CAGTTCGGT | (SEQ ID NO: 33) | 2.5 |
| TCGTCAAGC-PO$_3$-5' | (SEQ ID NO: 34) | |
| 5'-PO$_3$-CGAAGGAGT | (SEQ ID NO: 35) | 2.6 |
| TCGCTTCCT-PO$_3$-5' | (SEQ ID NO: 36) | |
| 5'-PO$_3$-CGGTGTTGT | (SEQ ID NO: 37) | 2.7 |
| TCGCCACAA-PO$_3$-5' | (SEQ ID NO: 38) | |
| 5'-PO$_3$-CGTTGCTGT | (SEQ ID NO: 39) | 2.8 |
| TCGCAACGA-PO$_3$-5' | (SEQ ID NO: 40) | |
| 5'-PO$_3$-CCGATCTGT | (SEQ ID NO: 41) | 2.9 |
| TCGGCTAGA-PO$_3$-5' | (SEQ ID NO: 42) | |
| 5'-PO$_3$-CCTTCTCGT | (SEQ ID NO: 43) | 2.10 |
| TCGGAAGAG-PO$_3$-5' | (SEQ ID NO: 44) | |
| 5'-PO$_3$-TGAGTCCGT | (SEQ ID NO: 45) | 2.11 |
| TCACTCAGG-PO$_3$-5' | (SEQ ID NO: 46) | |
| 5'-PO$_3$-TGCTACGGT | (SEQ ID NO: 47) | 2.12 |
| TCAGATTGC-PO$_3$-5' | (SEQ ID NO: 48) | |
| 5'-PO$_3$-GTGCGTTGA | (SEQ ID NO: 49) | 3.1 |
| CACACGCAA-PO$_3$-5' | (SEQ ID NO: 50) | |
| 5'-PO$_3$-GTTGGCAGA | (SEQ ID NO: 51) | 3.2 |
| CACAACCGT-PO$_3$-5' | (SEQ ID NO: 52) | |
| 5'-PO$_3$-CCTGTAGGA | (SEQ ID NO: 53) | 3.3 |
| CAGGACATC-PO$_3$-5' | (SEQ ID NO: 54) | |
| 5'-PO$_3$-CTGCGTAGA | (SEQ ID NO: 55) | 3.4 |
| CAGACGCAT-PO$_3$-5' | (SEQ ID NO: 56) | |
| 5'-PO$_3$-CTTACGCGA | (SEQ ID NO: 57) | 3.5 |
| CAGAATGCG-PO$_3$-5' | (SEQ ID NO: 58) | |
| 5'-PO$_3$-TGGTCACGA | (SEQ ID NO: 59) | 3.6 |
| CAACCAGTG-PO$_3$-5' | (SEQ ID NO: 60) | |
| 5'-PO$_3$-TCAGAGCGA | (SEQ ID NO: 61) | 3.7 |
| CAAGTCTCG-PO$_3$-5' | (SEQ ID NO: 62) | |
| 5'-PO$_3$-TTGCTCGGA | (SEQ ID NO: 63) | 3.8 |
| CAAACGAGC-PO$_3$-5' | (SEQ ID NO: 64) | |
| 5'-PO$_3$-GCAGTTGGA | (SEQ ID NO: 65) | 3.9 |
| CACGTCAAC-PO$_3$-5' | (SEQ ID NO: 66) | |
| 5'-PO$_3$-GCCTGAAGA | (SEQ ID NO: 67) | 3.10 |
| CACGGACTT-PO$_3$-5' | (SEQ ID NO: 68) | |
| 5'-PO$_3$-GTAGCCAGA | (SEQ ID NO: 69) | 3.11 |
| CACATCGGT-PO$_3$-5' | (SEQ ID NO: 70) | |
| 5'-PO$_3$-GTCGCTTGA | (SEQ ID NO: 71) | 3.12 |
| CACAGCCAA-PO$_3$-5' | (SEQ ID NO: 72) | |
| 5'-PO$_3$-GCCTAAGTT | (SEQ ID NO: 73) | 4.1 |
| CTCGGATTC-PO$_3$-5' | (SEQ ID NO: 74) | |
| 5'-PO$_3$-GTAGTGCTT | (SEQ ID NO: 75) | 4.2 |
| CTCATCACG-PO$_3$-5' | (SEQ ID NO: 76) | |
| 5'-PO$_3$-GTCGAAGTT | (SEQ ID NO: 77) | 4.3 |
| CTCAGCTTC-PO$_3$-5' | (SEQ ID NO: 78) | |
| 5'-PO$_3$-GTTTCGGTT | (SEQ ID NO: 79) | 4.4 |
| CTCAAAGCC-PO$_3$-5' | (SEQ ID NO: 80) | |
| 5'-PO$_3$-CAGCGTTTT | (SEQ ID NO: 81) | 4.5 |
| CTGTCGCAA-PO$_3$-5' | (SEQ ID NO: 82) | |
| 5'-PO$_3$-CATACGCTT | (SEQ ID NO: 83) | 4.6 |
| CTGTATGCG-PO$_3$-5' | (SEQ ID NO: 84) | |
| 5'-PO$_3$-CGATCTGTT | (SEQ ID NO: 85) | 4.7 |
| CTGCTAGAC-PO$_3$-5' | (SEQ ID NO: 86) | |
| 5'-PO$_3$-CGCTTTGTT | (SEQ ID NO: 87) | 4.8 |
| CTGCGAAAC-PO$_3$-5' | (SEQ ID NO: 88) | |
| 5'-PO$_3$-CCACAGTTT | (SEQ ID NO: 89) | 4.9 |
| CTGGTGTCA-PO$_3$-5' | (SEQ ID NO: 90) | |
| 5'-PO$_3$-CCTGAAGTT | (SEQ ID NO: 91) | 4.10 |
| CTGGACTTC-PO$_3$-5' | (SEQ ID NO: 92) | |
| 5'-PO$_3$-CTGACGATT | (SEQ ID NO: 93) | 4.11 |
| CTGACTGCT-PO$_3$-5' | (SEQ ID NO: 94) | |
| 5'-PO$_3$-CTCCACTTT | (SEQ ID NO: 95) | 4.12 |
| CTGAGGTGA-PO$_3$-5' | (SEQ ID NO: 96) | |
| 5'-PO$_3$-ACCAGAGCC | (SEQ ID NO: 97) | 5.1 |
| AATGGTCTC-PO$_3$-5' | (SEQ ID NO: 98) | |
| 5'-PO$_3$-ATCCGCACC | (SEQ ID NO: 99) | 5.2 |
| AATAGGCGT-PO$_3$-5' | (SEQ ID NO: 100) | |
| 5'-PO$_3$-GACGACACC | (SEQ ID NO: 101) | 5.3 |
| AACTGCTGT-PO$_3$-5' | (SEQ ID NO: 102) | |
| 5'-PO$_3$-GGATGGACC | (SEQ ID NO: 103) | 5.4 |
| AACCTACCT-PO$_3$-5' | (SEQ ID NO: 104) | |
| 5'-PO$_3$-GCAGAAGCC | (SEQ ID NO: 105) | 5.5 |
| AACGTCTTC-PO$_3$-5' | (SEQ ID NO: 106) | |
| 5'-PO$_3$-GCCATGTCC | (SEQ ID NO: 107) | 5.6 |
| AACGGTACA-PO$_3$-5' | (SEQ ID NO: 108) | |
| 5'-PO$_3$-GTCTGCTCC | (SEQ ID NO: 109) | 5.7 |
| AACAGACGA-PO$_3$-5' | (SEQ ID NO: 110) | |
| 5'-PO$_3$-CGACAGACC | (SEQ ID NO: 111) | 5.8 |
| AAGCTGTCT-PO$_3$-5' | (SEQ ID NO: 112) | |
| 5'-PO$_3$-CGCTACTCC | (SEQ ID NO: 113) | 5.9 |
| AAGCGATGA-PO$_3$-5' | (SEQ ID NO: 114) | |
| 5'-PO$_3$-CCACAGACC | (SEQ ID NO: 115) | 5.10 |
| AAGGTGTCT-PO$_3$-5' | (SEQ ID NO: 116) | |
| 5'-PO$_3$-CCTCTCTCC | (SEQ ID NO: 117) | 5.11 |
| AAGGAGAGA-PO$_3$-5' | (SEQ ID NO: 118) | |
| 5'-PO$_3$-CTCGTAGCC | (SEQ ID NO: 119) | 5.12 |
| AAGAGCATC-PO$_3$-5' | (SEQ ID NO: 120) | |

1× ligase buffer: 50 mM Tris, pH 7.5; 10 mM dithiothreitol; 10 mM MgCl$_2$; 2.5 mM ATP; 50 mM NaCl.

10× ligase buffer: 500 mM Tris, pH 7.5; 100 mM dithiothreitol; 100 mM MgCl$_2$; 25 mM ATP; 500 mM NaCl Cycle 1

To each of twelve PCR tubes was added 50 μL of a 1 mM solution of Compound 1 in water; 75 μL of a 0.80 mM solution of one of Tags 1.1-1.12; 15 μL 10× ligase buffer and 10 μL deionized water. The tubes were heated to 95° C. for 1 minute and then cooled to 16° C. over 10 minutes. To each tube was added 5,000 units T4 DNA ligase (2.5 μL of a 2,000,000 unit/mL solution (New England Biolabs, Cat. No. M0202)) in 50 μl 1× ligase buffer and the resulting solutions were incubated at 16° C. for 16 hours.

Following ligation, samples were transferred to 1.5 ml Eppendorf tubes and treated with 20 μL 5 M aqueous NaCl and 500 μL cold (−20° C.) ethanol, and held at −20° C. for 1 hour. Following centrifugation, the supernatant was removed and the pellet was washed with 70% aqueous ethanol at −20° C. Each of the pellets was then dissolved in 150 μL of 150 mM sodium borate buffer, pH 9.4.

Stock solutions comprising one each of building block precursors BB1 to BB12, N,N-diisopropylethanolamine and O-(7-azabenzotriazol-1-yl)-1,1,3,3-tetramethyluronium hexafluorophosphate, each at a concentration of 0.25 M, were prepared in DMF and stirred at room temperature for 20 minutes. The building block precursor solutions were added to each of the pellet solutions described above to provide a 10-fold excess of building block precursor relative to linker. The resulting solutions were stirred. An additional 10 equivalents of building block precursor was added to the reaction mixture after 20 minute, and another 10 equivalents after 40 minutes. The final concentration of DMF in the reaction mixture was 22%. The reaction solutions were then stirred overnight at 4° C. The reaction progress was monitored by RP-HPLC using 50 mM aqueous tetraethylammonium acetate (pH=7.5) and acetonitrile, and a gradient of 2-46% acetonitrile over 14 min. Reaction was stopped when ~95% of starting material (linker) is acylated. Following acylation the reaction mixtures were pooled and lyophilized to dryness. The lyophilized material was then purified by HPLC, and the fractions corresponding to the library (acylated product) were pooled and lyophilized.

The library was dissolved in 2.5 ml of 0.01M sodium phosphate buffer (pH=8.2) and 0.1 ml of piperidine (4% v/v) was added to it. The addition of piperidine results in turbidity which does not dissolve on mixing. The reaction mixtures were stirred at room temperature for 50 minutes, and then the turbid solution was centrifuged (14,000 rpm), the supernatant was removed using a 200 μl pipette, and the pellet was resuspended in 0.1 ml of water. The aqueous wash was combined with the supernatant and the pellet was discarded. The deprotected library was precipitated from solution by addition of excess ice-cold ethanol so as to bring the final concentration of ethanol in the reaction to 70% v/v. Centrifugation of the aqueous ethanol mixture gave a white pellet comprising the library. The pellet was washed once with cold 70% aq. ethanol. After removal of solvent the pellet was dried in air (~5 min.) to remove traces of ethanol and then used in cycle 2. The tags and corresponding building block precursors used in Round 1 are set forth in Table 1, below.

TABLE 1

| Building Block Precursor | Tag |
|---|---|
| BB1 | 1.11 |
| BB2 | 1.6 |
| BB3 | 1.2 |
| BB4 | 1.8 |
| BB5 | 1.1 |
| BB6 | 1.10 |
| BB7 | 1.12 |
| BB8 | 1.5 |

TABLE 1-continued

| Building Block Precursor | Tag |
|---|---|
| BB9 | 1.4 |
| BB10 | 1.3 |
| BB11 | 1.7 |
| BB12 | 1.9 |

Cycles 2-5

For each of these cycles, the combined solution resulting from the previous cycle was divided into 12 equal aliquots of 50 ul each and placed in PCR tubes. To each tube was added a solution comprising a different tag, and ligation, purification and acylation were performed as described for Cycle 1, except that for Cycles 3-5, the HPLC purification step described for Cycle 1 was omitted. The correspondence between tags and building block precursors for Cycles 2-5 is presented in Table 2.

The products of Cycle 5 were ligated with the closing primer shown below, using the method described above for ligation of tags.

5'-PO$_3$-GGCACATTGATTTGGGAGTCA           (SEQ ID NO: 918)
         GTGTAACTAAACCCTCAGT-PO$_3$-5' (SEQ ID NO: 919)

TABLE 2

| Building Block Precursor | Cycle 2 Tag | Cycle 3 Tag | Cycle 4 Tag | Cycle 5 Tag |
|---|---|---|---|---|
| BB1 | 2.7 | 3.7 | 4.7 | 5.7 |
| BB2 | 2.8 | 3.8 | 4.8 | 5.8 |
| BB3 | 2.2 | 3.2 | 4.2 | 5.2 |
| BB4 | 2.10 | 3.10 | 4.10 | 5.10 |
| BB5 | 2.1 | 3.1 | 4.1 | 5.1 |
| BB6 | 2.12 | 3.12 | 4.12 | 5.12 |
| BB7 | 2.5 | 3.5 | 4.5 | 5.5 |
| BB8 | 2.6 | 3.6 | 4.6 | 5.6 |
| BB9 | 2.4 | 3.4 | 4.4 | 5.4 |
| BB10 | 2.3 | 3.3 | 4.3 | 5.3 |
| BB11 | 2.9 | 3.9 | 4.9 | 5.9 |
| BB12 | 2.11 | 3.11 | 4.11 | 5.11 |

Figure 7:
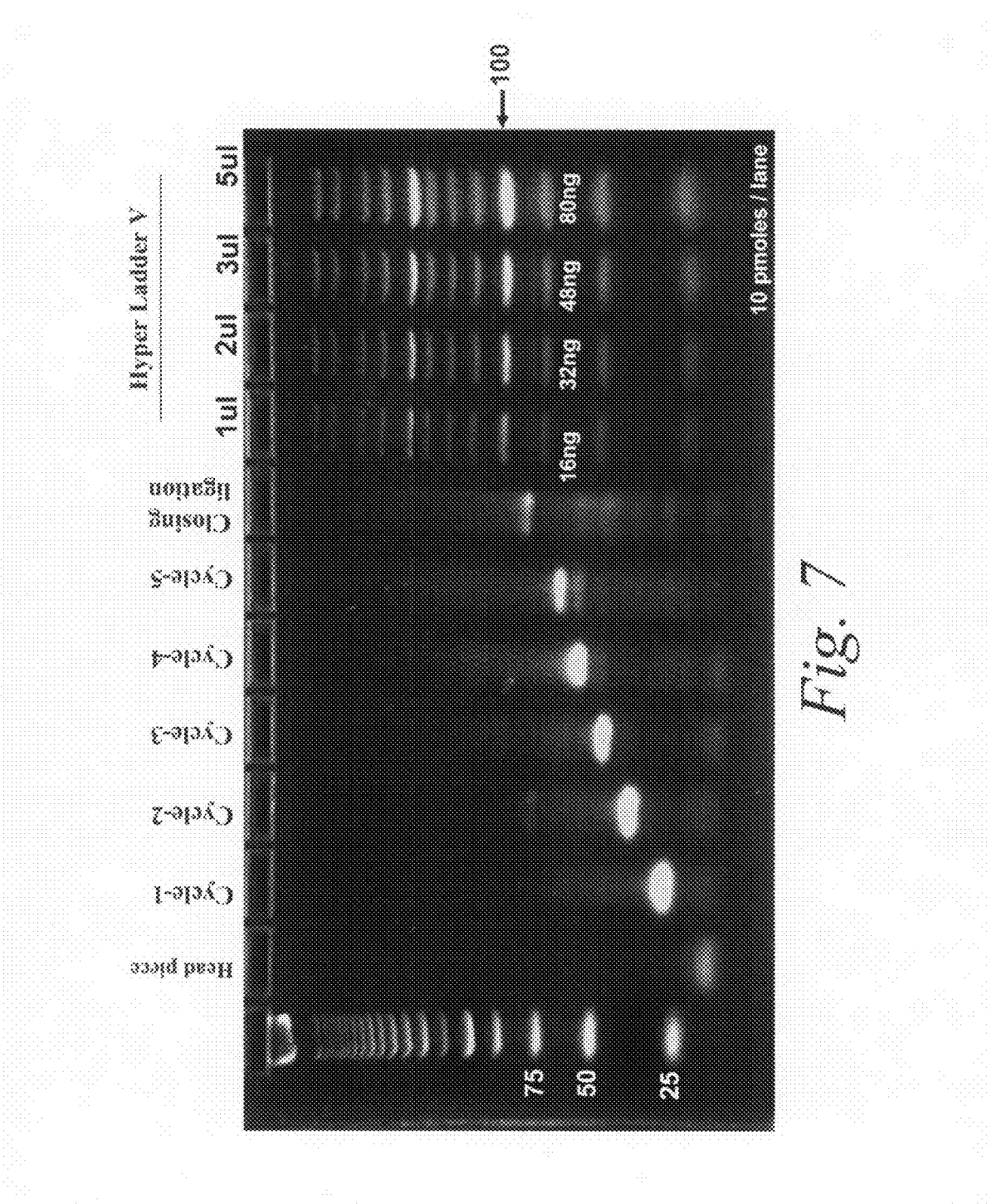
FIG. 7 is a gel resulting from electrophoresis of the products of each of cycles 1 to 5 described in Example 1 and following ligation of the closing primer. Molecular weight standards are shown in lane 1, and the indicated quantities of a hyperladder, for DNA quantitation, are shown in lanes 9 to 12.

Results:

The synthetic procedure described above has the capability of producing a library comprising $12^5$ (about 249,000) different structures. The synthesis of the library was monitored via gel electrophoresis of the product of each cycle. The results of each of the five cycles and the final library following ligation of the closing primer are illustrated in FIG. 7. The compound labeled "head piece" is Compound 1. The figure shows that each cycle results in the expected molecular weight increase and that the products of each cycle are substantially homogeneous with regard to molecular weight.

Example 2

Synthesis and Characterization of a Library on the Order of $10^8$ Members

The synthesis of a library comprising on the order of $10^5$ distinct members was accomplished using the following reagents:

Compound 2:
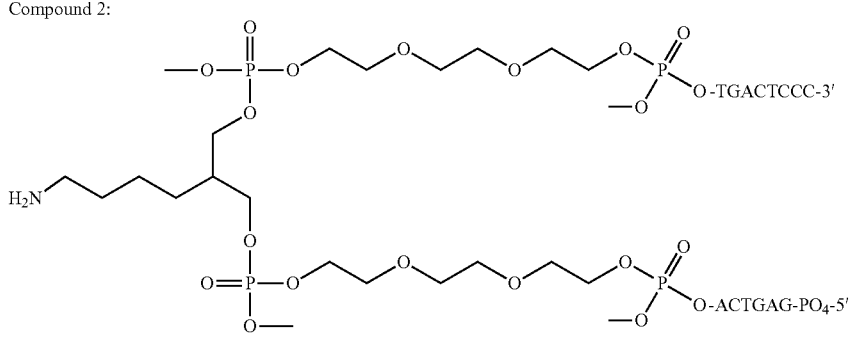
Single Letter Codes for Deoxyribonucleotides:
A=adenosine
C=cytidine
G=guanosine
T=thymidine
Building Block Precursors:
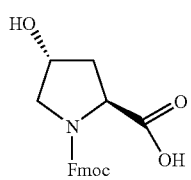
BB1
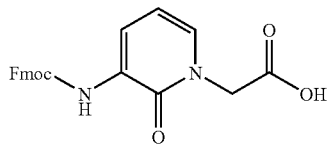
BB2
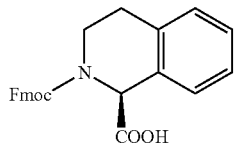
BB3
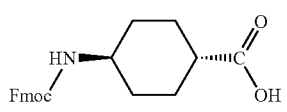
BB4
BB5
BB6
BB7
BB8
BB9
BB10
BB11
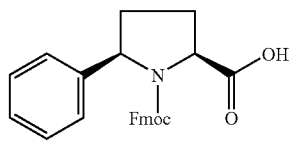
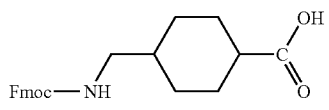
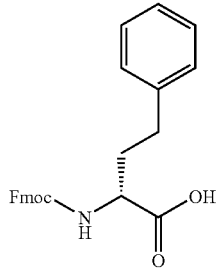

-continued
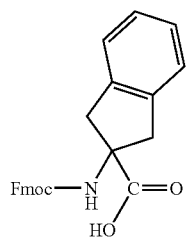
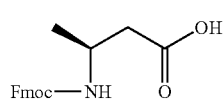
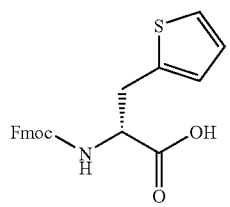
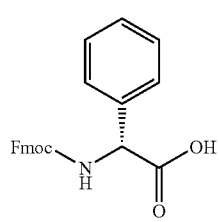
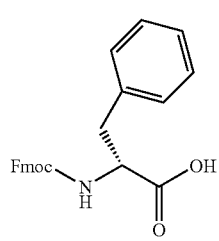
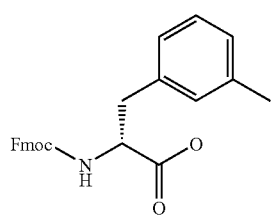
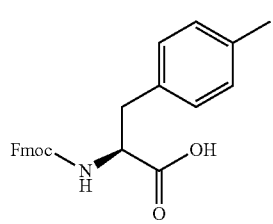
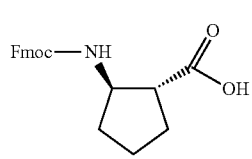
-continued
BB12
BB13
BB14
BB15
BB16
BB17
BB18
BB19
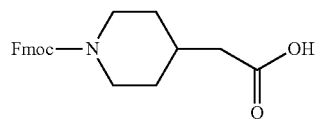
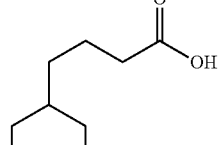
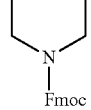
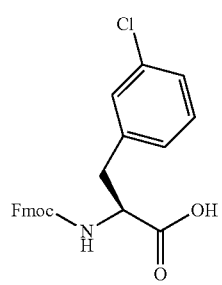
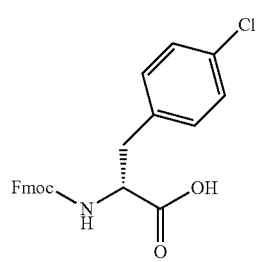
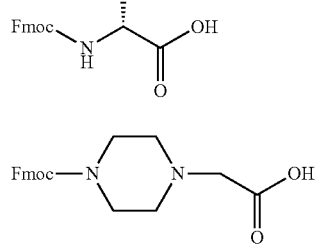
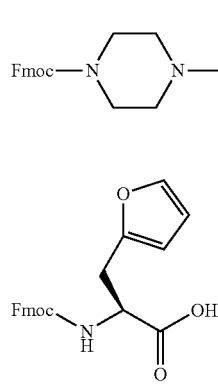
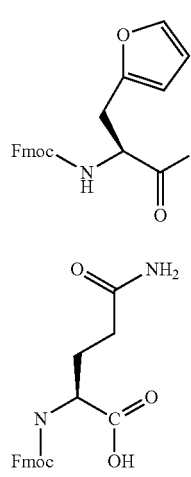
BB20
BB21
BB22
BB23
BB24
BB25
BB26

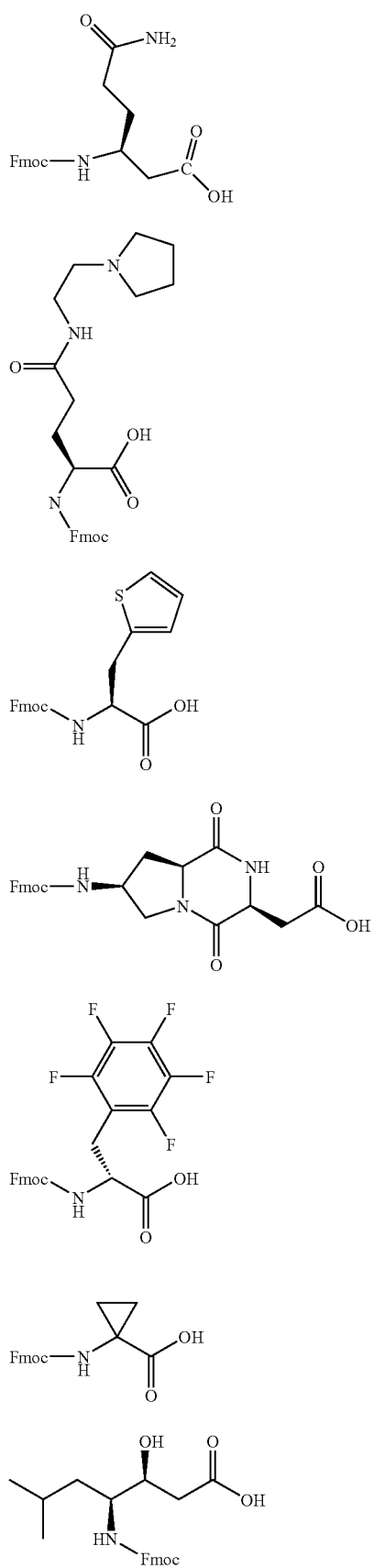
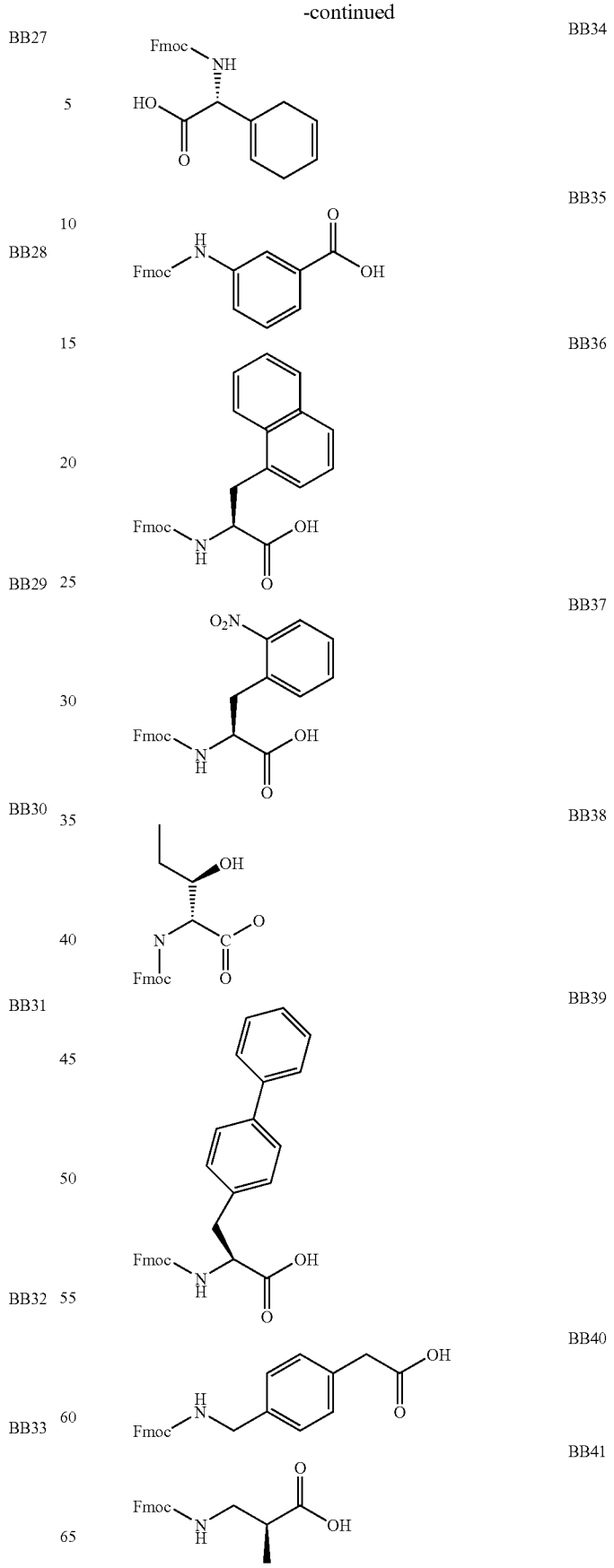

-continued
BB42 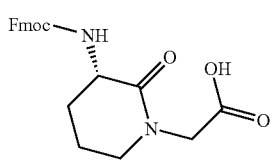
BB43 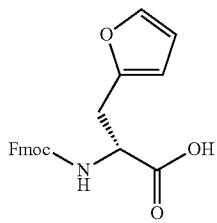
BB44 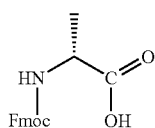
BB45 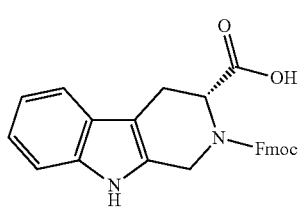
BB46 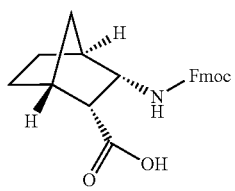
BB47 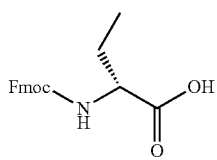
BB48 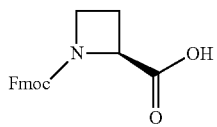
BB49 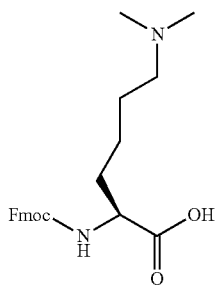
-continued
BB50 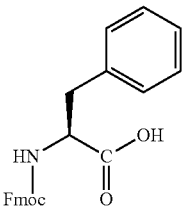
BB51
BB52
BB53
BB54
BB55
BB57
BB58

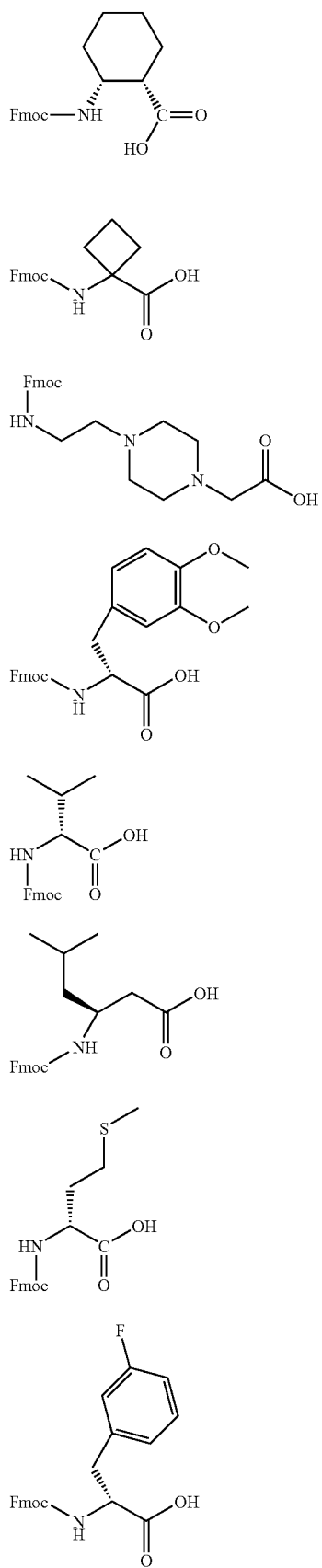
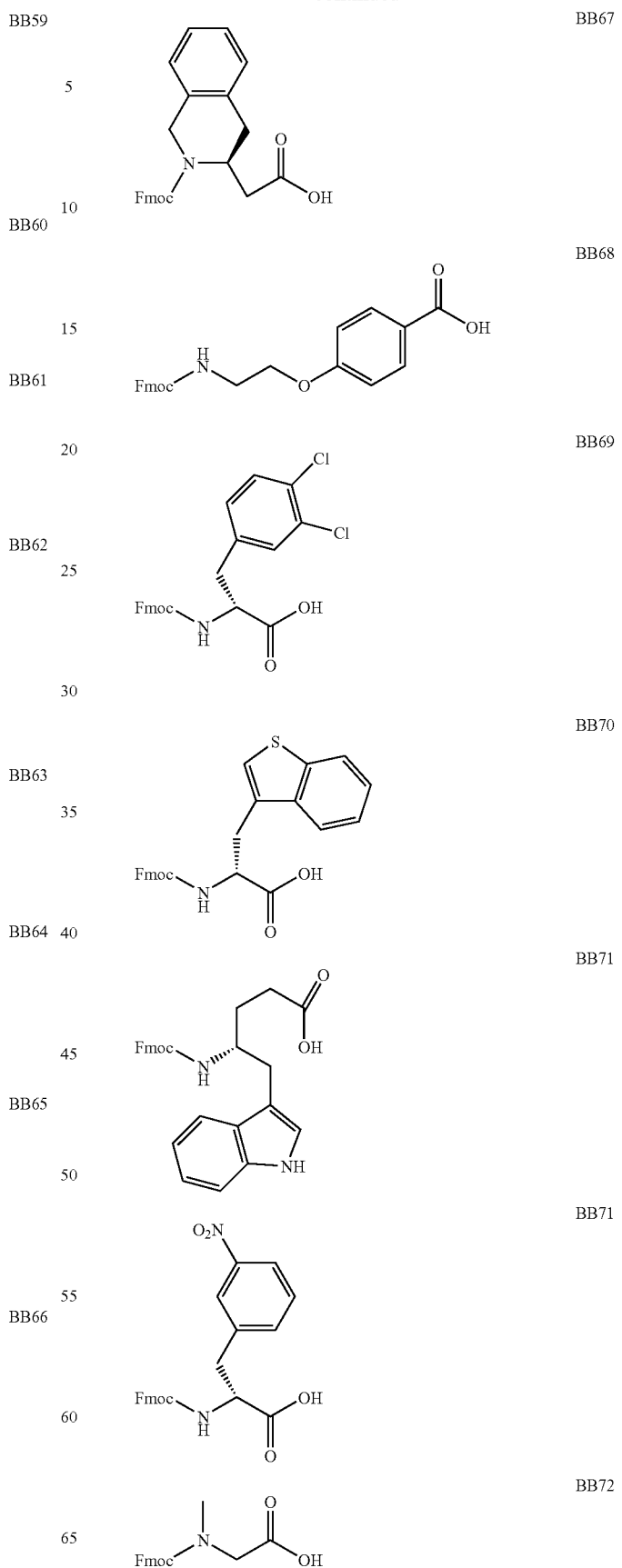

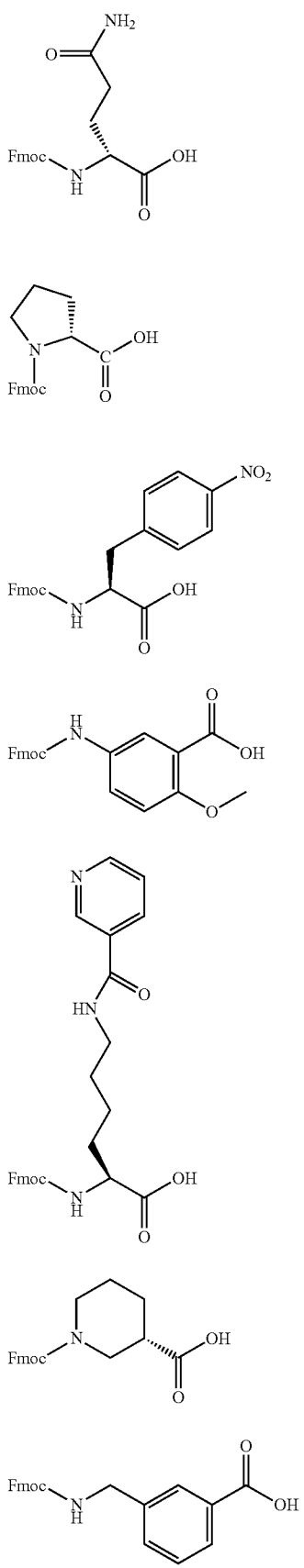
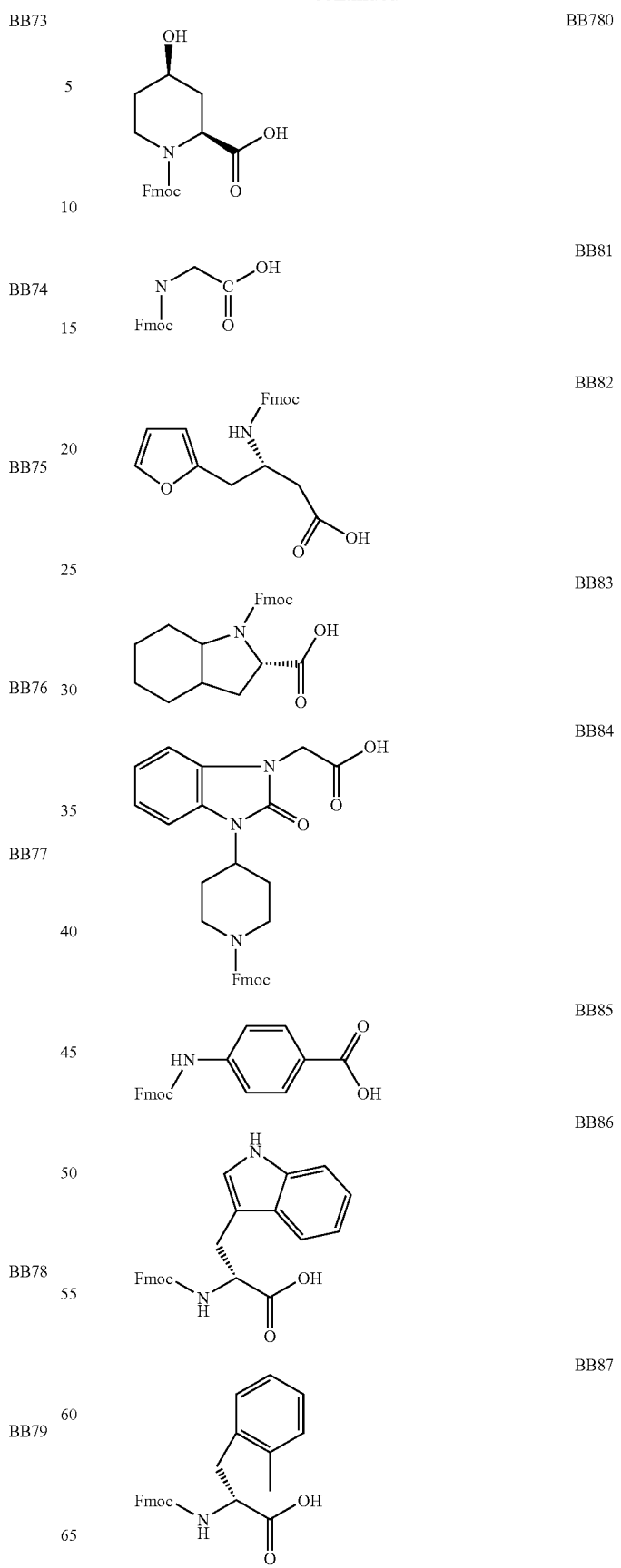

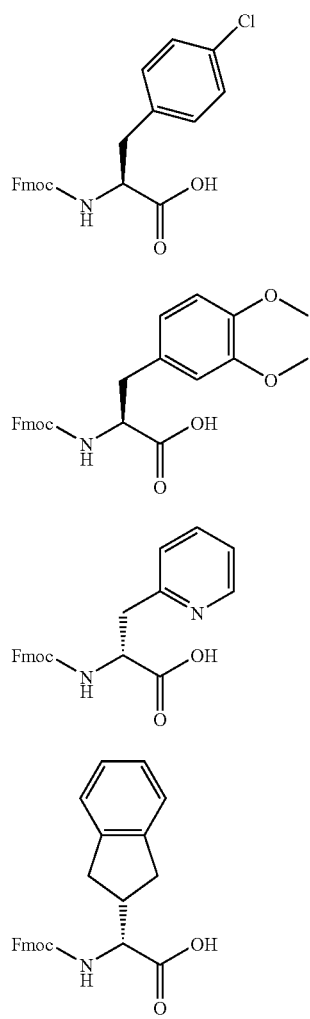

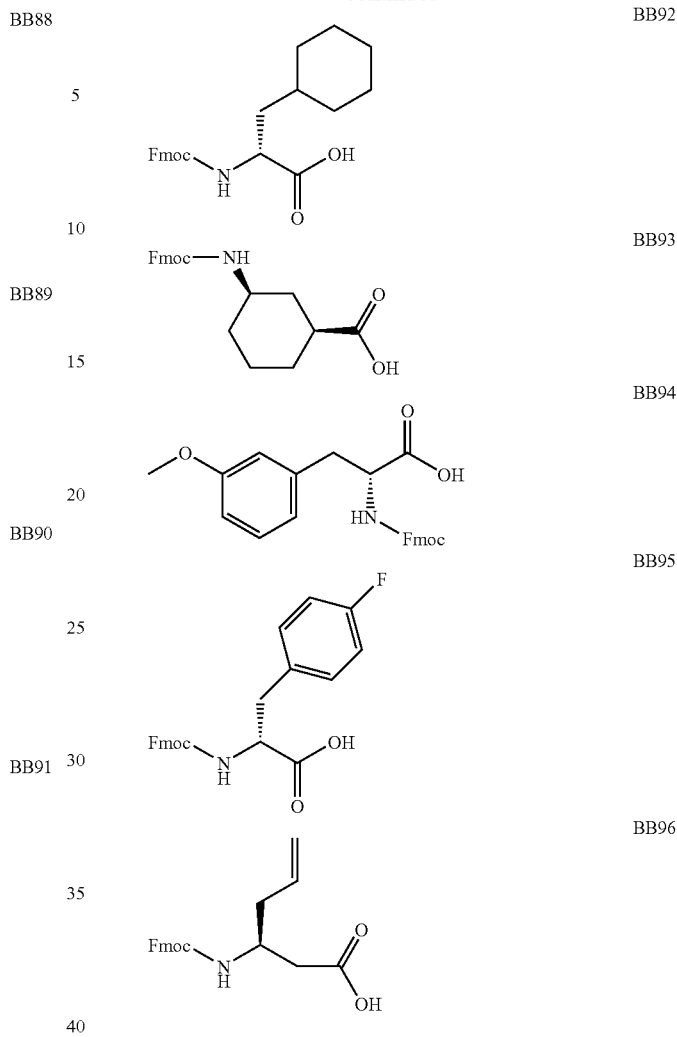

TABLE 3

| Oligonucleotide tags used in cycle 1: | | |
|---|---|---|
| Tag Number | Top Strand Sequence | Bottom Strand Sequence |
| 1.1 | 5'-PO3-AAATCGATGTGGTCACTCAG (SEQ ID NO: 121) | 5'-PO3-GAGTGACCACATCGATTTGG (SEQ ID NO: 122) |
| 1.2 | 5'-PO3-AAATCGATGTGGACTAGGAG (SEQ ID NO: 123) | 5'-PO3-CCTAGTCCACATCGATTTGG (SEQ ID NO: 124) |
| 1.3 | 5'-PO3-AAATCGATGTGCCGTATGAG (SEQ ID NO: 125) | 5'-PO3-CATACGGCACATCGATTTGG (SEQ ID NO: 126) |
| 1.4 | 5'-PO3-AAATCGATGTGCTGAAGGAG (SEQ ID NO: 127) | 5'-PO3-CCTTCAGCACATCGATTTGG (SEQ ID NO: 128) |
| 1.5 | 5'-PO3-AAATCGATGTGGACTAGCAG (SEQ ID NO: 129) | 5'-PO3-GCTAGTCCACATCGATTTGG (SEQ ID NO: 130) |
| 1.6 | 5'-PO3-AAATCGATGTGCGCTAAGAG (SEQ ID NO: 131) | 5'-PO3-CTTAGCGCACATCGATTTGG (SEQ ID NO: 132) |

TABLE 3-continued

Oligonucleotide tags used in cycle 1:

| Tag Number | Top Strand Sequence | Bottom Strand Sequence |
|---|---|---|
| 1.7 | 5'-PO3-AAATCGATGTGAGCCGAGAG (SEQ ID NO: 133) | 5'-PO3-CTCGGCTCACATCGATTTGG (SEQ ID NO: 134) |
| 1.8 | 5'-PO3-AAATCGATGTGCCGTATCAG (SEQ ID NO: 135) | 5'-PO3-GATACGGCACATCGATTTGG (SEQ ID NO: 136) |
| 1.9 | 5'-PO3-AAATCGATGTGCTGAAGCAG (SEQ ID NO: 137) | 5'-PO3-GCTTCAGCACATCGATTTGG (SEQ ID NO: 138) |
| 1.10 | 5'-PO3-AAATCGATGTGTGCGAGTAG (SEQ ID NO: 139) | 5'-PO3-ACTCGCACACATCGATTTGG (SEQ ID NO: 140) |
| 1.11 | 5'-PO3-AAATCGATGTGTTTGGCGAG (SEQ ID NO: 141) | 5'-PO3-CGCCAAACACATCGATTTGG (SEQ ID NO: 142) |
| 1.12 | 5'-PO3-AAATCGATGTGCGCTAACAG (SEQ ID NO: 143) | 5'-PO3-GTTAGCGCACATCGATTTGG (SEQ ID NO: 144) |
| 1.13 | 5'-PO3-AAATCGATGTGAGCCGACAG (SEQ ID NO: 145) | 5'-PO3-GTCGGCTCACATCGATTTGG (SEQ ID NO: 146) |
| 1.14 | 5'-PO3-AAATCGATGTGAGCCGAAAG (SEQ ID NO: 147) | 5'-PO3-TTCGGCTCACATCGATTTGG (SEQ ID NO: 148) |
| 1.15 | 5'-PO3-AAATCGATGTGTCGGTAGAG (SEQ ID NO: 149) | 5'-PO3-CTACCGACACATCGATTTGG (SEQ ID NO: 150) |
| 1.16 | 5'-PO3-AAATCGATGTGGTTGCCGAG (SEQ ID NO: 151) | 5'-PO3-CGGCAACCACATCGATTTGG (SEQ ID NO: 152) |
| 1.17 | 5'-PO3-AAATCGATGTGAGTGCGTAG (SEQ ID NO: 153) | 5'-PO3-ACGCAGTCACATCGATTTGG (SEQ ID NO: 154) |
| 1.18 | 5'-PO3-AAATCGATGTGGTTGCCAAG (SEQ ID NO: 155) | 5'-PO3-TGGCAACCACATCGATTTGG (SEQ ID NO: 156) |
| 1.19 | 5'-PO3-AAATCGATGTGTGCGAGGAG (SEQ ID NO: 157) | 5'-PO3-CCTCGCACACATCGATTTGG (SEQ ID NO: 158) |
| 1.20 | 5'-PO3-AAATCGATGTGGAACACGAG (SEQ ID NO: 159) | 5'-PO3-CGTGTTCCACATCGATTTGG (SEQ ID NO: 160) |
| 1.21 | 5'-PO3-AAATCGATGTGCTTGTCGAG (SEQ ID NO: 161) | 5'-PO3-CGACAAGCACATCGATTTGG (SEQ ID NO: 162) |
| 1.22 | 5'-PO3-AAATCGATGTGTTCCGGTAG (SEQ ID NO: 163) | 5'-PO3-A0CCGGAACACATCGATTTGG (SEQ ID NO: 164) |
| 1.23 | 5'-PO3-AAATCGATGTGTGCGAGCAG (SEQ ID NO: 165) | 5'-PO3-GCTCGCACACATCGATTTGG (SEQ ID NO: 166) |
| 1.24 | 5'-PO3-AAATCGATGTGGTCAGGTAG (SEQ ID NO: 167) | 5'-PO3-ACCTGACCACATCGATTTGG (SEQ ID NO: 168) |

TABLE 3-continued

Oligonucleotide tags used in cycle 1:

| Tag Number | Top Strand Sequence | Bottom Strand Sequence |
|---|---|---|
| 1.25 | 5'-PO3-AAATCGATGTGGCCTGTTAG (SEQ ID NO: 169) | 5'-PO3-AACAGGCCACATCGATTTGG (SEQ ID NO: 170) |
| 1.26 | 5'-PO3-AAATCGATGTGGAACACCAG (SEQ ID NO: 171) | 5'-PO3-GGTGTTCCACATCGATTTGG (SEQ ID NO: 172) |
| 1.27 | 5'-PO3-AAATCGATGTGCTTGTCCAG (SEQ ID NO: 173) | 5'-PO3-GGACAAGCACATCGATTTGG (SEQ ID NO: 174) |
| 1.28 | 5'-PO3-AAATCGATGTGTGCGAGAAG (SEQ ID NO: 175) | 5'-PO3-TCTCGCACACATCGATTTGG (SEQ ID NO: 176) |
| 1.29 | 5'-PO3-AAATCGATGTGAGTGCGGAG (SEQ ID NO: 177) | 5'-PO3-CCGCACTCACATCGATTTGG (SEQ ID NO: 178) |
| 1.30 | 5'-PO3-AAATCGATGTGTTGTCCGAG (SEQ ID NO: 179) | 5'-PO3-CGGACAACACATCGATTTGG (SEQ ID NO: 180) |
| 1.31 | 5'-PO3-AAATCGATGTGTGGAACGAG (SEQ ID NO: 181) | 5'-PO3-CGTTCCACACATCGATTTGG (SEQ ID NO: 182) |
| 1.32 | 5'-PO3-AAATCGATGTGAGTGCGAAG (SEQ ID NO: 183) | 5'-PO3-TCGCACTCACATCGATTTGG (SEQ ID NO: 184) |
| 1.33 | 5'-PO3-AAATCGATGTGTGGAACCAG (SEQ ID NO: 185) | 5'-PO3-GGTTCCACACATCGATTTGG (SEQ ID NO: 186) |
| 1.34 | 5'-PO3-AAATCGATGTGTTAGGCGAG (SEQ ID NO: 187) | 5'-PO3-CGCCTAACACATCGATTTGG (SEQ ID NO: 188) |
| 1.35 | 5'-PO3-AAATCGATGTGGCCTGTGAG (SEQ ID NO: 189) | 5'-PO3-CACAGGCCACATCGATTTGG (SEQ ID NO: 190) |
| 1.36 | 5'-PO3-AAATCGATGTGCTCCTGTAG (SEQ ID NO: 191) | 5'-PO3-ACAGGAGCACATCGATTTGG (SEQ ID NO: 192) |
| 1.37 | 5'-PO3-AAATCGATGTGGTCAGGCAG (SEQ ID NO: 193) | 5'-PO3-GCCTGACCACATCGATTTGG (SEQ ID NO: 194) |
| 1.38 | 5'-PO3-AAATCGATGTGGTGAGGAAG (SEQ ID NO: 195) | 5'-PO3-TCCTGACCACATCGATTTGG (SEQ ID NO: 196) |
| 1.39 | 5'-PO3-AAATCGATGTGGTAGCCGAG (SEQ ID NO: 197) | 5'-PO3-CGGCTACCACATCGATTTGG (SEQ ID NO: 198) |
| 1.40 | 5'-PO3-AAATCGATGTGGCCTGTAAG (SEQ ID NO: 199) | 5'-PO3-TACAGGCCACATCGATTTGG (SEQ ID NO: 200) |
| 1.41 | 5'-PO3-AAATCGATGTGCTTTCGGAG (SEQ ID NO: 201) | 5'-PO3-CCGAAAGCACATCGATTTGG (SEQ ID NO: 202) |
| 1.42 | 5'-PO3-AAATCGATGTGCGTAAGGAG (SEQ ID NO: 203) | 5'-PO3-CCTTACGCACATCGATTTGG (SEQ ID NO: 204) |

TABLE 3-continued

Oligonucleotide tags used in cycle 1:

| Tag Number | Top Strand Sequence | Bottom Strand Sequence |
|---|---|---|
| 1.43 | 5'-PO3-AAATCGATGTGAGAGCGTAG (SEQ ID NO: 205) | 5'-PO3-ACGCTCTCACATCGATTTGG (SEQ ID NO: 206) |
| 1.44 | 5'-PO3-AAATCGATGTGGACGGCAAG (SEQ ID NO: 207) | 5'-PO3-TGCCGTCCACATCGATTTGG (SEQ ID NO: 208) |
| 1.45 | 5'-PO3-AAATCGATGTGCTTTCGCAG (SEQ ID NO: 209) | 5'-PO3-GCGAAAGCACATCGATTTGG (SEQ ID NO: 210) |
| 1.46 | 5'-PO3-AAATCGATGTGCGTAAGCAG (SEQ ID NO: 211) | 5'-PO3-GCTTACGCACATCGATTTGG (SEQ ID NO: 212) |
| 1.47 | 5'-PO3-AAATCGATGTGGCTATGGAG (SEQ ID NO: 213) | 5'-PO3-CCATAGCCACATCGATTTGG (SEQ ID NO: 214) |
| 1.48 | 5'-PO3-AAATCGATGTGACTCTGGAG (SEQ ID NO: 215) | 5'-PO3-CCAGAGTCACATCGATTTGG (SEQ ID NO: 216) |
| 1.49 | 5'-PO3-AAATCGATGTGCTGGAAAG (SEQ ID NO: 217) | 5'-PO3-TTCCAGCACATCGATTTGG (SEQ ID NO: 218) |
| 1.50 | 5'-PO3-AAATCGATGTGCCGAAGTAG (SEQ ID NO: 219) | 5'-PO3-ACTTCGGCACATCGATTTGG (SEQ ID NO: 220) |
| 1.51 | 5'-PO3-AAATCGATGTGCTCCTGAAG (SEQ ID NO: 221) | 5'-PO3-TCAGGAGCACATCGATTTGG (SEQ ID NO: 222) |
| 1.52 | 5'-PO3-AAATCGATGTGTCCAGTCAG (SEQ ID NO: 223) | 5'-PO3-GACTGGACACATCGATTTGG (SEQ ID NO: 224) |
| 1.53 | 5'-PO3-AAATCGATGTGAGAGCGGAG (SEQ ID NO: 225) | 5'-PO3-CCGCTCTCACATCGATTTGG (SEQ ID NO: 226) |
| 1.54 | 5'-PO3-AAATCGATGTGAGAGCGAAG (SEQ ID NO: 227) | 5'-PO3-TCGCTCTCACATCGATTTGG (SEQ ID NO: 228) |
| 1.55 | 5'-PO3-AAATCGATGTGCCGAAGGAG (SEQ ID NO: 229) | 5'-PO3-CCTTCGGCACATCGATTTGG (SEQ ID NO: 230) |
| 1.56 | 5'-PO3-AAATCGATGTGCCGAAGCAG (SEQ ID NO: 231) | 5'-PO3-GCTTCGGCACATCGATTTGG (SEQ ID NO: 232) |
| 1.57 | 5'-PO3-AAATCGATGTGTGTTCCGAG (SEQ ID NO: 233) | 5'-PO3-CGGAACACACATCGATTTGG (SEQ ID NO: 234) |
| 1.58 | 5'-PO3-AAATCGATGTGTCTGGCGAG (SEQ ID NO: 235) | 5'-PO3-CGCCAGACACATCGATTTGG (SEQ ID NO: 236) |
| 1.59 | 5'-PO3-AAATCGATGTGCTATCGGAG (SEQ ID NO: 237) | 5'-PO3-CCGATAGCACATCGATTTGG (SEQ ID NO: 238) |
| 1.60 | 5'-PO3-AAATCGATGTGCGAAAGGAG (SEQ ID NO: 239) | 5'-PO3-CCTTTCGCACATCGATTTGG (SEQ ID NO: 240) |

TABLE 3-continued

Oligonucleotide tags used in cycle 1:

| Tag Number | Top Strand Sequence | Bottom Strand Sequence |
|---|---|---|
| 1.61 | 5'-PO3-AAATCGATGTGCCGAAGAAG (SEQ ID NO: 241) | 5'-PO3-TCTTCGGCACATCGATTTGG (SEQ ID NO: 242) |
| 1.62 | 5'-PO3-AAATCGATGTGGTTGCAGAG (SEQ ID NO: 243) | 5'-PO3-CTGCAACCACATCGATTTGG (SEQ ID NO: 244) |
| 1.63 | 5'-PO3-AAATCGATGTGGATGGTGAG (SEQ ID NO: 245) | 5'-PO3-CACCATCCACATCGATTTGG (SEQ ID NO: 246) |
| 1.64 | 5'-PO3-AAATCGATGTGCTATCGCAG (SEQ ID NO: 247) | 5'-PO3-GCGATAGCACATCGATTTGG (SEQ ID NO: 248) |
| 1.65 | 5'-PO3-AAATCGATGTGCGAAAGCAG (SEQ ID NO: 249) | 5'-PO3-GCTTTCGCACATCGATTTGG (SEQ ID NO: 250) |
| 1.66 | 5'-PO3-AAATCGATGTGACACTGGAG (SEQ ID NO: 251) | 5'-PO3-CCAGTGTCACATCGATTTGG (SEQ ID NO: 252) |
| 1.67 | 5'-PO3-AAATCGATGTGTCTGGCAAG (SEQ ID NO: 253) | 5'-PO3-TGCCAGACACATCGATTTGG (SEQ ID NO: 254) |
| 1.68 | 5'-PO3-AAATCGATGTGGATGGTCAG (SEQ ID NO: 255) | 5'-PO3-GACCATCCACATCGATTTGG (SEQ ID NO: 256) |
| 1.69 | 5'-PO3-AAATCGATGTGGTTGCACAG (SEQ ID NO: 257) | 5'-PO3-GTGCAACCACATCGATTTGG (SEQ ID NO: 258) |
| 1.70 | 5'-PO3-AAATCGATGTGGGCATCGAG (SEQ ID NO: 259) | 5'-PO3-CGATGCCCCATCCGATTT GG (SEQ ID NO: 260) |
| 1.71 | 5'-PO3-AAATCGATGTGTGCCTCCAG (SEQ ID NO: 261) | 5'-PO3-GGAGGCACACATCGATTTGG (SEQ ID NO: 262) |
| 1.72 | 5'-PO3-AAATCGATGTGTGCCTCAAG (SEQ ID NO: 263) | 5'-PO3-TGAGGCACACATCGATTTGG (SEQ ID NO: 264) |
| 1.73 | 5'-PO3-AAATCGATGTGGGCATCCAG (SEQ ID NO: 265) | 5'-PO3-GGATGCCCACATCGATTTGG (SEQ ID NO: 266) |
| 1.74 | 5'-PO3-AAATCGATGTGGGCATCAAG (SEQ ID NO: 267) | 5'-PO3-TGATGCCCA CAT CGA TTT GG (SEQ ID NO: 268) |
| 1.75 | 5'-PO3-AAATCGATGTGCCTGTCGAG (SEQ ID NO: 269) | 5'-PO3-CGA CAG GCA CAT CGA TTT GG (SEQ ID NO: 270) |
| 1.76 | 5'-PO3-AAATCGATGTGGACGGATAG (SEQ ID NO: 271) | 5'-PO3-ATC CGT CCA CAT CGA TTT GG (SEQ ID NO: 272) |
| 1.77 | 5'-PO3-AAATCGATGTGCCTGTCCAG (SEQ ID NO: 273) | 5'-PO3-GGA CAG GCA CAT CGA TTT GG (SEQ ID NO: 274) |
| 1.78 | 5'-PO3-AAATCGATGTGAAGCACGAG (SEQ ID NO: 275) | 5'-PO3-CGT GCT TCA CAT CGA TTT GG (SEQ ID NO: 276) |
| 1.79 | 5'-PO3-AAATCGATGTGCCTGTCAAG (SEQ ID NO: 277) | 5'-PO3-TGA CAG GCA CAT CGA TTT GG (SEQ ID NO: 278) |

TABLE 3-continued

Oligonucleotide tags used in cycle 1:

| Tag Number | Top Strand Sequence | Bottom Strand Sequence |
|---|---|---|
| 1.80 | 5'-PO3-AAATCGATGTGAAGCACCAG (SEQ ID NO: 279) | 5'-PO3-GGT GCT TCA CAT CGA TTT GG (SEQ ID NO: 280) |
| 1.81 | 5'-PO3-AAATCGATGTGCCTTCGTAG (SEQ ID NO: 281) | 5'-PO3-ACG AAG GCA CAT CGA TTT GG (SEQ ID NO: 282) |
| 1.82 | 5'-PO3-AAATCGATGTGTCGTCCGAG (SEQ ID NO: 283) | 5'-PO3-CGG ACG ACA CAT CGA TTT GG (SEQ ID NO: 284) |
| 1.83 | 5'-PO3-AAATCGATGTGGAGTCTGAG (SEQ ID NO: 285) | 5'-PO3-CAG ACT CCA CAT CGA TTT GG (SEQ ID NO: 286) |
| 1.84 | 5'-PO3-AAATCGATGTGTGATCCGAG (SEQ ID NO: 287) | 5'-PO3-CGG ATC ACA CAT CGA TTT GG (SEQ ID NO: 288) |
| 1.85 | 5'-PO3-AAATCGATGTGTCAGGCGAG (SEQ ID NO: 289) | 5'-PO3-CGC CTG ACA CAT CGA TTT GG (SEQ ID NO: 290) |
| 1.86 | 5'-PO3-AAATCGATGTGTCGTCCAAG (SEQ ID NO: 291) | 5'-PO3-TGG ACG ACA CAT CGA TTT GG (SEQ ID NO: 292) |
| 1.87 | 5'-PO3-AAATCGATGTGGACGGAGAG (SEQ ID NO: 293) | 5'-PO3-CTC CGT CCA CAT CGA TTT GG (SEQ ID NO: 294) |
| 1.88 | 5'-PO3-AAATCGATGTGGTAGCAGAG (SEQ ID NO: 295) | 5'-PO3-CTG CTA CCA CAT CGA TTT GG (SEQ ID NO: 296) |
| 1.89 | 5'-PO3-AAATCGATGTGGCTGTGTAG (SEQ ID NO: 297) | 5'-PO3-ACACAGCCACATCGATTTGG (SEQ ID NO: 298) |
| 1.90 | 5'-PO3-AAATCGATGTGGACGGACAG (SEQ ID NO: 299) | 5'-PO3-GTC CGT CCA CAT CGA TTT GG (SEQ ID NO: 300) |
| 1.91 | 5'-PO3-AAATCGATGTGTCAGGCAAG (SEQ ID NO: 301) | 5'-PO3-TGC CTG ACA CAT CGA TTT GG (SEQ ID NO: 302) |
| 1.92 | 5'-PO3-AAATCGATGTGGCTCGAAAG (SEQ ID NO: 303) | 5'-PO3-TTCGAGCCACATCGATTGG (SEQ ID NO: 304) |
| 1.93 | 5'-PO3-AAATCGATGTGCCTTCGGAG (SEQ ID NO: 305) | 5'-PO3-CCG AAG GCA CAT CGA TTT GG (SEQ ID NO: 306) |
| 1.94 | 5'-PO3-AAATCGATGTGGTAGCACAG (SEQ ID NO: 307) | 5'-PO3-GTG CTA CCA CAT CGA TTT GG (SEQ ID NO: 308) |
| 1.95 | 5'-PO3-AAATCGATGTGGAAGGTCAG (SEQ ID NO: 309) | 5'-PO3-GAC CTT CCA CAT CGA TTT GG (SEQ ID NO: 310) |
| 1.96 | 5'-PO3-AAATCGATGTGGTGCTGTAG (SEQ ID NO: 311) | 5'-PO3-ACA GCA CCA CAT CGA TTT GG (SEQ ID NO: 312) |

TABLE 4

Oligonucleotide tags used in cycle 2:

| Tag Number | Top strand sequence | Bottom strand sequence |
|---|---|---|
| 2.1 | 5'-PO3-GTT GCC TGT (SEQ ID NO: 313) | 5'-PO3-AGG CAA CCT (SEQ ID NO: 314) |
| 2.2 | 5'-PO3-CAG GAC GGT (SEQ ID NO: 315) | 5'-PO3-CGT CCT GCT (SEQ ID NO: 316) |
| 2.3 | 5'-PO3-AGA CGT GGT (SEQ ID NO: 317) | 5'-PO3-CAC GTC TCT (SEQ ID NO: 318) |
| 2.4 | 5'-PO3-CAG GAC CGT (SEQ ID NO: 319) | 5'-PO3-GGT CCT GCT (SEQ ID NO: 320) |
| 2.5 | 5'-PO3-CAG GAC AGT (SEQ ID NO: 321) | 5'-PO3-TGT CCT GCT (SEQ ID NO: 322) |
| 2.6 | 5'-PO3-CAC TCT GGT (SEQ ID NO: 323) | 5'-PO3-CAG AGT GCT (SEQ ID NO: 324) |
| 2.7 | 5'-PO3-GAC GGC TGT (SEQ ID NO: 325) | 5'-PO3-AGC CGT CCT (SEQ ID NO: 326) |
| 2.8 | 5'-PO3-CAC TCT CGT (SEQ ID NO: 327) | 5'-PO3-GAG AGT GCT (SEQ ID NO: 328) |
| 2.9 | 5'-PO3-GTA GCC TGT (SEQ ID NO: 329) | 5'-PO3-AGG CTA CCT (SEQ ID NO: 330) |
| 2.10 | 5'-PO3-GCC ACT TGT (SEQ ID NO: 331) | 5'-PO3-AAG TGG CCT (SEQ ID NO: 332) |
| 2.11 | 5'-PO3-CAT CGC TGT (SEQ ID NO: 333) | 5'-PO3-AGC GAT GCT (SEQ ID NO: 334) |
| 2.12 | 5'-PO3-CAC TGG TGT (SEQ ID NO: 335) | 5'-PO3-ACC AGT GCT (SEQ ID NO: 336) |
| 2.13 | 5'-PO3-GCC ACT GGT (SEQ ID NO: 337) | 5'-PO3-CAG TGG CCT (SEQ ID NO: 338) |
| 2.14 | 5'-PO3-TCT GGC TGT (SEQ ID NO: 339) | 5'-PO3-AGC CAG ACT (SEQ ID NO: 340) |
| 2.15 | 5'-PO3-GCC ACT CGT (SEQ ID NO: 341) | 5'-PO3-GAG TGG CCT (SEQ ID NO: 342) |
| 2.16 | 5'-PO3-TGC CTC TGT (SEQ ID NO: 343) | 5'-PO3-AGA GGC ACT (SEQ ID NO: 344) |
| 2.17 | 5'-PO3-CAT CGC AGT (SEQ ID NO: 345) | 5'-PO3-TGC GAT GCT (SEQ ID NO: 346) |
| 2.18 | 5'-PO3-CAG GAA GGT (SEQ ID NO: 347) | 5'-PO3-CTT CCT GCT (SEQ ID NO: 348) |
| 2.19 | 5'-PO3-GGC ATC TGT (SEQ ID NO: 349) | 5'-PO3-AGA TGC CCT (SEQ ID NO: 350) |
| 2.20 | 5'-PO3-CGG TGG TGT (SEQ ID NO: 351) | 5'-PO3-AGC ACC GCT (SEQ ID NO: 352) |
| 2.21 | 5'-PO3-CAC TGG CGT (SEQ ID NO: 353) | 5'-PO3-GCC AGT GCT (SEQ ID NO: 354) |
| 2.22 | 5'-PO3-TCTCCTCGT (SEQ ID NO: 355) | 5'-PO3-GAGGAGACT (SEQ ID NO: 356) |
| 2.23 | 5'-PO3-CCT GTC TGT (SEQ ID NO: 357) | 5'-PO3-AGA CAG GCT (SEQ ID NO: 358) |
| 2.24 | 5'-PO3-CAA CGC TGT (SEQ ID NO: 359) | 5'-PO3-AGC GTT GCT (SEQ ID NO: 360) |
| 2.25 | 5'-PO3-TGC CTC GGT (SEQ ID NO: 361) | 5'-PO3-CGA GGC ACT (SEQ ID NO: 362) |

TABLE 4-continued

Oligonucleotide tags used in cycle 2:

| Tag Number | Top strand sequence | Bottom strand sequence |
|---|---|---|
| 2.26 | 5'-PO3-ACA CTG CGT (SEQ ID NO: 363) | 5'-PO3-GCA GTG TCT (SEQ ID NO: 364) |
| 2.27 | 5'-PO3-TCG TCC TGT (SEQ ID NO: 365) | 5'-PO3-AGG ACG ACT (SEQ ID NO: 366) |
| 2.28 | 5'-PO3-GCT GCC AGT (SEQ ID NO: 367) | 5'-PO3-TGG CAG CCT (SEQ ID NO: 368) |
| 2.29 | 5'-PO3-TCA GCC TGT (SEQ ID NO: 369) | 5'-PO3-AGC CTG ACT (SEQ ID NO: 370) |
| 2.30 | 5'-PO3-GCC AGG TGT (SEQ ID NO: 371) | 5'-PO3-ACC TGG CCT (SEQ ID NO: 372) |
| 2.31 | 5'-PO3-CGG ACC TGT (SEQ ID NO: 373) | 5'-PO3-AGG TCC GCT (SEQ ID NO: 374) |
| 2.32 | 5'-PO3-CAA CGC AGT (SEQ ID NO: 375) | 5'-PO3-TGC GTT GCT (SEQ ID NO: 376) |
| 2.33 | 5'-PO3-CAC ACG AGT (SEQ ID NO: 377) | 5'-PO3-TCG TGT GCT (SEQ ID NO: 378) |
| 2.34 | 5'-PO3-ATG GCC TGT (SEQ ID NO: 379) | 5'-PO3-AGG CCA TCT (SEQ ID NO: 380) |
| 2.35 | 5'-PO3-CCA GTC TGT (SEQ ID NO: 381) | 5'-PO3-AGA CTG GCT (SEQ ID NO: 382) |
| 2.36 | 5'-PO3-GCC AGG AGT (SEQ ID NO: 383) | 5'-PO3-TCC TGG CCT (SEQ ID NO: 384) |
| 2.37 | 5'-PO3-CGG ACC AGT (SEQ ID NO: 385) | 5'-PO3-TGG TCC GCT (SEQ ID NO: 386) |
| 2.38 | 5'-PO3-CCT TCG CGT (SEQ ID NO: 387) | 5'-PO3-GCG AAG GCT (SEQ ID NO: 388) |
| 2.39 | 5'-PO3-GCA GCC AGT (SEQ ID NO: 389) | 5'-PO3-TGG CTG CCT (SEQ ID NO: 390) |
| 2.40 | 5'-PO3-CCA GTC GGT (SEQ ID NO: 391) | 5'-PO3-CGA CTG GCT (SEQ ID NO: 392) |
| 2.41 | 5'-PO3-ACT GAG CGT (SEQ ID NO: 393) | 5'-PO3-GCT GAG TCT (SEQ ID NO: 394) |
| 2.42 | 5'-PO3-CCA GTC CGT (SEQ ID NO: 395) | 5'-PO3-GGA CTG GCT (SEQ ID NO: 396) |
| 2.43 | 5'-PO3-CCA GTC AGT (SEQ ID NO: 397) | 5'-PO3-TGA CTG GCT (SEQ ID NO: 398) |
| 2.44 | 5'-PO3-CAT CGA GGT (SEQ ID NO: 399) | 5'-PO3-CTC GAT GCT (SEQ ID NO: 400) |
| 2.45 | 5'-PO3-CCA TCG TGT (SEQ ID NO: 401) | 5'-PO3-ACG ATG GCT (SEQ ID NO: 402) |
| 2.46 | 5'-PO3-GTG CTG CGT (SEQ ID NO: 403) | 5'-PO3-GCA GCA CCT (SEQ ID NO: 404) |
| 2.47 | 5'-PO3-GAC TAC GGT (SEQ ID NO: 405) | 5'-PO3-CGT AGT CCT (SEQ ID NO: 406) |
| 2.48 | 5'-PO3-GTG CTG AGT (SEQ ID NO: 407) | 5'-PO3-TCA GCA CCT (SEQ ID NO: 408) |
| 2.49 | 5'-PO3-GCTGCATGT (SEQ ID NO: 409) | 5'-PO3-ATGGAGCCT (SEQ ID NO: 410) |
| 2.50 | 5'-PO3-GAGTGGTGT (SEQ ID NO: 411) | 5'-PO3-ACCACTCCT (SEQ ID NO: 412) |

TABLE 4-continued

Oligonucleotide tags used in cycle 2:

| Tag Number | Top strand sequence | Bottom strand sequence |
|---|---|---|
| 2.51 | 5'-PO3-GACTACCGT (SEQ ID NO: 413) | 5'-PO3-GGTAGTCCT (SEQ ID NO: 414) |
| 2.52 | 5'-PO3-CGGTGATGT (SEQ ID NO: 415) | 5'-PO3-ATCACCGCT (SEQ ID NO: 416) |
| 2.53 | 5'-PO3-TGCGACTGT (SEQ ID NO: 417) | 5'-PO3-AGTCGCACT (SEQ ID NO: 418) |
| 2.54 | 5'-PO3-TCTGGAGGT (SEQ ID NO: 419) | 5'-PO3-CTCCAGACT (SEQ ID NO: 420) |
| 2.55 | 5'-PO3-AGCACTGGT (SEQ ID NO: 421) | 5'-PO3-CAGTGCTCT (SEQ ID NO: 422) |
| 2.56 | 5'-PO3-TCGCTTGGT (SEQ ID NO: 423) | 5'-PO3-CAAGCGACT (SEQ ID NO: 424) |
| 2.57 | 5'-PO3-AGCACTCGT (SEQ ID NO: 425) | 5'-PO3-GAGTGCTCT (SEQ ID NO: 426) |
| 2.58 | 5'-PO3-GCGATTGGT (SEQ ID NO: 427) | 5'-PO3-CAATCGCCT (SEQ ID NO: 428) |
| 2.59 | 5'-PO3-CCATCGCGT (SEQ ID NO: 429) | 5'-PO3-GCGATGGCT (SEQ ID NO: 430) |
| 2.60 | 5'-PO3-TCGCTTCGT (SEQ ID NO: 431) | 5'-PO3-GAAGCGACT (SEQ ID NO: 432) |
| 2.61 | 5'-PO3-AGTGCCTGT (SEQ ID NO: 433) | 5'-PO3-AGGCACTGT (SEQ ID NO: 434) |
| 2.62 | 5'-PO3-GGCATAGGT (SEQ ID NO: 435) | 5'-PO3-CTATGCCCT (SEQ ID NO: 436) |
| 2.63 | 5'-PO3-GCGATTCGT (SEQ ID NO: 437) | 5'-PO3-GAATCGCCT (SEQ ID NO: 438) |
| 2.64 | 5'-PO3-TGCGACGGT (SEQ ID NO: 439) | 5'-PO3-CGTCGCACT (SEQ ID NO: 440) |
| 2.65 | 5'-PO3-GAGTGGCGT (SEQ ID NO: 441) | 5'-PO3-GCCACTCCT (SEQ ID NO: 442) |
| 2.66 | 5'-PO3-CGGTGAGGT (SEQ ID NO: 443) | 5'-PO3-CTCACCGCT (SEQ ID NO: 444) |
| 2.67 | 5'-PO3-GCTGCAAGT (SEQ ID NO: 445) | 5'-PO3-TTGCAGCCT (SEQ ID NO: 446) |
| 2.68 | 5'-PO3-TTCCGCTGT (SEQ ID NO: 447) | 5'-PO3-AGCGGAACT (SEQ ID NO: 448) |
| 2.69 | 5'-PO3-GAGTGGAGT (SEQ ID NO: 449) | 5'-PO3-TCCACTCCT (SEQ ID NO: 450) |
| 2.70 | 5'-PO3-ACAGAGCGT (SEQ ID NO: 451) | 5'-PO3-GCTCTGTCT (SEQ ID NO: 452) |
| 2.71 | 5'-PO3-TGCGACCGT (SEQ ID NO: 453) | 5'-PO3-GGTCGCACT (SEQ ID NO: 454) |
| 2.72 | 5'-PO3-CCTGTAGGT (SEQ ID NO: 455) | 5'-PO3-CTACAGGCT (SEQ ID NO: 456) |
| 2.73 | 5'-PO3-TAGCCGTGT (SEQ ID NO: 457) | 5'-PO3-ACGGCTACT (SEQ ID NO: 458) |
| 2.74 | 5'-PO3-TGCGACAGT (SEQ ID NO: 459) | 5'-PO3-TGTCGCACT (SEQ ID NO: 460) |
| 2.75 | 5'-PO3-GGTCTGTGT (SEQ ID NO: 461) | 5'-PO3-ACAGACCCT (SEQ ID NO: 462) |
| 2.76 | 5'-PO3-CGGTGAAGT (SEQ ID NO: 463) | 5'-PO3-TTCACCGCT (SEQ ID NO: 464) |
| 2.77 | 5'-PO3-CAACGAGGT (SEQ ID NO: 465) | 5'-PO3-CTCGTTGCT (SEQ ID NO: 466) |
| 2.78 | 5'-PO3-GGAGCATGT (SEQ ID NO: 467) | 5'-PO3-ATGCTGCCT (SEQ ID NO: 468) |
| 2.79 | 5'-PO3-TCGTCAGGT (SEQ ID NO: 469) | 5'-PO3-CTGACGACT (SEQ ID NO: 470) |
| 2.80 | 5'-PO3-AGTGCCAGT (SEQ ID NO: 471) | 5'-PO3-TGGCACTCT (SEQ ID NO: 472) |
| 2.81 | 5'-PO3-TAGAGGCGT (SEQ ID NO: 473) | 5'-PO3-GCCTCTACT (SEQ ID NO: 474) |
| 2.82 | 5'-PO3-GTCAGCGGT (SEQ ID NO: 475) | 5'-PO3-CGCTGACCT (SEQ ID NO: 476) |
| 2.83 | 5'-PO3-TCAGGAGGT (SEQ ID NO: 477) | 5'-PO3-CTCCTGACT (SEQ ID NO: 478) |
| 2.84 | 5'-PO3-AGCAGGTGT (SEQ ID NO: 479) | 5'-PO3-ACCTGCTCT (SEQ ID NO: 480) |
| 2.85 | 5'-PO3-TTCCGCAGT (SEQ ID NO: 481) | 5'-PO3-TGCGGAACT (SEQ ID NO: 482) |
| 2.86 | 5'-PO3-GTCAGCCGT (SEQ ID NO: 483) | 5'-PO3-GGCTGACCT (SEQ ID NO: 484) |
| 2.87 | 5'-PO3-GGTCTGCGT (SEQ ID NO: 485) | 5'-PO3-GCAGACCCT (SEQ ID NO: 486) |
| 2.88 | 5'-PO3-TAGCCGAGT (SEQ ID NO: 487) | 5'-PO3-TCGGCTACT (SEQ ID NO: 488) |
| 2.89 | 5'-PO3-GTCAGCAGT (SEQ ID NO: 489) | 5'-PO3-TGCTGACCT (SEQ ID NQ:490) |
| 2.90 | 5'-PO3-GGTCTGAGT (SEQ ID NO: 491) | 5'-PO3-TCAGACCCT (SEQ ID NO: 492) |
| 2.91 | 5'-PO3-CGGACAGGT (SEQ ID NO: 493) | 5'-PO3-CTGTCCGCT (SEQ ID NO: 494) |
| 2.92 | 5'-PO3-TTAGCCGGT 5'-PO3-3' (SEQ ID NO: 495) | 5'-PO3-CGGCTAACT 5'-PO3-3' (SEQ ID NO: 496) |
| 2.93 | 5'-PO3-GAGACGAGT (SEQ ID NO: 497) | 5'-PO3-TCGTCTCCT (SEQ ID NQ:498) |
| 2.94 | 5'-PO3-CGTAACCGT (SEQ ID NO: 499) | 5'-PO3-GGTTACGCT (SEQ ID NO: 500) |
| 2.95 | 5'-PO3-TTGGCGTGT 5'-PO3-3' (SEQ ID NO: 501) | 5'-PO3-ACGCCAACT 5'-PO3-3' (SEQ ID NO: 502) |
| 2.96 | 5'-PO3-ATGGCAGGT (SEQ ID NO: 503) | 5'-PO3-CTGCCATCT (SEQ ID NO: 504) |

TABLE 5

Oligonucleotide tags used in cycle 3

| Tag number | Top strand sequence | Bottom strand sequence |
|---|---|---|
| 3.1 | 5'-PO3-CAG CTA CGA (SEQ ID NO: 505) | 5'-PO3-GTA GCT GAC (SEQ ID NO: 506) |
| 3.2 | 5'-PO3-CTC CTG CGA (SEQ ID NO: 507) | 5'-PO3-GCA GGA GAC (SEQ ID NO: 508) |
| 3.3 | 5'-PO3-GCT GCC TGA (SEQ ID NO: 509) | 5'-PO3-AGG CAG CAC (SEQ ID NO: 510) |
| 3.4 | 5'-PO3-CAG GAA CGA (SEQ ID NO: 511) | 5'-PO3-GTT CCT GAC (SEQ ID NO: 512) |
| 3.5 | 5'-PO3-CAC ACG CGA (SEQ ID NO: 513) | 5'-PO3-GCG TGT GAC (SEQ ID NO: 514) |
| 3.6 | 5'-PO3-GCA GCC TGA (SEQ ID NO: 515) | 5'-PO3-AGG CTG CAC (SEQ ID NO: 516) |
| 3.7 | 5'-PO3-CTG AAC GGA (SEQ ID NO: 517) | 5'-PO3-CGT TCA GAC (SEQ ID NO: 518) |
| 3.8 | 5'-PO3-CTG AAC CGA (SEQ ID NO: 519) | 5'-PO3-GGT TCA GAC (SEQ ID NO: 520) |
| 3.9 | 5'-PO3-TCT GGA CGA (SEQ ID NO: 521) | 5'-PO3-GTC CAG AAC (SEQ ID NO: 522) |
| 3.10 | 5'-PO3-TGC CTA CGA (SEQ ID NO: 523) | 5'-PO3-GTA GGC AAC (SEQ ID NO: 524) |
| 3.11 | 5'-PO3-GGC ATA CGA (SEQ ID NO: 525) | 5'-PO3-GTA TGC CAC (SEQ ID NO: 526) |
| 3.12 | 5'-PO3-CGG TGA CGA (SEQ ID NO: 527) | 5'-PO3-GTC ACC GAC (SEQ ID NO: 528) |
| 3.13 | 5'-PO3-CAA CGA CGA (SEQ ID NO: 529) | 5'-PO3-GTC GTT GAC (SEQ ID NO: 530) |
| 3.14 | 5'-PO3-CTC CTC TGA (SEQ ID NO: 531) | 5'-PO3-AGA GGA GAC (SEQ ID NO: 532) |
| 3.15 | 5'-PO3-TCA GGA CGA (SEQ ID NO: 533) | 5'-PO3-GTC CTG AAC (SEQ ID NO: 534) |
| 3.16 | 5'-PO3-AAA GGC GGA (SEQ ID NO: 535) | 5'-PO3-GGC CTT TAC (SEQ ID NO: 536) |
| 3.17 | 5'-PO3-CTC CTC GGA (SEQ ID NO: 537) | 5'-PO3-CGA GGA GAC (SEQ ID NO: 538) |
| 3.18 | 5'-PO3-CAG ATG CGA (SEQ ID NO: 539) | 5'-PO3-GCA TCT GAC (SEQ ID NO: 540) |
| 3.19 | 5'-PO3-GCA GCA AGA (SEQ ID NO: 541) | 5'-PO3-TTG CTG CAC (SEQ ID NO: 542) |
| 3.20 | 5'-PO3-GTG GAG TGA (SEQ ID NO: 543) | 5'-PO3-ACT CCA CAC (SEQ ID NO: 544) |
| 3.21 | 5'-PO3-CCA GTA GGA (SEQ ID NO: 545) | 5'-PO3-CTA CTG GAC (SEQ ID NO: 546) |
| 3.22 | 5'-PO3-ATG GCA CGA (SEQ ID NO: 547) | 5'-PO3-GTG CCA TAC (SEQ ID NO: 548) |
| 3.23 | 5'-PO3-GGA CTG TGA (SEQ ID NO: 549) | 5'-PO3-ACA GTC CAC (SEQ ID NO: 550) |
| 3.24 | 5'-PO3-CCG AAC TGA (SEQ ID NO: 551) | 5'-PO3-AGT TCG GAC (SEQ ID NO: 552) |
| 3.25 | 5'-PO3-CTC CTC AGA (SEQ ID NO: 553) | 5'-PO3-TGA GGA GAC (SEQ ID NO: 554) |
| 3.26 | 5'-PO3-CAC TGC TGA (SEQ ID NO: 555) | 5'-PO3-AGC AGT GAC (SEQ ID NO: 556) |
| 3.27 | 5'-PO3-AGC AGG CGA (SEQ ID NO: 557) | 5'-PO3-GCC TGC TAC (SEQ ID NO: 558) |
| 3.28 | 5'-PO3-AGC AGG AGA (SEQ ID NO: 559) | 5'-PO3-TCC TGC TAC (SEQ ID NO: 560) |
| 3.29 | 5'-PO3-AGA GCC AGA (SEQ ID NO: 561) | 5'-PO3-TGG CTC TAC (SEQ ID NO: 562) |
| 3.30 | 5'-PO3-GTC GTT GGA (SEQ ID NO: 563) | 5'-PO3-CAA CGA CAC (SEQ ID NO: 564) |
| 3.31 | 5'-PO3-CCG AAC GGA (SEQ ID NO: 565) | 5'-PO3-CGT TCG GAC (SEQ ID NO: 566) |
| 3.32 | 5'-PO3-CAC TGC GGA (SEQ ID NO: 567) | 5'-PO3-CGC AGT GAC (SEQ ID NO: 568) |
| 3.33 | 5'-PO3-GTG GAG CGA (SEQ ID NO: 569) | 5'-PO3-GCT CCA CAC (SEQ ID NO: 570) |
| 3.34 | 5'-PO3-GTG GAG AGA (SEQ ID NO: 571) | 5'-PO3-TCT CCA CAC (SEQ ID NO: 572) |
| 3.35 | 5'-PO3-GGA CTG CGA (SEQ ID NO: 573) | 5'-PO3-GCA GTC CAC (SEQ ID NO: 574) |
| 3.36 | 5'-PO3-CCG AAC CGA (SEQ ID NO: 575) | 5'-PO3-GGT TCG GAC (SEQ ID NO: 576) |
| 3.37 | 5'-PO3-CAC TGC CGA (SEQ ID NO: 577) | 5'-PO3-GGC AGT GAC (SEQ ID NO: 578) |
| 3.38 | 5'-PO3-CGA AAC GGA (SEQ ID NO: 579) | 5'-PO3-CGT TTC GAC (SEQ ID NO: 580) |
| 3.39 | 5'-PO3-GGA CTG AGA (SEQ ID NO: 581) | 5'-PO3-TCA GTC CAC (SEQ ID NO: 582) |
| 3.40 | 5'-PO3-CCG AAC AGA (SEQ ID NO: 583) | 5'-PO3-TGT TCG GAC (SEQ ID NO: 584) |
| 3.41 | 5'-PO3-CGA AAC CGA (SEQ ID NO: 585) | 5'-PO3-GGT TTC GAC (SEQ ID NO: 586) |
| 3.42 | 5'-PO3-CTG GCT TGA (SEQ ID NO: 587) | 5'-PO3-AAG CCA GAC (SEQ ID NO: 588) |
| 3.43 | 5'-PO3-CAC ACC TGA (SEQ ID NO: 589) | 5'-PO3-AGG TGT GAC (SEQ ID NO: 590) |
| 3.44 | 5'-PO3-AAC GAC CGA (SEQ ID NO: 591) | 5'-PO3-GGT CGT TAC (SEQ ID NO: 592) |
| 3.45 | 5'-PO3-ATC CAG CGA (SEQ ID NO: 593) | 5'-PO3-GCT GGA TAC (SEQ ID NO: 594) |
| 3.46 | 5'-PO3-TGC GAA GGA (SEQ ID NO: 595) | 5'-PO3-CTT CGC AAC (SEQ ID NO: 596) |
| 3.47 | 5'-PO3-TGC GAA CGA (SEQ ID NO: 597) | 5'-PO3-GTT CGC AAC (SEQ ID NO: 598) |
| 3.48 | 5'-PO3-CTG GCT GGA (SEQ ID NO: 599) | 5'-PO3-CAG CCA GAC (SEQ ID NO: 600) |
| 3.49 | 5'-PO3-CAC ACC GGA (SEQ ID NO: 601) | 5'-PO3-CGG TGT GAC (SEQ ID NO: 602) |
| 3.50 | 5'-PO3-AGT GCA GGA (SEQ ID NO: 603) | 5'-PO3-CTG CAC TAC (SEQ ID NO: 604) |

TABLE 5-continued

Oligonucleotide tags used in cycle 3

| Tag number | Top strand sequence | Bottom strand sequence |
|---|---|---|
| 3.51 | 5'-PO3-GAC CGT TGA (SEQ ID NO: 605) | 5'-PO3-AAC GGT CAC (SEQ ID NO: 606) |
| 3.52 | 5'-PO3-GGT GAG TGA (SEQ ID NO: 607) | 5'-PO3-ACT CAC CAC (SEQ ID NO: 608) |
| 3.53 | 5'-PO3-CCT TCC TGA (SEQ ID NO: 609) | 5'-PO3-AGG AAG GAC (SEQ ID NO: 610) |
| 3.54 | 5'-PO3-CTG GCT AGA (SEQ ID NO: 611) | 5'-PO3-TAG CCA GAC (SEQ ID NO: 612) |
| 3.55 | 5'-PO3-CAC ACC AGA (SEQ ID NO: 613) | 5'-PO3-TGG TGT GAC (SEQ ID NO: 614) |
| 3.56 | 5'-PO3-AGC GGT AGA (SEQ ID NO: 615) | 5'-PO3-TAC CGC TAC (SEQ ID NO: 616) |
| 3.57 | 5'-PO3-GTC AGA GGA (SEQ ID NO: 617) | 5'-PO3-CTC TGA CAC (SEQ ID NO: 618) |
| 3.58 | 5'-PO3-TTC CGA CGA (SEQ ID NO: 619) | 5'-PO3-GTC GGA AAC (SEQ ID NO: 620) |
| 3.59 | 5'-PO3-AGG CGT AGA (SEQ ID NO: 621) | 5'-PO3-TAC GCC TAC (SEQ ID NO: 622) |
| 3.60 | 5'-PO3-CTC GAC TGA (SEQ ID NO: 623) | 5'-PO3-AGT CGA GAC (SEQ ID NO: 624) |
| 3.61 | 5'-PO3-TAC GCT GGA (SEQ ID NO: 625) | 5'-PO3-CAG CGT AAC (SEQ ID NO: 626) |
| 3.62 | 5'-PO3-GTT CGG TGA (SEQ ID NO: 627) | 5'-PO3-ACC GAA CAC (SEQ ID NO: 628) |
| 3.63 | 5'-PO3-GCC AGC AGA (SEQ ID NO: 629) | 5'-PO3-TGC TGG CAC (SEQ ID NO: 630) |
| 3.64 | 5'-PO3-GAC CGT AGA (SEQ ID NO: 631) | 5'-PO3-TAC GGT CAC (SEQ ID NO: 632) |
| 3.65 | 5'-PO3-GTG CTC TGA (SEQ ID NO: 633) | 5'-PO3-AGA GCA CAC (SEQ ID NO: 634) |
| 3.66 | 5'-PO3-GGT GAG CGA (SEQ ID NO: 635) | 5'-PO3-GCT CAC CAC (SEQ ID NO: 636) |
| 3.67 | 5'-PO3-GGT GAG AGA (SEQ ID NO: 637) | 5'-PO3-TCT CAC CAC (SEQ ID NO: 638) |
| 3.68 | 5'-PO3-CCT TCC AGA (SEQ ID NO: 639) | 5'-PO3-TGG AAG GAC (SEQ ID NO: 640) |
| 3.69 | 5'-PO3-CTC CTA CGA (SEQ ID NO: 641) | 5'-PO3-GTA GGA GAC (SEQ ID NO: 642) |
| 3.70 | 5'-PO3-CTC GAC GGA (SEQ ID NO: 643) | 5'-PO3-CGT CGA GAC (SEQ ID NO: 644) |
| 3.71 | 5'-PO3-GCC GTT TGA (SEQ ID NO: 645) | 5'-PO3-AAA CGG CAC (SEQ ID NO: 646) |
| 3.72 | 5'-PO3-GCG GAG TGA (SEQ ID NO: 647) | 5'-PO3-ACT CCG CAC (SEQ ID NO: 648) |
| 3.73 | 5'-PO3-CGT GCT TGA (SEQ ID NO: 649) | 5'-PO3-AAG CAC GAC (SEQ ID NO: 650) |
| 3.74 | 5'-PO3-CTC GAC CGA (SEQ ID NO: 651) | 5'-PO3-GGT CGA GAC (SEQ ID NO: 652) |
| 3.75 | 5'-PO3-AGA GCA GGA (SEQ ID NO: 653) | 5'-PO3-CTG GTC TAC (SEQ ID NO: 654) |
| 3.76 | 5'-PO3-GTG CTC GGA (SEQ ID NO: 655) | 5'-PO3-CGA GCA CAC (SEQ ID NO: 656) |
| 3.77 | 5'-PO3-CTC GAC AGA (SEQ ID NO: 657) | 5'-PO3-TGT CGA GAC (SEQ ID NO: 658) |
| 3.78 | 5'-PO3-GGA GAG TGA (SEQ ID NO: 659) | 5'-PO3-ACT CTC CAC (SEQ ID NO: 660) |
| 3.79 | 5'-PO3-AGG CTG TGA (SEQ ID NO: 661) | 5'-PO3-ACA GCC TAC (SEQ ID NO: 662) |
| 3.80 | 5'-PO3-AGA GCA CGA (SEQ ID NO: 663) | 5'-PO3-GTG CTC TAC (SEQ ID NO: 664) |
| 3.81 | 5'-PO3-CCA TCC TGA (SEQ ID NO: 665) | 5'-PO3-AGG ATG GAC (SEQ ID NO: 666) |
| 3.82 | 5'-PO3-GTT CGG AGA (SEQ ID NO: 667) | 5'-PO3-TCC GAA CAC (SEQ ID NO: 668) |
| 3.83 | 5'-PO3-TGG TAG CGA (SEQ ID NO: 669) | 5'-PO3-GCT ACC AAC (SEQ ID NO: 670) |
| 3.84 | 5'-PO3-GTG CTC CGA (SEQ ID NO: 671) | 5'-PO3-GGA GCA CAC (SEQ ID NO: 672) |
| 3.85 | 5'-PO3-GTG CTC AGA (SEQ ID NO: 673) | 5'-PO3-TGA GCA CAC (SEQ ID NO: 674) |
| 3.86 | 5'-PO3-GCC GTT GGA (SEQ ID NO: 675) | 5'-PO3-CAA CGG CAC (SEQ ID NO: 676) |
| 3.87 | 5'-PO3-GAG TGC TGA 7 (SEQ ID NO: 677) | 5'-PO3-AGC ACT CAC (SEQ ID NO: 678) |
| 3.88 | 5'-PO3-GCT CCT TGA (SEQ ID NO: 679) | 5'-PO3-AAG GAG CAC (SEQ ID NO: 680) |
| 3.89 | 5'-PO3-CCG AAA GGA (SEQ ID NO: 681) | 5'-PO3-CTT TCG GAC (SEQ ID NO: 682) |
| 3.90 | 5'-PO3-CAC TGA GGA (SEQ ID NO: 683) | 5'-PO3-CTC AGT GAC (SEQ ID NO: 684) |
| 3.91 | 5'-PO3-CGT GCT GGA (SEQ ID NO: 685) | 5'-PO3-CAG CAC GAC (SEQ ID NO: 686) |
| 3.92 | 5'-PO3-CCG AAA CGA (SEQ ID NO: 687) | 5'-PO3-GTT TCG GAC (SEQ ID NO: 688) |
| 3.93 | 5'-PO3-GCG GAG AGA (SEQ ID NO: 689) | 5'-PO3-TCT CCG CAC (SEQ ID NO: 690) |
| 3.94 | 5'-PO3-GCC GTT AGA (SEQ ID NO: 691) | 5'-PO3-TAA CGG CAC (SEQ ID NO: 692) |
| 3.95 | 5'-PO3-TCT CGT GGA (SEQ ID NO: 693) | 5'-PO3-CAC GAG AAC (SEQ ID NO: 694) |
| 3.96 | 5'-PO3-CGT GCT AGA (SEQ ID NO: 695) | 5'-PO3-TAG CAC GAC (SEQ ID NO: 696) |

TABLE 6

Oligonucleotide tags used in cycle 4

| Tag number | Top strand sequence | Bottom strand sequence |
|---|---|---|
| 4.1 | 5'-PO3-GCCTGTCTT (SEQ ID NO: 697) | 5'-PO3-GAC AGG CTC (SEQ ID NO: 698) |

TABLE 6-continued

Oligonucleotide tags used in cycle 4

| Tag number | Top strand sequence | Bottom strand sequence |
|---|---|---|
| 4.2 | 5'-PO3-CTCCTGGTT (SEQ ID NO: 699) | 5'-PO3-CCA GGA GTC (SEQ ID NO: 700) |
| 4.3 | 5'-PO3-ACTCTGCTT (SEQ ID NO: 701) | 5'-PO3-GCA GAG TTC (SEQ ID NO: 702) |
| 4.4 | 5'-PO3-CATCGCCTT (SEQ ID NO: 703) | 5'-PO3-GGC GAT GTC (SEQ ID NO: 704) |
| 4.5 | 5'-PO3-GCCACTATT (SEQ ID NO: 705) | 5'-PO3-TAG TGG CTC (SEQ ID NO: 706) |
| 4.6 | 5'-PO3-CACACGGTT (SEQ ID NO: 707) | 5'-PO3-CCG TGT GTC (SEQ ID NO: 708) |
| 4.7 | 5'-PO3-CAACGCCTT (SEQ ID NO: 709) | 5'-PO3-GGC GTT GTC (SEQ ID NO: 710) |
| 4.8 | 5'-PO3-ACTGAGGTT (SEQ ID NO: 711) | 5'-PO3-CCT CAG TTC (SEQ ID NO: 712) |
| 4.9 | 5'-PO3-GTGCTGGTT (SEQ ID NO: 713) | 5'-PO3-CCA GCA CTC (SEQ ID NO: 714) |
| 4.10 | 5'-PO3-CATCGACTT (SEQ ID NO: 715) | 5'-PO3-GTC GAT GTC (SEQ ID NO: 716) |
| 4.11 | 5'-PO3-CCATCGGTT (SEQ ID NO: 717) | 5'-PO3-CCG ATG GTC (SEQ ID NO: 718) |
| 4.12 | 5'-PO3-GCTGCACTT (SEQ ID NO: 719) | 5'-PO3-GTG CAG CTC (SEQ ID NO: 720) |
| 4.13 | 5'-PO3-ACAGAGGTT (SEQ ID NO: 721) | 5'-PO3-CCT CTG TTC (SEQ ID NO: 722) |
| 4.14 | 5'-PO3-AGTGCCGTT (SEQ ID NO: 723) | 5'-PO3-CGG CAC TTC (SEQ ID NO: 724) |
| 4.15 | 5'-PO3-CGGACATTT (SEQ ID NO: 725) | 5'-PO3-ATG TCC GTC (SEQ ID NO: 726) |
| 4.16 | 5'-PO3-GGTCTGGTT (SEQ ID NO: 727) | 5'-PO3-CCA GAC CTC (SEQ ID NO: 728) |
| 4.17 | 5'-PO3-GAGACGGTT (SEQ ID NO: 729) | 5'-PO3-CCG TCT CTC (SEQ ID NO: 730) |
| 4.18 | 5'-PO3-CTTTCCGTT (SEQ ID NO: 731) | 5'-PO3-CGG AAA GTC (SEQ ID NO: 732) |
| 4.19 | 5'-PO3-CAGATGGTT (SEQ ID NO: 733) | 5'-PO3-CCA TCT GTC (SEQ ID NO: 734) |
| 4.20 | 5'-PO3-CGGACACTT (SEQ ID NO: 735) | 5'-PO3-GTG TCC GTC (SEQ ID NO: 736) |
| 4.21 | 5'-PO3-ACTCTCGTT (SEQ ID NO: 737) | 5'-PO3-CGA GAG TTC (SEQ ID NO: 738) |
| 4.22 | 5'-PO3-GCAGCACTT (SEQ ID NO: 739) | 5'-PO3-GTG CTG CTC (SEQ ID NO: 740) |
| 4.23 | 5'-PO3-ACTCTCCTT (SEQ ID NO: 741) | 5'-PO3-GGA GAG TTC (SEQ ID NO: 742) |
| 4.24 | 5'-PO3-ACCTTGGTT (SEQ ID NO: 743) | 5'-PO3-CCA AGG TTC (SEQ ID NO: 744) |
| 4.25 | 5'-PO3-AGAGCCGTT (SEQ ID NO: 745) | 5'-PO3-CGG CTC TTC (SEQ ID NO: 746) |
| 4.26 | 5'-PO3-ACCTTGCTT (SEQ ID NO: 747) | 5'-PO3-GCA AGG TTC (SEQ ID NO: 748) |
| 4.27 | 5'-PO3-AAGTCCGTT (SEQ ID NO: 749) | 5'-PO3-CGG ACT TTC (SEQ ID NO: 750) |
| 4.28 | 5'-PO3-GGA CTG GTT (SEQ ID NO: 751) | 5'-PO3-CCA GTC CTC (SEQ ID NO: 752) |
| 4.29 | 5'-PO3-GTCGTTCTT (SEQ ID NO: 753) | 5'-PO3-GAA CGA CTC (SEQ ID NO: 754) |
| 4.30 | 5'-PO3-CAGCATCTT (SEQ ID NO: 755) | 5'-PO3-GAT GCT GTC (SEQ ID NO: 756) |
| 4.31 | 5'-PO3-CTATCCGTT (SEQ ID NO: 757) | 5'-PO3-CGG ATA GTC (SEQ ID NO: 758) |
| 4.32 | 5'-PO3-ACACTCGTT (SEQ ID NO: 759) | 5'-PO3-CGA GTG TTC (SEQ ID NO: 760) |
| 4.33 | 5'-PO3-ATCCAGGTT (SEQ ID NO: 761) | 5'-PO3-CCT GGA TTC (SEQ ID NO: 762) |
| 4.34 | 5'-PO3-GTTCCTGTT (SEQ ID NO: 763) | 5'-PO3-CAG GAA CTC (SEQ ID NO: 764) |
| 4.35 | 5'-PO3-ACACTCCTT (SEQ ID NO: 765) | 5'-PO3-GGA GTG TTC (SEQ ID NO: 766) |
| 4.36 | 5'-PO3-GTTCCTCTT (SEQ ID NO: 767) | 5'-PO3-GAG GAA CTC (SEQ ID NO: 768) |
| 4.37 | 5'-PO3-CTGGCTCTT (SEQ ID NO: 769) | 5'-PO3-GAG CCA GTC (SEQ ID NO: 770) |
| 4.38 | 5'-PO3-ACGGCATTT (SEQ ID NO: 771) | 5'-PO3-ATG CCG TTC (SEQ ID NO: 772) |
| 4.39 | 5'-PO3-GGTGAGGTT (SEQ ID NO: 773) | 5'-PO3-CCT CAC CTC (SEQ ID NO: 774) |
| 4.40 | 5'-PO3-CCTTCCGTT (SEQ ID NO: 775) | 5'-PO3-CGG AAG GTC (SEQ ID NO: 776) |
| 4.41 | 5'-PO3-TACGCTCTT (SEQ ID NO: 777) | 5'-PO3-GAG CGT ATC (SEQ ID NO: 778) |
| 4.42 | 5'-PO3-ACGGCAGTT (SEQ ID NO: 779) | 5'-PO3-CTG CCG TTC (SEQ ID NO: 780) |
| 4.43 | 5'-PO3-ACTGACGTT (SEQ ID NO: 781) | 5'-PO3-CGT CAG TTC (SEQ ID NO: 782) |
| 4.44 | 5'-PO3-ACGGCACTT (SEQ ID NO: 783) | 5'-PO3-GTG CCG TTC (SEQ ID NO: 784) |
| 4.45 | 5'-PO3-ACTGACCTT (SEQ ID NO: 785) | 5'-PO3-GGT CAG TTC (SEQ ID NO: 786) |
| 4.46 | 5'-PO3-TTTGCGGTT (SEQ ID NO: 787) | 5'-PO3-CCG CAA ATC (SEQ ID NO: 788) |
| 4.47 | 5'-PO3-TGGTAGGTT (SEQ ID NO: 789) | 5'-PO3-CCT ACC ATC (SEQ ID NO: 790) |
| 4.48 | 5'-PO3-GTTCGGCTT (SEQ ID NO: 791) | 5'-PO3-GCC GAA CTC (SEQ ID NO: 792) |
| 4.49 | 5'-PO3-GCC GTT CTT (SEQ ID NO: 793) | 5'-PO3-GAA CGG CTC (SEQ ID NO: 794) |
| 4.50 | 5'-PO3-GGAGAGGTT (SEQ ID NO: 795) | 5'-PO3-CCT CTC CTC (SEQ ID NO: 796) |
| 4.51 | 5'-PO3-CACTGACTT (SEQ ID NO: 797) | 5'-PO3-GTC AGT GTC (SEQ ID NO: 798) |

TABLE 6-continued

Oligonucleotide tags used in cycle 4

| Tag number | Top strand sequence | Bottom strand sequence |
|---|---|---|
| 4.52 | 5'-PO3-CGTGCTCTT (SEQ ID NO: 799) | 5'-PO3-GAG CAC GTC (SEQ ID NO: 800) |
| 4.53 | 5'-PO3-AATCCGCTT (SEQ ID NO: 801) | 5'-PO3-GCGGATTTC (SEQ ID NO: 802) |
| 4.54 | 5'-PO3-AGGCTGGTT (SEQ ID NO: 803) | 5'-PO3-CCA GCC TTC (SEQ ID NO: 804) |
| 4.55 | 5'-PO3-GCTAGTGTT (SEQ ID NO: 805) | 5'-PO3-CAC TAG CTC (SEQ ID NO: 806) |
| 4.56 | 5'-PO3-GGAGAGCTT (SEQ ID NO: 807) | 5'-PO3-GCT CTC CTC (SEQ ID NO: 808) |
| 4.57 | 5'-PO3-GGAGAGATT (SEQ ID NO: 809) | 5'-PO3-TCT CTC CTC (SEQ ID NO: 810) |
| 4.58 | 5'-PO3-AGGCTGCTT (SEQ ID NO: 811) | 5'-PO3-GCA GCC TTC (SEQ ID NO: 812) |
| 4.59 | 5'-PO3-GAGTGCGTT (SEQ ID NO: 813) | 5'-PO3-CGC ACT CTC (SEQ ID NO: 814) |
| 4.60 | 5'-PO3-CCATCCATT (SEQ ID NO: 815) | 5'-PO3-TGG ATG GTC (SEQ ID NO: 816) |
| 4.61 | 5'-PO3-GCTAGTCTT (SEQ ID NO: 817) | 5'-PO3-GAC TAG CTC (SEQ ID NO: 818) |
| 4.62 | 5'-PO3-AGGCTGATT (SEQ ID NO: 819) | 5'-PO3-TCA GCC TTC (SEQ ID NO: 820) |
| 4.63 | 5'-PO3-ACAGACGTT (SEQ ID NO: 821) | 5'-PO3-CGT CTG TTC (SEQ ID NO: 822) |
| 4.64 | 5'-PO3-GAGTGCCTT (SEQ ID NO: 823) | 5'-PO3-GGC ACT CTC (SEQ ID NO: 824) |
| 4.65 | 5'-PO3-ACAGACCTT (SEQ ID NO: 825) | 5'-PO3-GGT CTG TTC (SEQ ID NO: 826) |
| 4.66 | 5'-PO3-CGAGCTTTT (SEQ ID NO: 827) | 5'-PO3-AAG CTC GTC (SEQ ID NO: 828) |
| 4.67 | 5'-PO3-TTAGCGGTT (SEQ ID NO: 829) | 5'-PO3-CCG CTA ATC (SEQ ID NO: 830) |
| 4.68 | 5'-PO3-CCTCTTGTT (SEQ ID NO: 831) | 5'-PO3-CAA GAG GTC (SEQ ID NO: 832) |
| 4.69 | 5'-PO3-GGTCTCTTT (SEQ ID NO: 833) | 5'-PO3-AGA GAC CTC (SEQ ID NO: 834) |
| 4.70 | 5'-PO3-GCCAGATTT (SEQ ID NO: 835) | 5'-PO3-ATC TGG CTC (SEQ ID NO: 836) |
| 4.71 | 5'-PO3-GAGACCTTT (SEQ ID NO: 837) | 5'-PO3-AGG TCT CTC (SEQ ID NO: 838) |
| 4.72 | 5'-PO3-CACACAGTT (SEQ ID NO: 839) | 5'-PO3-CTG TGT GTC (SEQ ID NO: 840) |
| 4.73 | 5'-PO3-CCTCTTCTT (SEQ ID NO: 841) | 5'-PO3-GAA GAG GTC (SEQ ID NO: 842) |
| 4.74 | 5'-PO3-TAGAGCGTT (SEQ ID NO: 843) | 5'-PO3-CGC TCT ATC (SEQ ID NO: 844) |
| 4.75 | 5'-PO3-GCACCTTTT (SEQ ID NO: 845) | 5'-PO3-AAG GTG CTC (SEQ ID NO: 846) |
| 4.76 | 5'-PO3-GGCTTGTTT (SEQ ID NO: 847) | 5'-PO3-ACA AGC CTC (SEQ ID NO: 848) |
| 4.77 | 5'-PO3-GACGCGATT (SEQ ID NO: 849) | 5'-PO3-TCG CGT CTC (SEQ ID NO: 850) |
| 4.78 | 5'-PO3-CGAGCTGTT (SEQ ID NO: 851) | 5'-PO3-CAG CTC GTC (SEQ ID NO: 852) |
| 4.79 | 5'-PO3-TAGAGCCTT (SEQ ID NO: 853) | 5'-PO3-GGC TCT ATC (SEQ ID NO: 854) |
| 4.80 | 5'-PO3-CATCCGTTT (SEQ ID NO: 855) | 5'-PO3-ACG GAT GTC (SEQ ID NO: 856) |
| 4.81 | 5'-PO3-GGTCTCGTT (SEQ ID NO: 857) | 5'-PO3-CGA GAC CTC (SEQ ID NO: 858) |
| 4.82 | 5'-PO3-GCCAGAGTT (SEQ ID NO: 859) | 5'-PO3-CTC TGG CTC (SEQ ID NO: 860) |
| 4.83 | 5'-PO3-GAGACCGTT (SEQ ID NO: 861) | 5'-PO3-CGG TCT CTC (SEQ ID NO: 862) |
| 4.84 | 5'-PO3-CGAGCTATT (SEQ ID NO: 863) | 5'-PO3-TAG CTC GTC (SEQ ID NO: 864) |
| 4.85 | 5'-PO3-GCAAGTGTT (SEQ ID NO: 865) | 5'-PO3-CAC TTG CTC (SEQ ID NO: 866) |
| 4.86 | 5'-PO3-GGTCTCCTT (SEQ ID NO: 867) | 5'-PO3-GGA GAC CTC (SEQ ID NO: 868) |
| 4.87 | 5'-PO3-GCCAGACTT (SEQ ID NO: 869) | 5'-PO3-GTC TGG CTC (SEQ ID NO: 870) |
| 4.88 | 5'-PO3-GGTCTCATT (SEQ ID NO: 871) | 5'-PO3-TGA GAC CTC (SEQ ID NO: 872) |
| 4.89 | 5'-PO3-GAGACCATT (SEQ ID NO: 873) | 5'-PO3-TGG TCT CTC (SEQ ID NO: 874) |
| 4.90 | 5'-PO3-CCTTCAGTT (SEQ ID NO: 875) | 5'-PO3-CTG AAG GTC (SEQ ID NO: 876) |
| 4.91 | 5'-PO3-GCACCTGTT (SEQ ID NO: 877) | 5'-PO3-CAG GTG CTC (SEQ ID NO: 878) |
| 4.92 | 5'-PO3-AAAGGCGTT (SEQ ID NO: 879) | 5'-PO3-CGC CTT TTC (SEQ ID NO: 880) |
| 4.93 | 5'-PO3-CAGATCGTT (SEQ ID NO: 881) | 5'-PO3-CGA TCT GTC (SEQ ID NO: 882) |
| 4.94 | 5'-PO3-CATAGGCTT (SEQ ID NO: 883) | 5'-PO3-GCC TAT GTC (SEQ ID NO: 884) |
| 4.95 | 5'-PO3-CCTTCACTT (SEQ ID NO: 885) | 5'-PO3-GTG AAG GTC (SEQ ID NO: 886) |
| 4.96 | 5'-PO3-GCACCTCTT (SEQ ID NO: 887) | 5'-PO3-GAG GTG CTC (SEQ ID NO: 888) |

TABLE 7

Correspondence between building blocks and oligonucleotide tags for Cycles 1-4.

| Building block | Cycle 1 | Cycle 2 | Cycle 3 | Cycle 4 |
|---|---|---|---|---|
| BB1 | 1.1 | 2.1 | 3.1 | 4.1 |
| BB2 | 1.2 | 2.2 | 3.2 | 4.2 |
| BB3 | 1.3 | 2.3 | 3.3 | 4.3 |

TABLE 7-continued

Correspondence between building blocks and oligonucleotide tags for Cycles 1-4.

| Building block | Cycle 1 | Cycle 2 | Cycle 3 | Cycle 4 |
|---|---|---|---|---|
| BB4 | 1.4 | 2.4 | 3.4 | 4.4 |
| BB5 | 1.5 | 2.5 | 3.5 | 4.5 |
| BB6 | 1.6 | 2.6 | 3.6 | 4.6 |
| BB7 | 1.7 | 2.7 | 3.7 | 4.7 |
| BB8 | 1.8 | 2.8 | 3.8 | 4.8 |
| BB9 | 1.9 | 2.9 | 3.9 | 4.9 |
| BB10 | 1.10 | 2.10 | 3.10 | 4.10 |
| BB11 | 1.11 | 2.11 | 3.11 | 4.11 |
| BB12 | 1.12 | 2.12 | 3.12 | 4.12 |
| BB13 | 1.13 | 2.13 | 3.13 | 4.13 |
| BB14 | 1.14 | 2.14 | 3.14 | 4.14 |
| BB15 | 1.15 | 2.15 | 3.15 | 4.15 |
| BB16 | 1.16 | 2.16 | 3.16 | 4.16 |
| BB17 | 1.17 | 2.17 | 3.17 | 4.17 |
| BB18 | 1.18 | 2.18 | 3.18 | 4.18 |
| BB19 | 1.19 | 2.19 | 3.19 | 4.19 |
| BB20 | 1.20 | 2.20 | 3.20 | 4.20 |
| BB21 | 1.21 | 2.21 | 3.21 | 4.21 |
| BB22 | 1.22 | 2.22 | 3.22 | 4.22 |
| BB23 | 1.23 | 2.23 | 3.23 | 4.23 |
| BB24 | 1.24 | 2.24 | 3.24 | 4.24 |
| BB25 | 1.25 | 2.25 | 3.25 | 4.25 |
| BB26 | 1.26 | 2.26 | 3.26 | 4.26 |
| BB27 | 1.27 | 2.27 | 3.27 | 4.27 |
| BB28 | 1.28 | 2.28 | 3.28 | 4.28 |
| BB29 | 1.29 | 2.29 | 3.29 | 4.29 |
| BB30 | 1.30 | 2.30 | 3.30 | 4.30 |
| BB31 | 1.31 | 2.31 | 3.31 | 4.31 |
| BB32 | 1.32 | 2.32 | 3.32 | 4.32 |
| BB33 | 1.33 | 2.33 | 3.33 | 4.33 |
| BB34 | 1.34 | 2.34 | 3.34 | 4.34 |
| BB35 | 1.35 | 2.35 | 3.35 | 4.35 |
| BB36 | 1.36 | 2.36 | 3.36 | 4.36 |
| BB37 | 1.37 | 2.37 | 3.37 | 4.37 |
| BB38 | 1.38 | 2.38 | 3.38 | 4.38 |
| BB39 | 1.39 | 2.39 | 3.39 | 4.39 |
| BB40 | 1.44 | 2.44 | 3.44 | 4.44 |
| BB41 | 1.41 | 2.41 | 3.41 | 4.41 |
| BB42 | 1.42 | 2.42 | 3.42 | 4.42 |
| BB43 | 1.43 | 2.43 | 3.43 | 4.43 |
| BB44 | 1.40 | 2.40 | 3.40 | 4.40 |
| BB45 | 1.45 | 2.45 | 3.45 | 4.45 |
| BB46 | 1.46 | 2.46 | 3.46 | 4.46 |
| BB47 | 1.47 | 2.47 | 3.47 | 4.47 |
| BB48 | 1.48 | 2.48 | 3.48 | 4.48 |
| BB49 | 1.49 | 2.49 | 3.49 | 4.49 |
| BB50 | 1.50 | 2.50 | 3.50 | 4.50 |
| BB51 | 1.51 | 2.51 | 3.51 | 4.51 |
| BB52 | 1.52 | 2.52 | 3.52 | 4.52 |
| BB53 | 1.53 | 2.53 | 3.53 | 4.53 |
| BB54 | 1.54 | 2.54 | 3.54 | 4.54 |
| BB55 | 1.55 | 2.55 | 3.55 | 4.55 |
| BB56 | 1.56 | 2.56 | 3.56 | 4.56 |
| BB57 | 1.57 | 2.57 | 3.57 | 4.57 |
| BB58 | 1.58 | 2.58 | 3.58 | 4.58 |
| BB59 | 1.59 | 2.59 | 3.59 | 4.59 |
| BB60 | 1.60 | 2.60 | 3.60 | 4.60 |
| BB61 | 1.61 | 2.61 | 3.61 | 4.61 |
| BB62 | 1.62 | 2.62 | 3.62 | 4.62 |
| BB63 | 1.63 | 2.63 | 3.63 | 4.63 |
| BB64 | 1.64 | 2.64 | 3.64 | 4.64 |
| BB65 | 1.65 | 2.65 | 3.65 | 4.65 |
| BB66 | 1.66 | 2.66 | 3.66 | 4.66 |
| BB67 | 1.67 | 2.67 | 3.67 | 4.67 |
| BB68 | 1.68 | 2.68 | 3.68 | 4.68 |
| BB69 | 1.69 | 2.69 | 3.69 | 4.69 |
| BB70 | 1.70 | 2.70 | 3.70 | 4.70 |
| BB71 | 1.71 | 2.71 | 3.71 | 4.71 |
| BB72 | 1.72 | 2.72 | 3.72 | 4.72 |
| BB73 | 1.73 | 2.73 | 3.73 | 4.73 |
| BB74 | 1.74 | 2.74 | 3.74 | 4.74 |
| BB75 | 1.75 | 2.75 | 3.75 | 4.75 |
| BB76 | 1.76 | 2.76 | 3.76 | 4.76 |
| BB77 | 1.77 | 2.77 | 3.77 | 4.77 |
| BB78 | 1.78 | 2.78 | 3.78 | 4.78 |
| BB79 | 1.79 | 2.79 | 3.79 | 4.79 |
| BB80 | 1.80 | 2.80 | 3.80 | 4.80 |
| BB81 | 1.81 | 2.81 | 3.81 | 4.81 |
| BB82 | 1.82 | 2.82 | 3.82 | 4.82 |
| BB83 | 1.96 | 2.96 | 3.96 | 4.96 |
| BB84 | 1.83 | 2.83 | 3.83 | 4.83 |
| BB85 | 1.84 | 2.84 | 3.84 | 4.84 |
| BB86 | 1.85 | 2.85 | 3.85 | 4.85 |
| BB87 | 1.86 | 2.86 | 3.86 | 4.86 |
| BB88 | 1.87 | 2.87 | 3.87 | 4.87 |
| BB89 | 1.88 | 2.88 | 3.88 | 4.88 |
| BB90 | 1.89 | 2.89 | 3.89 | 4.89 |
| BB91 | 1.90 | 2.90 | 3.90 | 4.90 |
| BB92 | 1.91 | 2.91 | 3.91 | 4.91 |
| BB93 | 1.92 | 2.92 | 3.92 | 4.92 |
| BB94 | 1.93 | 2.93 | 3.93 | 4.93 |
| BB95 | 1.94 | 2.94 | 3.94 | 4.94 |
| BB96 | 1.95 | 2.95 | 3.95 | 4.95 |

1× ligase buffer: 50 mM Tris, pH 7.5; 10 mM dithiothreitol; 10 mM $MgCl_2$; 2 mM ATP; 50 mM NaCl.

10× ligase buffer: 500 mM Tris, pH 7.5; 100 mM dithiothreitol; 100 mM $MgCl_2$; 20 mM ATP; 500 mM NaCl Attachment of Water Soluble Spacer to Compound 2

To a solution of Compound 2 (60 mL, 1 mM) in sodium borate buffer (150 mM, pH 9.4) that was chilled to 4° C. was added 40 equivalents of N-Fmoc-15-amino-4,7,10,13-tetraoxaoctadecanoic acid (S-Ado) in N,N-dimethylformamide (DMF) (16 mL, 0.15 M) followed by 40 equivalents of 4-(4,6-dimethoxy[1.3.5]triazin-2-yl)-4-methylmorpholinium chloride hydrate (DMTMM) in water (9.6 mL, 0.25 M). The mixture was gently shaken for 2 hours at 4° C. before an additional 40 equivalents of S-Ado and DMTMM were added and shaken for a further 16 hours at 4° C.

Following acylation, a 0.1× volume of 5 M aqueous NaCl and a 2.5× volume of cold (−20° C.) ethanol was added and the mixture was allowed to stand at −20° C. for at least one hour. The mixture was then centrifuged for 15 minutes at 14,000 rpm in a 4° C. centrifuge to give a white pellet which was washed with cold EtOH and then dried in a lyophilizer at room temperature for 30 minutes. The solid was dissolved in 40 mL of water and purified by Reverse Phase HPLC with a Waters Xterra $RP_{18}$ column. A binary mobile phase gradient profile was used to elute the product using a 50 mM aqueous triethylammonium acetate buffer at pH 7.5 and 99% acetonitrile/1% water solution. The purified material was concentrated by lyophilization and the resulting residue was dissolved in 5 mL of water. A 0.1× volume of piperidine was added to the solution and the mixture was gently shaken for 45 minutes at room temperature. The product was then purified by ethanol precipitation as described above and isolated by centrifugation. The resulting pellet was washed twice with cold EtOH and dried by lyophilization to give purified Compound 3.

Cycle 1

To each well in a 96 well plate was added 12.5 μL of a 4 mM solution of Compound 3 in water; 100 μL of a 1 mM solution of one of oligonucleotide tags 1.1 to 1.96, as shown in Table 3 (the molar ratio of Compound 3 to tags was 1:2). The plates were heated to 95° C. for 1 minute and then cooled to 16° C. over 10 minutes. To each well was added 10 μL of 10× ligase buffer, 30 units T4 DNA ligase (1 μL of a 30 unit/μL solution (FermentasLife Science, Cat. No. EL0013)), 76.5 µl of water and the resulting solutions were incubated at 16° C. for 16 hours.

After the ligation reaction, 20 µL of 5 M aqueous NaCl was added directly to each well, followed by 500 µL cold (−20° C.) ethanol, and held at −20° C. for 1 hour. The plates were centrifugated for 1 hour at 3200 g in a Beckman Coulter Allegra 6R centrifuge using Beckman Microplus Carriers. The supernatant was carefully removed by inverting the plate and the pellet was washed with 70% aqueous cold ethanol at −20° C. Each of the pellets was then dissolved in sodium borate buffer (50 µL, 150 mM, pH 9.4) to a concentration of 1 mM and chilled to 4° C.

To each solution was added 40 equivalents of one of the 96 building block precursors in DMF (13 µL, 0.15 M) followed by 40 equivalents of DMT-MM in water (8 µL, 0.25M), and the solutions were gently shaken at 4° C. After 2 hours, an additional 40 equivalents of one of each building block precursor and DMTMM were added and the solutions were gently shaken for 16 hours at 4° C. Following acylation, 10 equivalents of acetic acid-N-hydroxy-succinimide ester in DMF (2 µL, 0.25M) was added to each solution and gently shaken for 10 minutes.

Following acylation, the 96 reaction mixtures were pooled and 0.1 volume of 5M aqueous NaCl and 2.5 volumes of cold absolute ethanol were added and the solution was allowed to stand at −20° C. for at least one hour. The mixture was then centrifuged. Following centrifugation, as much supernatant as possible was removed with a micropipette, the pellet was washed with cold ethanol and centrifuged again. The supernatant was removed with a 200 µL pipet. Cold 70% ethanol was added to the tube, and the resulting mixture was centrifuged for 5 min at 4° C.

The supernatant was removed and the remaining ethanol was removed by lyophilization at room temperature for 10 minutes. The pellet was then dissolved in 2 mL of water and purified by Reverse Phase HPLC with a Waters Xterra $RP_{18}$ column. A binary mobile phase gradient profile was used to elute the library using a 50 mM aqueous triethylammonium acetate buffer at pH 7.5 and 99% acetontrile/1% water solution. The fractions containing the library were collected, pooled, and lyophilized. The resulting residue was dissolved in 2.5 mL of water and 250 µL of piperidine was added. The solution was shaken gently for 45 minutes and then precipitated with ethanol as previously described. The resulting pellet was dried by lyophilization and then dissolved in sodium borate buffer (4.8 mL, 150 mM, pH 9.4) to a concentration of 1 mM.

The solution was chilled to 4° C. and 40 equivalents each of N-Fmoc-propargylglycine in DMF (1.2 mL, 0.15 M) and DMT-MM in water (7.7 mL, 0.25 M) were added. The mixture was gently shaken for 2 hours at 4° C. before an additional 40 equivalents of N-Fmoc-propargylglycine and DMT-MM were added and the solution was shaken for a further 16 hours. The mixture was later purified by EtOH precipitation and Reverse Phase HPLC as described above and the N-Fmoc group was removed by treatment with piperidine as previously described. Upon final purification by EtOH precipitation, the resulting pellet was dried by lyophilization and carried into the next cycle of synthesis Cycles 2-4

For each of these cycles, the dried pellet from the previous cycle was dissolved in water and the concentration of library was determined by spectrophotometry based on the extinction coefficient of the DNA component of the library, where the initial extinction coefficient of Compound 2 is 131,500 L/(mole.cm). The concentration of the library was adjusted with water such that the final concentration in the subsequent ligation reactions was 0.25 mM. The library was then divided into 96 equal aliquots in a 96 well plate. To each well was added a solution comprising a different tag (molar ratio of the library to tag was 1:2), and ligations were performed as described for Cycle 1. Oligonucleotide tags used in Cycles 2, 3 and 4 are set forth in Tables 4, 5 and 6, respectively. Correspondense between the tags and the building block precursors for each of Cycles 1 to 4 is provided in Table 7. The library was precipitated by the addition of ethanol as described above for Cycle 1, and dissolved in sodium borate buffer (150 mM, pH 9.4) to a concentration of 1 mM. Subsequent acylations and purifications were performed as described for Cycle 1, except HPLC purification was omitted during Cycle 3.

The products of Cycle 4 were ligated with the closing primer shown below, using the method described above for ligation of tags.

(SEQ ID NO: 889)
5'-PO₃-CAG AAG ACA GAC AAG CTT CAC CTG C (SEQ ID NO: 890)
5'-PO₃-GCA GGT GAA GCT TGT CTG TCT TCT GAA

Results:

The synthetic procedure described above has the capability of producing a library comprising $96^4$ (about $10^8$) different structures. The synthesis of the library was monitored via gel electrophoresis and LC/MS of the product of each cycle. Upon completion, the library was analyzed using several techniques. FIG. 13a is a chromatogram of the library following Cycle 4, but before ligation of the closing primer; FIG. 13b is a mass spectrum of the library at the same synthetic stage. The average molecular weight was determined by negative ion LC/MS analysis. The ion signal was deconvoluted using ProMass software. This result is consistent with the predicted average mass of the library.

The DNA component of the library was analyzed by agarose gel electrophoresis, which showed that the majority of library material corresponds to ligated product of the correct size. DNA sequence analysis of molecular clones of PCR product derived from a sampling of the library shows that DNA ligation occurred with high fidelity and to near completion.

Library Cyclization

At the completion of Cycle 4, a portion of the library was capped at the N-terminus using azidoacetic acid under the usual acylation conditions. The product, after purification by EtOH precipitation, was dissolved in sodium phosphate buffer (150 mM, pH 8) to a concentration of 1 mM and 4 equivalents each of $CuSO_4$ in water (200 mM), ascorbic acid in water (200 mM), and a solution of the compound shown below in DMF (200 mM) were added. The reaction mixture was then gently shaken for 2 hours at room temperature.

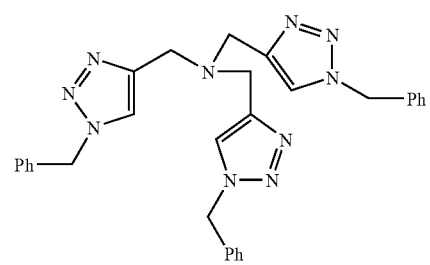

To assay the extent of cyclization, 5 μL aliquots from the library cyclization reaction were removed and treated with a fluorescently-labeled azide or alkyne (1 μL of 100 mM DMF stocks) prepared as described in Example 4. After 16 hours, neither the alkyne or azide labels had been incorporated into the library by HPLC analysis at 500 nm. This result indicated that the library no longer contained azide or alkyne groups capable of cycloaddition and that the library must therefore have reacted with itself, either through cyclization or intermolecular reactions. The cyclized library was purified by Reverse Phase HPLC as previously described. Control experiments using uncyclized library showed complete incorporation of the fluorescent tags mentioned above.

Example 4

Preparation of Fluorescent Tags for Cyclization Assay

In separate tubes, propargyl glycine or 2-amino-3-phenyl-propylazide (8 μmol each) was combined with FAM-OSu (Molecular Probes Inc.) (1.2 equiv.) in pH 9.4 borate buffer (250 μL). The reactions were allowed to proceed for 3 h at room temperature, and were then lyophilized overnight. Purification by HPLC afforded the desired fluorescent alkyne and azide in quantitative yield.

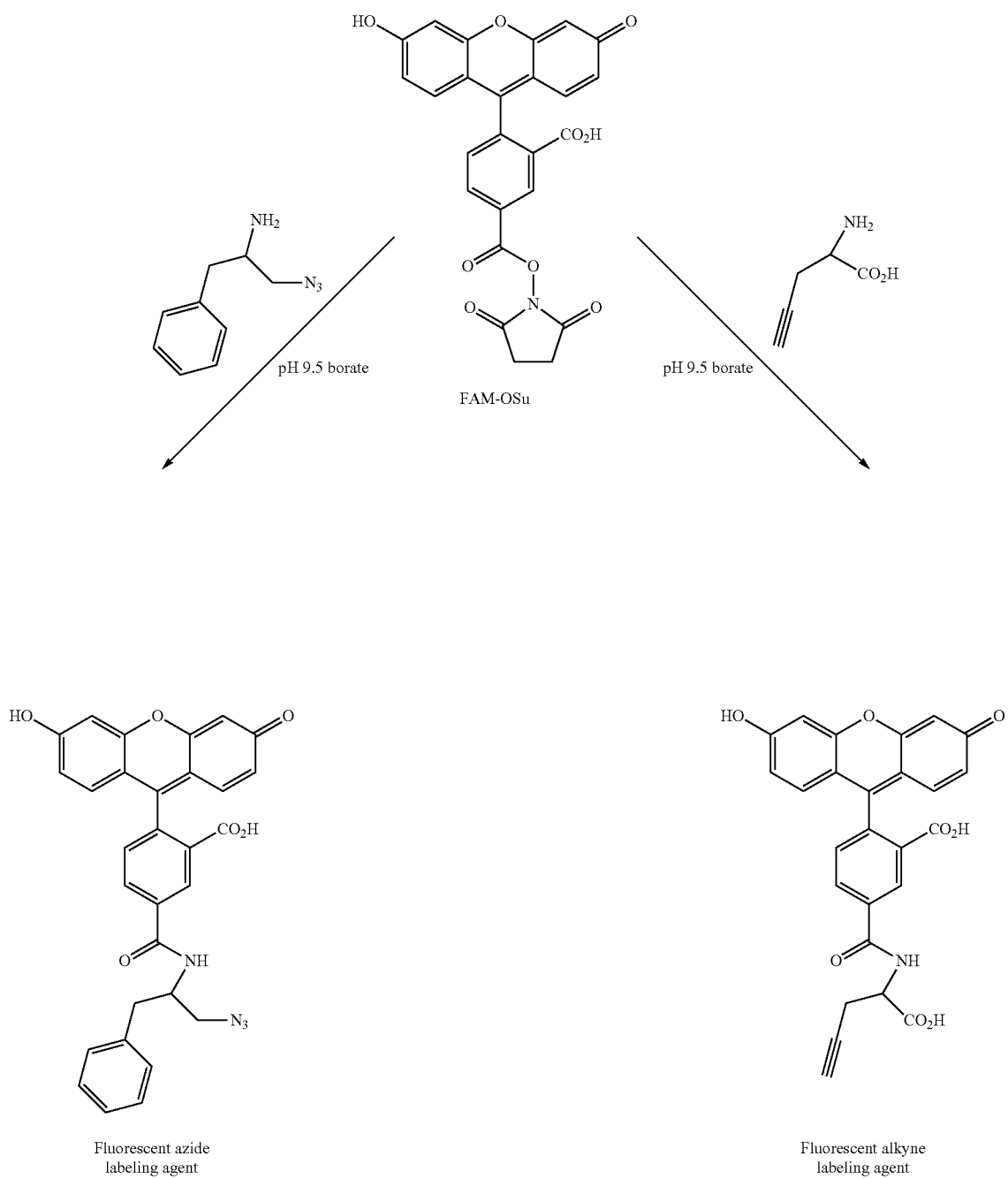

Fluorescent azide labeling agent

Fluorescent alkyne labeling agent

Example 5

Cyclization of Individual Compounds Using the Azide/Alkyne Cycloaddition Reaction Preparation of Azidoacetyl-Gly-Pro-Phe-Pra-NH$_2$:

Using 0.3 mmol of Rink-amide resin, the indicated sequence was synthesized using standard solid phase synthesis techniques with Fmoc-protected amino acids and HATU as activating agent (Pra=C-propargylglycine). Azidoacetic acid was used to cap the tetrapeptide. The peptide was cleaved from the resin with 20% TFA/DCM for 4 h. Purification by RP HPLC afforded product as a white solid (75 mg, 51%). $^1$H NMR (DMSO-d$_6$, 400 MHz): 8.4-7.8 (m, 3H), 7.4-7.1 (m, 7H), 4.6-4.4 (m, 1H), 4.4-4.2 (m, 2H), 4.0-3.9 (m, 2H), 3.74 (dd, 1H, J=6 Hz, 17 Hz), 3.5-3.3 (m, 2H), 3.07 (dt, 1H, J=5 Hz, 14 Hz), 2.92 (dd, 1H, J=5 Hz, 16 Hz), 2.86 (t, 1H, J=2 Hz), 2.85-2.75 (m, 1H), 2.6-2.4 (m, 2H), 2.2-1.6 (m, 4H). IR (mull) 2900, 2100, 1450, 1300 cm$^{-1}$. ESIMS 497.4 ([M+H], 100%), 993.4 ([2M+H], 50%). ESIMS with ion-source fragmentation: 519.3 ([M+Na], 100%), 491.3 (100%), 480.1 ([M-NH$_2$], 90%), 452.2 ([M-NH$_2$—CO], 20%), 424.2 (20%), 385.1 ([M-Pra], 50%), 357.1 ([M-Pra-CO], 40%), 238.0 ([M-Pra-Phe], 100%).

Cyclization of Azidoacetyl-Gly-Pro-Phe-Pra-NH$_2$:

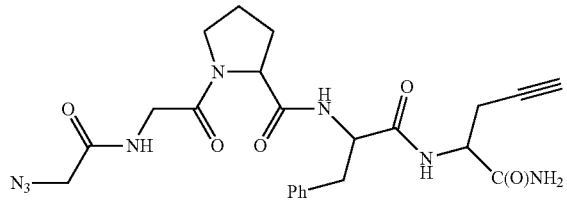 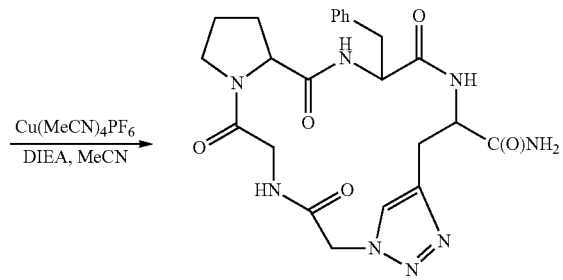

The azidoacetyl peptide (31 mg, 0.62 mmol) was dissolved in MeCN (30 mL). Diisopropylethylamine (DIEA, 1 mL) and Cu(MeCN)$_4$PF$_6$ (1 mg) were added. After stirring for 1.5 h, the solution was evaporated and the resulting residue was taken up in 20% MeCN/H$_2$O. After centrifugation to remove insoluble salts, the solution was subjected to preparative reverse phase HPLC. The desired cyclic peptide was isolated as a white solid (10 mg, 32%). $^1$H NMR (DMSO-d$_6$, 400 MHz): 8.28 (t, 1H, J=5 Hz), 7.77 (s, 1H), 7.2-6.9 (m, 9H), 4.98 (m, 2H), 4.48 (m, 1H), 4.28 (m, 1H), 4.1-3.9 (m, 2H), 3.63 (dd, 1H, J=5 Hz, 16 Hz), 3.33 (m, 2H), 3.0 (m, 3H), 2.48 (dd, 1H, J=11 Hz, 14 Hz), 1.75 (m, 1H0, 1.55 (m, 1H), 1.32 (m, 1H), 1.05 (m, 1H). IR (mull) 2900, 1475, 1400 cm$^{-1}$. ESIMS 497.2 ([M+H], 100%), 993.2 ([2M+H], 30%), 1015.2 ([2M+Na], 15%). ESIMS with ion-source fragmentation: 535.2 (70%), 519.3 ([M+Na], 100%), 497.2 ([M+H], 80%), 480.1 ([M-NH$_2$], 30%), 452.2 ([M-NH$_2$—CO], 40%), 208.1 (60%).

Preparation of Azidoacetyl-Gly-Pro-Phe-Pra-Gly-OH (SEQ ID NO:920):

Using 0.3 mmol of Glycine-Wang resin, the indicated sequence was synthesized using Fmoc-protected amino acids and HATU as the activating agent. Azidoacetic acid was used in the last coupling step to cap the pentapeptide. Cleavage of the peptide was achieved using 50% TFA/DCM for 2 h. Purification by RP HPLC afforded the peptide as a white solid (83 mg; 50%). $^1$H NMR (DMSO-d$_6$, 400 MHz): 8.4-7.9 (m, 4H), 7.2 (m, 5H), 4.7-4.2 (m, 3H), 4.0-3.7 (m, 4H), 3.5-3.3 (m, 2H), 3.1 (m, 1H), 2.91 (dd, 1H, J=4 Hz, 16 Hz), 2.84 (t, 1H, J=2.5 Hz), 2.78 (m, 1H), 2.6-2.4 (m, 2H), 2.2-1.6 (m, 4H). IR (mull) 2900, 2100, 1450, 1350 cm$^{-1}$. ESIMS 555.3 ([M+H], 100%). ESIMS with ion-source fragmentation: 577.1 ([M+Na], 90%), 555.3 ([M+H], 80%), 480.1 ([M-Gly], 100%), 385.1 ([M-Gly-Pra], 70%), 357.1 ([M-Gly-Pra-CO], 40%), 238.0 ([M-Gly-Pra-Phe], 80%).

Cyclization of Azidoacetyl-Gly-Pro-Phe-Pra-Gly-OH (SEQ ID NO:920):

The peptide (32 mg, 0.058 mmol) was dissolved in MeCN (60 mL). Diisopropylethylamine (1 mL) and Cu(MeCN)$_4$PF$_6$ (1 mg) were added and the solution was stirred for 2 h. The solvent was evaporated and the crude product was subjected to RP HPLC to remove dimers and trimers. The cyclic monomer was isolated as a colorless glass (6 mg, 20%). ESIMS 555.6 ([M+H], 100%), 1109.3 ([2M+H], 20%), 1131.2 ([2M+Na], 15%).

ESIMS with ion source fragmentation: 555.3 ([M+H], 100%), 480.4 ([M-Gly], 30%), 452.2 ([M-Gly-CO], 25%), 424.5 ([M-Gly-2CO], 10%, only possible in a cyclic structure).

Conjugation of Linear Peptide to DNA:

Compound 2 (45 nmol) was dissolved in 45 µL sodium borate buffer (pH 9.4; 150 mM). At 4° C., linear peptide (18 µL of a 100 mM stock in DMF; 180 nmol; 40 equiv.) was added, followed by DMT-MM (3.6 µL of a 500 mM stock in water; 180 nmol; 40 equiv.). After agitating for 2 h, LCMS showed complete reaction, and product was isolated by ethanol precipitation. ESIMS 1823.0 ([M-3H]/3, 20%), 1367.2 ([M-4H]/4, 20%), 1093.7 ([M-5H]/5, 40%), 911.4 ([M-6H]/6, 100%).

Conjugation of Cyclic Peptide to DNA:

Compound 2 (20 nmol) was dissolved in 20 µL sodium borate buffer (pH 9.4, 150 mM). At 4° C., linear peptide (8 µL of a 100 mM stock in DMF; 80 nmol; 40 equiv.) was added, followed by DMT-MM (1.6 µL of a 500 mM stock in water; 80 nmol; 40 equiv.). After agitating for 2 h, LCMS showed complete reaction, and product was isolated by ethanol precipitation. ESIMS 1823.0 ([M-3H]/3, 20%), 1367.2 ([M-4H]/4, 20%), 1093.7 ([M-5H]/5, 40%), 911.4 ([M-6H]/6, 100%).

Cyclization of DNA-Linked Peptide:

Linear peptide-DNA conjugate (10 nmol) was dissolved in pH 8 sodium phosphate buffer (10 µL, 150 mm). At room temperature, 4 equivalents each of CuSO$_4$, ascorbic acid, and the Sharpless ligand were all added (0.2 µL of 200 mM stocks). The reaction was allowed to proceed overnight. RP HPLC showed that no linear peptide-DNA was present, and that the product co-eluted with authentic cyclic peptide-DNA. No traces of dimers or other oligomers were observed.

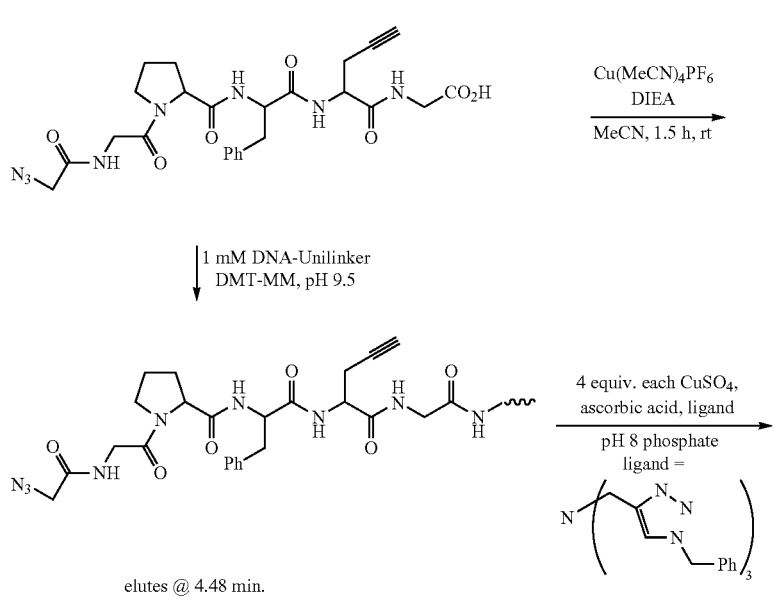
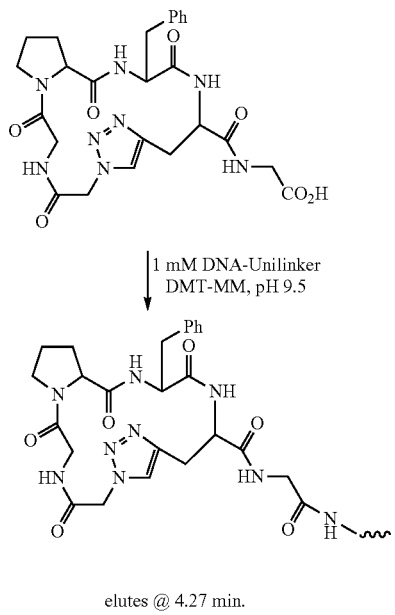

elutes @ 4.48 min.
LC conditions: Targa C18, 2.1 × 40 mm, 10-40% MeCN in 40 mM aq. TEAA over 8 min.

elutes @ 4.27 min.

Example 6

Application of Aromatic Nucleophilic Substitution Reactions to Functional Moiety Synthesis General Procedure for Arylation of Compound 3 with Cyanuric Chloride:

Compound 2 is dissolved in pH 9.4 sodium borate buffer at a concentration of 1 mM. The solution is cooled to 40° C. and 20 equivalents of cyanuric chloride is then added as a 500 mM solution in MeCN. After 2 h, complete reaction is confirmed by LCMS and the resulting dichlorotriazine-DNA conjugate is isolated by ethanol precipitation.

Procedure for Amine Substitution of Dichlorotriazine-DNA:

The dichlorotriazine-DNA conjugate is dissolved in pH 9.5 borate buffer at a concentration of 1 mM. At room temperature, 40 equivalents of an aliphatic amine is added as a DMF solution. The reaction is followed by LCMS and is usually complete after 2 h. The resulting alkylamino-monochlorotriazine-DNA conjugate is isolated by ethanol precipitation.

Procedure for Amine Substitution of Monochlorotriazine-DNA:

The alkylamino-monochlorotriazine-DNA conjugate is dissolved in pH 9.5 borate buffer at a concentration of 1 mM. At 42° C., 40 equivalents of a second aliphatic amine is added as a DMF solution. The reaction is followed by LCMS and is usually complete after 2 h. The resulting diaminotriazine-DNA conjugate is isolated by ethanol precipitation.

Example 7

Application of Reductive Amination Reactions to Functional Moiety Synthesis

General Procedure for Reductive Amination of DNA-Linker Containing a Secondary Amine with an Aldehyde Building Block:

Compound 2 was coupled to an N-terminal proline residue. The resulting compound was dissolved in sodium phosphate buffer (50 μL, 150 mM, pH 5.5) at a concentration of 1 mM. To this solution was added 40 equivalents each of an aldehyde building block in DMF (8 μL, 0.25M) and sodium cyanoborohydride in DMF (8 μL, 0.25M) and the solution was heated at 80° C. for 2 hours. Following alkylation, the solution was purified by ethanol precipitation.

General Procedure for Reductive Aminations of DNA-Linker Containing an Aldehyde with Amine Building Blocks:

Compound 2 coupled to a building block comprising an aldehyde group was dissolved in sodium phosphate buffer (50 μL, 250 mM, pH 5.5) at a concentration of 1 mM. To this solution was added 40 equivalents each of an amine building block in DMF (8 μL, 0.25M) and sodium cyanoborohydride in DMF (8 μL, 0.25M) and the solution was heated at 80° C. for 2 hours. Following alkylation, the solution was purified by ethanol precipitation.

Example 8

Application of Peptoid Building Reactions to Functional Moiety Synthesis

General Procedure for Peptoid Synthesis on DNA-Linker:

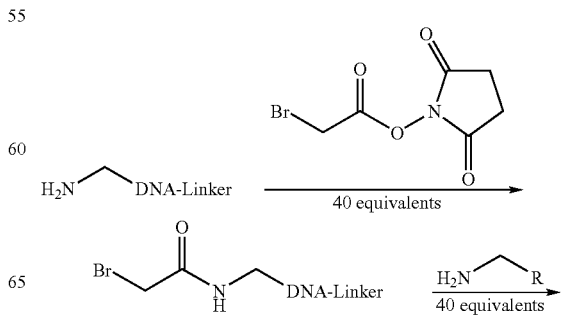

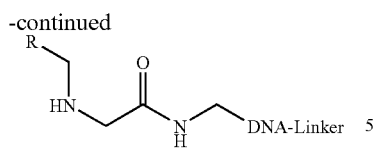

Compound 2 was dissolved in sodium borate buffer (50 μL, 150 mM, pH 9.4) at a concentration of 1 mM and chilled to 4° C. To this solution was added 40 equivalents of N-hydroxysuccinimidyl bromoacetate in DMF (13 μL, 0.15 M) and the solution was gently shaken at 4° C. for 2 hours. Following acylation, the DNA-Linker was purified by ethanol precipitation and redissolved in sodium borate buffer (50 μL, 150 mM, pH 9.4) at a concentration of 1 mM and chilled to 4° C. To this solution was added 40 equivalents of an amine building block in DMF (13 μL, 0.15 M) and the solution was gently shaken at 4° C. for 16 hours. Following alkylation, the DNA-linker was purified by ethanol precipitation and redissolved in sodium borate buffer (50 μL, 150 mM, pH 9.4) at a concentration of 1 mM and chilled to 4° C. Peptoid synthesis is continued by the stepwise addition of N-hydroxysuccinimidyl bromoacetate followed by the addition of an amine building block.

Example 9

Application of the Azide-Alkyne Cycloaddition Reaction to Functional Moiety Synthesis General Procedure An alkyne-containing DNA conjugate is dissolved in pH 8.0 phosphate buffer at a concentration of ca. 1 mM. To this mixture is added 10 equivalents of an organic azide and 5 equivalents each of copper (II) sulfate, ascorbic acid, and the ligand (tris-((1-benzyltriazol-4-yl)methyl)amine all at room temperature. The reaction is followed by LCMS, and is usually complete after 1-2 h. The resulting triazole-DNA conjugate can be isolated by ethanol precipitation.

Example 10

Identification of a ligand to Abl Kinase from within an Encoded Library

The ability to enrich molecules of interest in a DNA-encoded library above undesirable library members is paramount to identifying single compounds with defined properties against therapeutic targets of interest. To demonstrate this enrichment ability a known binding molecule (described by Shah et al., Science 305, 399-401 (2004), incorporated herein by reference) to rhAbl kinase (GenBank U07563) was synthesized. This compound was attached to a double stranded DNA oligonucleotide via the linker described in the preceding examples using standard chemistry methods to produce a molecule similar (functional moiety linked to an oligonucleotide) to those produced via the methods described in Examples 1 and 2. A library generally produced as described in Example 2 and the DNA-linked Abl kinase binder were designed with unique DNA sequences that allowed qPCR analysis of both species. The DNA-linked Abl kinase binder was mixed with the library at a ratio of 1:1000. This mixture was equilibrated with to rhAble kinase, and the enzyme was captured on a solid phase, washed to remove non-binding library members and binding molecules were eluted. The ratio of library molecules to the DNA-linked Abl kinase inhibitor in the eluate was 1:1, indicating a greater than 500-fold enrichment of the DNA-linked Abl-kinase binder in a 1000-fold excess of library molecules.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for identifying one or more compounds which bind to a biological target, said method comprising:
   (A) synthesizing a library of compounds, wherein the compounds comprise a functional moiety comprising two or more building blocks which is operatively linked to an encoding oligonucleotide which identifies the structure of the functional moiety by:
      (i) providing a solution comprising m initiator compounds, wherein m is an integer of 1 or greater, where the initiator compounds consist of an initial functional moiety comprising n building blocks comprising at least one reactive group, where n is an integer of 1 or greater, which is operatively linked to an initial oligonucleotide which identifies the n building blocks; wherein the initial functional moiety and the initial oligonucleotide are linked by a linking moiety and wherein the initial oligonucleotide is double-stranded and the linking moiety is covalently coupled to the initial functional moiety and to both strands of the initial oligonucleotide;
      (ii) dividing the solution of step (A)(i) into r reaction vessels, wherein r is an integer of 2 or greater, thereby producing r aliquots of the solution;
      (iii) reacting the initiator compounds in each reaction vessel with one of r building blocks, said building blocks comprising at least one complementary reactive group, which complementary reactive group is complementary to the reactive group of step (A)(i), under conditions suitable for reaction of the complementary reactive group to form a covalent bond, thereby producing r aliquots comprising compounds consisting of a functional moiety comprising n+1 building blocks operatively linked to the initial oligonucleotide; and
      (iv) reacting the initial oligonucleotide in each aliquot with one of a set of r distinct incoming oligonucleotides corresponding to the building block of step (A)(iii) in the presence of an enzyme which catalyzes the ligation of the incoming oligonucleotide and the initial oligonucleotide, under conditions suitable for enzymatic ligation of the incoming oligonucleotide and the initial oligonucleotide to form an encoding oligonucleotide;
      thereby producing r aliquots of molecules consisting of a functional moiety comprising n+1 building blocks operatively linked to an encoding oligonucleotide which identifies the structure of the functional moiety comprising the n+1 building blocks;
   (B) contacting the biological target with the library of compounds, or a portion thereof, under conditions suitable for at least one member of the library of compounds to bind to the target;
   (C) removing library members that do not bind to the target;
   (D) sequencing the encoding oligonucleotides of the at least one member of the library of compounds which binds to the target, and
   (E) using the sequences determined in step (D) to determine the structure of the functional moieties of the members of the library of compounds which bind to the biological target, thereby identifying one or more compounds which bind to the biological target.

2. The method of claim 1, further comprising amplifying the encoding oligonucleotides of the at least one member of the library of compounds which binds to the target.

3. The method of claim 2, wherein said amplifying step comprises:
   (i) forming a water-in-oil emulsion to create a plurality of aqueous microreactors, wherein at least one of the microreactors comprises the at least one member of the library of compounds that binds to the target, a single bead capable of binding to the encoding oligonucleotide of the at least one member of the library of compounds that binds to the target, and amplification reaction solution containing reagents necessary to perform nucleic acid amplification;
   (ii) amplifying the encoding oligonucleotide in the microreactors to form amplified copies of said encoding oligonucleotide; and
   (iii) binding the amplified copies of the encoding oligonucleotide to the beads in the microreactors.

4. The method of claim 2, wherein said sequencing step (D) comprises:
   (i) annealing an effective amount of a sequencing primer to the amplified copies of the encoding oligonucleotide and extending the sequencing primer with a polymerase and a predetermined nucleotide triphosphate to yield a sequencing product and, if the predetermined nucleotide triphosphate is incorporated onto a 3' end of said sequencing primer, a sequencing reaction byproduct; and
   (ii) identifying the sequencing reaction byproduct, thereby determining the sequence of the encoding oligonucleotide.

5. The method of claim 2, wherein said amplification of the encoding oligonucleotides is carried out by a method selected from the group consisting of: the polymerase chain reaction (PCR); transcription-based amplification, rapid amplification of cDNA ends, continuous flow amplification, and rolling circle amplification.

6. The method of claim 1 or 4, wherein said sequencing of the encoding oligonucleotides is carried out by a pyrophosphate-based sequencing reaction or a single molecule sequencing by synthesis method.

7. The method of claim 6, wherein the sequencing reaction byproduct is PPi and a coupled sulfurylase/luciferase reaction is used to generate light for detection.

8. The method of claim 3, further comprising the step of enriching for beads which bind amplified copies of the encoding oligonucleotide away from beads to which no encoding oligonucleotide is bound.

9. The method of claim 8, wherein the method for said enrichment step is selected from the group consisting of affinity purification, and electrophoresis.

10. The method of claim 3, further comprising breaking the emulsion to retrieve one or more of the amplified copies of the encoding oligonucleotide.

11. The method of claim 1, further comprising the step of
   (A)(v) combining two or more of the r aliquots, thereby producing a solution comprising molecules consisting of a functional moiety comprising n+1 building blocks, which is operatively linked to an elongated oligonucleotide which encodes the n+1 building blocks.

12. The method of claim 11, wherein r aliquots are combined.

13. The method of claim 11, wherein the steps (A)(i) to (A)(v) are conducted one or more times to yield cycles 1 to i, where i is an integer of 2 or greater, wherein in cycle s+1, where s is an integer of i−1 or less, the solution comprising m initiator compounds of step (A)(i) is the solution of step (A)(v) of cycle s.

14. The method of claim 1, wherein at least one of the building blocks is an amino acid.

15. The method of claim 1, wherein the incoming oligonucleotide is a double-stranded oligonucleotide.

16. The method of claim 1, wherein the linking moiety is of the structure

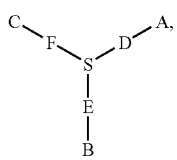

wherein
A is a functional group adapted to bond to a building block;
B is a functional group adapted to bond to the 5'-end of an oligonucleotide;
C is a functional group adapted to bond to the 3'-end of an oligonucleotide;
S is an atom or a scaffold;
D is a chemical structure that connects A to S;
E is a chemical structure that connects B to S; and
F is a chemical structure that connects C to S.

17. The method of claim 16, wherein:
A is an amino group;
B is a phosphate group; and
C is a phosphate group.

18. The method of claim 16, wherein D, E and F are each, independently, an alkylene group or an oligo(ethylene glycol) group.

19. The method of claim 16, wherein S is a carbon atom, a nitrogen atom, a phosphorus atom, a boron atom, a phosphate group, a cyclic group or a polycyclic group.

20. The method of claim 19, wherein the linking moiety is of the structure

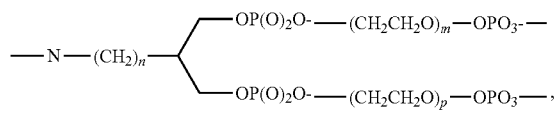

wherein each of n, m and p is, independently, an integer from 1 to about 20.

21. The method of claim 20, wherein each of n, m and p is independently an integer from 2 to 8.

22. The method of claim 21, wherein each of n, m and p is independently an integer from 3 to 6.

23. The method of claim 20, wherein the linking moiety has the structure

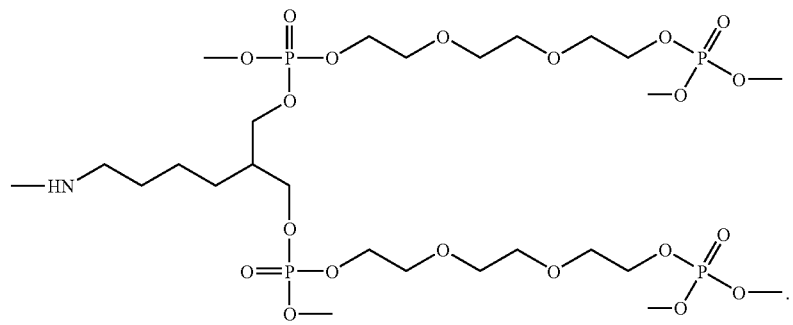

24. The method of claim 1, wherein the reactive group is an amino group and the complementary reactive group is selected from the group consisting of a carboxyl group; a sulfonyl group; a phosphonyl group; an epoxide group; an aziridine group; and an isocyanate group.

25. The method of claim 1, wherein reactive group or the complementary reactive group are independently selected from the group consisting of a hydroxyl group; a carboxyl group; a sulfonyl group; a phosphonyl group; an epoxide group; an aziridine group; and an isocyanate group.

26. The method of claim 1, wherein the reactive group is an amino group and the complementary reactive group is selected from the group consisting of an aldehyde group and a ketone group.

27. The method of claim 1, wherein the reaction between the reactive group and the complementary reactive group is conducted under reducing conditions.

28. The method of claim 1, wherein the reactive group is a phosphorous ylide group and the complementary reactive group is selected from the group consisting of an aldehyde group and a ketone group.

29. The method of claim 1, wherein the reactive group and the complementary reactive group react via cycloaddition to form a cyclic structure.

30. The method of claim 29, wherein the reactive group and the complementary reactive group are selected from the group consisting of an alkyne and an azide.

31. The method of claim 29, wherein the reactive group and the complementary functional group are selected from the group consisting of a halogenated heteroaromatic group and a nucleophile.

32. The method of claim 31, wherein the halogenated heteroaromatic group is selected from the group consisting of chlorinated pyrimidines, chlorinated triazines and chlorinated purines.

33. The method of claim 31, wherein the nucleophile is an amino group.

34. The method of claim 13, further comprising following cycle i, the step of:
(A)(vi) cyclizing one or more of the functional moieties.

35. The method of claim 34, wherein a functional moiety of step (A)(vi) comprises an azido group and an alkynyl group.

36. The method of claim 35, wherein the functional moiety is maintained under conditions suitable for cycloaddition of the azido group and the alkynyl group to form a triazole group, thereby forming a cyclic functional moiety.

37. The method of claim 36, wherein the cycloaddition reaction is conducted in the presence of a copper catalyst.

38. The method of claim 37, wherein at least one of the one or more functional moieties of step (A)(vi) comprises at least two sulfhydryl groups, and said functional moiety is maintained under conditions suitable for reaction of the two sulfhydryl groups to form a disulfide group, thereby cyclicizing the functional moiety.

39. The method of claim 1, wherein the initial oligonucleotide comprises a PCR primer sequence.

40. The method of claim 13, wherein the incoming oligonucleotide of cycle i comprises a PCR closing primer.

41. The method of claim 13, further comprising following cycle i, the step of
ligating an oligonucleotide comprising a closing PCR primer sequence to the encoding oligonucleotide.

42. The method of claim 41, wherein the oligonucleotide comprising a closing PCR primer sequence is ligated to the encoding oligonucleotide in the presence of an enzyme which catalyzes said ligation.

43. The method of claim 1, wherein the reactions of step (A)(i) through (A)(iv) are conducted in an aqueous solution.

44. The method of claim 1, wherein the synthesized molecules are polymeric compounds.

45. The method of claim 1, wherein the synthesized molecules are small non-polymeric compounds.

46. The method of claim 1, wherein the reactions of step (A)(i) through (A)(iv) are conducted in a mixed aqueous/organic media.

* * * * *